US008545856B2

(12) United States Patent
Boyden et al.

(10) Patent No.: US 8,545,856 B2
(45) Date of Patent: *Oct. 1, 2013

(54) COMPOSITIONS AND METHODS FOR DELIVERY OF FROZEN PARTICLE ADHESIVES

(75) Inventors: Edward S. Boyden, Cambridge, MA (US); Daniel B. Cook, Seattle, WA (US); Roderick A. Hyde, Redmond, WA (US); Eric C. Leuthardt, St. Louis, MO (US); Nathan P. Myhrvold, Medina, WA (US); Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 311 days.

This patent is subject to a terminal disclaimer.

(21) Appl. No.: 12/383,264

(22) Filed: Mar. 20, 2009

(65) Prior Publication Data

US 2010/0113614 A1 May 6, 2010

Related U.S. Application Data

(63) Continuation-in-part of application No. 12/383,263, filed on Mar. 20, 2009, and a continuation-in-part of application No. 12/383,260, filed on Mar. 20, 2009, and a continuation-in-part of application No. 12/383,265, filed on Mar. 20, 2009, and a continuation-in-part of application No. 12/290,671, filed on Oct. 31, 2008, and a continuation-in-part of application No. 12/290,683, filed on Oct. 31, 2008, and a continuation-in-part of application No. 12/290,685, filed on Oct. 31, 2008, and a continuation-in-part of application No. 12/290,686, filed on Oct. 31, 2008, and a continuation-in-part of application No. 12/290,690, filed on Oct. 31, 2008, and a continuation-in-part of application No. 12/290,691, filed on Oct. 31, 2008, and a continuation-in-part of application No. 12/290,684, filed on Oct. 31, 2008, and a continuation-in-part of application No. 12/290,670, filed on Oct. 31, 2008, and a continuation-in-part of application No. 12/290,664, filed on Oct. 31, 2008, and a continuation-in-part of application No. 12/290,659, filed on Oct. 31, 2008, and a continuation-in-part of application No. 12/290,658, filed on Oct. 31, 2008, and a continuation-in-part of application No. 12/290,665, filed on Oct. 31, 2008, and a continuation-in-part of application No. 12/290,677, filed on Oct. 31, 2008, and a continuation-in-part of application No. 12/290,687, filed on Oct. 31, 2008, and a continuation-in-part of application No. 12/290,676, filed on Oct. 31, 2008.

(51) Int. Cl.
*A61K 51/00* (2006.01)
*A61K 9/14* (2006.01)
*A61K 9/00* (2006.01)

(52) U.S. Cl.
USPC .......... 424/400; 424/1.11; 424/1.29; 424/489; 606/22; 606/131

(58) Field of Classification Search
USPC ........................................................ 424/400
See application file for complete search history.

(56) References Cited

U.S. PATENT DOCUMENTS

| | | | |
|---|---|---|---|
| 1,433,628 A | 10/1922 | Knaust, Henry E. |
| 2,182,952 A | 12/1939 | Todd et al. |
| 3,089,775 A | 5/1963 | Lindall |
| 3,276,880 A | 10/1966 | Torr |
| 3,491,170 A | 1/1970 | Roe, Jr. |
| 3,500,242 A | 3/1970 | Young |
| 3,551,535 A | 12/1970 | Henderson et al. |
| 3,733,158 A | 5/1973 | Ruekberg |
| 3,787,302 A | 1/1974 | Ijichi et al. |
| 3,808,097 A | 4/1974 | Fowler et al. |
| 3,868,997 A | 3/1975 | Pogers |
| 3,889,002 A | 6/1975 | Clausi et al. |
| 3,911,601 A | 10/1975 | Maheu |
| 3,914,441 A | 10/1975 | Finney et al. |
| 4,016,264 A | 4/1977 | Clark |
| 4,102,765 A | 7/1978 | Fey et al. |
| 4,146,029 A | 3/1979 | Ellinwood, Jr. |
| 4,152,231 A | 5/1979 | St. Clair et al. |

(Continued)

FOREIGN PATENT DOCUMENTS

| | | |
|---|---|---|
| CA | 992756 A | 7/1976 |
| GB | 2439092 A | 12/2007 |
| WO | WO 00/09670 | 2/2000 |
| WO | WO 2007/064204 A2 | 6/2007 |
| WO | WO 2007/149868 A2 | 12/2007 |
| WO | WO 2009/113856 A1 | 9/2009 |

OTHER PUBLICATIONS

Lin, H., et al., "Endoscopic injection with fibrin sealant versus epinephrine for arrest of peptic ulcer bleeding: a randomized, comparatie trial", 2002, J. Clin. Gastroent., 35, Abstract (p. 1-2).*
Babicki, A., et al., "Evaluation of using fibrin tissue adhesive (Beriplast) and preparations of thrombin and adrenalin in injection hemostasis methods for gastric and doudenal ulcer heorrhage. Randomized, prospective clinical trial", 1997, 50, Abstract (p. 1).*
Escamex, M.J., et al., "An in vivo model of wound healing in genetically modified skin-humanized mice", 2004, 123, pp. 1182-1191.*

(Continued)

*Primary Examiner* — Michael G Hartley
*Assistant Examiner* — Lance W. Rider

(57) ABSTRACT

Certain embodiments disclosed herein relate to compositions, methods, devices, systems, and products regarding frozen particles. In certain embodiments, the frozen particles include materials at low temperatures. In certain embodiments, the frozen particles provide vehicles for delivery of particular agents. In certain embodiments, the frozen particles are administered to at least one biological tissue.

19 Claims, 81 Drawing Sheets

(56) References Cited

U.S. PATENT DOCUMENTS

| | | | |
|---|---|---|---|
| 4,207,360 A | 6/1980 | Padovani | |
| 4,297,379 A | 10/1981 | Topalian et al. | |
| 4,312,850 A | 1/1982 | Dietl et al. | |
| 4,394,370 A | 7/1983 | Jefferies | |
| 4,442,082 A | 4/1984 | Sanjurjo | |
| 4,512,160 A | 4/1985 | Arias Mas | |
| 4,590,043 A | 5/1986 | Sanjurjo | |
| 4,603,051 A | 7/1986 | Rubenstein et al. | |
| 4,637,905 A | 1/1987 | Gardner | |
| 4,704,873 A | 11/1987 | Imaike et al. | |
| 4,712,920 A | 12/1987 | Ames et al. | |
| 4,751,020 A | 6/1988 | Marten et al. | |
| 4,861,714 A | 8/1989 | Dean, Jr. et al. | |
| 4,907,415 A | 3/1990 | Stewart, Jr. et al. | |
| 4,921,720 A | 5/1990 | Davis | |
| 4,951,197 A | 8/1990 | Mellinger | |
| 4,958,014 A | 9/1990 | Shirokaze | |
| 4,962,091 A | 10/1990 | Eppstein et al. | |
| 4,981,625 A | 1/1991 | Rhim et al. | |
| 5,006,338 A | 4/1991 | Luenemann | |
| 5,008,116 A | 4/1991 | Cahn | |
| 5,049,328 A | 9/1991 | Meyer et al. | |
| 5,072,596 A | 12/1991 | Gilbertson et al. | |
| 5,090,208 A | 2/1992 | Aono et al. | |
| 5,102,983 A | 4/1992 | Kennedy | |
| 5,114,957 A | 5/1992 | Hendler et al. | |
| 5,126,156 A | 6/1992 | Jones | |
| 5,132,101 A | 7/1992 | Vogel et al. | |
| 5,158,760 A | 10/1992 | Phillips et al. | |
| 5,216,890 A | 6/1993 | Ban et al. | |
| 5,219,746 A | 6/1993 | Brinegar et al. | |
| 5,231,015 A | 7/1993 | Cummins et al. | |
| 5,269,682 A | 12/1993 | Kesling | |
| 5,283,985 A | 2/1994 | Browning | |
| 5,283,989 A | 2/1994 | Hisasue et al. | |
| 5,307,640 A | 5/1994 | Fawzy et al. | |
| 5,315,793 A | 5/1994 | Peterson et al. | |
| 5,328,517 A | 7/1994 | Cates et al. | |
| 5,341,608 A | 8/1994 | Mains, Jr. | |
| 5,352,673 A | 10/1994 | Dennis | |
| 5,365,699 A | 11/1994 | Armstrong et al. | |
| 5,375,432 A | 12/1994 | Cur | |
| 5,390,450 A | 2/1995 | Goenka | |
| 5,394,705 A | 3/1995 | Torii et al. | |
| 5,433,654 A | 7/1995 | Clark, Jr. et al. | |
| 5,436,039 A | 7/1995 | Miura et al. | |
| 5,438,071 A | 8/1995 | Clauss et al. | |
| 5,444,986 A | 8/1995 | Hino | |
| 5,599,223 A | 2/1997 | Mains Jr. | |
| 5,631,023 A | 5/1997 | Kearney et al. | |
| 5,632,150 A | 5/1997 | Henzler | |
| 5,656,317 A | 8/1997 | Smits et al. | |
| 5,690,940 A | 11/1997 | Joo | |
| 5,707,667 A | 1/1998 | Galt et al. | |
| 5,725,579 A | 3/1998 | Fages et al. | |
| 5,745,377 A | 4/1998 | Power et al. | |
| 5,753,234 A | 5/1998 | Lee et al. | |
| 5,764,493 A | 6/1998 | Liao | |
| 5,785,581 A | 7/1998 | Settles | |
| 5,877,819 A | 3/1999 | Branson | |
| 5,883,078 A * | 3/1999 | Seelich et al. | 424/443 |
| 5,931,721 A | 8/1999 | Rose et al. | |
| 5,954,640 A | 9/1999 | Szabo | |
| 5,962,018 A | 10/1999 | Curtis et al. | |
| 5,976,505 A | 11/1999 | Henderson | |
| 6,017,973 A | 1/2000 | Tamura et al. | |
| 6,080,329 A | 6/2000 | Dobry | |
| 6,092,235 A | 7/2000 | Santa Cruz et al. | |
| 6,103,528 A | 8/2000 | An et al. | |
| 6,129,290 A | 10/2000 | Nikkanen | |
| 6,130,206 A | 10/2000 | Carter | |
| 6,192,693 B1 | 2/2001 | Kloppenberg et al. | |
| 6,203,406 B1 | 3/2001 | Rose et al. | |
| 6,204,309 B1 | 3/2001 | Misiak et al. | |
| 6,241,704 B1 | 6/2001 | Peterson et al. | |
| 6,242,504 B1 | 6/2001 | Meyer-Roscher et al. | |
| 6,248,063 B1 | 6/2001 | Barnhill et al. | |
| 6,270,723 B1 | 8/2001 | Laugharn, Jr. et al. | |
| 6,284,283 B1 | 9/2001 | Costantino et al. | |
| 6,311,639 B1 | 11/2001 | Stickney | |
| 6,349,549 B1 | 2/2002 | Angus et al. | |
| 6,350,185 B1 | 2/2002 | Robins et al. | |
| 6,366,206 B1 | 4/2002 | Ishikawa et al. | |
| 6,379,324 B1 | 4/2002 | Gartstein et al. | |
| 6,383,329 B1 | 5/2002 | Agarwala et al. | |
| 6,436,422 B1 | 8/2002 | Trogolo et al. | |
| 6,464,570 B1 | 10/2002 | Shaw et al. | |
| 6,464,999 B1 | 10/2002 | Huo et al. | |
| 6,500,187 B1 | 12/2002 | Petersen | |
| 6,569,458 B1 | 5/2003 | Gombotz et al. | |
| 6,623,457 B1 | 9/2003 | Rosenberg | |
| 6,659,844 B2 | 12/2003 | Shaw | |
| 6,678,669 B2 | 1/2004 | Lapointe et al. | |
| 6,695,686 B1 | 2/2004 | Frohlich et al. | |
| 6,705,194 B2 | 3/2004 | Geskin et al. | |
| 6,712,237 B2 | 3/2004 | Medina et al. | |
| 6,713,083 B1 | 3/2004 | McGregor et al. | |
| 6,726,693 B2 | 4/2004 | Weber et al. | |
| 6,732,424 B2 | 5/2004 | Nadicksbernd | |
| 6,764,493 B1 * | 7/2004 | Weber et al. | 606/131 |
| 6,807,717 B2 | 10/2004 | Daehn | |
| 6,838,089 B1 | 1/2005 | Carlsson et al. | |
| 6,845,631 B1 | 1/2005 | Hallin et al. | |
| 6,875,984 B2 | 4/2005 | Kakibayashi et al. | |
| 6,991,515 B2 | 1/2006 | Akedo | |
| 7,033,249 B2 | 4/2006 | Spalteholz et al. | |
| 7,040,962 B2 | 5/2006 | Makino et al. | |
| 7,075,658 B2 | 7/2006 | Izatt et al. | |
| 7,140,954 B2 | 11/2006 | Johnson et al. | |
| 7,143,967 B2 | 12/2006 | Heinrich et al. | |
| 7,284,390 B2 | 10/2007 | Van Meter et al. | |
| 7,321,004 B2 | 1/2008 | Melikechi et al. | |
| 7,350,374 B1 | 4/2008 | Tashlitsky | |
| 7,393,468 B2 | 7/2008 | Lu et al. | |
| 7,407,616 B2 | 8/2008 | Melikechi et al. | |
| 7,421,872 B2 | 9/2008 | Indlekofer | |
| 7,442,112 B2 | 10/2008 | Yoon | |
| 7,547,292 B2 | 6/2009 | Sheldrake et al. | |
| 7,666,778 B2 | 2/2010 | Young | |
| 7,917,298 B1 | 3/2011 | Scher et al. | |
| 7,922,565 B2 | 4/2011 | Knisel et al. | |
| 8,128,872 B2 | 3/2012 | Lentz et al. | |
| 8,256,233 B2 | 9/2012 | Boyden et al. | |
| 8,292,698 B1 | 10/2012 | Shih et al. | |
| 2001/0005504 A1 | 6/2001 | Matsuda et al. | |
| 2001/0025495 A1 | 10/2001 | Newman et al. | |
| 2001/0038338 A1 | 11/2001 | Kadwell et al. | |
| 2002/0002474 A1 | 1/2002 | Michelson et al. | |
| 2002/0068510 A1 | 6/2002 | Okazawa et al. | |
| 2002/0082543 A1 | 6/2002 | Park et al. | |
| 2002/0098534 A1 | 7/2002 | McCaskey-Feazel et al. | |
| 2002/0107199 A1 | 8/2002 | Walker | |
| 2002/0111362 A1 | 8/2002 | Rubinfeld et al. | |
| 2002/0169411 A1 | 11/2002 | Sherman et al. | |
| 2003/0003105 A1 | 1/2003 | Gerber | |
| 2003/0012741 A1 | 1/2003 | Furlan et al. | |
| 2003/0041602 A1 | 3/2003 | Williams, III et al. | |
| 2003/0049320 A1 | 3/2003 | Bhagwatwar et al. | |
| 2003/0065535 A1 | 4/2003 | Karlov et al. | |
| 2003/0072814 A1 | 4/2003 | Maibach et al. | |
| 2003/0104764 A1 | 6/2003 | Preising | |
| 2003/0127054 A1 | 7/2003 | Hebrank | |
| 2003/0135201 A1 | 7/2003 | Gonnelli | |
| 2003/0147995 A1 | 8/2003 | Koss et al. | |
| 2003/0166594 A1 | 9/2003 | Blum et al. | |
| 2003/0181826 A1 | 9/2003 | Smith et al. | |
| 2003/0181863 A1 | 9/2003 | Ackley et al. | |
| 2003/0207655 A1 | 11/2003 | Jackson | |
| 2004/0026617 A1 | 2/2004 | Gregori et al. | |
| 2004/0029774 A1 | 2/2004 | Gamay | |
| 2004/0049150 A1 | 3/2004 | Dalton et al. | |
| 2004/0075196 A1 | 4/2004 | Leyden et al. | |
| 2004/0076319 A1 | 4/2004 | Fauver et al. | |
| 2004/0092920 A1 | 5/2004 | Rozenshpeer | |

| | | | |
|---|---|---|---|
| 2004/0093240 | A1 | 5/2004 | Shah |
| 2004/0097990 | A1 | 5/2004 | Zhao |
| 2004/0106904 | A1 | 6/2004 | Gonnelli et al. |
| 2004/0176732 | A1 | 9/2004 | Frazier et al. |
| 2004/0180846 | A1 | 9/2004 | Huang et al. |
| 2004/0193019 | A1 | 9/2004 | Wei |
| 2004/0244508 | A1 | 12/2004 | Keskinen et al. |
| 2004/0254525 | A1 | 12/2004 | Uber, III et al. |
| 2004/0260234 | A1 | 12/2004 | Srinivasan et al. |
| 2005/0019380 | A1 | 1/2005 | Hoon et al. |
| 2005/0057366 | A1 | 3/2005 | Kadwell et al. |
| 2005/0059940 | A1 | 3/2005 | Weber et al. |
| 2005/0086961 | A1 | 4/2005 | McKay |
| 2005/0107006 | A1 | 5/2005 | Makino et al. |
| 2005/0107832 | A1 | 5/2005 | Bernabei |
| 2005/0193451 | A1 | 9/2005 | Quistgaard et al. |
| 2005/0271733 | A1 | 12/2005 | Burkoth et al. |
| 2006/0045881 | A1 | 3/2006 | Molldrem |
| 2006/0105011 | A1 | 5/2006 | Sun et al. |
| 2006/0123801 | A1 | 6/2006 | Jackson |
| 2006/0123819 | A1 | 6/2006 | Choe et al. |
| 2006/0129326 | A1 | 6/2006 | Braconnier et al. |
| 2006/0153927 | A1 | 7/2006 | Xu |
| 2006/0166233 | A1 | 7/2006 | Wu et al. |
| 2006/0177564 | A1 | 8/2006 | Diaz et al. |
| 2006/0178688 | A1 | 8/2006 | Freeman et al. |
| 2006/0182738 | A1 | 8/2006 | Holmes |
| 2006/0190195 | A1 | 8/2006 | Watanabe et al. |
| 2006/0195179 | A1 | 8/2006 | Sun et al. |
| 2006/0195269 | A1 | 8/2006 | Yeatman et al. |
| 2006/0200369 | A1 | 9/2006 | Batch et al. |
| 2006/0202385 | A1 | 9/2006 | Xu et al. |
| 2006/0228465 | A1 | 10/2006 | Zurecki |
| 2006/0233454 | A1 | 10/2006 | Cheng et al. |
| 2006/0254039 | A1 | 11/2006 | Daehn |
| 2006/0258986 | A1 | 11/2006 | Hunter et al. |
| 2007/0013910 | A1 | 1/2007 | Jiang et al. |
| 2007/0020273 | A1 | 1/2007 | Arlen et al. |
| 2007/0021816 | A1 | 1/2007 | Rudin |
| 2007/0112598 | A1 | 5/2007 | Heckerman et al. |
| 2007/0113639 | A1 | 5/2007 | DiFoggio et al. |
| 2007/0161964 | A1 | 7/2007 | Yuzhakov |
| 2007/0178811 | A1 | 8/2007 | Sundaram et al. |
| 2007/0196437 | A1 | 8/2007 | Hamaker et al. |
| 2008/0031934 | A1* | 2/2008 | MacPhee et al. ............. 424/449 |
| 2008/0039773 | A1 | 2/2008 | Py |
| 2008/0070304 | A1 | 3/2008 | Forgacs et al. |
| 2008/0085286 | A1 | 4/2008 | Kalkum et al. |
| 2008/0145639 | A1 | 6/2008 | Sun et al. |
| 2009/0011087 | A1 | 1/2009 | Rabault et al. |
| 2009/0062737 | A1 | 3/2009 | Sun |
| 2009/0062783 | A1 | 3/2009 | Sun |
| 2009/0232849 | A1 | 9/2009 | Gallez et al. |
| 2009/0317759 | A1 | 12/2009 | Groman |
| 2010/0111854 | A1 | 5/2010 | Boyden et al. |
| 2010/0133195 | A1 | 6/2010 | Gane et al. |
| 2011/0150765 | A1 | 6/2011 | Boyden et al. |
| 2011/0277679 | A1 | 11/2011 | Good et al. |

OTHER PUBLICATIONS

Definition from Hutchinson Unabridged Encyclopedia with Atlas and Weather guide; "Polymers"; The Hutchinson Unabridged Encyclopedia with Atlas and Weather guide; total of 3 pages; located at: http://www.credoreference.com/entry/heliconhe/polymers; © 2010 Helicon Publishing/RM.

Definition from The Crystal Reference Encyclopedia; "Horse"; The Crystal Reference Encyclopedia; total of 1 page; located at: http://www.credoreference.com/entry/cre/horse; Crystal Semantics Ltd.

Aarabi et al.; "Hypertrophic Scar Formation Following Burns and Trauma: New Approaches to Treatment"; PLoS Medicine; Sep. 2007; pp. 1464-1470; vol. 4, Issue 9.

Ashkenazi, Avi; "Directing cancer cells to self-destruct with pro-apoptotic receptor agonists"; Nature Reviews; Dec. 2008; pp. 1001-1012; vol. 7; Macmillan Publishers Limited.

Barry et al.; "Supercritical carbon dioxide: putting the fizz into biomaterials"; Phil. Trans. R. Soc. A; 2006; pp. 249-261; vol. 364; The Royal Society.

Berger et al.; "Adoptive transfer of effector CD8+ T cells derived from central memory cells establishes persistent T cell memory in primates"; The Journal of Clinical Investigation; Jan. 2008; pp. 294-305; vol. 118, No. I.

Boateng et al.; "Wound Healing Dressings and Drug Delivery Systems: A Review"; Journal of Pharmaceutical Sciences; Aug. 2008; pp. 2892-2923; vol. 97; No. 8; Wiley-Liss, Inc. and the American Pharmacists Association.

Bosch et al.; "Fluorescent Probes for Sensing Processes in Polymers"; Abstract; Chemistry—A European Journal; Apr. 5, 2005; pp. 4314-4325; vol. 11, Issue 15.

Bosch et al.; "New Fluorescent Probes for Monitoring Polymerization Reactions: Photocuring of Acrylic Adhesives, 2"; Abstract; Macromolecular Chemistry and Physics; Jan. 31, 2002; pp. 336-345; vol. 203, Issue 2.

Cheung et al.; "The Applications of Stereolithography in Facial Reconstructive Surgery"; IEEE; 2001; pp. 10-15.

Davies et al.; "Applications of supercritical $CO_2$ in the fabrication of polymer systems for drug delivery and tissue engineering"; Advanced Drug Delivery Reviews; 2008; pp. 373-387; vol. 60; Elsevier B.V.

Evans et al.; "Current Applications of Fibrin Sealant in Urologic Surgery"; Int Braz J Urol.; 2006; pp. 131-141; vol. 32; downloaded on Nov. 17, 2008 from http://www.brazjurol.com.br/march_april_Evans_ing_131_141.htm.

Fuller et al.; "Computer applications in facial plastic and reconstructive surgery"; Current Opinion in Otolaryngology & Head and Neck Surgery; 2007; pp. 233-237; vol. 15; Lippincott Williams & Wilkins.

Girod et al.; "Computer-aided 3-D simulation and prediction of craniofacial surgery: a new approach"; Journal of Cranio-Maxillofacial Surgery; 2001; pp. 156-158; vol. 29; European Association for Cranio-Maxillofacial Surgery.

Hou et al.; "Injectable scaffolds for tissue regeneration"; J. Mater. Chem.; 2004; pp. 1915-1923; vol. 14; The Royal Society of Chemistry.

Jakab et al.; "Tissue Engineering by Self-Assembly of Cells Printed into Topologically Defined Structures"; Tissue Engineering: Part A; 2008; pp. 413-421; vol. 14, No. 3; Mary Ann Liebert, Inc.

Kanczler et al.; "The effect of mesenchymal populations and vascular endothelial growth factor delivered from biodegradable polymer scaffolds on bone formation"; Biomaterials; 2008; pp. 1892-1900; vol. 29; Elsevier Ltd.

Kolorjet Chemicals Pvt.Ltd.; "Synthetic Food Colors"; pp. 1-3; downloaded on Nov. 25, 2008 from http://www.kolorjetchemicals.com/synthetic-food-colors.html.

Kufer et al.; "A revival of bispecific antibodies"; TRENDS in Biotechnology; May 2004; pp. 238-244; vol. 22, No. 5; Elsevier Ltd.

Lei et al.; "Incorporating fluorescent quantum dots into water-soluble polymer"; Abstract; Journal of Luminescence; Mar. 2008; pp. 277-281; vol. 128, Issue 3.

Mahabeleshwar et al.; "Angiogenesis in Melanoma"; Semin Oncol.; Dec. 2007; pp. 555-565; vol. 34, No. 6.

Martin-Manso et al.; "Thrombospondin 1 Promotes Tumor Macrophage Recruitment and Enhances Tumor Cell Cytotoxicity of Differentiated U937 Cells"; Cancer Res; Sep. 1, 2008; pp. 7090-7099; vol. 68, No. 17; American Association for Cancer Research.

McWilliams et al.; "Treatment of Brain Metastases From Melanoma"; Mayo Clin Proc.; 2003; pp. 1529-1536; vol. 78; Mayo Foundation for Medical Education and Research.

Mironov et al.; "Organ printing: computer-aided jet-based 3D tissue engineering"; TRENDS in Biotechnology; Apr. 2003; pp. 157-161; vol. 21, No. 4; Elsevier Science Ltd.

Mironov V. et al.; "Organ printing: promises and challenges"; Regen Med.; Jan. 2008; pp. 93-103; vol. 3, No. 1.

Mironov Vladimir; "Organ printing: Understanding and employing multicellular self-assembly"; pp. 1-4; located at http://organprint.missouri.edu/talks.php; printed on Jan. 7, 2009.

Nam et al.; "Computer Aided Tissue Engineering for Modeling and Design of Novel Tissue Scaffolds"; J. of Computer-Aided Design and App.; 2004; pp. 633-640; vol. 1, Nos. 1-4.

Nishikawa et al.; "Honeycomb Films of Biodegradable Polymers for Tissue Engineering"; Mat. Res. Soc. Symp. Proc.; 2002; pp. N11.7.1-N11.7.6; vol. 724; Materials Research Society.

Nolte et al.; "Diversity of Fibroblasts—A Review on Implications for Skin Tissue Engineering"; Cells Tissues Organs; 2008; pp. 165-176; vol. 187; S. Karger AG, Basel.

Peinado et al.; "Fluorescent Probes for Monitoring the UV Curing of Acrylic Adhesives, 1. FTIR and Fluorescence in Real Time"; Macromolecular Chemistry and Physics; Jul. 4, 2001; pp. 1924-1934; vol. 202, Issue 9.

Pham et al.; "Computer modeling and intraoperative navigation in maxillofacial surgery"; Otolaryngology-Head and Neck Surgery; 2007; pp. 624-631; vol. 137; American Academy of Otolaryngology-Head and Neck Surgery Foundation.

Piatt, Jr. et al.; "Application of computer-assisted design in craniofacial reconstructive surgery using a commercial image guidance system"; J Neurosurg (1 Suppl Pediatrics); 2006; pp. 64-67; vol. 104.

Pokroy et al.; "Self-Organization of a Mesoscale Bristle into Ordered, Hierarchical Helical Assemblies"; Science; Jan. 9, 2009; pp. 237-240; vol. 323.

Ripamonti et al.; "Soluble and insoluble signals and the induction of bone formation: molecular therapeutics recapitulating development"; J. Anat.; 2006; pp. 447-468; Anatomical Society of Great Britain and Ireland.

Sabat et al.; "Immunopathogenesis of psoriasis"; Experimental Dermatology; 2007; pp. 779-798; vol. 16; Blackwell Munksgaard.

Shenoy et al.; "Poly(Ethylene Oxide)-Modified Poly(β-Amino Ester) Nanoparticles as a pH-Sensitive System for Tumor-Targeted Delivery of Hydrophobic Drugs: Part 2. In Vivo Distribution and Tumor Localization Studies"; Pharm Res.; Dec. 2005: pp. 2107-2114; vol. 22, No. 12.

Spotnitz et al.; "Hemostats, sealants, and adhesives: components of the surgical toolbox"; Transfusion; Jul. 2008; pp. 1502-1516; vol. 48.

Strong et al.; "Comparison of 3 Optical Navigation Systems for Computer-Aided Maxillofacial Surgery"; Arch Otolaryngol Head Neck Surg; Oct. 2008; pp. 1080-1084; vol. 134; No. 10; American Medical Association.

Sun et al.; "Computer-aided tissue engineering: overview, scope and challenges"; Biotechnol. Appl. Biochem.; 2004; pp. 29-47; vol. 39; Portland Press Ltd.

Wagner et al.; "Protein and bacterial fouling characteristics of peptide and antibody decorated surfaces of PEG-poly(acrylic acid) co-polymers"; Biomaterials; 2004; pp. 2247-2263; vol. 25; Elsevier Ltd.

Whitaker et al.; "The production of protein-loaded microparticles by supercritical fluid enhanced mixing and spraying"; Journal of Controlled Release; 2005; pp. 85-92; vol. 101; Elsevier B.V.

Bertie, J. E. et al.; "Transformations of Ice II, Ice III, and Ice V at Atmospheric Pressure"; The Journal of Chemical Physics; bearing a date of Feb. 15, 1963; pp. 840-846; vol. 38, No. 4; Journal of Chemical Physics.

Buck, Christopher B. et al.; "Carrageenan Is a Potent Inhibitor of Papillomavirus Infection"; PLoS Pathogens; bearing a date of Jul. 2006; pp. 0671-0680; vol. 2, Issue 7; PLoS Pathogens.

Clements, Harry F.; "Life and the Wonders of Water"; Harold L. Lyon Arboretum Lecture No. Seven; bearing a date of Apr. 21, 1976; pp. 1-34; Harold L. Lyon Arboretum, University of Hawaii, Honolulu, Hawaii.

Definition from Dorland's Illustrated Medical Dictionary "Nanoparticle"; bearing a date of 2007; total of 1 page; Elsevier; located at: www.credoreference.com/entry/ehsdorland/nanoparticle.

Goodman, J. M.; "Liquid Nitrogen Therapy of Warts and Other Skin Lesions"; Canad. M. A. J.; bearing a date of Mar. 19, 1960; pp. 628-630; vol. 82.

Hansen, T. C. et al.; "Modelling Ice Ic of Different Origin and Stacking-Faulted Hexagonal Ice Using Neutron Powder Diffraction Data"; Physics and Chemistry of Ice: Proceedings of the 11$^{th}$ International Conference on the Physics and Chemistry of Ice held at Bremerhaven; 2006; pp. 1-8.

KidsHealth.org; "Dehydration"; Internet Archive WayBackMachine; bearing a date of 2002, pp. 1-5; located at: http:replay.waybackmachine.org/20021117135207/http://endoflifecare.tripod.com/juvenilehuntingtonsdisease/id51.html.

Minaev, V. S. et al.; "Polymorphous-Crystalloid Nature of Vitreous and Liquid $H_2O$"; Journal of Optoelectronics and Advanced Materials; bearing a date of Mar. 2004; pp. 103-112; vol. 6, No. 1.

Moffatt, Stanley et al.; "Uptake characteristics of NGR-coupled stealth PEI/pDNA nanoparticles loaded with PLGA-PEG-PLGA triblock copolymer for targeted delivery to human monocyte-derived dendritic cells"; International Journal of Pharmaceutics; bearing a date of 2006; pp. 143-154; vol. 321; Elsevier B.V.

Oeschger, H. et al.; "Atmospheric $CO_2$ Content in the Past Deduced from Ice-Core Analyses"; Annals of Glaciology; bearing a date of 1982; pp. 227-232; vol. 3; © International Glaciological Society.

Want, Roy; "RFID: A Key to Automating Everything"; Scientific American; bearing a date of Jan. 2004, printed on Feb. 21, 2004; pp. 1-10; vol. 290, No. 1; Scientific American.

Kidshealth.org; "Dehydration"; bearing a date of 2002; located at: http://endoflifecare.tripod.com/juvenilehuntingtonsdisease/id51.html; printed on Mar. 17, 2011; pp. 1-5.

Butler, A.R. et al.; "Therapeutic Uses of Inorganic Nitrite and Nitrate: From the Past to the Future"; Circulation; bearing a date of 2008; pp. 2151-2159; vol. 117; Journal of the American Heart Association.

Schmidt, A.I. et al.; "Exposure to carbon dioxide and helium reduces in vitro proliferation of pediatric tumor cells"; Pediatric Surgical Int. bearing a date of 2006; pp. 72-77; vol. 22; Springer-Verlag.

Oeschger, H. et al.; "Atmospheric $CO_2$ Content in the Past Deduced From Ice-Core Analyses"; Annals of Glaciology; bearing a date of 1982; pp. 227-232; vol. 3; International Glaciological Society.

Edwards, R. et al.; "Iron in East Antarctic snow: Implications for atmospheric iron deposition and algal production in Antarctic waters"; Geophysical Research Letters; bearing a date of 2001; 1 page; vol. 28; No. 20; American Geophysical Union (Abstract only).

Uauy, C. et al.; "A NAC Gene Regulating Senescence Improves Grain Protein, Zinc, and Iron Content in Wheat"; Science; bearing a date of Nov. 24, 2006; pp. 1298-1301; vol. 314; No. 1298; American Association for the Advancement of Science.

Abnet, Christian C. et al.; "Zinc Concentration in Esophageal Biopsy Specimens Measured by X-Ray Fluorescence and Esophageal Cancer Risk"; Journal of the National Cancer Institute, bearing a date of Feb. 15, 2005; pp. 301-306; vol. 97, No. 4; Oxford University Press.

Herman, F. A. et al.; "Total Mineral Material, Acidity, Sulphur and Nitrogen in Rain and Snow at Kentville, Nova Scotia"; Tellus; bearing a date of 1957; pp. 180-183; vol. IX, No. 2.

"A Guide to Snowflakes"; SnowCrystals.com; printed on May 19, 2012; 10 pages; located at http://www.its.caltech.edu/~atomic/snowcrystals/class/class.htm.

Berleant, Daniel; "New Plant Paradigms (Part X: Power Plants, Greening the Desert, Phyto-Terraforming, and Recommendations)"; Lifeboat News: The Blog; Sep. 19, 2010; 3 pages; located at http://lifeboat.com/blog/2010/09/new-plant-paradigms-part-x-power-plants-greening-the-desert-phyto-terraforming-and-recommendations.

"Bullet"; definition of Bullet; dictionary.reference.com; printed on May 19, 2012; 4 pages; located at http://dictionary.reference.com/browse/bullet.

Campo et al.; "Super-exchange interactions enhanced through spin delocalisation in $K_2FeCl_5 \cdot H_2O$"; Scientific Highlights; bearing a date of 2002; pp. 18-19; located at http://www.unizar.es/icma/depart/termomag/lineas/h11.pdf.

"Cryonomic Dry Ice Cleaning Technology"; CRYONOMIC;bearing a date of 2006; 2 pages; located at http://www.cryonomic.ro/produse.php?lang=en&p_id=.

"Fixative"; definition of Fixative; TheFreeOnlineDictionary.com; printed on May 19, 2012; 2 pages; located at http://www.thefreedictionary.com/fixative.

"Freeze"; definition of Freeze; American Heritage Dictionary; printed on May 19, 2012; 6 pages; located at http://www.answers.com/topic/freeze.

"Freeze-Dry"; The Penguin English Dictionary; bearing a date of 2000, 2003; 2 pages; Penguin Books.

Gromball, F.; "Nanometer-Scale Height Measurements in Micromachined Picoliter Vials Based on Interference Fringe Analysis"; ACM Digital Library (US Patent & Trademark Office); bearing a date of 2000; 1 page; located at http://dl.acm.org/citation.cfm?id=877015.

Minnery, John; "Kill Without Joy! The Complete How to Kill Book"; bearing a date of 1992; cover page, publication information, and p. 149; Paladin Press.

"Robot"; definition of Robot; TheFreeOnlineDictionary.com; printed on May 7, 2012; 3 pages; located at http://www.thefreedictionary.com/robot.

Ryalls, Charles Wager; Transactions of the National Association for the Promotion of Social Science; Glasgow Meeting, 1874; bearing dates of 1874 and 1875; 2 pages; Longmans, Green, and Co., London (best copy available).

Tamai et al.; "Percutaneous injection of a low-concentration alkaline solution targeting hepatocellular carcinoma"; Oncol. Rep.; bearing a date of Jul.-Aug. 2000; pp. 719-723; vol. 7, No. 4; located at http://www.ncbi.nlm.nih.gov/pubmed/10854532 (abstract only—1 page).

Wiseman, John "Lofty"; "The Ultimate Survival Guide"; bearing dates of 1986, 1993, 2004; cover page, copyright page and p. 140; Harper-Collins Publishers Inc.

Van Baare et al.; "Microbiological Evaluation of Glycerolized Cadaveric Donor Skin"; Transplantation; bearing a date of Apr. 15, 1998; pp. 1-7 (966-970); vol. 65, No. 7; Williams & Wilkins.

Berman, S. et al.; "Tracking stem cells using magnetic nanoparticles"; WIREs Nanomedicine and Nanobiotechnology; Jul./Aug. 2011; pp. 343-355; vol. 3; John Wiley & Sons, Inc.

Bourgeois, Jocelyne C..; "Seasonal and interannual pollen variability in snow layers of arctic ice caps"; Review of Palaeobotany & Palynology; 2000; pp. 17-36; vol. 108; Elsevier Science B.V.

Clinical Trial; Pharmaceutical Medicine Dictionary; 2001; one page; located at: http://www.credoreference.com/entry/pmd/clinical_trial retrieved online on Sep. 18, 2011 by examiner.

ECO-USA.NET; "Benzene"; eco-usa.net; pp. 1-4; printed on Oct. 24, 2011; located at: htlp://www.eco-usa.net/toxics/chemicals/benzene.shtml; Information is excerpted from: "Toxicological Profile for Benzene, 2005 Draft for Public Comment"; Agency for Toxic Substances and Disease Registry, United States Public Health Service.

Kluz, K. et al.; "Application of ice-air jet blasting in treatment of sensitive surfaces"; Int. J. Abrasive Technology; May 30, 2007; pp. 59-77; vol. 1, No. 1; Inderscience Enterprises Ltd.

Mayo Clinic; "Impacted wisdom teeth"; mayoclinic.com special in association with cnn.com; Health/Library; Apr. 21, 2006; printed on Oct. 3, 2011; 4 pages; located at http://premium.asia.cnn.com/HEALTH/library/DS/00679.html.

MIStupid; "Composition of Air"; MIStupid.com; pp. 1-2; printed on Oct. 3, 2011; located at: http://mistupid.com/chemistry/aircomp.htm.

Pacini, E. et al.; "Pollen carbohydrates and water content during development, presentation, and dispersal: a short review"; Protoplasma; published Aug. 31, 2006; pp. 73-77; vol. 228; Springer-Verlag.

Sasaki, A. et al.; "Bisphosphonate Risedronate Reduces Metastatic Human Breast Cancer Burden in Bone in Nude Mice"; Cancer Research; Aug. 15, 1995; pp. 3551-3557; vol. 55; American Association for Cancer Research.

Shaw, G. et al.; "Chemical Studies on the Constitution of Some Pollen and Spore Membranes"; Grana Palynologica; published 1964; printed on Oct. 23, 2011; pp. 247-252 (& cover information, 2 pages); vol. 5, No. 2; Taylor & Francis Informa Ltd.

Taylor, C. H.; "Cancer"; 1915; p. 64; Lea & Febiger.

Toshiyuki, O. et al.; "Dermabrasion Technique for Peri-implant Soft Tissue Management in the Mandible Reconstructed by Free Osteocutaneous Flap"; Science Links Japan; 2004; pp. 1-2; Nippon Koku Inpuranto Gakkaishi; printed on Oct. 3, 2011; located at http://sciencelinks.jp/j-east/article/200424/000020042404A0800133.php.

Warts; Black's Medical Dictionary, 42$^{nd}$ Edition; 2010; one page; retrieved on Sep. 18, 2011; located at: http://www.credoreference.com/entry/blackmed/warts; A & C Black Publishers Ltd.

Wilhardt, M. et al.; "National PBM Drug Monograph Papain-Urea (Accuzyme®) and Papain-Urea-Chlorophyllin Copper Complex Sodium (Panafil®)"; 10 pages; Jan. 2004; located at: http://www.vapbm.org or http://vaww.pbm.med.va.gov.

Al-Amoudi A. et al.; "Amorphous solid water produced by cryosectioning of crystalline ice at 113 K."; J. Microsc.; Aug. 2002; pp. 146-153; vol. 207 (Pt 2); (Abstract Only).

Barnes, Piers R.F. et al.; "Distribution of soluble impurities in cold glacial ice"; Journal of Glaciology; Jun. 2004; pp. 311-324(14); vol. 50, No. 170; (Abstract Only).

Chen, Si et al.; "In-situ Observations of Snow Sublimation using Scanning Electron Microscopy"; 66$^{th}$ Eastern Snow Conference; 2009; pp. 5-9.

"Clathrate"; Merriam-Webster; accessed Jan. 3, 2012; pp. 1-3; located at http://www.merriam-webster.com/dictionary/clathrate.

Fischer, Ralf G. et al.; "Levels and Pattern of alkyl nitrates, multifunctional alkyl nitrates, and halocarbons in the air over the Atlantic Ocean"; Journal of Geophysical Research; bearing a date of 2000; pp. 14,473-14,494; American Geophysical Union; (Abstract Only).

Hervig, Mark et al.; "First confirmation that water ice is the primary component of polar mesospheric clouds"; Geophysical Research Letters; Mar. 15, 2001; pp. 971-974; vol. 28, No. 6; American Geophysical Union.

Law, Marcus; "A 100-year-old Mystery: Nitrate Tolerance"; HKPJ; Jul.-Sep. 2003; p. 117; vol. 12, No. 3.

McFeeters, Roger F.; "Single-Injection HPLC Analysis of Acids, Sugars, and Alcohols in Cucumber Fermentations"; J. Agric. Food Chem.; 1993; pp. 1439-1443; vol. 41, No. 9.

Melville, Kate; "The incredible noise of snow flakes!"; scienceagogo.com; Mar. 16, 2000; pp. 1-3; located at http://www.scienceagogo.com/news/20000216171241data_trunc_sys.shtml.

Miedaner, Markus Maria; "Characterization of inclusions and their distribution in natural and artificial ice samples by synchrotron cryo-micro-tomography (SCXRT)"; bearing a date of May 15, 2007; 121 pages.

Painter, Thomas H. et al.; "Detection and Quantification of Snow Algae with an Airborne Imaging Spectrometer"; Applied and Environmental Microbiology; Nov. 2001; pp. 5267-5272 plus cover page; vol. 67, No. 11; American Society for Microbiology.

Platt, Ulrich F. et al.; "Measurement of Nitrate Radical Concentrations in Continental Air"; Environ. Sci. Technol.; 1984; pp. 365-369; vol. 18, No. 5; American Chemical Society.

Raman, Chandrashekar et al./ "Modeling small-molecule release from PLG microspheres: effects of polymer degradation and nonuniform drug distribution"; Journal of Controlled Release; bearing a date of Dec. 7, 2004; pp. 149-158; vol. 103; Elsevier B.V.

Singh, Manmohan et al.; "Charged polylactide co-glycolide microparticles as antigen delivery systems"; Expert Opin. Biol. Ther.; 2004; pp. 483-491; vol. 4, No. 4; Ashley Publications Ltd.

Adams et al.; "Update in Vitamin D"; J Clin Endocrinol Metab; bearing a date of Feb. 2010; pp. 471-478; vol. 95, No. 2; The Endocrine Society.

Armstrong et al.; "Vasodilator Therapy in Acute Myocardial Infarction. A Compassion of Sodium Nitoprusside and Nitroglycerin"; Circulation, Journal of the American Heart Association; bearing a date Dec. 1975; pp. 1118-1122 and 1 cover-page; vol. 52; American Heart Association; Dallas, TX.

Cornell University Cooperative Extension; "Water Quality Information for Consumers"; accessed at http://waterquality.cce.cornell.edu/bottled.htm; accessed on Mar. 14, 2012; pp. 1-6; Cornell University.

"Dynamite"; Classic Encyclopedia 1911; located at: http://1911encylopedia.org/Dynamite; printed on May 5, 2012; pp. 1-2.

Holmes et al.; "Nitroglycerin: The Explosive Drug"; Journal of Chemical Education; bearing a date of Sep. 1971; pp. 573-576; vol. 48, No. 9.

Leroux et al.; "Biodegradable Nanoparticles—From Sustained Release Formulations to Improved Site Specific Drug Delivery"; Journal of Controlled Release; bearing a date of 1996; pp. 339-350; vol. 39; Elsevier Science B. V.

Murray, Benjamin J.; "Enhanced Formation of Cubic Ice in Aqueous Organic Acid Droplets"; Environmental Research Letters; published May 30, 2008; pp. 1-7; vol. 3; IOP Publishing Ltd.

NASA Tech Brief; "Tools Made of Ice Facilitate Forming of Soft, Sticky Materials"; Brief 69-10199; bearing a date of Jun. 1969; pp. 1-2.

Nomura et al.; "Interaction of Water with Native Collagen"; Biopolymers; bearing a date of 1977: pp. 231-246; vol. 16; John Wiley & Sons, Inc.

Overholt et al.; "Photodynamic Therapy with Porfimer Sodium for Ablation of High-Grade Dysplasia in Barrett's Esophagus; International, Partially Blinded, Randomized Phase III Trial (CME)"; Gastrointestinal Endoscopy; bearing a date of 2005; pp. 488-498; vol. 62, No. 4; The American Society for Gastrointestinal Endoscopy.

RxList; "Nystatin and Triamcinoline Acetonide"; located at http://www.rxlist.com/nystatin-and-trianicinolone-acetonide-drug.htm; printed on Mar. 10, 2012; pp. 1-3; WebMD, LLC.

Vogl et al.; "Colorectal Carcinoma Metastases in Liver: Laser-Induced Interstitial Thermotherapy—Local Tumor Control Rate and Survival Data"; Radiology; bearing a date of 2004; pp. 450-458; vol. 230, No. 2; RSNA.

Wissner-Goss et al.; "Diamond Stabilization of Ice Multilayers at Human Body Temperature"; Physical Review E; published on Aug. 27, 2007; pp. 020501-1 through 020501-4; vol. 76, No. 020501(R); The American Physical Society.

Gorman et al.; Effects of Topical Nitroglycerin and Flurbiprofen in the Rat Comb Burn Model; Annals of Plastic Surgery; May 1999; 1 page (abstract only); Lippincott Williams & Wilkins, Inc.

Ito et al.; "Evaluation of self-dissolving needles containing low molecular weight heparin (LMWH) in rats"; International Journal of Pharmaceutics; bearing a date of 2008; available online Aug. 6, 2007; pp. 124-129; vol. 349; Elsevier B. V.

Nagourney, Eric; "Vital Signs: Sensations; A Needle on Ice to Ease the Pain"; The New York Times; Oct. 16, 2001; 2 pages; located online at : http://www.nytimes.com/2001/10/16/health/vital-signs-sensations-a-needle-on-ice-to-ease-the-pain.html ; The New York Times Company.

Ali et al.; "Lid for a Vacuum Line Cooling Trap"; J. Chem. Educ.; bearing a date of Jun. 1995; p. 549; vol. 72, No. 6.

"Dell Precision™ Workstation 650"; Product brochure, bearing a date of Nov. 2002; pp. 1-2; Dell Computer Corporation.

He et al.; "A Virtual Prototype Manufacturing Software System for Mems"; International Workshop on Micro Electromechanical Systems, bearing a date of 1996; pp. 122-126; IEEE.

Henry et al.; "Microfabricated Microneedles: A Novel Approach to Transdermal Drug Delivery"; Journal of Pharmaceutical Sciences; bearing a date of Aug. 1998; pp. 922-925; vol. 87, No. 8; American Chemical Society and American Pharmaceutical Association.

McAllister et al.; "Microfabricated Microneedles for Gene and Drug Delivery"; Annual Review of Biomedical Engineering; bearing a date of 2000; pp. 289-313; Annual Reviews.

McAllister et al.; "Microfabricated Needles for Transdermal Delivery of Macromolecules and Nanoparticles: Fabrication Methods and Transport Studies"; Proceedings of the National Academy of Sciences USA; bearing a date of Nov. 25, 2003; pp. 13755-13760; vol. 100, No. 24; The National Academy of Sciences of the USA.

Belitsky, Rosalind B. et al.; "Evaluation of the Effectiveness of Wet Ice, Dry Ice, and Cryogen Packs in Reducing Skin Temperature"; Physical Therapy; Jul. 1987; pp. 1080-1084; vol. 67, No. 7.

Currie, L. A. et al.; "Long range transport of biomass aerosol to Greenland: Multi-spectroscopic investigation of particles deposited in the snow"; Journal of Radioanalytical and Nuclear Chemistry; 2005; pp. 399-411; vol. 263, No. 2; Akadémiai Kiadó, Budapest.

Kennedy, Muiris T. et al.; "Hypertonic saline reduces inflammation and enhances the resolution of oleic acid induced acute lung injury"; BMC Pulmonary Medicine; Jul. 8, 2008; pp. 1-7; vol. 8, Issue 9; BioMed Central Ltd.

"Martian Snowflakes"; exo.net; printed on Nov. 14, 2011; 11 pages; located at http://www.exo.net/~pauld/Mars/4snowflakes/martiansnowflakes.html.

"Precursor"; AudioEnglish.net; printed on Nov. 14, 2011; 2 pages; located at http://www.audioenglish.net/dictionary/precursor.htm.

Rifkin, Barry R. et al.; "Osteoid Resorption by Mononuclear Cells in vitro"; Cell and Tissue Research; 1980; pp. 493-500; vol. 210; Springer-Verlag.

"Snow"; wikipedia.org; printed on Nov. 14, 2011; 18 pages; located at http://en.wikipedia.org/wiki/Snow.

Ansiaux, R. et al.; "Use of botulinum toxins in cancer therapy"; Expert Opinion in Investig. Drugs; bearing a date of 2007; pp. 209-218; vol. 16, No. 2; Informa UK Ltd.

Bhalla, M. et al.; "Microdermabrasion: Reappraisal and Brief Review of Literature"; American Society for Dermatologic Surgery, Inc.; bearing a date of Jun. 2006; pp. 809-814; vol. 32; Blackwell Publishing.

Davari, P. et al.; "A randomized investigator-blind trial of different passes of microdermabrasion therapy and their effects on skin biophysical characteristics"; International Journal of Dermatology; bearing a date of 2008; pp. 508-513; vol. 47; The International Society of Dermatology.

Fang, J.-Y. et al.; "Enhancement of topical 5-aminolaevulinic acid delivery by erbium:YAG laser and microdermabrasion: a comparison with iontophoresis and electroporation"; The British Journal of Dermatology; bearing a date of 2004; pp. 132- 140; vol. 151; British Association of Dermatologists.

Gelderblom, H. et al.; "Disposition of [G-$^3$H]Paclitaxel and Cremophor El in a Patient With Severely Impaired Renal Function"; Drug Metabolism and Disposition; bearing a date of 1999; pp. 1300-1305; vol. 27, No. 11; The American Society for Pharmacology and Experimental Therapeutics.

Grimes, P. E.; "Microdermabrasion"; The American Society for Dermatologic Surgery, Inc.; bearing a date of Sep. 2005; pp. 1160-1165; vol. 31, No. 9, Part 2; BC Decker, Inc.

Lee, Woan-Ruoh et al.; "Microdermabrasion as a Novel Tool to Enhance Drug Delivery via the Skin: An Animal Study"; The American Society for Dermatologic Surgery, Inc.; bearing a date of Aug. 2006; pp. 1013-1022; vol. 32, No. 8; Blackwell Publishing.

Rajan, P. et al.; "Skin Barrier Changes Induced by Aluminum Oxide and Sodium Chloride Microdermabrasion"; The American Society for Dermatologic Surgery, Inc.; bearing a date of May 2002; pp. 390-393; vol. 28, No. 5; Blackwell Publishing.

Spencer, J. M. et al.; "Approaches to Document the Efficacy and Safety of Microdermabrasion Procedure"; The American Society for Dermatologic Surgery, Inc.; bearing a date of Nov. 2006; pp. 1353-1357; vol. 32, No. 11; Blackwell Publishing.

"Capecitabine"; from Wikipedia, the free encyclopedia; pp. 1-3; located at http://en.wikipedia.org/wiki/Capecitabine; printed on Nov. 11, 2008.

"Liposuction"; from Wikipedia, the free encyclopedia; pp. 1-6; located at http://en.wikipedia.org/wiki/Liposuction; printed on Nov. 13, 2008.

"Psoriasis"; from Wikipedia, the free encyclopedia; pp. 1-10; located at http://en.wikipedia.org/wiki/Psoriasis; printed on Nov. 13, 2008.

"Inkjet printer"; from Wikipedia, the free encyclopedia; pp. 1-5; located at http://en.wikipedia.org/wiki/Inkjet_printer; last accessed Oct, 28, 2008.

"Computer assisted surgery"; from Wikipedia, the free encyclopedia; pp. 1-5; located at http://en.wikipedia.org/wiki/Computer_assisted_surgery; printed on Jan. 12, 2009.

* cited by examiner

FIG. 9

900 receipt by the at least one subject of at least one frozen particle therapeutic composition is pursuant to at least one clinical trial 910 creating at least one inclusion criterion and at least one exclusion criterion for a clinical trial involving the at least one frozen particle therapeutic composition 920 suggesting the inclusion of one or more of the at least one subject in at least one clinical trial 930 suggesting the exclusion of one or more of the at least one subject in at least one clinical trial 940 using one or more comparisons to predict at least one clinical outcome regarding at least one second subject 950 the at least one second subject has not received the at least one frozen particle therapeutic composition 960 predicting at least one clinical outcome involving the at least one second subject, wherein the at least one second subject is a plurality of people; and segregating subject identifiers associated with the plurality of people in reference to the predicted at least one clinical outcome 970 determining the eligibility of the at least one second subject for the at least one clinical trial

FIG. 10

1000 A method of predicting a clinical outcome of administering at least one frozen particle therapeutic composition to at least one biological tissue of at least one first subject, comprising:

1010 determining a similarity or a dissimilarity in information regarding at least one aspect of administering at least one therapeutic composition to the at least one biological tissue of the at least one first subject to information regarding at least one aspect of administering at least one therapeutic composition to the at least one biological tissue of the at least one second subject, wherein the at least one second subject attained a clinical outcome following receipt of the at least one frozen particle therapeutic composition; and providing output information optionally based on the determination 1020 information regarding the amount of at least one frozen particle therapeutic composition or therapeutic agent administered to at least one biological tissue of at least one subject 1030 information regarding at least one dimension of biological tissue penetration 1040 information regarding at least one depth, width, or breadth of administration of at least one frozen particle therapeutic composition to at least one biological tissue of at least one subject 1050 information regarding two or more subjects with one or more common attributes 1060 genetic attributes, mental attributes, or psychological attributes 1070 genotype attributes or phenotype attributes 1080 at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; partial or whole proteomic sequence; medical history; or blood condition

FIG. 12

1200 receipt by the at least one subject of at least one frozen particle therapeutic composition is pursuant to at least one clinical trial 1210 determining at least one correlation before the administration of the at least one frozen particle therapeutic composition 1220 creating at least one inclusion criterion and at least one exclusion criterion for a clinical trial involving the at least one frozen particle therapeutic composition 1230 suggesting the inclusion of one or more of the at least one subject in at least one clinical trial 1240 suggesting the exclusion of one or more of the at least one subject in at least one clinical trial 1250 using one or more of the at least one determination to predict at least one clinical outcome regarding at least one second subject 1260 the at least one second subject has not received the at least one frozen particle therapeutic composition 1270 predicting at least one clinical outcome involving the at least one second subject, wherein the at least one second subject is a plurality of people; and segregating subject identifiers associated with the plurality of people in reference to the predicted at least one clinical outcome 1280 determining the eligibility of the at least one second subject for the at least one clinical trial

FIG. 13

1300 A system comprising:

1310 at least one computer program, configured with a computer-readable medium, for use with at least one computer system and wherein the computer program includes a plurality of instructions including but not limited to:

1320 one or more instructions for comparing information regarding at least one aspect of at least one therapeutic administration of at least one frozen particle therapeutic composition to at least one biological tissue of at least one subject, and information regarding at least one clinical outcome following receipt by the at least one subject of at least one frozen particle therapeutic composition 1330 information regarding amount of the at least one therapeutic composition or therapeutic agent administered to at least one biological tissue of at least one subject 1340 information regarding at least one dimension of biological tissue penetration 1350 information regarding at least one depth, width, or breadth of administration of at least one frozen particle therapeutic composition to at least one biological tissue of at least one subject 1360 information regarding two or more subjects with one or more common attributes 1370 computing device is configured to communicate with at least one printing device, at least one imaging device, or at least one input device

FIG. 15

1500 receipt by the at least one subject of at least one frozen particle therapeutic composition is pursuant to at least one clinical trial 1510 determining at least one correlation before the administration of the at least one frozen particle therapeutic composition 1520 creating at least one inclusion criterion and at least one exclusion criterion for a clinical trial involving the at least one frozen particle therapeutic composition 1530 suggesting the inclusion of one or more of the at least one subject in at least one clinical trial 1540 suggesting the exclusion of one or more of the at least one subject in at least one clinical trial 1550 using one or more of the at least one comparison to predict at least one clinical outcome regarding at least one second subject 1560 the at least one second subject has not received the at least one frozen particle therapeutic composition 1570 predicting at least one clinical outcome involving the at least one second subject, wherein the at least one second subject is a plurality of people; and segregating subject identifiers associated with the plurality of people in reference to the predicted at least one clinical outcome 1580 determining the eligibility of the at least one second subject for the at least one clinical trial

FIG. 16

1600 A system comprising:

1610 at least one computer program, configured with a computer-readable medium, for use with at least one computer system and wherein the computer program includes a plurality of instructions including but not limited to:

1620 one or more instructions for comparing information regarding at least one aspect of at least one therapeutic administration of at least one frozen particle therapeutic composition to at least one subject, and information regarding at least one frozen particle therapeutic composition involving at least one biological tissue of at least one subject; and one or more instructions for applying one or more comparisons to the information regarding the at least one aspect of therapeutic administration of at least one frozen particle therapeutic composition to a plurality of people 1630 one or more instructions for segregating subject identifiers associated with the plurality of people in reference to at least one of the one or more applied comparisons 1640 information regarding the amount of therapeutic composition or therapeutic agent administered to at least one biological tissue of at least one subject 1650 information regarding at least one dimension of biological tissue penetration 1660 information regarding at least one depth, width, or breadth of administration of at least one frozen particle therapeutic composition to at least one biological tissue of at least one subject 1670 one or more instructions for segregating individual identifiers associated with the plurality of people in reference to at least one characteristic shared by two or more subjects in the plurality of people

FIG. 17

1700 A computer program product comprising:

1710 a signal-bearing medium bearing at least one of 1720 one or more instructions for receiving a first input associated with a first possible dataset, the first possible dataset including data representative of one or more measurements relating to one or more physical attributes of a first subject;

1730 one or more instructions for comparing a value associated with the first possible dataset with a second dataset including values representative of predictive regimen parameters from a second subject with one or more similar or dissimilar physical attributes;

1740 one or more instructions for determining from the comparison at least one frozen particle therapeutic composition regimen for the first subject; and output information optionally based on the comparison 1750 one or more instructions for accessing the first possible dataset in response to the first input 1760 one or more instructions for generating the first possible dataset in response to the first input 1770 one or more instructions for determining a graphical illustration of the first possible dataset 1780 one or more instructions for determining a graphical illustration of the second possible dataset

| 1790 computer-readable medium | 1792 recordable medium | 1794 communications medium |

FIG. 19

1900 A computer program product comprising:

1910 a signal-bearing medium bearing at least one of 1920 one or more instructions responsive to a first possible dataset, the first possible dataset including data representative of one or more measurements relating to one or more physical attributes of a first subject;

1930 one or more instructions for comparing a value associated with the first possible dataset with a second dataset including values representative of predictive regimen parameters for a second subject with one or more similar or dissimilar physical attributes;

1940 one or more instructions for determining from the comparison at least one frozen particle composition or therapeutic composition treatment regimen for the first subject; and output information

FIG. 20

2000 A computer program product comprising:

2010 a signal-bearing medium bearing at least one of 2020 one or more instructions for receiving a first input associated with a first possible dataset, the first possible dataset including data representative of one or more measurements relating to one or more physical attributes of a subject;

2030 one or more instructions for comparing a value associated with the first possible dataset with a second dataset including values representative of parameters relating to one or more expected biological changes following administration of one or more frozen particle therapeutic compositions;

2040 one or more instructions for determining from the comparison at least one biological change following administration of one or more frozen particle therapeutic compositions to the subject; and output information optionally based on the comparison 2050 one or more instructions for accessing the first possible dataset in response to the first input 2060 one or more instructions for generating the first possible dataset in response to the first input 2070 one or more instructions for determining a graphical illustration of the first possible dataset 2080 one or more instructions for determining a graphical illustration of the second possible dataset 2090 computer-readable medium | 2092 recordable medium | 2094 communications medium

FIG. 21

2100 A computer program product comprising:

2110 a signal-bearing medium bearing at least one of 2120 one or more instructions for processing a first input associated with a first possible dataset, the first possible dataset including data representative of one or more measurements relating to one or more physical attributes of a subject;

2130 one or more instructions for comparing a value associated with the first possible dataset with a second dataset including values representative of parameters relating to one or more expected biological changes following administration of one or more frozen particle therapeutic compositions;

2140 one or more instructions for determining from the comparison at least one biological change following administration of one or more frozen particle therapeutic compositions to the subject; and output information optionally based on the comparison

FIG. 22

2200 A computer program product comprising:

2210 a signal-bearing medium bearing at least one of 2220 one or more instructions responsive to a first possible dataset, the first possible dataset including data representative of one or more measurements relating to one or more physical attributes of a subject;

2230 one or more instructions for comparing a value associated with the first possible dataset with a second dataset including values representative of parameters relating to one or more expected biological changes following administration of one or more frozen particle therapeutic compositions;

2240 one or more instructions for determining from the comparison at least one biological change following administration of one or more frozen particle therapeutic compositions to the subject; and output information optionally based on the comparison

FIG. 23

2300 A method comprising:

2310 comparing information regarding at least one aspect of cellular or tissue abrasion or ablation of at least one biological tissue of at least one subject and information regarding at least one clinical outcome following receipt by the at least one subject of at least one frozen particle composition; and providing output information optionally based on the comparison 2320 determining at least one statistical correlation 2330 counting the occurrence of at least one clinical outcome 2340 information regarding quantity of cells or tissue removed or destroyed 2350 information regarding at least one dimension of cellular, tissue, or other material removal or destruction 2360 information regarding at least one depth, width, or breadth of cellular, tissue, or other material removal or destruction 2370 information regarding two or more subjects with one or more common attributes 2380 genetic attributes, mental attributes, or psychological attributes 2390 genotype attributes or phenotype attributes 2397 at least one of height; weight; medical diagnosis, familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; partial or whole proteomic sequence; medical condition; medical history, or blood condition

FIG. 26

2600 A method of predicting a clinical outcome of at least one frozen particle composition treatment for at least one first subject, comprising:

2610 determining a similarity or a dissimilarity in information regarding at least one aspect of cellular or tissue abrasion or ablation of at least one biological tissue of at least one first subject to information regarding at least one aspect of cellular or tissue abrasion or ablation of at least one biological tissue of at least one second subject, wherein the at least one second subject attained a clinical outcome following receipt of the at least one frozen particle composition; and providing output information optionally based on the determination 2620 information regarding quantity of cells or tissue removed or destroyed 2630 information regarding at least one dimension of cellular, tissue or other material removal or destruction 2640 information regarding at least one depth, width, or breadth of cellular, tissue, or other material removal or destruction 2650 information regarding two or more subjects with one or more common attributes 2660 genetic attributes, mental attributes, or psychological attributes 2670 genotype attributes or phenotype attributes 2680 at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; partial or whole proteomic sequence; medical condition; or blood condition

FIG. 29

2900 A system comprising:

2910 at least one computing device;

2920 one or more instructions that when executed on the at least one computing device cause the at least one computing device to receive a first input associated with a first possible dataset, the first possible dataset including data representative of one or more measurements relating to one or more physical attributes of a first subject;

2930 one or more instructions that when executed on the at least one computing device cause the at least one computing device to compare a value associated with the first possible dataset with a second dataset including values representative of predictive regimen parameters related to a second subject with one or more similar or dissimilar physical attributes;

2940 one or more instructions that when executed on the at least one computing device cause the at least one computing device to determine from the comparison at least one frozen particle composition treatment regimen for the first subject; and at least one output optionally based on the determination 2950 one or more instructions that when executed on the at least one computing device cause the at least one computing device to access the first possible dataset in response to the first input 2960 one or more instructions that when executed on the at least one computing device cause the at least one computing device to generate the first possible dataset in response to the first input 2970 one or more instructions that when executed on the at least one computing device cause the at least one computing device to determine a graphical illustration of the possible dataset

FIG. 30

3000 one or more instructions that when executed on the at least one computing device cause the at least one computing device to determine a graphical illustration of the second possible dataset 3005 the treatment regimen includes at least one of cellular or tissue removal, cellular or tissue ablation, debridement, delivery of at least one therapeutic agent, cleaning one or more wounds, removing material from at least one biological tissue, or removing material from at least one blood vessel 3008 at least one frozen particle composition includes at least one of nitrogen, carbon dioxide, hydrogen oxide, helium, neon, xenon, krypton, air, oxygen, chlorine, bromine, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether 3010 one or more desktop computer, workstation computer, computing system including a cluster of processors, a networked computer, a tablet personal computer, a laptop computer, a mobile device, a mobile telephone, or a personal digital assistant computer 3020 wherein the at least one computing device is configured to communicate with a database to access the first possible dataset 3030 wherein the at least one computing device is configured to communicate with a frozen particle composition selecting apparatus or a frozen particle composition generating apparatus, or both

FIG. 31

3100 A system comprising:

3110 circuitry for receiving a first input associated with a first possible dataset, the first possible dataset including data representative of one or more measurements relating to one or more physical attributes of a first subject;

3120 circuitry for comparing a value associated with the first possible dataset with a second dataset including values representative of predictive regimen parameters related to a second subject with one or more similar or dissimilar physical attributes;

3125 circuitry for determining from the comparison at least one frozen particle composition treatment regimen for the first subject 3128 circuitry for selecting at least one of quality or quantity related to one or more frozen particle compositions, method of administration of one or more frozen particle compositions, administration location of one or more frozen particle compositions, content of one or more frozen particle compositions, timing of administration of one or more frozen particle compositions, decrease in physical dimension of one or more frozen particle compositions, or time interval between at least two deliveries with one or more frozen particle compositions 3130 circuitry for determining from the comparison at least one frozen particle composition treatment regimen for the first subject; and 3140 circuitry for providing output information optionally based on the determination

FIG. 33

3300 A system comprising:

3310 at least one computer program, configured with a computer-readable medium, for use with at least one computer system and wherein the computer program includes a plurality of instructions including but not limited to:

3320 one or more instructions for comparing information regarding at least one aspect of cellular or tissue abrasion or ablation of at least one biological tissue of at least one subject and information regarding at least one clinical outcome following receipt by the at least one subject of at least one frozen particle composition 3330 one or more instructions for determining at least one statistical correlation 3340 one or more instructions for counting the occurrence of at least one clinical outcome 3350 information regarding quantity of cells or tissue removed or destroyed 3360 information regarding at least one dimension of cellular, tissue, or other material removal or destruction 3370 information regarding at least one depth, width, or breadth of cellular, tissue, or other material removal or destruction 3380 information regarding two or more subjects with one or more common attributes

FIG. 34

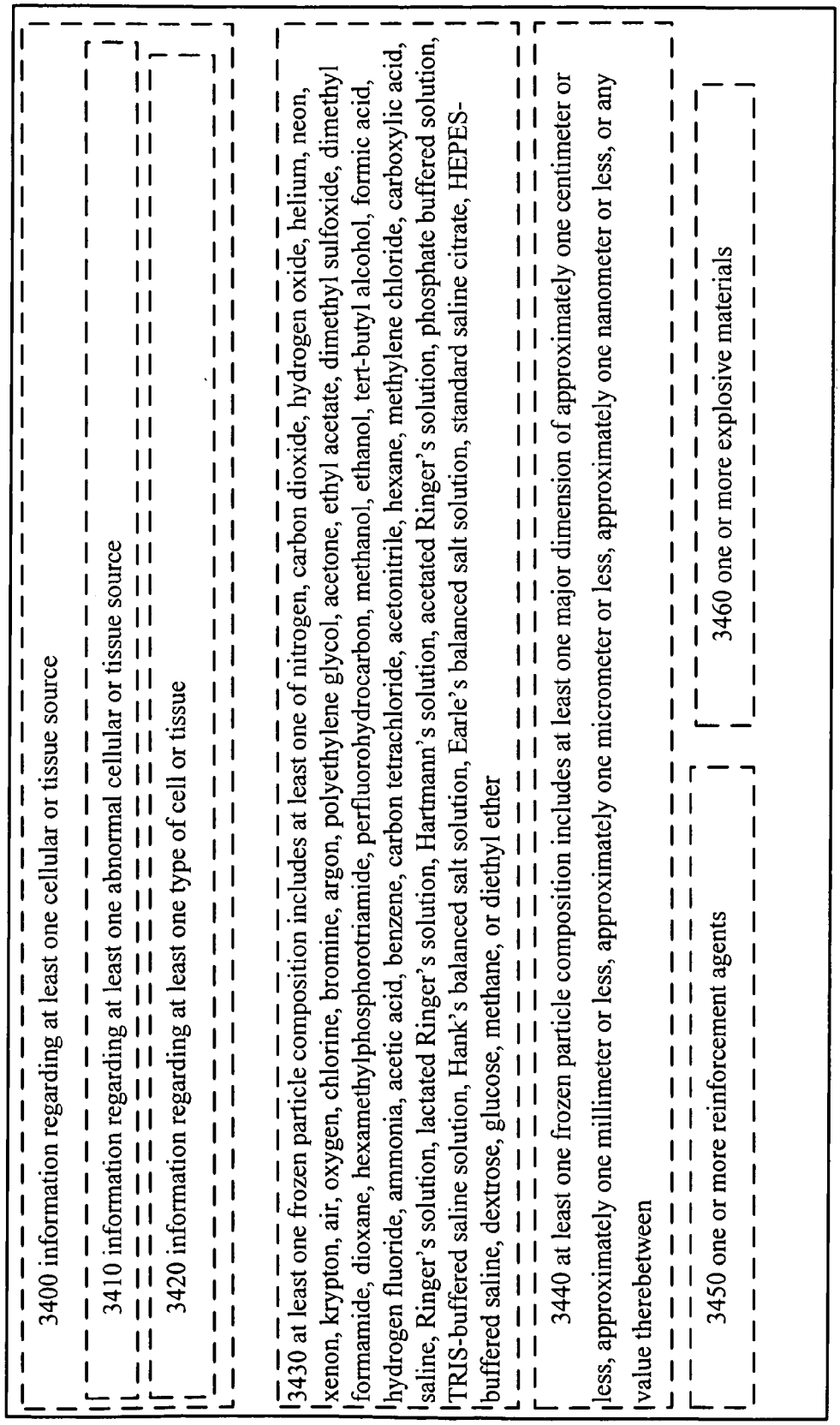

3400 information regarding at least one cellular or tissue source 3410 information regarding at least one abnormal cellular or tissue source 3420 information regarding at least one type of cell or tissue 3430 at least one frozen particle composition includes at least one of nitrogen, carbon dioxide, hydrogen oxide, helium, neon, xenon, krypton, air, oxygen, chlorine, bromine, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether 3440 at least one frozen particle composition includes at least one major dimension of approximately one centimeter or less, approximately one millimeter or less, approximately one micrometer or less, approximately one nanometer or less, or any value therebetween 3450 one or more reinforcement agents 3460 one or more explosive materials

FIG. 35

3500 receipt by the at least one subject of at least one frozen particle composition is pursuant to at least one clinical trial 3510 one or more instructions for determining at least one comparison before the administration of the at least one frozen particle composition to at least one subject 3520 one or more instructions for creating at least one inclusion criterion and at least one exclusion criterion for a clinical trial involving the at least one frozen particle composition 3530 one or more instructions for suggesting the inclusion of one or more of the at least one subject in at least one clinical trial 3540 one or more instructions for suggesting the exclusion of one or more of the at least one subject in at least one clinical trial 3550 one or more instructions for using one or more of the at least one comparison to predict at least one clinical outcome regarding at least one second subject 3560 the at least one second subject has not received the at least one frozen particle composition 3570 one or more instructions for predicting at least one clinical outcome involving the at least one second subject, wherein the at least one second subject is a plurality of people; and segregating subject identifiers associated with the plurality of people in reference to the predicted at least one clinical outcome 3580 wherein the at least one second subject is a plurality of people; and determining the eligibility of the at least one second subject for the at least one clinical trial

FIG. 36

3600 A system comprising:

3610 at least one computer program, configured with a computer-readable medium, for use with at least one computer system and wherein the computer program includes a plurality of instructions including but not limited to:

3620 one or more instructions for comparing information regarding at least one aspect of cellular or tissue abrasion or ablation of at least one biological tissue of at least one subject, and information regarding at least one frozen particle composition involving the at least one biological tissue of at least one subject; and 3630 one or more instructions for applying one or more comparisons to information regarding at least one aspect of cellular or tissue abrasion or ablation regarding a plurality of people 3640 one or more instructions for segregating subject identifiers associated with the plurality of people in reference to at least one of the one or more applied comparisons 3650 information regarding quantity of cells or tissue removed or destroyed 3660 information regarding at least one dimension of cellular, tissue, or other material removal or destruction 3670 information regarding at least one depth, width, or breadth of cellular, tissue, or other material removal or destruction 3680 one or more instructions for segregating individual identifiers associated with the plurality of people in reference to at least one characteristic shared by two or more subjects of the plurality of people

FIG. 37

3700 A method comprising:

3710 accepting a first input associated with at least one characteristic of at least one biological tissue to be at least partially constructed or at least partially reconstructed;

3720 accepting a second input associated with at least one parameter of at least partially constructing or at least partially reconstructing the at least one biological tissue by administering one or more frozen particle compositions including at least one agent;

3730 wherein the at least one agent includes one or more of a therapeutic agent, adhesive agent, abrasive, reinforcement agent, explosive material, or biological remodeling agent 3740 wherein the administering one or more frozen particle compositions includes administering the one or more frozen particle compositions to at least one substrate 3750 wherein the at least one substrate includes one or more of a cell, tissue, organ, structure, or device 3760 processing results of the first input and the second input 3770 processing results of the first input and the second input includes electronically processing results of the first input and the second input 3780 electronically processing results of the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, or modification of a CAD design

FIG. 38

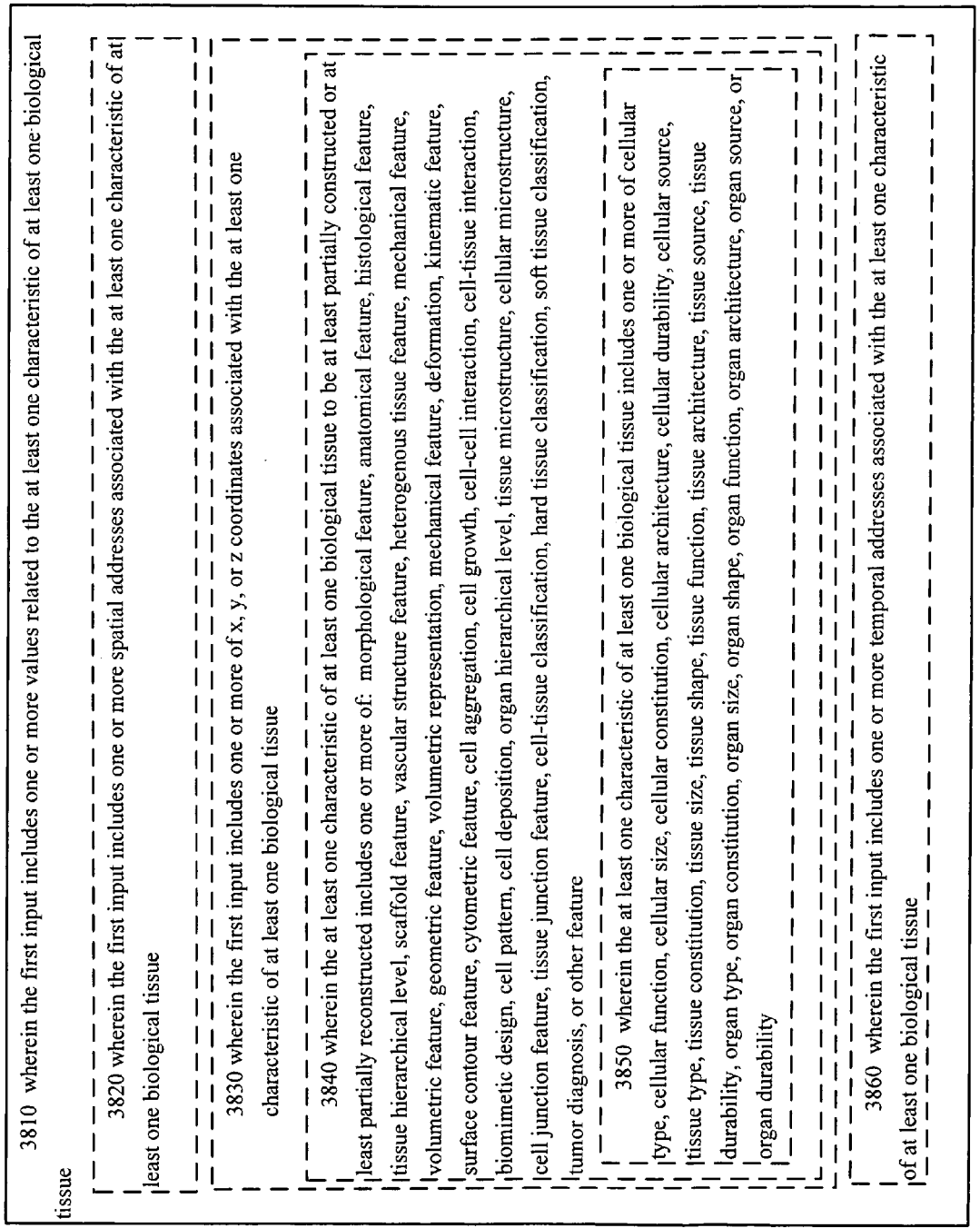

3810 wherein the first input includes one or more values related to the at least one characteristic of at least one biological tissue 3820 wherein the first input includes one or more spatial addresses associated with the at least one characteristic of at least one biological tissue 3830 wherein the first input includes one or more of x, y, or z coordinates associated with the at least one characteristic of at least one biological tissue 3840 wherein the at least one characteristic of at least one biological tissue to be at least partially constructed or at least partially reconstructed includes one or more of: morphological feature, anatomical feature, histological feature, tissue hierarchical level, scaffold feature, vascular structure feature, heterogenous tissue feature, mechanical feature, volumetric feature, geometric feature, volumetric representation, mechanical feature, deformation, kinematic feature, surface contour feature, cytometric feature, cell aggregation, cell growth, cell-cell interaction, cell-tissue interaction, biomimetic design, cell pattern, cell deposition, organ hierarchical level, tissue microstructure, cellular microstructure, cell junction feature, tissue junction feature, cell-tissue classification, hard tissue classification, soft tissue classification, tumor diagnosis, or other feature 3850 wherein the at least one characteristic of at least one biological tissue includes one or more of cellular type, cellular function, cellular size, cellular constitution, cellular architecture, cellular durability, cellular source, tissue type, tissue constitution, tissue size, tissue shape, tissue function, tissue architecture, tissue source, tissue durability, organ type, organ constitution, organ size, organ shape, organ function, organ architecture, organ source, or organ durability 3860 wherein the first input includes one or more temporal addresses associated with the at least one characteristic of at least one biological tissue

FIG. 39

3910 wherein the first input includes one or more values derived from at least one image of the at least one biological tissue 3920 wherein the at least one image includes one or more images acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, multiphoton calcium-imaging, photography, or *in silico* generation 3930 wherein the at least one biological tissue is located in at least one of *in situ*, *in vitro*, *in vivo*, *in utero*, *in planta*, *in silico*, or *ex vivo*

3940 wherein the at least one biological tissue is at least partially located in at least one subject 3950 further comprising accepting a third input associated with at least one feature of the at least one subject 3960 wherein the at least one feature of the at least one subject includes one or more of age, gender, genotype, phenotype, proteomic profile, or health condition

FIG. 40

4010 wherein the processing results of the first input and the second input includes determining at least one parameter of at least partially constructing or at least partially reconstructing the at least one biological tissue with one or more frozen particle compositions from one 4020 wherein the second input includes one or more values related to the at least one parameter of at least partially constructing or at least partially reconstructing the at least one biological tissue by administering one or more frozen particle compositions to the at least one substrate 4030 wherein the at least one parameter of at least partially constructing or at least partially reconstructing the at least one biological tissue includes one or more of porosity of the at least one substrate, pore size of the at least one substrate, interconnectivity of the pores of the at least one substrate, transport properties of the at least one substrate, cell-tissue formation of the at least one substrate, mechanical strength of the at least one substrate, ability for attachment or distribution of the at least one agent included in the one or more frozen particle compositions to the at least one substrate, ability for attachment or distribution of one or more cells or tissues to the at least one substrate, facilitation of at least one nutrient, or tissue formation or tissue growth associated with the at least one substrate 4040 wherein the at least one parameter of at least partially constructing or at least partially reconstructing the at least one biological tissue by administering one or more frozen particle compositions includes one or more of: design of plot or model for administration of one or more frozen particle compositions, constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, method of administration of one or more frozen particle compositions, timing of administration of one or more frozen particle compositions, modulation of administration of one or more frozen particle compositions, deposition of one or more frozen particle compositions, or rate of deposition of at least one agent

FIG. 41

4110 wherein the at least one parameter of at least partially constructing or at least partially reconstructing the at least one biological tissue by administering one or more frozen particle compositions includes at least one parameter relating to at least partially ablating or at least partially abrading one or more surfaces of the at least one biological tissue with the one or more frozen particle compositions 4120 wherein the at least one parameter of at least partially constructing or at least partially reconstructing the at least one biological tissue by administering one or more frozen particle compositions includes at least one parameter relating to administering at least one of a therapeutic agent, adhesive agent, biological remodeling agent, reinforcement agent, abrasive, or explosive material with the one or more frozen particle compositions 4130 wherein the one or more values related to the at least one parameter of constructing or reconstructing the at least one biological tissue includes one or more predictive values 4140 wherein the spatial location for administration of one or more frozen particle compositions includes one or more of x, y, or z coordinates 4150 wherein the processing results includes comparing at least one value related to the first input associated with the at least one characteristic of at least one biological tissue to be at least partially constructed or at least partially reconstructed with at least one value related to at least one image of a target biological tissue 4160 wherein the image of a target biological tissue includes an image of a similar biological tissue, or an image of a dissimilar biological tissue

FIG. 46

4610 wherein the one or more frozen particle compositions includes one or more frozen particles of at least one of: hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

4620 wherein the at least one agent includes one or more of an adhesive agent, therapeutic agent, reinforcement agent, abrasive, explosive material, or biological remodeling agent 4630 wherein at least one of the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer

FIG. 47

4710 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal 4720 wherein the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polyhydroxyhexanoate, polyhydroxyoctanoate, polycaprolactone, poly (e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, polyisohexylcyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin 4730 wherein the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter

FIG. 48

4810 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof 4820 wherein the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast 4830 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin 4840 wherein the at least one biological remodeling agent includes one or more of Type I collagen, Type II collagen, Type III collagen, Type VII collagen, Type X collagen, elastin fibers, or soluble elastin 4850 wherein the at least one biological remodeling agent is included as part of a carrier that assists in synthesis or activation of the at least one biological remodeling agent

FIG. 49

4900 A method comprising:

4910 accepting input associated with at least one parameter of at least partially constructing or at least partially reconstructing at least one biological tissue by administering one or more frozen particle compositions;

4920 administering one or more frozen particle compositions including at least one agent;

4930 wherein the at least one agent includes one or more of a therapeutic agent, adhesive agent, abrasive, reinforcement agent, explosive material, or biological remodeling agent 4940 evaluating the at least one biological tissue for one or more indicators related to deposition of at least one agent, tissue formation, or tissue growth;

4950 wherein the evaluating at least one biological tissue for one or more indicators includes evaluating at least one of an assay, image, or gross assessment of the at least one biological tissue prior to, during, or subsequent to at least one administration of the one or more frozen particle compositions 4960 wherein the assay includes at least one technique that includes sp

FIG. 50

5020 wherein the image includes at least one image acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, multiphoton calcium-imaging, photography, or *in silico* generation 5030 wherein the one or more indicators of tissue formation or growth include at least one of cell migration, cell attachment, cell retention, cell differentiation, cell proliferation, apoptosis, diffusion of materials, angiogenesis, nucleic acid expression, protein translation, protein modification, carbohydrate production, carbohydrate secretion, fat production, fat secretion, or protein secretion 5040 wherein the input associated with at least one parameter of at least partially constructing or at least partially reconstructing the at least one biological tissue by administering one or more frozen particle compositions includes one or more of: constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, method of administration of one or more frozen particle compositions, timing of administration of one or more frozen particle compositions, modulation of administration of one or more frozen particle compositions, deposition of one or more frozen particle compositions, or rate of deposition of at least one agent

FIG. 51

5110 transmitting one or more signals that include information related to the accepting input and information related to the evaluating the at least one biological tissue 5120 wherein the transmitting one or more signals includes transmitting one or more signals associated with selection of one or more frozen particle compositions for administration 5130 wherein the transmitting one or more signals includes transmitting one or more signals associated with selection of one or more of a biological remodeling agent, adhesive agent, abrasive, therapeutic agent, reinforcement agent, or explosive material associated with the one or more frozen particle compositions 5140 wherein the administering one or more frozen particle compositions includes administering the one or more frozen particle compositions to at least one substrate 5150 wherein the at least one substrate includes one or more of a cell, tissue, organ, structure, or device 5160 wherein the one or more frozen particle compositions include one or more frozen particles of at least one of: hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

FIG. 52

5210 wherein the at least one agent includes one or more of an adhesive agent, therapeutic agent, reinforcement agent, abrasive, explosive material, or biological remodeling agent 5220 wherein the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer 5230 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal 5240 wherein the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polyhydroxyhexanoate, polyhydroxyoctanoate, polycaprolactone, poly (e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin

FIG. 53

5310 wherein the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter 5320 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof 5330 wherein the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast 5340 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin 5350 wherein the at least one biological remodeling agent includes one or more of Type I collagen, Type II collagen, Type III collagen, Type VII collagen, Type X collagen, elastin fibers, or soluble elastin

FIG. 54

5400 A method comprising:

5410 receiving one or more signals that include information related to accepting input associated with at least one parameter of at least partially constructing or at least partially reconstructing the at least one biological tissue by administering one or more frozen particle compositions 5420 receiving one or more signals that include information related to evaluating the at least one biological tissue for one or more indicators of tissue formation or growth;

5430 processing the information related to the input associated with at least one parameter of at least partially constructing or at least partially reconstructing the at least one biological tissue and the information related to the evaluating the lat least one biological tissue 5440 wherein the evaluating at least one biological tissue for one or more indicators includes evaluating at least one of an assay, image, or gross assessment of the at least one biological tissue prior to, during, or subsequent to at least one administration of the one or more frozen particle compositions 5450 wherein the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay 5460 wherein the image includes at least one image acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, multiphoton calcium-imaging, photography, or *in silico* generation

FIG. 55

5510 wherein the one or more indicators of tissue formation or growth include at least one of cell migration, cell attachment, cell retention, cell differentiation, cell proliferation, apoptosis, diffusion of materials, angiogenesis, nucleic acid expression, protein translation, protein modification, carbohydrate production, carbohydrate secretion, fat production, fat secretion, or protein secretion 5520 wherein the input associated with at least one parameter of at least partially constructing or at least partially reconstructing the at least one biological tissue by administering one or more frozen particle compositions includes one or more of: constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, method of administration of one or more frozen particle compositions, timing of administration of one or more frozen particle compositions, modulation of administration of one or more frozen particle compositions, deposition of one or more frozen particle compositions, or rate of deposition of at least one agent 5530 wherein the receiving one or more signals includes receiving one or more signals associated with selection of one or more frozen particle compositions for administration 5540 wherein the receiving one or more signals includes receiving one or more signals associated with the selection of at least one of a biological remodeling agent, adhesive agent, abrasive, therapeutic agent, reinforcement agent, or explosive material associated with the one or more frozen particle compositions

FIG. 56

5610 wherein the administering one or more frozen particle compositions includes administering the one or more frozen particle compositions to at least one substrate 5620 wherein the at least one substrate includes one or more of a cell, tissue, organ, structure, or device 5630 wherein the one or more frozen particle compositions includes one or more frozen particles of at least one of: hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetronitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

5640 wherein the at least one agent includes one or more of an adhesive agent, therapeutic agent, reinforcement agent, abrasive, explosive material, or biological remodeling agent 5650 wherein the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer

FIG. 57

5710 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal 5720 wherein the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly (e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin 5730 wherein the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter 5740 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof

FIG. 58

5810 wherein the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast 5820 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin 5830 wherein the at least one biological remodeling agent includes one or more of Type I collagen, Type II collagen, Type III collagen, Type VII collagen, Type X collagen, elastin fibers, or soluble elastin 5840 wherein the at least one biological remodeling agent is included as part of a carrier that assists in synthesis or activation of the at least one biological remodeling agent

FIG. 59

5900 A method comprising:

5910 comparing information regarding at least one parameter for at least partially constructing or at least partially reconstructing at least one biological tissue of a subject by administering one or more frozen particle compositions to the at least one subject and information regarding at least one clinical outcome following receipt by the at least one subject of one or more frozen particle compositions;

5920 providing output information 5930 wherein the output information is based on the comparison 5940 further comprising determining at least one statistical correlation 5950 further comprising counting the occurrence of at least one clinical outcome 5960 wherein the information regarding at least one parameter of at least partially constructing or at least partially reconstructing at least one biological tissue of a subject includes information regarding quantity of cells or tissue at least partially constructed or at least partially reconstructed 5970 wherein the information regarding at least one parameter of at least partially constructing or at least partially reconstructing at least one biological tissue of a subject includes information regarding at least one cellular or tissue source 5980 wherein the information regarding at least one parameter of at least partially constructing or at least partially reconstructing at least one biological tissue of a subject includes information regarding at least one abnormal cellular or tissue source 5990 wherein the information regarding at least one parameter of at least partially constructing or at least partially reconstructing at least one biological tissue of a subject includes information regarding at least one type of cell or tissue

FIG. 60

6010 wherein the at least one agent includes one or more of an adhesive agent, therapeutic agent, reinforcement agent, abrasive, explosive material, or biological remodeling agent 6020 wherein the information regarding at least one parameter of at least partially constructing or at least partially reconstructing at least one biological tissue of a subject includes information regarding at least one dimension of at least one agent deposited 6030 wherein the information regarding at least one parameter of at least partially constructing or at least partially reconstructing at least one biological tissue of at least one subject includes information regarding at least one dimension of at least one depth, width, or breadth of cellular, tissue, or other material removal or destruction 6040 wherein the information regarding at least one clinical outcome following receipt by the at least one subject of one or more frozen particle compositions includes information regarding two or more subjects with one or more common attributes 6050 wherein the one or more common attributes include one or more of genetic attributes, mental attributes, proteomic attributes, phenotypic attributes, or psychological attributes 6060 wherein the one or more common attributes include one or more of height, weight, medical diagnosis, familial background, results on one or more medical tests, ethnic background, body mass index, age, presence or absence of at least one disease or condition, species, ethnicity, race, allergies, gender, thickness of tissue, blood vessel condition, hair or fur condition, skin condition, tissue condition, muscle condition, organ condition, nerve condition, brain condition, presence or absence of at least one biological, chemical, or therapeutic agent in the subject, pregnancy status, lactation status, genetic profile, proteomic profile, partial or whole genetic sequence, partial or whole proteomic sequence, medical condition, medical history, or blood condition

FIG. 61

6110 wherein the output information includes at least one of a response signal, comparison plot, diagnostic code, treatment code, test code, code indicative of at least one treatment received, code indicative of at least one prescribed treatment step, code indicative of at least one vaccination administered, code indicative of at least one therapeutic agent administered, code indicative of at least one diagnostic agent administered, code indicative of at least one interaction of an administered agent and at least one biological or chemical agent in the subject; a code indicative of at least one dispersion or location of at least one administered agent; code indicative of at least one detection material administered; code indicative of the depth of penetration of an administered agent, code indicative of the depth of deposition of an administered agent, or a code indicative of the condition of at least one location of an administered frozen particle composition 6120 wherein receipt by the at least one subject of one or more frozen particle compositions is pursuant to at least one clinical trial 6130 further comprising determining at least one correlation before the administration of the one or more frozen particle compositions to the at least one subject 6140 further comprising creating at least one inclusion criterion and at least one exclusion criterion for a clinical trial involving the one or more frozen particle compositions 6150 further comprising suggesting the inclusion of one or more of the at least one subject in at least one clinical trial 6160 further comprising suggesting the exclusion of one or more of the at least one subject in at least one clinical trial

FIG. 62

6210 further comprising using one or more of the at least one correlation to predict at least one clinical outcome regarding at least one second subject 6220 wherein the at least one second subject has not received the one or more frozen particle compositions 6230 further comprising predicting at least one clinical outcome involving the at least one second subject, wherein the at least one second subject is a plurality of people; and segregating subject identifiers associated with the plurality of people in reference to the predicted at least one clinical outcome 6240 further comprising determining the eligibility of the at least one second subject for the at least one clinical trial 6250 wherein the one or more frozen particle compositions includes one or more frozen particles of at least one of: hydrogen oxide, nitrogen, oxygen, air, helium, neon, argon, xenon, chlorine, bromine, carbon dioxide, polyethylene glycol, hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

FIG. 63

6310 wherein the at least one agent includes one or more of an adhesive agent, therapeutic agent, reinforcement agent, abrasive, explosive material, or biological remodeling agent 6320 wherein the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer 6330 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal 6340 wherein the at least one adhesive agent includes one or more of an acrylic polymer or copolymer, acrylamide polymer or copolymer, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyhroxyoctanoate, polycaprolactone, poly (e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin

FIG. 64

6410 wherein the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter 6420 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof 6430 wherein the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast

FIG. 65

6510 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin 6520 wherein the at least one biological remodeling agent includes one or more of Type I collagen, Type II collagen, Type III collagen, Type VII collagen, Type X collagen, elastin fibers, or soluble elastin 6530 wherein the at least one biological remodeling agent is included as part of a carrier that assists in synthesis or activation of the at least one biological remodeling agent

FIG. 66

6600 A method of predicting a clinical outcome of one or more frozen particle composition treatments for at least one first subject, comprising:

6610 determining a similarity or a dissimilarity in information regarding at least one parameter for at least partially constructing or at least partially reconstructing at least one biological tissue of at least one first subject by administering one or more frozen particle compositions to the at least one first subject with information regarding at least one parameter of at least partially constructing or at least partially reconstructing at least one biological tissue of at least one second subject 6620 wherein the at least one second subject attained a clinical outcome following receipt of one or more frozen particle compositions;

6630 providing output information 6640 wherein providing output information is based on the determination 6650 wherein the information regarding at least one parameter of at least partially constructing or at least partially reconstructing at least one biological tissue of at least second subject includes information regarding quantity of cells or tissue at least partially constructed or at least partially reconstructed 6660 wherein the information regarding at least one parameter of at least partially constructing or at least partially reconstructing at least one biological tissue of at least one first subject includes information regarding at least one cellular or tissue source 6670 wherein the information regarding at least one parameter of at least partially constructing or at least partially reconstructing at least one biological tissue of at least one first subject includes information regarding at least one abnormal cellular or tissue source

FIG. 67

6710 wherein the information regarding at least one parameter of at least partially constructing or at least partially reconstructing at least one biological tissue of at least one first subject includes information regarding at least one type of cell or tissue 6720 wherein the information regarding at least one parameter of at least partially constructing or at least partially reconstructing at least one biological tissue of at least one second subject includes information regarding at least one type of cell or tissue 6730 wherein the at least one agent includes one or more of an adhesive agent, abrasive, reinforcement agent, therapeutic agent, biological remodeling agent, or explosive material 6740 wherein the information regarding at least one parameter of at least partially constructing or at least partially reconstructing at least one biological tissue of at least one first subject includes information regarding at least one dimension of at least one agent deposited 6750 wherein the information regarding at least one parameter of at least partially constructing or at least partially reconstructing at least one biological tissue of at least one second subject includes information regarding at least one dimension of at least one agent deposited 6760 wherein the information regarding at least one parameter of at least partially constructing or at least partially reconstructing at least one biological tissue of at least one second subject includes information regarding at least one dimension of at least one depth, width, or breadth of cellular, tissue, or other material removal or destruction 6770 wherein the information regarding at least one parameter of at least partially constructing or at least partially reconstructing at least one biological tissue of at least one first subject includes information regarding at least one dimension of at least one depth, width, or breadth of cellular, tissue, or other material removal or destruction

FIG. 70

7010 wherein the one or more frozen particle compositions include one or more frozen particles including at least one of: hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

7020 wherein the one or more frozen particle compositions includes one or more of an adhesive agent, therapeutic agent, reinforcement agent, abrasive, explosive material, or biological remodeling agent 7030 wherein the adhesive agent, therapeutic agent, reinforcement agent, abrasive, explosive material, or biological remodeling agent includes at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer 7040 wherein the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal

FIG. 71

7110 wherein the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly (e-caprolactone), sialyl Lewis[x], heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin 7120 wherein the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter 7130 wherein the therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof

FIG. 72

7210 wherein the at least one biological remodeling agent includes one or more of a blood cell, chondrocyte, endothelial cell, hepatocyte, keratinocyte, myocyte, osteocyte, osteoblast, osteoclast, mesenchymal cell, stem cell, progenitor cell, or fibroblast 7220 wherein the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin 7230 wherein the at least one biological remodeling agent includes one or more of Type I collagen, Type II collagen, Type III collagen, Type VII collagen, Type X collagen, elastin fibers, or soluble elastin 7240 wherein the at least one biological remodeling agent is included as part of a carrier that assists in synthesis or activation of the at least one biological remodeling agent

FIG. 74

7410 — one or more instructions that when executed on the at least one computing device cause the at least one computing device to determine from the comparison at least one parameter for administering one or more frozen particle compositions 7420 — one or more instructions that when executed on the at least one computing device cause the at least one computing device to generate at least one response based on the determination 7430 — one or more instructions that when executed on the at least one computing device cause the at least one computing device to access the first possible dataset in response to the first input 7440 — one or more instructions that when executed on the at least one computing device cause the at least one computing device to generate the first possible dataset in response to the first input 7450 — one or more instructions that when executed on the at least one computing device cause the at least one computing device to determine a graphical illustration of the first possible dataset 7460 — one or more instructions that when executed on the at least one computing device cause the at least one computing device to determine a graphical illustration of the second dataset

FIG. 76

7610 — one or more instructions that when executed on the at least one computing device cause the at least one computing device to determine from the comparison at least one characteristic of the at least one biological tissue or organ to be at least partially constructed or at least partially reconstructed by administering one or more frozen particle compositions 7620 — one or more instructions that when executed on the at least one computing device cause the at least one computing device to generate at least one response based on the determination 7630 — one or more instructions that when executed on the at least one computing device cause the at least one computing device to access the first possible dataset in response to the first input 7640 — one or more instructions that when executed on the at least one computing device cause the at least one computing device to generate the first possible dataset in response to the first input 7650 — one or more instructions that when executed on the at least one computing device cause the at least one computing device to determine a graphical illustration of the first possible dataset 7660 — one or more instructions that when executed on the at least one computing device cause the at least one computing device to determine a graphical illustration of the second dataset

FIG. 78

7800 A computer program product comprising:

7810 a signal-bearing medium bearing 7820 one or more instructions for accepting a first input associated with at least one characteristic of at least one biological tissue to be at least partially constructed or at least partially reconstructed by administering one or more frozen particle compositions, 7830 one or more instructions for accepting a second input associated with at least one characteristic of at least one parameter of at least partially constructing or at least partially reconstructing the at least one biological tissue by administering one or more frozen particle compositions that include at least one agent;

7840 one or more instructions for processing results of the first input and the second input 7850 one or more instructions for displaying results of the processing 7860 one or more instructions for transmitting one or more signals that include information related to the processing results of the first input and the second input 7870 one or more instructions for administering one or more frozen particle compositions that include at least one agent including a biological remodeling agent, therapeutic agent, adhesive agent, abrasive, reinforcement agent, or explosive material 7880 one or more instructions for evaluating the at last one biological tissue for one or more indicators relating to one or more of deposition of at least one agent, tissue formation, or tissue growth 7890 computer-readable medium | 7895 recordable medium | 7897 communications medium

FIG. 79

7900 A system comprising:

7910 circuitry for accepting a first input associated with at least one characteristic of at least one biological tissue to be at least partially constructed or at least partially reconstructed by administering one or more frozen particle compositions;

7920 circuitry for accepting a second input associated with at least one characteristic of at least one parameter of at least partially constructing or at least partially reconstructing the at least one biological tissue by administering one or more frozen particle compositions that include at least one agent;

7930 circuitry for processing results of the first input and the second input 7940 circuitry for displaying results of the processing 7950 circuitry for transmitting one or more signals that include information related to the processing results of the first input and the second input 7960 circuitry for administering one or more frozen particle compositions that include at least one agent including a biological remodeling agent, therapeutic agent, adhesive agent, abrasive, reinforcement agent, or explosive material 7970 circuitry for evaluating the at last one biological tissue for one or more indicators relating to one or more of deposition of at least one agent, tissue formation, or tissue growth

FIG. 80

8000 A system comprising:

8010 at least one computer program, configured with a computer-readable medium, for use with at least one computer system and wherein the computer program includes a plurality of instructions including but not limited to:

8020 one or more instructions for accepting a first input associated with at least one characteristic of at least one biological tissue to be at least partially constructed or at least partially reconstructed by administering one or more frozen particle compositions, 8030 one or more instructions for accepting a second input associated with at least one characteristic of at least one parameter of at least partially constructing or at least partially reconstructing the at least one biological tissue by administering one or more frozen particle compositions that include at least one agent;

8040 one or more instructions for processing results of the first input and the second input 8050 one or more instructions for displaying results of the processing 8060 one or more instructions for transmitting one or more signals that include information related to the processing results of the first input and the second input 8070 one or more instructions for administering one or more frozen particle compositions that include at least one agent including a biological remodeling agent, therapeutic agent, adhesive agent, abrasive, reinforcement agent, or explosive material 8080 one or more instructions for evaluating the at last one biological tissue for one or more indicators relating to one or more of deposition of at least one agent, tissue formation, or tissue growth

COMPOSITIONS AND METHODS FOR DELIVERY OF FROZEN PARTICLE ADHESIVES

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/290,671, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,683, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,685, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,686, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,690, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,691, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,684, entitled COMPOSITIONS AND METHODS FOR THERAPEUTIC DELIVERY WITH FROZEN PARTICLES, naming Edward S. Boyden, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,670, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,664, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,659, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,658, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,665, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,677, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,687, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/290,676, entitled COMPOSITIONS AND METHODS FOR SURFACE ABRASION WITH FROZEN PARTICLES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 31 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,263, entitled COMPOSITIONS AND METHODS FOR DELIVERY OF FROZEN PARTICLE ADHESIVES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 20 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,260, entitled COMPOSITIONS AND METHODS FOR DELIVERY OF FROZEN PARTICLE ADHESIVES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 20 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,265, entitled COMPOSITIONS AND METHODS FOR DELIVERY OF FROZEN PARTICLE ADHESIVES, naming Edward S. Boyden, Daniel B. Cook, Roderick A. Hyde, Eric C. Leuthardt, Nathan P. Myhrvold, Elizabeth A. Sweeney and Lowell L. Wood, Jr. as inventors, filed 20 Mar. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

Compositions, methods, systems, and other embodiments related to one or more frozen particle compositions are described herein. One embodiment includes a composition comprising one or more frozen particle compositions including at least one adhesive agent.

In one embodiment, the frozen particle compositions include one or more frozen particles and at least one adhesive agent.

In one embodiment, a frozen particle composition, comprises: one or more frozen hydrogen oxide particles including at least one adhesive agent; wherein the one or more frozen hydrogen oxide particles are in one or more phases including at least one of amorphous solid water, low density amorphous ice, high density amorphous ice, very high density amorphous ice, clathrate ice, hyperquenched glassy water, ice Ic, ice II, ice III, ice IV, ice V, ice VI, ice VII, ice VIII, ice IX, ice X, ice XI, ice XII, ice XIII, ice XIV, or ice XV.

In one embodiment, a frozen particle composition, comprises: one or more frozen solution particles including at least one adhesive agent; wherein the one or more frozen solution particles have at least one major dimension of approximately one centimeter or less, approximately one millimeter or less, approximately one micrometer or less, approximately one nanometer or less, or any value therebetween.

In one embodiment, a frozen particle composition comprises: one or more non-hydrogen oxide frozen solvent particles including at least one adhesive agent. In one embodiment, the one or more non-hydrogen-oxide frozen solvent particles include frozen particles of at least one of acetone, ethyl acetate, dimethyl sulfoxide, dimethyl formamide, dioxane, tetrahydrofuran, acetronitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, or diethyl ether. In one embodiment, the frozen particle composition further comprises at least one of polyethylene glycol, Ringer's solution, lactated Ringer's solution, Hartmann's solution, acetated Ringer's solution, phosphate buffered solution, TRIS-buffered saline solution, Hank's balanced salt solution, Earle's balanced salt solution, HEPES-buffered saline, dextrose, or glucose. In one embodiment, a frozen particle composition comprises: one or more non-hydrogen oxide frozen solute particles including at least one adhesive agent.

In one embodiment, a frozen particle composition, comprises: one or more frozen adhesive particles; wherein the one or more frozen adhesive particles have at least one major dimension of approximately one hundred nanometers or less, approximately one nanometer or less, or any value therebetween.

In one embodiment, a frozen particle composition, comprises: one or more frozen particles of at least one component, wherein the one or more frozen particles include at least one adhesive agent; and wherein the at least one component is in a gaseous state at or above 1 bar pressure, and at or above approximately 10° C., approximately 15° C., approximately 20° C., approximately 25° C., approximately 30° C., approximately 37° C., approximately 40° C., approximately 45° C., or approximately 50° C. In one embodiment, the at least one component includes one or more of nitrogen, helium, neon, xenon, oxygen, air, krypton, chlorine, bromine, or argon.

In one embodiment, the frozen particle composition includes one or more frozen particles that exist at about 30° C., about 20° C., about 10° C., about 5° C., about 0° C., about −10° C., about −20° C., about −30° C., about −40° C., about −50° C., about −60° C., about −70° C., about −75° C., about −80° C., about −85° C., about −90° C., about −95° C., about −100° C., about −120° C., about −150° C., about −180° C., about −200° C., about −220° C., about −250° C., or any temperature less than or therebetween.

In one embodiment, the one or more frozen particles have at least one major dimension of approximately one centimeter or less, approximately one millimeter or less, approximately one micrometer or less, approximately one nanometer or less, or any value therebetween. In one embodiment, the at least one major dimension includes at least one of the radius, diameter, length, width, height, or perimeter.

In one embodiment, the at least one adhesive agent includes at least one of a monomer, prepolymer, polymer, or copolymer. In one embodiment, the at least one adhesive agent includes at least one monomer of a self-polymerizing agent. In one embodiment, the at least one adhesive agent includes at least one nontoxic, biocompatible, bioresorbable, or biodegradable agent. In one embodiment, the at least one adhesive agent is configured to polymerize upon administration to at least one substrate. In one embodiment, the at least one adhesive agent is configured to polymerize at or above the temperature of the at least one substrate. In one embodiment, the at least one adhesive agent is configured to polymerize at or above the temperature of at least one biological tissue. In one embodiment, the at least one adhesive agent is configured to polymerize at or above the temperature of at least one subject.

In one embodiment, the at least one adhesive agent is located in at least one cavity of the one or more frozen particles. In one embodiment, the at least one cavity includes at least one different phase state than the one or more frozen particles. In one embodiment, the at least one cavity includes at least one of a solid, liquid, or gas. In one embodiment, the at least one cavity includes at least one of a liquid or gas, and the one or more frozen particles include a solid. In one embodiment, the at least one cavity includes at least one of a solid or liquid, and at least one other cavity includes a solid.

In one embodiment, the at least one adhesive agent includes one or more components that are inactive. In one embodiment, the one or more components are configured to be activated by administration. In one embodiment, at least two of the one or more components are included in the same or different frozen particle compositions. In one embodiment, at least two of the one or more components are located in cavities of the same or different frozen particle compositions. In one embodiment, at least two of the one or more components each is located in a separate cavity of the same or different frozen particle compositions.

In one embodiment, the at least one agent is configured to modify its adhesive properties upon administration of the frozen particle composition. In one embodiment, the frozen particle composition further includes at least one material that modulates the rate of diffusion or degradation of the at least one adhesive agent. In one embodiment, the at least one material reduces the rate of diffusion or degradation of the at least one adhesive agent. In one embodiment, the at least one adhesive agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

In one embodiment, the at least one adhesive agent includes one or more of an acrylic polymer or copolymer, acrylamide polymer or copolymer, polyacrylic acid, epoxy, urethane, gum arabic, polyester, polyhydroxyalkanoate, poly (L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, polysulfide, polyanhydride, polydioxanone, poly-p-dioxanone, albumin, glutaraldehyde, polyethylene glycol, hydrogel, soy, or gelatin.

In one embodiment, the at least one adhesive agent is configured to form one or more of a hydrogen bond, ionic bond, covalent bond, or non-covalent bond with at least one substrate. In one embodiment, the at least one adhesive agent includes at least one crosslinking or derivatized agent. In one embodiment, the at least one adhesive agent is configured to form a crosslink bond with at least one component of at least one substrate. In one embodiment, the crosslink bond of the at least one adhesive agent is configured for modulation by one or more of a chemical agent, change in pH, change in exposure to air, vacuum, change in moisture content, change in pressure, or change in temperature. In one embodiment, the formation of a crosslink bond of the at least one adhesive agent is configured for modulation by exposure of the at least one adhesive agent to one or more of electromagnetic energy, optical energy, thermal energy, laser energy, ionizing radiation, non-ionizing radiation, or sonic energy.

In one embodiment, the frozen particle composition further includes at least one therapeutic agent. In one embodiment, the at least one therapeutic agent and the at least one adhesive agent are the same agent. In one embodiment, the at least one therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotoic promoting factor, enzymatic agent, histatin, honey, calcium alginate, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof.

In one embodiment, the at least one adhesive agent is configured to convert to at least one therapeutic agent upon administration of the at least one adhesive agent. In one embodiment, the at least one adhesive agent configured to undergo one or more of hydration, hydrolysis, hydrogenolysis, condensation, dehydration, or polymerization, upon administration of the at least one adhesive agent. In one embodiment, the at least one adhesive agent includes a methacrylate. In one embodiment, the at least one adhesive agent includes at least one of poly(N,N-dimethyl-N-(ethoxycarbonylmethyl)-N-[2'-(methacryloyloxy)ethyl]-ammonium bromide) or poly(sulfobetaine methacrylate).

In one embodiment, the one or more frozen particles include one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

In one embodiment, the one or more frozen particles approximate the shape of at least one of a sphere, bullet, flechette, cone, needle, arrow, spear, diamond, pyramid, cylinder, minie ball, shuttlecock, spiral, bell, pear, crystal, cube, spheroid, tetrahedron, crescent, or possess a high aspect ratio shape.

In one embodiment, the one or more frozen particles include a plurality of frozen particles that are approximately uniform in size, shape, weight, or density. In one embodiment, the frozen particle composition includes at least one of a frozen liquid, or frozen gas. In one embodiment, the frozen particle composition includes one or more of a suspension, mixture, solution, sol, clathrate, colloid, emulsion, microemulsion, aerosol, ointment, capsule, powder, tablet, suppository, cream, device, paste, liniment, lotion, ampule, elixir, spray, suspension, syrup, tincture, detection material, polymer, biopolymer, buffer, adjuvant, diluent, lubricant, disintegration agent, suspending agent, solvent, light-emitting agent, colorimetric agent, glidant, anti-adherent, anti-static agent, surfactant, plasticizer, emulsifying agent, flavor, gum, sweetener, coating, binder, filler, compression aid, encapsulation aid, preservative, granulation agent, spheronization agent, stabilizer, adhesive, pigment, sorbent, nanoparticle, or gel.

In one embodiment, the frozen particle composition further includes one or more reinforcement agents. In one embodiment, at least one of the one or more reinforcement agents are the same as the at least one adhesive agent. In one embodiment, the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic polymer or copolymer, acrylamide polymer or copolymer, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, aluminum, magnesium, silicon, silica, frozen hydrogen oxide ice, plant matter, animal matter, or mineral matter.

In one embodiment, the frozen particle composition further includes one or more abrasives.

In one embodiment, the frozen particle composition further includes at least one of a nanoparticle, detection material, sensor, micro-syringe, or circuit. In one embodiment, the detection material includes at least one electronic identification device. In one embodiment, the at least one electronic identification device includes at least one radio frequency identification device. In one embodiment, the detection material includes at least one radioactive element. In one embodiment, the at least one radioactive element includes one or more of $^{32}P$, $^{35}S$, $^{13}C$, $^{131}I$, $^{191}Ir$, $^{192}Ir$, $^{193}Ir$, $^{201}Tl$, or $^{3}H$. In one embodiment, the detection material includes at least one radioactive, luminescent, colorimetric, or odorous substance. In one embodiment, the detection material includes at least one of a diamagnetic particle, ferromagnetic particle, paramagnetic particle, super paramagnetic contrast agent, or other magnetic particle.

In one embodiment, the frozen particle composition is formulated to be administered to at least one substrate, including one or more of a cell, tissue, organ, structure, or device. In one embodiment, the frozen particle composition is formulated to be administered by one or more of topical administration, oral administration, enteral administration, mucosal administration, percutaneous administration, or parenteral administration. In one embodiment, the parenteral administration includes at least one of intravenous administration, intra-arterial administration, intracardiac administration, subcutaneous administration, intraperitoneal administration, or intramuscular administration. In one embodiment, the frozen particle composition is formulated to be administered by high velocity impact. In one embodiment, the frozen particle composition is formulated to be administered by one or more devices.

In one embodiment, the frozen particle composition further includes at least one pharmaceutically-acceptable carrier or excipient. In one embodiment, the frozen particle composition further includes one or more explosive materials. In one embodiment, at least one of the one or more explosive materials are the same as the at least one adhesive agent. In one embodiment, the one or more explosive materials include at least one of a carbonate, carbon dioxide, nitroglycerine, acid, base, epoxy, acrylic polymer or copolymer, acrylamide polymer or copolymer, urethane, hypoxyapatite, or a reactive metal. In one embodiment, the at least one adhesive agent is included as part of a carrier that assists in synthesis or activation of the at least one adhesive agent. In one embodiment, the at least one adhesive agent is frozen.

In one embodiment, the at least one adhesive agent includes two or more components configured to combine upon administration to at least one substrate. In one embodiment, the combination of the two or more components modifies at least one property of the adhesive agent. In one embodiment, the at least one property includes one or more of initiation of adhesive bond formation, strength of adhesive bond, adhesive bonding time, bond flexibility, bond biodegradability, bond bioresorbability, bond biocompatibility, or durability of adhesive bond. In one embodiment, the at least one property includes one or more of polymerization of the adhesive agent, or crosslinking of the adhesive agent. In one embodiment, the frozen particle composition further comprises administering two or more frozen particle compositions; wherein at least one administration parameter is different for the two or more frozen particle compositions.

In one embodiment, the at least one administration parameter includes at least one of: constitution of the frozen particle composition, formulation of the frozen particle composition, size of the frozen particle compositions, shape of the frozen particle composition, angle of administration of the frozen particle composition, velocity of administration of the frozen particle composition, quantity of frozen particle compositions administered, rate of administration of more than one frozen particle composition, spatial location for administration of the frozen particle compositions, temporal location for administration of the frozen particle compositions, method of administration of the frozen particle compositions, timing of administration of the frozen particle compositions, modulation of administration of the frozen particle compositions, deposition of the frozen particle compositions, or rate of deposition of at least one agent included in the frozen particle compositions.

In one embodiment, a method for providing at least one adhesive agent to at least one substrate comprises: administering at least one frozen particle composition to at least one substrate, wherein the at least one frozen particle composition includes one or more frozen hydrogen oxide particles including at least one adhesive agent; wherein the one or more frozen hydrogen oxide particles are in one or more phases including at least one of amorphous solid water, low density amorphous ice, high density amorphous ice, very high density amorphous ice, clathrate ice, hyperquenched glassy water, ice Ic, ice II, ice III, ice IV, ice V, ice VI, ice VII, ice VIII, ice IX, ice X, ice XI, ice XII, ice XIII, ice XIV, or ice XV.

In one embodiment, a method for providing at least one adhesive agent to at least one substrate comprises: administering at least one frozen particle composition to at least one substrate, wherein the at least one frozen particle composition includes one or more frozen solution particles including at least one adhesive agent. In one embodiment, the at least one frozen particle composition is in at least one crystalline or amorphous phase.

In one embodiment, a method for providing at least one adhesive agent to at least one substrate comprises: administering at least one frozen particle composition to at least one substrate, wherein the at least one frozen particle composition includes one or more non-hydrogen oxide frozen solvent particles and at least one adhesive agent. In one embodiment, the one or more non-hydrogen-oxide frozen solvent particles include frozen particles of at least one of acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, or diethyl ether. In one embodiment, the method further comprises at least one of polyethylene glycol, Ringer's solution, lactated Ringer's solution, Hartmann's solution, acetated Ringer's solution, phosphate buffered solution, TRIS-buffered saline solution, Hank's balanced salt solution, Earle's balanced salt solution, HEPES-buffered saline, dextrose, or glucose.

In one embodiment, a method for providing at least one adhesive agent to at least one substrate comprises: administering at least one frozen particle composition to at least one substrate, wherein the at least one frozen particle composition includes one or more frozen particles of at least one component, and at least one adhesive agent; and wherein the at least one component is in a gaseous state at or above 1 bar pressure, and at or above approximately 10° C., approximately 15° C., approximately 20° C., approximately 25° C., approximately 30° C., approximately 37° C., approximately 40° C., approximately 45° C., or approximately 50° C. In one embodiment, the at least one component includes one or more of nitrogen, helium, neon, xenon, oxygen, air, krypton, chlorine, bromine, or argon.

In one embodiment, the method includes administering at least one frozen particle composition that further includes at least one pharmaceutically-acceptable carrier or excipient. In one embodiment, the at least one adhesive agent includes at least one of a monomer, prepolymer, polymer, or copolymer. In one embodiment, the at least one adhesive agent includes at least one monomer of a self-polymerizing agent. In one embodiment, the at least one adhesive agent includes at least one nontoxic, biocompatible, bioresorbable, or biodegradable agent. In one embodiment, the at least one adhesive agent is configured to polymerize upon administration to at least one substrate. In one embodiment, the at least one adhesive agent is configured to polymerize at or above the temperature of the at least one substrate. In one embodiment, the at least one adhesive agent is configured to polymerize at or above the temperature of at least one biological tissue. In one embodiment, the at least one adhesive agent is configured to polymerize at or above the temperature of at least one subject.

In one embodiment, the at least one substrate includes at least one nontoxic, biocompatible, bioresorbable, or biodegradable substrate. In one embodiment, the substrate includes at least a portion of which is naturally, artificially, or synthetically derived. In one embodiment, the substrate includes at least a portion of which is genetically altered. In one embodiment, the at least one substrate includes one or more of a cell, tissue, organ, structure, or device. In one embodiment, the structure includes one or more of a prosthesis, cell matrix, or tissue matrix. In one embodiment, the device includes at least one mechanical or electrical device. In one embodiment, the at least one substrate includes at least one implantable substrate. In one embodiment, the at least one substrate is located in at least one of in situ, in vitro, in vivo, in utero, in planta, in silico, or ex vivo. In one embodiment, the at least one substrate is transplanted or implanted into at least one subject. In one embodiment, the at least one substrate is ingested by at least one subject. In one embodiment, the at least one substrate includes at least one biological tissue from at least one donor or recipient. In one embodiment, the at least one donor includes at least one cadaver. In one embodiment, the at least one substrate includes one or more of skin, scalp, hair, nail, nail bed, teeth, eye, ear, ovary, oviduct, tongue, tonsil, adenoid, liver, bone, pancreas, stomach, blood vessel, blood, lymph, heart, lung, brain, breast, kidney, bladder, urethra, ureter, gall bladder, uterus, prostate, testes, vas deferens, fallopian tubes, large intestine, small intestine, esophagus, oral cavity, nasal cavity, otic cavity, connective tissue, peritoneal tissue, muscle tissue, or adipose tissue. In one embodiment, the at least one substrate includes one or more of a stalk, stem, leaf, root, plant, or tendril.

In one embodiment, the at least substrate includes at least one cell mass. In one embodiment, the at least one cell mass includes at least one of a scar, pore, pit, eschar, granuloma, keloid, artheromatous plaque, abscess, pustule, scaling, infected tissue, hair follicle, necrotic tissue, stratum corneum, wrinkle, wound, tumor, skin structure, nevus, cyst, lesion, callus, neoplastic tissue, gangrenous tissue, or cellular deposit. In one embodiment, the at least one cell mass is related to at least one blood clot, microorganism accumulation, blood vessel obstruction, duct obstruction, bowel obstruction, infection, gangrene, connective tissue destruction, tissue or organ damage, injury, white blood cell accumulation, or cancer. In one embodiment, the at least one substrate includes one or more wounds. In one embodiment, the one or more wounds are located in at least one biological tissue. In one embodiment, the at least one biological tissue includes at least one of skin tissue, peritoneal tissue, muscle tissue, eye tissue, an organ, peritoneal tissue, nervous tissue, connective tissue, neoplastic tissue, or bone tissue. In one embodiment, the one or more wounds are located in at least one subject. In one embodiment, the one or more wounds include at least one of an fracture, incision, laceration, abrasion, irritation, puncture wound, penetration wound, gunshot wound, iatrogenic wound, severing, infection, ulcer, pressure sore, lesion, chemical burn, animal bite, dental caries, first-degree burn, second-degree burn, third-degree burn, or fourth-degree burn.

In one embodiment, the at least one substrate includes at least a portion of at least one subject. In one embodiment, the at least one subject includes at least one invertebrate or vertebrate animal. In one embodiment, the at least one subject includes at least one of a reptile, mammal, amphibian, bird, or fish. In one embodiment, the at least one subject includes at least one human. In one embodiment, the at least one subject includes at least one of livestock, pet, undomesticated herd animal, wild animal, zoo animal, or product animal. In one embodiment, the at least one subject includes at least one of a sheep, goat, frog, dog, cat, rat, mouse, vermin, monkey, duck, horse, cow, pig, chicken, shellfish, fish, turkey, llama, alpaca, bison, buffalo, ape, primate, ferret, wolf, coyote, deer, rabbit, guinea pig, yak, chinchilla, mink, reindeer, camel, fox, raccoon, elk, deer, donkey, or mule.

In one embodiment, the at least one adhesive agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

In one embodiment, the at least one adhesive agent includes one or more of an acrylic polymer or copolymer, acrylamide polymer or copolymer, polyacrylic acid, epoxy, urethane, gum arabic, polyester, polyhydroxyalkanoate, poly (L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, polysulfide, polyanhydride, polydioxanone, poly-p-dioxanone, albumin, glutaraldehyde, polyethylene glycol, hydrogel, soy, or gelatin.

In one embodiment, the at least one adhesive agent includes one or more components that are inactive. In one embodiment, the one or more components are configured to be activated by administration. In one embodiment, administering at least one frozen particle composition to at least one substrate includes accelerating, propelling, or ejecting the frozen particle composition toward the at least one substrate. In one embodiment, administering the at least one frozen particle composition to at least one substrate includes propelling, ejecting, or accelerating the at least one frozen particle composition toward the at least one substrate at a predetermined angle, predetermined velocity, or predetermined rate of administration. In one embodiment, the method further includes varying the rate, velocity, or angle at which the at least one frozen particle composition is administered to at least one substrate. In one embodiment, administering the at least one frozen particle composition to at least one substrate includes propelling, ejecting, or accelerating a plurality of frozen particle compositions toward the at least one substrate. In one embodiment, two or more of the plurality of frozen particle compositions include two or more adhesive agents that are configured to physically or chemically bind upon administration. In one embodiment, administering the at least one frozen particle composition to at least one substrate includes contacting the at least one substrate with the at least one frozen particle composition. In one embodiment, administering the at least one frozen particle composition to at least one substrate includes contacting the at least one substrate with the at least one adhesive agent. In one embodiment, administering the at least one frozen particle composition occurs prior to, during, or subsequent to surgery.

In one embodiment, the method further includes administering to the at least one substrate at least one of a nanoparticle, detection material, sensor, micro-syringe, or circuit. In one embodiment, the detection material is intermixed with the at least one frozen particle composition. In one embodiment, the detection material is located in the at least one frozen particle composition. In one embodiment, the detection material is located in the one or more frozen hydrogen oxide particles. In one embodiment, the detection material includes at least one electronic identification device. In one embodiment, the at least one electronic identification device includes at least one radio frequency identification device. In one embodiment, the detection material includes at least one radioactive element. In one embodiment, the at least one radioactive element includes one or more of $^{32}P$, $^{35}S$, $^{13}C$, $^{131}I$, $^{191}Ir$, $^{192}Ir$, $^{193}Ir$, $^{201}Tl$, $^{3}H$. In one embodiment, the detection material includes at least one luminescent, radioactive, colorimetric, or odorous substance. In one embodiment, the detection material includes at least one of a diamagnetic particle, ferromagnetic particle, paramagnetic particle, super paramagnetic contrast agent, or other magnetic particle.

In one embodiment, the method includes one or more frozen particle composition that further includes one or more of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

In one embodiment, the method includes at least one frozen particle composition that further includes one or more of a reinforcement agent, abrasive, explosive material, or biological remodeling agent.

In one embodiment, the at least one adhesive agent includes a detectable state that varies with its adhesive state. In one embodiment, the at least one adhesive agent includes one or more epoxy adhesive, acrylic adhesive, urethane adhesive, polyurethane adhesive, silicone adhesive, cationic adhesive, anerobic adhesive, urethane acrylate, polyester acrylate, methyacrylate, or cyanoacrylate. In one embodiment, the at least one adhesive agent includes at least one α-cyanoacrylate and a fluorescent compound including at least one of a bis-benzoxazolyl compound, pyrylium salt, quantum dot, or coumarin compound. In one embodiment, the at least one adhesive agent includes an α-cyanoacrylate and 2,5-bis-(5-tert-butyl-2-benzoxasolyl)-thiophene. In one embodiment, the at least one adhesive agent further includes one or more of a base component, initiator component, or activator component. In one embodiment, the at least one adhesive agent further includes at least one curing component. In one embodiment, the at least one adhesive agent includes at least one photopolymerizable adhesive, photocurable adhesive, thermal curable adhesive, free radical curable adhesive, or aerobic curable adhesive. In one embodiment, the at least one adhesive agent includes one or more adhesive agent configured to polymerize upon exposure to infrared light, ultraviolet light, x-ray, visible light, or other electromagnetic radiation. In one embodiment, the adhesive agent includes at least one dye coinitiator.

In one embodiment, the at least one dye coinitiator includes at least one of a bis-benzoxazolyl compound, pyrylium salt, QTX, safranine O, fluorescein, eosin yellow, eosin Y, eosin B, ethyl eosin, eosin bluish, erythrosine B, erythrosine yellowish blend, toluidine blue, 4',5'-dibromofluorescein, Rose Bengal B, cyanine, pyronin GY, cresyl violet, brilliant green, lissamine green BN, rhodamine B, methylene blue, crystal violet, phosphine oxide, or coumarin compound.

In one embodiment, the at least one adhesive agent includes one or more components that are inactive. In one embodiment, the one or more components are configured to be activated by administration. In one embodiment, the at least one adhesive agent includes two or more components configured to combine upon administration to at least one substrate. In one embodiment, the combination of the two or more components modifies at least one property of the adhesive agent. In one embodiment, the at least one property includes one or more of initiation of adhesive bond formation, strength of adhesive bond, adhesive bonding time, bond flexibility, bond biodegradability, bond bioresorbability, bond biocompatibility, or durability of adhesive bond. In one embodiment, the at least one property includes one or more of polymerization of the adhesive agent, or cross-linking of the adhesive agent.

In one embodiment, the method further comprises administering two or more frozen particle compositions; wherein at least one administration parameter is different for the two or more frozen particle compositions. In one embodiment, the at least one administration parameter includes at least one of: constitution of the frozen particle composition, formulation of the frozen particle composition, size of the frozen particle compositions, shape of the frozen particle composition, angle of administration of the frozen particle composition, velocity of administration of the frozen particle composition, quantity of frozen particle compositions administered, rate of administration of more than one frozen particle composition, spatial location for administration of the frozen particle compositions, temporal location for administration of the frozen particle compositions, method of administration of the frozen particle compositions, timing of administration of the frozen particle compositions, modulation of administration of the frozen particle compositions, deposition of the frozen particle compositions, or rate of deposition of at least one agent included in the frozen particle compositions.

In one embodiment, a method of maintaining the approximation of tissue of at least one wound of a subject comprises: administering at least one frozen particle composition to at least one wound of a subject for a time sufficient to maintain the approximation of tissue of the at least one wound; wherein the at least one frozen particle composition includes one or more frozen hydrogen oxide particles including at least one adhesive, and wherein the one or more frozen hydrogen oxide particles have one or more phases including at least one of amorphous solid water, low density amorphous ice, high density amorphous ice, very high density amorphous ice, clathrate ice, hyperquenched glassy water, ice Ic, ice II, ice III, ice IV, ice V, ice VI, ice VII, ice VIII, ice IX, ice X, ice XI, ice XII, ice XIII, ice XIV, or ice XV.

In one embodiment, a method of maintaining the approximation of tissue of the at least one wound of a subject comprises: administering at least one frozen particle composition to at least one wound of a subject for a time sufficient to maintain the approximation of tissue of the at least one wound; wherein the at least one frozen particle composition includes one or more frozen solution particles including at least one adhesive agent. In one embodiment, the at least one frozen particle composition is in at least one crystalline or amorphous phase.

In one embodiment, a method of maintaining the approximation of tissue of at least one wound of a subject comprises: administering at least one frozen particle composition to at least one wound of a subject for a time sufficient to maintain the approximation of tissue of the at least one wound; wherein the at least one frozen particle composition includes one or more non-hydrogen oxide frozen solvent particles and at least one adhesive agent. In one embodiment, the one or more non-hydrogen-oxide frozen solvent particles include frozen particles of at least one of acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, or diethyl ether. In one embodiment, the method includes one or more frozen particle compositions further comprising at least one of polyethylene glycol, Ringer's solution, lactated Ringer's solution, Hartmann's solution, acetated Ringer's solution, phosphate buffered solution, TRIS-buffered saline solution, Hank's balanced salt solution, Earle's balanced salt solution, HEPES-buffered saline, dextrose, or glucose.

In one embodiment, a method of maintaining the approximation of tissue of at least one wound of a subject comprises: administering at least one frozen particle composition to at least one wound of a subject for a time sufficient to maintain the approximation of tissue of the at least one wound; wherein the at least one frozen particle composition includes one or more frozen particles of at least one component, and at least one adhesive agent; and wherein the at least one component is in a gaseous state at or above 1 bar pressure, and at or above approximately 10° C., approximately 15° C., approximately 20° C., approximately 25° C., approximately 30° C., approximately 37° C., approximately 40° C., approximately 45° C., or approximately 50° C. In one embodiment, the at least one component includes one or more of nitrogen, helium, neon, xenon, oxygen, air, krypton, chlorine, bromine, or argon.

In one embodiment, the at least one frozen particle composition further includes at least one pharmaceutically-acceptable carrier or excipient. In one embodiment, the at least one adhesive agent includes at least one of a monomer, prepolymer, polymer, or copolymer. In one embodiment, the at least one adhesive agent includes at least one monomer of a self-polymerizing agent.

In one embodiment, the at least one adhesive agent is configured to polymerize upon administration to the at least one wound. In one embodiment, the at least one adhesive agent is configured to polymerize at or above the temperature of the at least one wound. In one embodiment, the at least one adhesive agent is configured to polymerize at or above the temperature of at least one biological tissue. In one embodiment, the at least one adhesive agent is configured to polymerize at or above the temperature of at least one subject. In one embodiment, the at least one wound is located in one or more of a cell, tissue, or organ. In one embodiment, the tissue or organ includes at least one of skin tissue, muscle tissue, eye tissue, an organ, nervous tissue, peritoneal tissue, connective tissue, neoplastic tissue, or bone tissue.

In one embodiment, the subject includes at least one invertebrate or vertebrate animal. In one embodiment, the subject includes at least one of a reptile, mammal, amphibian, bird, or fish. In one embodiment, the subject includes at least one human. In one embodiment, the subject includes at least one of livestock, pet, undomesticated herd animal, zoo animal, wild animal, or product animal. In one embodiment, the subject includes at least one of a sheep, goat, frog, dog, cat, rat, mouse, vermin, monkey, duck, horse, cow, pig, chicken, shellfish, fish, turkey, llama, alpaca, bison, buffalo, ape, primate, ferret, wolf, coyote, deer, rabbit, guinea pig, yak, chinchilla, mink, reindeer, camel, fox, raccoon, elk, deer, donkey, or mule.

In one embodiment, the at least one adhesive agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

In one embodiment, the at least one adhesive agent includes one or more of an acrylic polymer or copolymer, acrylamide polymer or copolymer, polyacrylic acid, epoxy, urethane, gum arabic, polyester, polyhydroxyalkanoate, poly (L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, polysulfide, polyanhydride, polydioxanone, poly-p-dioxanone, albumin, glutaraldehyde, polyethylene glycol, hydrogel, soy, or gelatin.

In one embodiment, the at least one adhesive agent includes one or more components that are inactive. In one embodiment, the one or more components are configured to be activated by administration. In one embodiment, administering at least one frozen particle composition to at least one wound includes accelerating, propelling, or ejecting the frozen particle composition toward the at least one wound. In one embodiment, administering the at least one frozen particle composition to at least one wound includes propelling, ejecting, or accelerating the at least one frozen particle composition toward the at least one wound at a predetermined angle, predetermined velocity, or predetermined rate of administration. In one embodiment, the method further includes varying the rate, velocity, or angle at which the at least one frozen particle composition is administered to at least one wound. In one embodiment, administering at least one frozen particle composition to at least one wound includes propelling, ejecting, or accelerating a plurality of frozen particle compositions toward the at least one wound.

In one embodiment, two or more of the plurality of frozen particle compositions include two or more adhesive agents configured to physically or chemically bind upon administration. In one embodiment, administering at least one frozen particle composition to at least one wound includes contacting the at least one wound with the at least one frozen particle composition. In one embodiment, administering at least one frozen particle composition to at least one wound includes contacting the at least one wound with the at least one adhesive agent. In one embodiment, administering the at least one frozen particle composition occurs prior to, during, or subsequent to surgery. In one embodiment, the at least one wound is located in at least one of in situ, in vitro, in vivo, in utero, in planta, in silico, or ex vivo. In one embodiment, the at least one wound is located in one or more of skin, scalp, hair, nail, nail bed, teeth, eye, ear, ovary, oviduct, tongue, tonsil, adenoid, liver, bone, pancreas, stomach, blood vessel, blood, lymph, heart, lung, brain, breast, kidney, bladder, urethra, ureter, gall bladder, uterus, prostate, testes, vas deferens, fallopian tubes, large intestine, small intestine, esophagus, oral cavity, nasal cavity, otic cavity, connective tissue, muscle tissue, peritoneal tissue, or adipose tissue. In one embodiment, the at least one wound is related to at least one blood clot, microorganism accumulation, blood vessel obstruction, duct obstruction, bowel obstruction, infection, gangrene, connective tissue destruction, tissue or organ damage, injury, white blood cell accumulation, or cancer. In one embodiment, the at least one wound includes at least one of an incision, fracture, irritation, laceration, abrasion, puncture wound, penetration wound, gunshot wound, iatrogenic wound, severing, infection, ulcer, pressure sore, lesion, chemical burn, animal bite, dental caries, first-degree burn, second-degree burn, third-degree burn, or fourth-degree burn.

In one embodiment, the method further includes administering to the at least one substrate at least one of a nanoparticle, detection material, sensor, micro-syringe, or circuit. In one embodiment, the detection material is intermixed with the at least one frozen particle composition. In one embodiment, the detection material is located in the at least one frozen particle composition. In one embodiment, the detection material is located in the one or more frozen particles. In one embodiment, the detection material includes at least one electronic identification device. In one embodiment, the at least one electronic identification device includes at least one radio frequency identification device. In one embodiment, the detection material includes at least one radioactive element. In one embodiment, the at least one radioactive element includes one or more of $^{32}P$, $^{35}S$, $^{13}C$, $^{131}I$, $^{191}Ir$, $^{192}Ir$, $^{193}Ir$, $^{201}Tl$, or $^{3}H$. In one embodiment, the detection material includes at least one radioactive, luminescent, colorimetric, or odorous substance. In one embodiment, the detection material includes at least one of a diamagnetic particle, ferromagnetic particle, paramagnetic particle, super paramagnetic contrast agent, or other magnetic particle. In one embodiment, the at least one frozen particle composition includes at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

In one embodiment, the at least one frozen particle composition further includes one or more of a reinforcement agent, abrasive, explosive material, or biological remodeling agent.

BRIEF DESCRIPTION OF THE FIGURES

FIG. 9 illustrates a partial view of FIG. 7 in which embodiments may be implemented.

FIG. 10 illustrates a partial view of a method 1000 that includes generating at least one response.

FIG. 12 illustrates a partial view of FIG. 10 in which embodiments may be implemented.

FIG. 13 illustrates a partial view of a system 1300 that includes a computer program for executing a computing process on a computing device.

FIG. 15 illustrates a partial view of FIG. 13 in which embodiments may be implemented.

FIG. 16 illustrates a partial view of a system 1600 that includes a computer program for executing a computing process on a computing device.

FIG. 17 illustrates a partial view of a computer program product 1700 for executing a computing process on a computing device.

FIG. 19 illustrates a partial view of a computer program product 1900 for executing a computing process on a computing device.

FIG. 20 illustrates a partial view of a computer program product 2000 for executing a computing process on a computing device.

FIG. 21 illustrates a partial view of a computer program product 2100 for executing a computing process on a computing device.

FIG. 22 illustrates a partial view of a computer program product 2200 for executing a computing process on a computing device.

FIG. 23 illustrates a partial view of a method 2300 that includes generating at least one response.

FIG. 26 illustrates a partial view of a method 2600 that includes generating at least one response.

FIG. 29 illustrates a partial view of a system 2900 that includes a computer program for executing a computing process on a computing device.

FIG. 30 illustrates a partial view of FIG. 29 in which embodiments may be implemented.

FIG. 31 illustrates a partial view of a system 3100 that includes a computer program for executing a computing process on a computing device.

FIG. 33 illustrates a partial view of a system 3300 that includes a computer program for executing a computing process on a computing device.

FIG. 34 illustrates a partial view of FIG. 33 in which embodiments may be implemented.

FIG. 35 illustrates a partial view of FIG. 33 in which embodiments may be implemented.

FIG. 36 illustrates a partial view of a system 3600 that includes a computer program for executing a computing process on a computing device.

FIG. 37 illustrates a partial view of a method 3700 in which embodiments may be implemented.

FIG. 38 illustrates a partial view of FIG. 37 in which embodiments may be implemented.

FIG. 39 illustrates a partial view of FIG. 37 in which embodiments may be implemented.

FIG. 40 illustrates a partial view of FIG. 37 in which embodiments may be implemented.

FIG. 41 illustrates a partial view of FIG. 37 in which embodiments may be implemented.

FIG. 46 illustrates a partial view of FIG. 37 in which embodiments may be implemented.

FIG. 47 illustrates a partial view of FIG. 37 in which embodiments may be implemented.

FIG. 48 illustrates a partial view of FIG. 37 in which embodiments may be implemented.

FIG. 49 illustrates a partial view of a method 4900 in which embodiments may be implemented.

FIG. 50 illustrates a partial view of FIG. 49 in which embodiments may be implemented.

FIG. 51 illustrates a partial view of FIG. 49 in which embodiments may be implemented.

FIG. 52 illustrates a partial view of FIG. 49 in which embodiments may be implemented.

FIG. 53 illustrates a partial view of FIG. 49 in which embodiments may be implemented.

FIG. 54 illustrates a partial view of a method 5400 in which embodiments may be implemented.

FIG. 55 illustrates a partial view of FIG. 54 in which embodiments may be implemented.

FIG. 56 illustrates a partial view of FIG. 54 in which embodiments may be implemented.

FIG. 57 illustrates a partial view of FIG. 54 in which embodiments may be implemented.

FIG. 58 illustrates a partial view of FIG. 54 in which embodiments may be implemented.

FIG. 59 illustrates a partial view of a method 5900 in which embodiments may be implemented.

FIG. 60 illustrates a partial view of a method 6000 in which embodiments may be implemented.

FIG. 61 illustrates a partial view of FIG. 60 in which embodiments may be implemented.

FIG. 62 illustrates a partial view of FIG. 60 in which embodiments may be implemented.

FIG. 63 illustrates a partial view of FIG. 60 in which embodiments may be implemented.

FIG. 64 illustrates a partial view of FIG. 60 in which embodiments may be implemented.

FIG. 65 illustrates a partial view of FIG. 60 in which embodiments may be implemented.

FIG. 66 illustrates a partial view of a method 6600 in which embodiments may be implemented.

FIG. 67 illustrates a partial view of FIG. 66 in which embodiments may be implemented.

FIG. 70 illustrates a partial view of FIG. 66 in which embodiments may be implemented.

FIG. 71 illustrates a partial view of FIG. 66 in which embodiments may be implemented.

FIG. 72 illustrates a partial view of FIG. 66 in which embodiments may be implemented.

FIG. 74 illustrates a partial view of FIG. 73 in which embodiments may be implemented.

FIG. 76 illustrates a partial view of FIG. 75 in which embodiments may be implemented.

FIG. 78 illustrates a partial view of a computer program product 7800 in which embodiments may be implemented.

FIG. 79 illustrates a partial view of a system 7900 in which embodiments may be implemented.

FIG. 80 illustrates a partial view of a system 8000 in which embodiments may be implemented.

DETAILED DESCRIPTION

Figure 1:
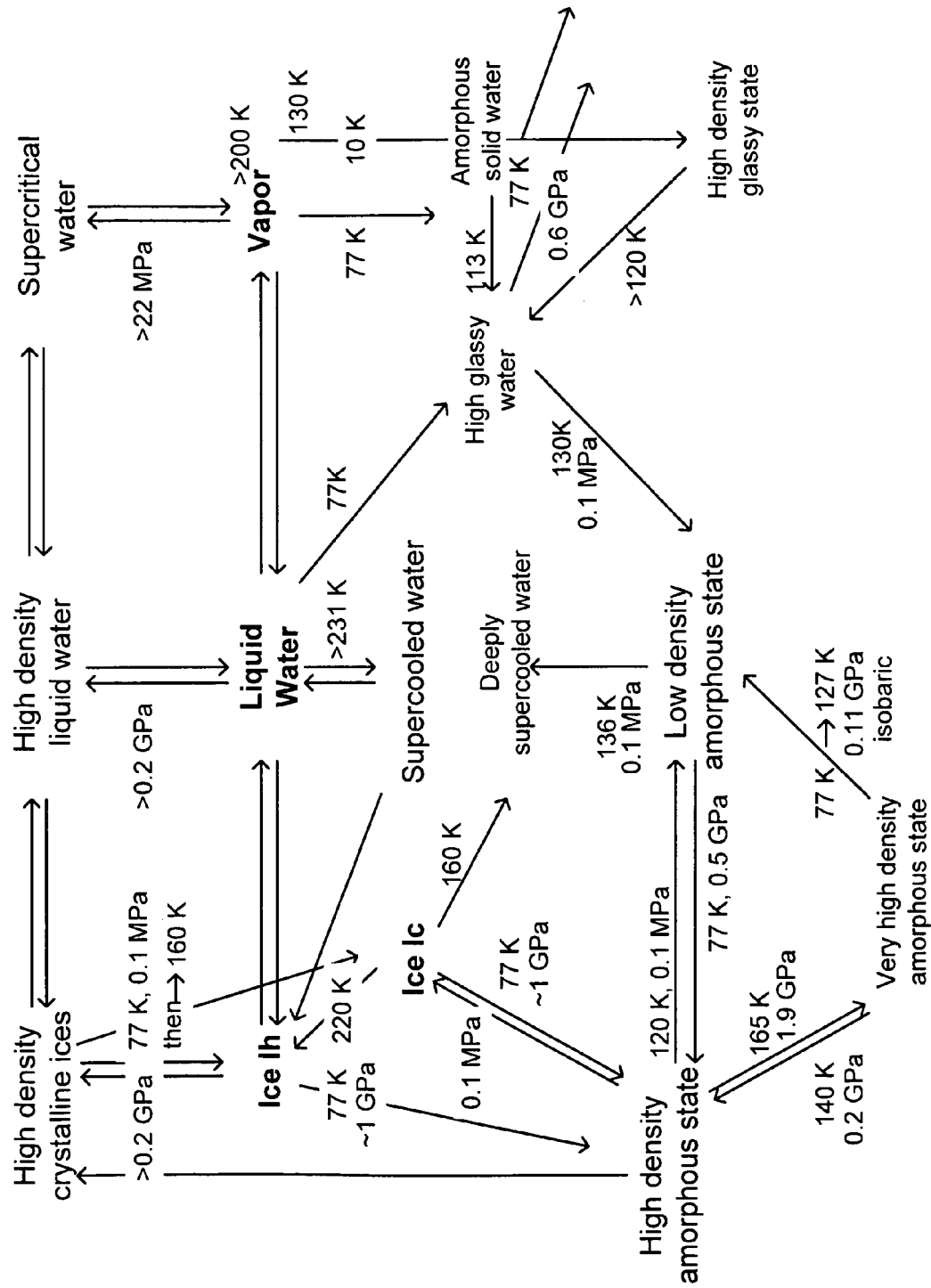
FIG. 1 illustrates particular phases of hydrogen oxide.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

In one embodiment, at least one frozen particle composition (including therapeutic compositions), device, system, product, machine, or method disclosed herein relates to making, administering, or utilizing one or more frozen particle compositions for various purposes.

Frozen Particles

In one embodiment, the one or more frozen particle compositions include one or more frozen particles and optionally, at least one other agent. In one embodiment, the at least one agent includes at least one of a therapeutic agent, reinforcement agent, abrasive, biological remodeling agent, explosive material, or adhesive agent. In one embodiment, the frozen particle composition includes at least one material that modulates the rate of diffusion or degradation of the at least one agent. In one embodiment, the at least one material reduces the rate of diffusion or degradation of the at least one agent.

In one embodiment, the at least one agent includes or is substantially in the form of at least one of substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

In one embodiment, the one or more frozen particle compositions include one or more frozen particles made up of at least one frozen constituent. In one embodiment, the one or more frozen particle compositions include one or more frozen particles including a single frozen constituent. In one embodiment, the one or more frozen particles include multiple frozen constituents. In one embodiment, the one or more frozen particles include frozen solute particles, and optionally, at least one agent. In one embodiment, the one or more frozen particles include non-hydrogen oxide frozen solute particles, and optionally, at least one agent. In one embodiment, the one or more frozen particles include frozen solvent particles, and optionally, at least one agent. In one embodiment, the one or more frozen particles include non-hydrogen oxide frozen solvent particles and optionally, at least one agent. In one embodiment, the one or more frozen particles include frozen solution particles, and optionally, at least one agent. In one embodiment, a composition includes one or more frozen solution particles and at least one agent; wherein the frozen particle composition is in at least one crystalline or amorphous phase.

In one embodiment, the one or more frozen particles include frozen particles of at least one component that is in a gaseous state at or above 1 bar pressure and at or above approximately 10° C., approximately 15° C., approximately 20° C., approximately 25° C., approximately 30° C., approximately 35° C., approximately 37° C., approximately 40° C., approximately 45° C., approximately 50° C. In one embodiment, the one or more frozen particles include one or more frozen hydrogen oxide particles.

In one embodiment, the frozen particle composition includes one or more frozen particles including at least one of hydrogen oxide, helium, neon, krypton, argon, xenon, nitrogen, chlorine, bromine, methane, oxygen, air, carbon dioxide, polyethylene glycol, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, diethyl ether, or any solution, suspension, mixture, or colloid including one or more thereof.

In one embodiment, the frozen particle composition includes one or more frozen particles, wherein the frozen hydrogen oxide particle is in one or more phases including at least one of amorphous solid water, low density amorphous ice, high density amorphous ice, very high density amorphous ice, clathrate ice, hyperquenched glassy water, ice Ic, ice II, ice III, ice IV, ice V, ice VI, ice VII, ice VIII, ice IX, ice X, ice XI, ice XII, ice XIII, ice XIV, or ice XV.

In one embodiment, the frozen particle composition includes one or more frozen solution particles, optionally including at least one agent; wherein the one or more frozen solution particles have at least one major dimension of approximately one centimeter or less, approximately one millimeter or less, approximately one micrometer or less, approximately one nanometer or less, or any value therebetween.

In one embodiment, at least one of the constituents of the one or more frozen particle compositions is frozen. In one embodiment, all of the constituents of the one or more frozen particle compositions are frozen. In one embodiment, the one or more frozen particle compositions have at least one major dimension of approximately one decimeter or less, approximately one centimeter or less, approximately one millimeter or less, approximately one micrometer or less, approximately one nanometer or less, approximately one picometer or less, or any value therebetween. In one embodiment, a plurality of frozen particle compositions is delivered or administered, and the plurality includes at least two subsets of frozen particle compositions which can be differentiated based on size. In one embodiment, a plurality of frozen particle compositions includes at least one subset of frozen particle compositions that have at least one major dimension of approximately ten micrometers or less. In one embodiment, the at least one major dimension of the one or more frozen particle compositions includes at least one of radius, diameter, length, width, height, or perimeter.

In one embodiment, the one or more frozen particle compositions approximate the shape of at least one of a sphere, bullet, flechette, cone, needle, arrow, spear, diamond, pyramid, cylinder, mini ball, shuttlecock, spiral, bell, pear, crystal, cube, spheroid, tetrahedron, crescent, or high aspect ratio shape. The size, shape, weight, or density, as well as other physical parameters of the one or more frozen particle compositions can be adjusted according to a frozen particle composition, or desired goal in utilizing the frozen particle composition(s). In one embodiment, the one or more frozen particle compositions include a plurality of frozen particles that are approximately uniform with regard to size, shape, weight, or density. In one embodiment, the one or more frozen particle compositions include an array of different sizes, shapes, weights, or densities.

In one embodiment, the one or more frozen particle compositions exist at about 30° C., about 20° C., about 10° C., about 5° C., about 0° C., about −10° C. about −20° C., about −30° C., about −40° C., about −50° C., about −60° C., about −70° C., about −75° C., about −80° C., about −85° C., about −90° C., about −95° C., about −100° C., about −120° C., about −150° C., about −180° C., about −200° C., about −220° C., about −250° C., or any temperature less than or therebetween.

In one embodiment, the frozen particle composition includes at least one of a solid, liquid, or gas. In one embodiment, the frozen particle composition includes at least one of a frozen liquid, or frozen gas. In one embodiment, the frozen particle composition includes at least one pharmaceutically acceptable carrier or excipient. In one embodiment, the frozen particle composition is formulated to be administered by one or more of topical administration, oral administration, enteral administration, mucosal administration, percutaneous administration, or parenteral administration. In one embodiment, parenteral administration includes at least one of intravenous administration, intra-arterial administration, intracardiac administration, subcutaneous administration, intraperitioneal administration, or intramuscular administration. In one embodiment, the frozen particle composition is formulated to be administered by high velocity impact. In one embodiment, the frozen particle composition is formulated to be administered by one or more devices.

In one embodiment, the frozen particle composition includes one or more of a suspension, mixture, solution, sol, clathrate, colloid, emulsion, microemulsion, aerosol, ointment, capsule, powder, tablet, suppository, cream, device, paste, resin, liniment, lotion, ampule, elixir, spray, suspension, syrup, tincture, detection material, polymer, biopolymer, buffer, adjuvant, diluent, lubricant, disintegration agent, suspending agent, solvent, light-emitting agent, colorimetric agent, glidant, anti-adherent, anti-static agent, surfactant, plasticizer, emulsifying agent, flavor, gum, sweetener, coating, binder, filler, compression aid, encapsulation aid, preservative, granulation agent, spheronization agent, stabilizer, adhesive, pigment, sorbent, nanoparticle, or gel.

In one embodiment, the one or more frozen particle compositions include frozen hydrogen oxide particles. Frozen hydrogen oxide, or typical water ice, exists in several non-crystalline forms. Each of these forms has specific physical characteristics such as density and vibrational spectra. Some examples of frozen hydrogen oxide phase transformations are shown in FIG. 1. (See e.g., Chaplin, the worldwide web at lsbu.ac.uk/water; Ivanov et al., Russian J. Gen. Chem. vol. 75, pp. 1851-1856 (2005), each of which is incorporated herein by reference).

Hydrogen oxide (water) has many frozen phases (ices), including crystalline and non-crystalline phases. The crystalline phases generally have the common structure of having hydrogen bonds to four neighboring water molecules, such as two hydrogen atoms near each oxygen atom. Structural data on the known frozen hydrogen oxide polymorphs are shown in Table I, with two known phases of ice XI. (See, e.g., Chaplin, Ibid; and Zheligovskaya, et al., Russian Chem. Rev. 75, pp. 57-76, 2006, each of which is incorporated herein by reference).

TABLE I

Structural Data on the Ice Polymorphs

| Ice polymorph | Density, g/cm$^3$ | Protons | Crystal | Symmetry | Dielectric constant, $\epsilon_S$ | Notes |
|---|---|---|---|---|---|---|
| Hexagonal ice, Ih | 0.92 | disordered | Hexagonal | One $C_6$ | 97.5 | |
| Cubic ice, Ic | 0.92 | disordered | Cubic | four $C_3$ | | |
| LDA, Ia | 0.94 | disordered | Non-crystalline | | | As prepared, can be mixtures of several types |
| HAD | 1.17 | disordered | Non-crystalline | | | As prepared, can be mixtures of several types |
| VHDA | 1.25 | disordered | Non-crystalline | | | |
| II | 1.17 | ordered | Rhombohedral | One $C_3$ | 3.66 | |
| III | 1.14 | disordered | Tetragonal | One $C_4$ | 117 | protons can be partially ordered |
| IV | 1.27 | disordered | Rhombohedral | One $C_3$ | | metastable in ice V phase space |
| V | 1.23 | disordered | Monoclinic | One $C_2$ | 144 | protons can be partially ordered |
| VI | 1.31 | disordered | Tetragonal | One $C_4$ | 193 | protons can be partly ordered |
| VII | 1.50 | disordered | Cubic | four $C_3$ | 150 | two interpenetrating ice Ic frameworks |
| VIII | 1.46 | ordered | Tetragonal | One $C_4$ | 4 | low temperature form of ice VII |
| IX | 1.16 | ordered | Tetragonal | One $C_4$ | 3.74 | low temperature form of ice III, metastable in ice II space |

TABLE I-continued

Structural Data on the Ice Polymorphs

| Ice polymorph | Density, g/cm$^3$ | Protons | Crystal | Symmetry | Dielectric constant, $\epsilon_S$ | Notes |
|---|---|---|---|---|---|---|
| X | 2.51 | symmetric | Cubic | four C$_3$ | | symmetric proton form of ice VII |
| XI | 0.92 | ordered | Orthorhombic | there C$_2$ | | low temperature form of ice Ih |
| XI | >2.51 | symmetric | Hexagonal close packed | distorted | | Found in simulations only |
| XII | 1.29 | disordered | Tetragonal | One C$_4$ | | metastable in ice V phase space |
| XIII | 1.23 | ordered | Monoclinic | One C$_2$ | | ordered form of ice V phase |
| XIV | 1.29 | mostly ordered | Orthorhombic | One C$_4$ | | ordered form of ice XII phase |
| XV | 1.31 (?) | ordered | ? | ? | | ordered form of ice VI phase |

Cooling liquid hydrogen oxide below its standard freezing point typically results in the formation of frozen hexagonal ice. However, if the hydrogen oxide is pure and cooled slowly, the liquid hydrogen oxide can be supercooled to approximately −42° C. Amorphous solids harden without crystallizing, such that if hydrogen oxide is cooled rapidly it results in formation of a glass-like state, for example, hyperquenched glassy water. (See e.g., Debenedetti, J. Phys. Condens. Matter, vol. 15, pp. R1669-R1726 (2003), and as cited by Chaplin, worldwideweb at lsbu.ac.uk/water; each of which is incorporated herein by reference.) Generally, hyperquenched glassy water is formed by rapidly spraying a fine mist of micrometer-sized hydrogen oxide droplets into very cold liquefied gas, such as propane. Alternatively, a fine mist of hydrogen oxide can be sprayed onto a very cold frozen cell or tissue, for example, at or below approximately −193° C. Hyperquenched glassy water may also be formed by cooling capillary tubes containing bulk liquid water (~100 μm diameter) with liquid helium, for example, at approximately −269° C.

Figure 2:
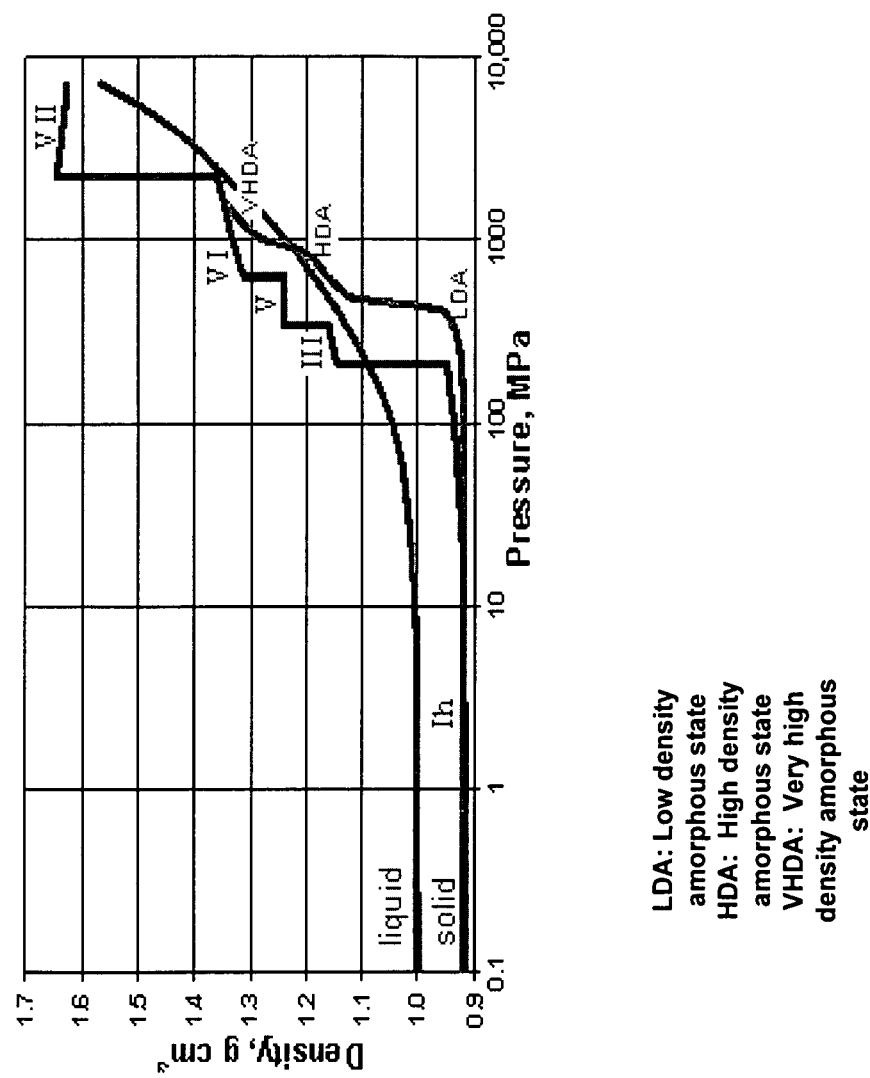
FIG. 2 illustrates the density of hydrogen oxide at various pressure points.
Figure 3:
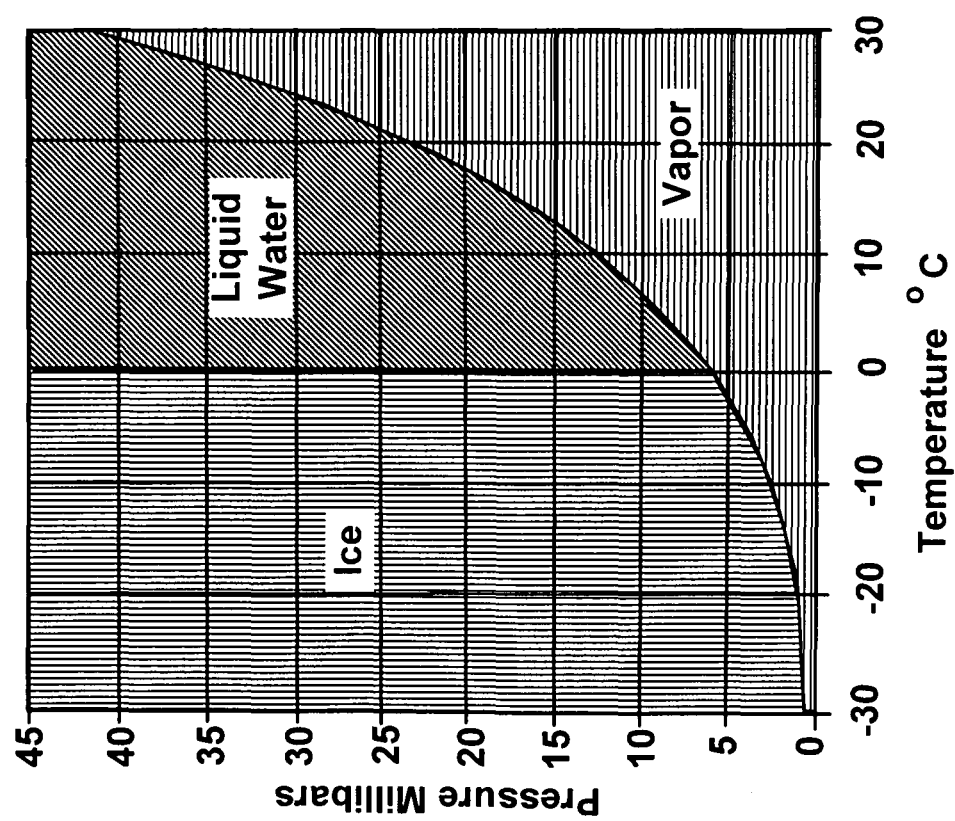
FIG. 3 illustrates particular phases of hydrogen oxide at various pressure and temperature points.
Figure 4:
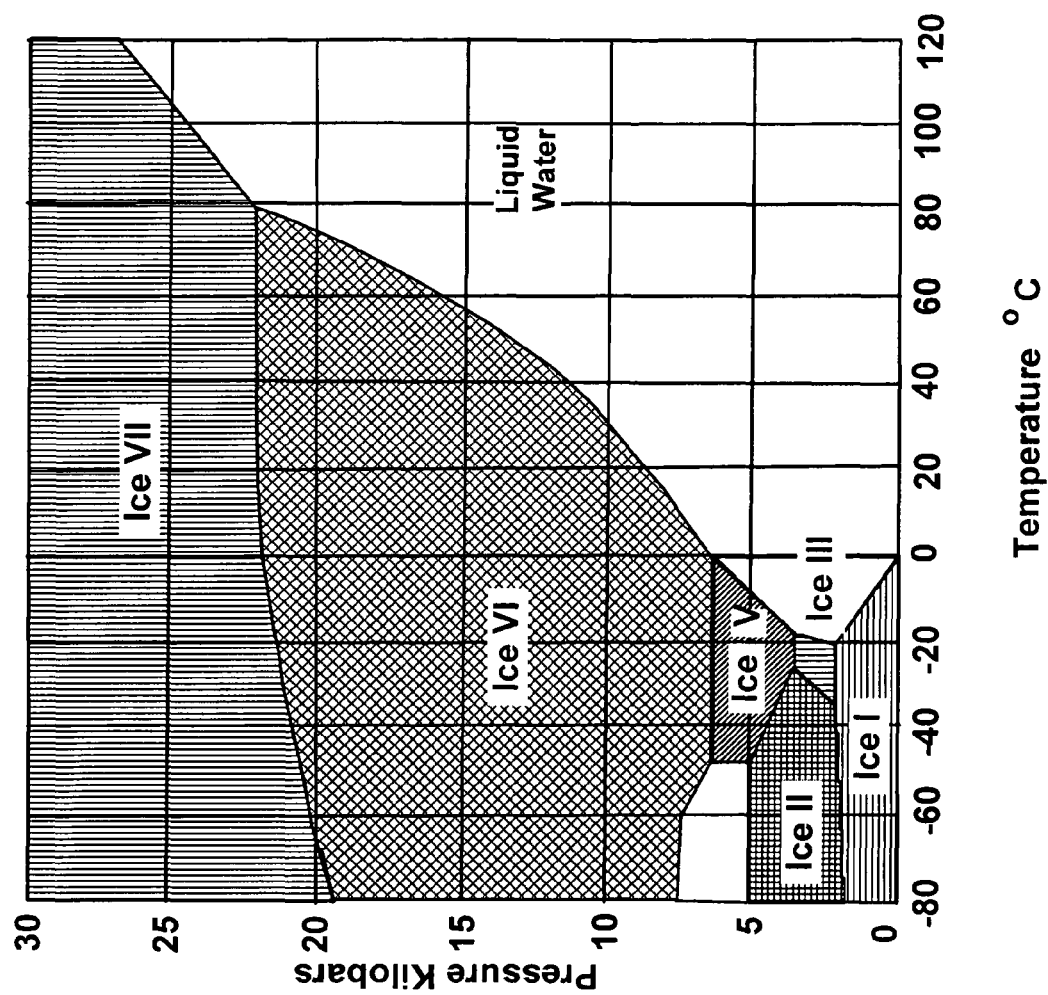
FIG. 4 illustrates particular phases of hydrogen oxide at various pressure and temperature points.

As shown in FIGS. 1-4, hydrogen oxide attains various structures and phases depending upon the temperature or pressure of the environment. As indicated in FIG. 1, for example, hydrogen oxide ice Ic is derived from high density amorphous water or deeply supercooled liquid water, when put under low temperature or higher pressure. Likewise, as indicated in FIG. 2, the hydrogen oxide has a greater density as a liquid than as a solid under ambient conditions (ice Ih). However, at increasing pressure, at least ice stages III, V, VI, and VII exhibit a greater density than liquid hydrogen oxide. FIG. 3 indicates the phase diagram for hydrogen oxide based on pressure and temperature variance, while FIG. 4 shows the specific sub-categories of hydrogen oxide based on physical properties, such as structure and density, among others, as the temperature and pressure vary.

Similarly, amorphous solid water is formed from the slow deposition of hydrogen oxide vapor on a cold metal crystal surface (for example, at less than approximately 2 nm/s), below the temperature of approximately −153° C. Amorphous solid water is a viscous semi-solid material that has a density of approximately 0.94 g/cm$^3$ and harbors gaps and spaces in its structure, as well as reactive hydrogen bonds. These structures are removed by annealing under vacuum pressure, which allows the material to convert to a high density glassy water or low density amorphous ice, depending on the temperature. Typically, high density glassy water, which has a density of approximately 1.1 g/cm$^3$, is formed by vapor deposition at approximately −263° C.

Low-density amorphous (LDA) ice also occurs from heating high-density amorphous (HDA) ice to just above approximately −153° C. at atmospheric pressure, and transforms to cubic ice at approximately −113° C. to −123° C. Low-density amorphous ice is also prepared by submitting low-pressure phases (Ih, Ic, XI, etc.) to high pressure (e.g., approximately 1.0 GPa) at low temperatures (e.g., below approximately −148° C.).

Very-high density amorphous (VHDA) ice is a viscous water state with a density of approximately 1.25 g/cm$^3$, and is prepared by heating high-density amorphous ice to just above approximately −113° C. and approximate pressure of 1.15 GPa. When very-high density amorphous ice is heated at different pressures between, e.g., 0.3 and 2 GPa, it re-crystallizes into only the proton disordered ices III, IV, V, XII, VI and VII in order of increasing pressure, but does not typically re-crystallize into the proton ordered phases (e.g., ice II).

Typically, the density of liquid water increases with increased pressure. When liquid water approaches the critical point in the liquid-vapor phase, water enters a supercritical phase where it exists as small but liquid-like hydrogen-bonded clusters dispersed within a gas-like phase and its physical properties vary according to changing density. Supercritical water is an excellent solvent for non-polar molecules, due to its low dielectric constant and poor hydrogen bonding. Due to these same properties, supercritical water is typically not a good solvent for electrolytes, which tend to form ionic bonds.

As indicated in FIG. 2, hexagonal ice is less dense than liquid water, whereas the other ice phases are all denser and phase changes occur near the liquid and solid densities (See e.g., Loerting et al., J. Phys.: Condens. Matter vol. 18, R919-R977 (2006), which is incorporated herein by reference). Liquid water density varies with change in temperature or pressure, whereas the density of amorphous ice varies only with change in pressure, but not temperature.

Hydrogen oxide has a high heat of vaporization (approximately 40.7 kJ/mol), and a high heat of sublimation (approximately 51.059 kJ/mol at 0° C.), which allows for the frozen particle compositions to remain intact for a short time period during which the particles are delivered to one or more cells or tissues. These properties further enable the frozen particle compositions to serve as particles for delivery of at least one therapeutic composition to one or more cells or tissues.

Frozen particle compositions may include a "solid," such as true solids, semi-solids, and viscous fluid, such as gels, hydrogels, or sols. Frozen particle compositions including one or more frozen particles may include particles that are at least partially frozen, or are entirely frozen. Frozen particle compositions including one or more frozen particles may include one or more subset groups of one or more particles, some of which are entirely frozen and some of which are at least partially frozen. Such frozen particle compositions may include multiple different constitutions, wherein a group of frozen particle compositions includes at least one subset of multiple frozen particles, wherein each frozen particle has an individual therapeutic agent, adhesive agent, biological remodeling agent, abrasive, explosive material, reinforcement agent, other agent, a common constitution, or unique constitution. The group of frozen particle compositions may also include at least one subset of multiple frozen particles, wherein each frozen particle includes multiple agents.

A particular plurality of frozen particle compositions may include multiple frozen particles where various multiple agents are associated with a single particle. Likewise, a particular plurality of frozen particle compositions may include various multiple agents, where each individual agent is associated with a single frozen particle. In one embodiment, a plurality of frozen particle compositions includes any number of subsets of frozen particles associated with a particular agent, or other constituent. During the course of any particular method described herein, one or more plurality of frozen particle compositions, or any particular subset thereof, can be administered in a single treatment or in multiple treatments. A frozen particle composition including at least one therapeutic agent may be referred to as a "therapeutic composition" or "frozen particle therapeutic composition" herein.

In certain instances, the one or more frozen particle compositions are utilized at a very low temperature, which may increase the degree of penetration of the one or more particles or the one or more compositions for a biological tissue. In certain instances, the one or more frozen particle compositions are utilized at higher temperatures, depending on the freezing temperature of the constituents of the one or more particles, the goals of administration or treatment, or other factors. For example, the freezing point of nitrogen is approximately −210° C., whereas the freezing point of dimethyl sulfoxide (DMSO) is approximately 18.45° C.

Hydrogen oxide becomes more viscous as the temperature is decreased to below approximately 33° C., or the pressure is increased. Ice Ic is generally formed by condensation of water vapor, at ambient pressure and low temperatures (less than approximately −80° C.), or below approximately −38° C. as a mist. (See e.g., Murray et al., Phys. Chem. Chem. Phys. Vol. 8, pp. 186-192 (2006), which is incorporated herein by reference). Ice Ic is also prepared by reducing the pressure on high-pressure hydrogen oxide ice at approximately −196° C. It can be the preferred phase for ice formed from hydrogen oxide droplets smaller than about 15 nm in radius, particularly at low temperatures (e.g., −113° C. to −53° C.). (See e.g., Johari, J. Chem. Phys. vol. 122 pp. 194504 (2005); Zhang, et al., Chem. Phys. Lett. vol. 421, pp. 251-255 (2006), each of which is incorporated herein by reference).

Ice Ih constitutes a large portion of naturally-occurring snow and ice. Since hexagonal ice exhibits changes in the hydrogen bonding, ice Ih shows anomalous reduction in thermal conductivity with increasing pressure (as does cubic ice and low-density amorphous ice). (See e.g., Andersson et al., Phys. Rev. B vol. 65 pp. 140201.1-14201.4 (2002), which is incorporated herein by reference).

Ice II maintains a general rhombohedral unit shape, similar to ice I. The density of ice II is approximately 1.17 g/cm$^3$. Ice III maintains a general tetragonal unit shape, with a density of approximately 1.14 g/cm$^3$. Ice VI also maintains a general tetragonal unit shape, with a density of approximately 1.31 g/cm$^3$. Ice VII is primarily composed of multiple intercalating ice Ic lattices, and has a density of approximately 1.66 g/cm$^3$.

Examples of materials that are included in one or more compositions described herein include, but are not limited to, liquid nitrogen, which is nontoxic and inert, with a freezing point at 1 atm pressure of approximately −210° C. Liquid helium is nontoxic and inert, with a freezing point at 367 psi of approximately −272.2° C. Liquid argon is nontoxic and inert with a freezing point at 1 atm pressure of approximately −189.4° C. Liquid neon has a freezing point of approximately −245.95° C., while liquid xenon has a freezing point of approximately −111.9° C. The freezing point of liquid dimethyl sulfoxide (DMSO) is approximately 18.45° C., and water or other co-solvents can decrease the freezing point. The freezing point of lactated Ringer's solution is approximately −45° C. These and other materials can be utilized as described herein either alone, or in combination with other materials.

In one embodiment, the frozen particle composition includes a clathrate. Clathrate ice forms from water or other liquids, and contains small amounts of non-polar molecules (generally gases) under moderate pressure of a few MPa, and temperatures close to 0° C. Clathrate structures can vary, but generally allow a minimum amount of small molecules to fit into and stabilize gaps without forming covalent or hydrogen bonds with the hydrogen oxide molecules. Certain clathrates are formed at the interface of the liquid phase, under atmospheric pressure. Clathrates include but are not limited to the structural forms of sI, sII, and sh. In certain instances, noble gases can be used to form clathrate compounds with hydrogen oxide or other molecules. Noble gases generally have low polarizability, and tend to be spherically symmetrical, which allows for solubility with the hydrogen oxide cage. In addition, the solubility of the noble gases increases considerably as the temperature is lowered.

The solubility properties of particular noble gases as clathrates with hydrogen oxide are shown in Table IV. (See e.g., Dec et al., J. Solution Chem. vol. 14, pp. 417-429 (1985); Ivanov, et al., J. Struct. Chem. vol. 46, pp. 253-263 (2005); Fernandez-Prini, et al., Elsvier, pp. 73-98 (2004); Ivanov, et al., Russian J. Gen. Chem. vol. 75, pp. 1851-1856 (2005), each of which is incorporated herein by reference.)

TABLE IV

Solubility Properties of the Noble Gases

| Property | He | Ne | Ar | Kr | Xe | Rn |
|---|---|---|---|---|---|---|
| Atomic number | 2 | 10 | 18 | 36 | 54 | 86 |
| Atomic radius, Å | 1.08 | 1.21 | 1.64 | 1.78 | 1.96 | 2.11 |
| ΔG° of solution in H$_2$O at 25° C., kJ/mol | 29.41 | 29.03 | 26.25 | 24.80 | 23.42 | |

TABLE IV-continued

Solubility Properties of the Noble Gases

| Property | | He | Ne | Ar | Kr | Xe | Rn |
|---|---|---|---|---|---|---|---|
| $\Delta H°$ of solution in $H_2O$ at 25° C., kJ/mol | | −0.59 | −3.80 | −11.98 | −15.29 | −18.99 | |
| $\Delta S°$ of solution in $H_2O$ at 25° C., J/molK | | −100.6 | −110.1 | −128.2 | −134.5 | −142.2 | |
| Solubility, mM, 5° C., 101,325 Pa | $H_2O$ | 0.41 | 0.53 | 2.11 | 4.20 | 8.21 | 18.83 |
| | $D_2O$ | 0.49 | 0.61 | 2.38 | 4.61 | 8.91 | 20.41 |
| Solubility minima, ° C. | $H_2O$ | 30 | 50 | 90 | 108 | 110 | |
| | $D_2O$ | 53 | 53 | 98 | 108 | 116 | |

In one embodiment, the frozen particle composition is substantially in the form of a microneedle, microscalpel, or other tool. In one embodiment, the frozen particle composition includes means for piercing, stitching, extracting material, or administering at least one agent to a substrate.

Cavitized or Compartmentalized Frozen Particle Compositions

In one embodiment, the frozen particle composition includes at least one frozen particle defining at least one cavity or compartment configured for holding at least one agent. In one embodiment, the frozen particle includes at least one inlet port in fluid communication with the at least one cavity. In one embodiment, the frozen particle includes at least one status indicator. In one embodiment, the at least one status indicator indicates one or more of: content of the at least one cavity, amount of cavity space occupied, or amount of cavity space available. In one embodiment, the at least one status indicator includes at least one of a sensor, a magnet, a colorimetric substance, or a physical measuring device. In one embodiment, the at least one status indicator measures one or more of a change in cavity volume, a change in cavity shape, a change in cavity temperature, a change in cavity pressure, a change in cavity pH, a change in frozen particle density, a change in frozen particle volume, a change in frozen particle weight, a change in frozen particle temperature, a change in frozen particle shape, a change in electrical field, a change in vehicle magnetic field, a change in frozen particle pH, a change in the state of an activatable agent of the composition, or a change in the state of an activating factor or inactivating factor of the composition.

In one embodiment, the at least one cavity includes at least one of a permeable, semi-permeable or impermeable partition. In one embodiment, the at least one cavity includes at least one of at least one means for at least partially sealing the cavity. In one embodiment, the at least one cavity includes at least one cap, seal, screw, door, or hinge. In one embodiment, the at least one cavity is substantially in the form of at least one of a space-filling curve, a depression, a cylinder, a spheroid, a cuboid, a high aspect ratio shape, a tetrahedron, a pyramid, a channel, or a cone.

In one embodiment, the at least one cavity differs in physical or chemical composition from at least one other cavity of the frozen particle. In one embodiment, the frozen particle composition including at least one frozen particle defining at least one cavity or compartment further comprises at least one agent located in the at least one cavity or compartment.

In one embodiment, the cavity or compartment is configured to physically or chemically separate the at least one agent from at least one other cavity of the frozen particle. In one embodiment, the at least one cavity or compartment is configured to physically or chemically separate from at least one other cavity or compartment of the frozen particle during administration. In one embodiment the frozen particle composition includes at least one agent, and the at least one agent includes at least one agent in a different phase state than the frozen particle. In one embodiment, the at least one cavity or compartment includes at least one of a solid, liquid, or gas. In one embodiment, the at least one cavity or compartment includes at least one of a liquid or gas, and at least one other cavity or compartment includes a solid.

In one embodiment, the at least one cavity or compartment includes at least one clathrate. In one embodiment, the at least one cavity or compartment includes at least one matrix. In one embodiment, the at least one cavity or compartment is an inner core cavity of at least one frozen particle. In one embodiment, the at least one cavity or compartment includes an inner core region and wherein the at least one agent is at least one of a liquid or gas. In one embodiment, the at least one cavity or compartment is intercalated with at least one other cavity or compartment.

In one embodiment, the at least one cavity or compartment has a higher concentration of the at least one agent than any other cavity or compartment. In one embodiment, the at least one cavity or compartment includes a graduated concentration of the at least one agent. In one embodiment, the at least one cavity or compartment includes varying levels of the at least one agent. In one embodiment, the at least one agent is fractionated. In one embodiment, the cavity or compartment includes one or more layers of at least one agent. In one embodiment, the cavity or compartment includes one or more layers of multiple agents. In one embodiment, the at least one agent includes one or more of a pro-drug or precursor compound. In one embodiment, the at least one agent includes one or more time-release or extended-release formulations. In one embodiment, the at least one agent includes an activatable agent. In one embodiment, the at least one agent is configured to activate upon administration of the frozen particle composition. In one embodiment, the at least one activatable agent is configured to activate by one or more of an enzymatic reaction, a reduction reaction, an oxidation reaction, a reduction-oxidation reaction, a hydrolysis reaction, a dehydration synthesis reaction, a glycosylation reaction, a phosphorylation reaction, a dehydration reaction, a hydration reaction, a decarboxylation reaction, a condensation reaction, a polymerization reaction, a glycolysis reaction, a gluconeogenesis reaction, a fermentation reaction, a photo chemical reaction, a thermal reaction, a magnetic reaction, an electrical reaction, an electrochemical reaction, a photolysis reaction, a photosynthetic reaction, an esterification reaction, altering the pressure on at least one frozen particle composition, altering the content of at least one frozen particle composition, altering at least one chemical property of at least one frozen particle composition, altering at least one physical property of at least one frozen particle composition, or applying at least one external stimulus to at least one frozen particle composition.

In one embodiment, the at least one external stimulus includes one or more of light, heat, electrical field, magnetic field, or electromagnetic energy. In one embodiment, the frozen particle composition further comprises at least one activating factor or at least one inactivating factor capable of modulating the activity of the at least one agent. In one embodiment, the at least one activating factor or the at least one inactivating factor forms at least part of one or more of a lipid conjugate, carbohydrate conjugate, peptide conjugate, polymer-lipid conjugate, fusion protein, antibody or antibody fragment, receptor or receptor fragment, reversible inhibitor, irreversible inhibitor, enzyme, gene repressor, gene suppressor, microRNA, siRNA, kinase, gene activator, DNA-binding protein, polymerase, gene promoter, gene enhancer, diamagnetic chemical, explosive material, reactive metal, adhesive agent, abrasive, reinforcement agent, biological remodeling agent, or therapeutic agent.

In one embodiment, the at least one activating or inactivating agent is configured to activate by one or more of altering the temperature of at least one frozen particle composition, altering the pressure on at least one frozen particle composition, altering the content of at least one frozen particle composition, altering at least one electrical property of at least one frozen particle composition, altering at least one magnetic property of at least one frozen particle composition, altering at least one chemical property of at least one frozen particle composition, altering at least one physical property of at least one frozen particle composition, or applying at least one external stimulus to at least one frozen particle composition.

In one embodiment, the at least one cavity or compartment is in substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

Agents

In one embodiment, the frozen particle composition includes at least one agent. In one embodiment, the frozen particle provides a vehicle for the at least one agent. In one embodiment, the frozen particle is constituted solely by the at least one agent. In one embodiment, the agent includes at least one nontoxic, biocompatible, bioresorbable, or biodegradable agent. In one embodiment, the one or more agents are manufactured into a plate or spheroid. In certain instances, the one or more reinforcement agents, one or more explosive materials, one or more abrasives, one or more adhesive agents, or one or more therapeutic agents, or one or more biological remodeling agents are utilized in the form of a resin, powder, solution, flake, sheet, film, ribbon, gel, ball, pellet, or bead. (See e.g., U.S. Pat. No. 5,534,584; U.S. Pat. No. 5,331,046; each of which is incorporated herein by reference). The one or more materials or agents of the frozen particle compositions can be in the form of a solid, liquid, or gas. In one embodiment, one or more of the agents are the same agent. For example, in one embodiment, the frozen particle composition includes at least one therapeutic agent that is the same as a reinforcement agent, an adhesive agent, an abrasive, an explosive material, or a biological remodeling agent. In one embodiment, any one single agent is the same as any single other agent (ie the constitution of an agent may be the same as another agent, or the function of an agent may be the same as another agent).

In one embodiment, the at least one therapeutic agent and the at least one adhesive agent, biological remodeling agent, abrasive, reinforcement agent, or explosive material are the same agent. In one embodiment, the at least one adhesive agent and the at least one biological remodeling agent, therapeutic agent, abrasive, reinforcement agent, or explosive material are the same. In one embodiment, the at least one biological remodeling agent and the at least one adhesive agent, therapeutic agent, abrasive, reinforcement agent, or explosive material are the same agent. In one embodiment, the at least one reinforcement agent and the at least one adhesive agent, therapeutic agent, biological remodeling agent, abrasive, or explosive material are the same. In one embodiment, the at least one abrasive and the at least one adhesive agent, therapeutic agent, biological remodeling agent, explosive material, or reinforcement agent are the same. In one embodiment, the at least one explosive material and abrasive, adhesive agent, therapeutic agent, biological remodeling agent, or explosive material are the same.

In one embodiment, the at least one is included as part of at least one carrier that assists in synthesis or activation of the at least one agent. In one embodiment, the at least one carrier encompasses the at least one agent. In one embodiment, the carrier includes a microbe, other cell (such as a cell from a subject or related to a particular subject, including but not limited to a transgenic cell). In one embodiment, the cellular carrier is included in the one or more frozen particle compositions described. In one embodiment, the carrier includes or is substantially in the form of at least one of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, glycopeptide, glycolipid, sphingolipid, glycosphingolipid, glycoprotein, peptidoglycan, lipid, carbohydrate, metalloprotein, proteoglycan, chromosome, nucleus, acid, base, buffer, protic solvent, aprotic solvent, nitric oxide, nitrous oxide, nitric oxide synthase, amino acid, micelle, polymer, copolymer, monomer, prepolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

In one embodiment, the at least one agent is frozen. In one embodiment, the at least one agent is at least partially frozen. In at least one embodiment, the frozen particle composition includes one or more frozen particles and at least one agent that is not frozen. In one embodiment, the at least one agent includes two or more components configured to combine upon administration of the at least one agent.

In one embodiment, the at least one agent includes one or more inactive components. In one embodiment, the at least one agent includes two or more components that are configured to activate when combined. In one embodiment, the at least one agent includes one or more components that are configured to activate when administered. In one embodiment, at least two of the one or more components are included in the same or different frozen particle composition. In one embodiment, at least two of the one or more components each reside in a separate cavity of the same or a different frozen particle composition. In one embodiment, at least one agent is included as a precursor molecule.

In one embodiment, at least one agent is configured to be activated prior to or subsequent to administration. In one embodiment, at least one agent is configured to be activated after a prolonged time subsequent to administration. For example, in cases where the agent is encased or associated with a polymer or other agent that may insulate one or more reactant or retard the explosive or decomposition process, the release of the agent can be delayed. In one embodiment, the frozen particle composition includes at least one activatable agent. In one embodiment, the frozen particle composition includes at least one activating agent or at least one inactivating agent, or both. In one embodiment, the at least one agent includes two or more components that are configured to fuse upon deposition.

In one embodiment, the one or more frozen particle compositions including at least one agent are part of a kit for administration, optionally to at least one substrate (including at least one biological cell or tissue). In one embodiment, one or more subsets of frozen particle compositions include different agents or different components of an agent and are administered in a kit or device wherein one subset is kept separate from another subset until administration of the frozen particle compositions.

Reinforcement Agents

In one embodiment disclosed herein, one or more reinforcement agents are included in the frozen particle composition. Examples of some reinforcement agents include, but are not limited to, polyaramid, vinylester matrix, metal (including but not limited to gold, silver, copper, zinc, brass, tin, bronze, gallium, sodium, potassium, tungsten, steel, iron, carbon, aluminum, copper, platinum, tantalum, rhodium, or alloys thereof), ceramic, fiberglass, cellulose, broad carbide, aromatic polyamide, nylon, silk, rayon, acetate, modacrylic, olefin, acrylic polymer or copolymer, acrylamide polymer or copolymer, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, alluvium, sand, sugar, calcite, emery, diamond, novaculite, pumice, rouge, borazon, corundum, zirconia alumina, silicon, silica, frozen hydrogen oxide ice, plant matter, animal matter, or mineral matter. In one embodiment, plant matter may include vegetable matter, nuts or nut products or pieces (e.g., almonds), grains (e.g., oatmeal), wood (e.g., wood fibers) or other stalk material, leaf matter, fruit matter (including pits or seeds or parts thereof), and other plant material.

In one embodiment, one or more reinforcement agents are made by spinning into a fiber, wire, or filament. Some non-limiting examples of reinforcement fibers can be found at, for example, U.S. Pat. No. 5,855,663; U.S. Pat. No. 5,652,058; KEVLAR® technical guide, Polymer Bulletin, vol. 16, pp. 167-174 (1986), and WO/2003/060002, each of which is incorporated herein by reference.

The one or more agents are positioned on or in the one or more frozen particle compositions depending on a given context. For example, the positioning of one or more agents may consider the particular goal of administering the one or more frozen particle compositions, the components of the at least one frozen particle composition, or the needs or desires of a particular outcome of treatment or administration of the one or more frozen particle compositions. In one embodiment, the one or more agents are located at least on the surface or beneath the surface of the one or more frozen particle compositions. In one embodiment, the one or more agents are located within the one or more frozen particle compositions.

As shown in FIGS. 5 and 6, the strength of hydrogen oxide ice samples increases when particular reinforcement agents are added, as published. As indicated in FIG. 5, ice samples exhibit increased strength, as measured by beam deflection as an angle of shear when reinforced with fiberglass or kaolin. As indicated in FIG. 6, the maximum stress (in MPa) and strain rate increases when particular reinforcement agents are added to the hydrogen oxide ice samples.

Abrasives

In certain instances, the frozen particle composition described herein includes one or more abrasives. The one or more abrasives may include treated or untreated abrasives, coated abrasives, bonded abrasives, powders, aggregates, composites, or other forms. In one embodiment, the one or more abrasives include, but are not limited to, polyaramid, vinylester matrix, metal, ceramic, fiberglass, cellulose, broad carbide, aromatic polyamide, nylon, silk, rayon, acetate, modacrylic, olefin, acrylic polymer or copolymer, acrylamide polymer or copolymer, polyester, aromatic polyester, polylactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, alluvium, sand, sugar, calcite, emery, diamond, novaculite, pumice, rouge, borazon, corundum, zirconia alumina, silicon, silica, frozen hydrogen oxide ice, plant matter, animal matter, or mineral matter. In one embodiment, plant matter may include vegetable matter, nuts or nut products or pieces (e.g., almonds), grains (e.g., oatmeal), wood (e.g., wood fibers) or other stalk material, leaf matter, fruit matter (including pits or seeds or parts thereof), or other plant material.

Explosive Materials

In one embodiment, one or more frozen particle compositions include one or more explosive materials. Explosive materials are typically chemically or energetically unstable or produce a sudden expansion of the material with a change in pressure. Such a sudden expansion of the material under pressure changes is generally accompanied by the production of heat. Explosive materials are generally differentiated according to their decomposition rates. Generally, a chemical decomposition rate of an explosive material takes years, days, hours, minutes, seconds, or a fraction of a second. Certain explosive materials are relatively stable, and may maintain their explosive ability for some amount of time. Other explosive materials have relatively high rates of decomposition and detonate rapidly.

In one embodiment, frozen particle compositions include one or more explosive materials that may include, for example, at least one of a high explosive or a low explosive. In one embodiment, the one or more explosive materials include at least one of carbonate, carbon dioxide, nitroglycerine, acid, base, epoxy, acrylic polymer or copolymer, acrlyamide polymer or copolymer, urethane, hypoxyapatite, or a reactive metal. In certain instances, the one or more explosive properties are the result of activation of one or more explosive materials.

In certain instances, the one or more explosive properties are the result of inherent tendencies of the frozen particle compositions themselves. In certain instances, the one or more explosive properties relate to an external event or stimulus, such as a change in temperature or pressure. In certain instances, the one or more explosive properties relate to a change in light intensity. In certain instances, the one or more explosive properties relate to a change in the composition upon administration or contact with at least one composition, cell, tissue, or subject. In certain instances, the one or more explosive properties result from a temperature or pressure increase relating to penetration of at least one cell, tissue, or subject. In certain instances, the one or more explosive properties result from contact with water or other moisture in a cell or tissue. In certain instances, the one or more explosive properties result from contact with at least one substrate. In addition to the intensity of the one or more explosives, the one or more explosive materials may differ with regard to the volatility, density, toxicity, hygroscopicity, or brisance of a particular explosive material.

Explosive materials may contain at least one oxidizer that provides fuel for certain explosive materials. In certain instances, the oxidizer can be an oxidizing element, such as oxygen. In certain instances, the oxidizer reacts with a reactive metal; an example of such a compound includes reacting fine metal powder (e.g., aluminum or magnesium) with an oxidizer (e.g., potassium chlorate or perchlorate). Chemically pure compounds may have high decomposition rates and lead to an explosion, including but not limited to nitroglycerin, acetone peroxide, trinitrotoluene, nitrocellulose, carbon, carbon monoxide, chlorine, potassium nitrate, sulfur, nitrogen compounds (such as nitrite, nitrate, and azide), potassium chlorate and potassium nitrate, hydrogen, ammonium nitrate, phosphorous, dinitrogen tetroxide, or others. In one embodiment, one or more mixtures of organic materials and oxidizers are included. In one embodiment, one or more mixtures of reactive metals and oxidizers or oils are included.

In one embodiment, the one or more explosive materials include carbon dioxide gas. In one embodiment, carbon dioxide gas is entrapped in the frozen particle composition. One method of incorporating carbon dioxide gas into at least one frozen particle composition includes liquefying the frozen particle composition and introducing carbon dioxide gas while maintaining the mixture under pressure. (See e.g., U.S. Pat. Nos. 4,289,794; 4,289,790; 4,262,029; 5,439,698, each of which is incorporated herein by reference). The carbon dioxide may also be present as a clathrate compound.

In one embodiment, at least one gasified frozen particle is formed, for example, by contacting fluid with gas under high pressure for a sufficient time period to form a gas hydrate. This gas hydrate is then cooled to a lower temperature in order to freeze the remaining unreacted fluid and entrap the gas hydrate. As one non-limiting example, aqueous liquid and carbon dioxide are kept in contact at approximately 0° C. for a time sufficient under a pressure range including at least approximately 200 psig to approximately 600 psig, while permitting absorption in the liquid of the gas in bound form and formation of the gasified ice. This process yields approximately 25-27.5 milliliters of gas per gram of ice. (See e.g., U.S. Pat. Nos. 4,487,023; 2,975,603; 3,086,370; 3,217,503, and 4,404,807, each of which is incorporated herein by reference).

Similarly, as described in U.S. Pat. No. 2,975,603, which is incorporated herein by reference, water contacted with carbon dioxide at a pressure of approximately 400 psig, in a temperature bath of approximately 0° C., is subsequently placed at −10° C. for 24 hours to effect degasification. As described in U.S. Pat. No. 2,975,603, the resulting product yields approximately 75 volumes of carbon dioxide per gram of ice. Additionally, as described in U.S. Pat. No. 3,086,370, which is incorporated herein by reference, gasified ice products are produced in a similar manner that contain other gases, such as nitrous oxide, sulfur-containing gases, chlorine-containing gases, inert gases, or carbon monoxide.

In one embodiment, the one or more explosive materials include at least one of sodium bicarbonate, citric acid, or both. In one embodiment, the one or more explosive materials include hydrogen peroxide.

In certain instances, the at least one frozen particle composition is configured to explodes during or upon administration. In certain instances, the at least one frozen particle composition is configured to explode prior to or subsequent to administration. In certain instances, the at least one frozen particle composition explodes after a prolonged time subsequent to administration or delivery to at least one biological tissue, or other substrate. For example, in one embodiment, the one or more explosive materials are encased or associated with a polymer or other agent that may insulate one or more reactant or retard the explosive or decomposition process.

Therapeutic Agents

In one embodiment, the at least one frozen particle composition includes at least one therapeutic agent. (See, e.g., The Merck Index, 14$^{th}$ Ed. Merck & Co., Inc., Whitehouse Station, N.J. (2006), which is incorporated herein by reference). Other therapeutic agents that are approved for use in humans can be utilized as at least one therapeutic agent described herein, and can be found at the U.S. Food and Drug Administration website on the worldwide web at fda.gov, the information at which is incorporated herein by reference.

In certain instances, the one or more frozen particles themselves provide at least one therapeutic benefit. In certain instances, the one or more frozen particles act as vehicles for one or more therapeutic agents that provide at least one therapeutic benefit. In one embodiment, the one or more frozen particles including at least one therapeutic agent is inert.

In one embodiment, the at least one therapeutic agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, chemical debridement agent, immunogen, antigen, radioactive agent, apoptotic promoting factor, angiogenic factor, anti-angiogenic factor, hormone, enzymatic factor, enzyme, papain, collagenase, protease, peptidase, elastase, urea, vitamin, mineral, nutraceutical, histatin, honey, alcium alginate, antiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof. In one embodiment, the nutraceutical includes one or more of a flavonoid, antioxidant, beta-carotene, anthocyanin, alpha-linolenic acid, omega-3 fatty acids, yeast, bacteria, algae, other microorganisms, plant products, or animal products. In one embodiment, the analgesic or anesthetic includes one or more of any aminoamid or aminoester local anesthetic, ibuprofen, morphine, codeine, aspirin, acetaminophen, lidocaine/lignocaine, ropivacaine, mepivacaine, benzocaine, chloroprocaine, cocaine, cyclomethycaine, dimethocaine/larocaine, propoxycaine, procaine/novocaine, proparacaine, tetracaine/amethocaine, articaine, bupivacaine, carticaine, cinchocaine/dibucaine, etidocaine, levobupivacaine, piperocaine, prilocaine, trimecaine, saxitoxin, or tetrodotoxin.

In one embodiment, the therapeutic agent includes at least one anti-inflammatory agent, including but not limited to steroids, non-steroidal anti-inflammatory drugs, topical anti-inflammatory agents, or subcutaneously administered non-steroidal anti-inflammatory drugs (e.g. diclofenac).

In one embodiment, the analgesic includes but is not limited to one or more of paracetamol (acetaminophen), non-steroidal anti-inflammatory drugs (NSAIDs), salicylates, narcotics, or tramadol. In one embodiment, the analgesic includes but is not limited to aspirin, rofecoxib, celecoxib, morphine, codeine, oxycodone, hydrocodone, diamorphine, pethidine, buprenorphine, amitriptyline, carbamazepine, bagapentin, pregabalin, ibuprofen, naproxen, lidocaine, a psychotropic agent, orphenadrine, cyclobenzaprine, scopolamine, atropine, gabapentin, methadone, ketobemidone, or piritramide.

In one embodiment, the at least one therapeutic agent includes one or more antiseptic, including but not limited to one or more of an alcohol, a quaternary ammonium compound, boric acid, hydrogen peroxide, chlorhexidine gluconate, iodine, mercurochrome, octenidine dihydrochloride, phenol (carbolic acid) compounds, sodium chloride, or sodium hypochlorite.

In one embodiment, the antiseptic includes but is not limited to one or more of povidone-iodine, iodine, ethanol, 1-propanol, 2-propanol/isopropanol, benzalkonium chloride, cetyl trimethylammonium bromide, cetylpyridinium chloride, benzethonium chloride, chlorhexidine, octenidine dihydrochloride, or carbolic acid.

In one embodiment, the at least one therapeutic agent is an antimicrobial agent, and includes at least one of an antifungal agent, antibiotic agent, anti-bacterial, anti-parasitic agent, or anti-worm agent. In certain instances, the antimicrobial agent may occur in nature, or it can be synthetic.

In one embodiment, the at least one therapeutic agent includes one or more of a penicillin, cephalosporin, polymixin, sulfonamide, beta-lactam antibiotic, beta-lactamase inhibitor, enediynes, lincosamide antibiotic, nitroimidazole antibiotic, pleuromutilin antibiotic, polyketide antibiotic, polymyxin antibiotic, polypeptide antibiotic, antimicrobial peptides, quinolone antibiotic, rifamycin antibiotic, sulfonamide antibiotic, tetracycline antibiotic, aminoglycoside antibiotic, macrolide, tetracycline, cyclic lipopeptide, glycylcycline, or oxazolidinone. In one embodiment, the at least one therapeutic agent includes one or more of amoxicillin, tobramycin, levofloxacin, gatifloxacin, moxifloxacin, streptomycin, oxytetracycline, chloramphenicol, or ampicillin.

In one embodiment, the at least one therapeutic agent includes one or more anti-tumor agent, at least one of which may also be identified as a cytotoxic agent, or chemotherapy agent. Non-limiting examples of an anti-tumor agent for use as described herein include at least one of an alkylating agent, antimetabolite, anthracycline, plant alkaloid (such as paclitaxel), topoisomerase inhibitor, monoclonal antibody, or tyrosine kinase inhibitor. In one embodiment, the therapeutic agent includes one or more of imatinib, mechlorethamine, cyclophosphamide, chlorambucil, azathioprine, mercaptopurine, vinca alkaloid, taxane, vincristine, vinblastine, vinorelbine, vindesine, podophyllotoxin, etoposide, teniposide, amsacrine, dactinomycin, trastuzumab, cetuximab, rituximab, bevacizumab, dexamethasone, finasteride, tamoxifen, goserelin, telomerase inhibitor, dichloroacetate, aminopterin, methotrexate, pemetrexed, raltitrexed, cladribine, clofarabine, fludarabine, pentostatin, thioguanine, cytarabine, decitabine, fluorouracil/capecitabine, floxuridine, gemcitabine, enocitabine, sapacitabine, chloromethine, cyclophosphamide, ifosfamide, melphalan, bendamustine, trofosfamide, uramustine, carmustine, fotemustine, lomustine, nimustine, prednimustine, ranimustine, semustine, spretpozocin, carboplatin, cisplatin, nedaplatin, oxaliplatin, triplatin tetranitrate, satraplatin, busulfan, mannosulfan, treosulfan, procarbazine, decarbazine, temozolomide, carboquone, ThioTEPA, triazi-quone, triethylenemelamine, docetaxel, larotaxel, ortataxel, tesetaxel, vinflunine, ixabepilone, aclarubicin, daunorubicin, doxorubicin, epirubicin, idarubicin, amrubicin, pirarubicin, valrubicin, zorubicin, metoxantrone, pixantrone, actinomycin, bleomycin, mitomycin, plicamycin, hydroxyurea, camptothecin, topotecan, irinotecan, rubitecan, belotecan, altretamine, amsacrine, bexarotene, estramustine, irofulven, trabectedin, cetuximab, panitumumab, trastuzumab, rituximab, tositumomab, alemtuzumab, bevacizumab, edrecolomab, gemtuzumab, axitinib, bosutinib, cediranib, dasatinib, erlotinib, gefitinib, imatinib, lapatinib, lestaurtinib, nilotinib, semaxanib, sorafenib, sunitinib, vandetanib, alvocidib, seliciclib, aflibercept, denileukin diftitox, aminolevulnic acid, efaproxiral, porfimer sodium, talaporfin, temoporfin, verteporfin, alitretinoin, tretinoin, anagrelide, arsenic trioxide, asparaginase/pegaspergase, atrasentan, bortezomib, carmofur, celecoxib, demecolcine, elesclomol, elasamitrucin, etoglucid, lonidamine, lucanthone, masoprocol, mitobronitol, mitoguanzone, mitotane, oblimersen, omacetaxine, sitimagene ceradenovec, tegafur, testolactone, tiazofurine, tipifarnib, or vorinostat.

In one embodiment, at least one nutraceutical is included. At least one nutraceutical includes but is not limited to, one or more of an extract of plant or animal matter (e.g., an oil, aqueous, or solid extract), a vitamin, a mineral, a mixture or solution, a food supplement, a food additive, a food fortification element, or other nutraceutical. In one embodiment, at least one nutraceutical includes but is not limited to resveratrol, an antioxidant, psyllium, sulforaphane, isoflavonoid, alpha-linolenic acid, beta-carotene, anthocyanins, phytoestrogens, polyphenols, polyphenons, catechins, benzenediols, tannins, phenylpropanoids, caffeine, alcohol, or others.

In one embodiment, at least one therapeutic agent includes one or more vaccine. In one embodiment, the composition including at least one vaccine includes at least one prophylactic vaccine or therapeutic vaccine. In one embodiment, the at least one therapeutic vaccine includes at least one anti-cancer vaccine. In one embodiment, the at least one vaccine includes at least one of an anti-tumor agent, antimicrobial agent, anti-viral agent, immunogen, antigen, live microbe, dead microbe, attenuated microbe, microbe or component thereof, live virus, recombinant virus, killed virus, attenuated virus, virus component, plasmid DNA, nucleic acid, amino acid, peptide, protein, glycopeptide, proteoglycan, glycoprotein, glycolipid, sphingolipid, glycosphingolipid, cancer cell or component thereof, organic or inorganic small molecule, or toxoid.

One or more vaccine may include but not be limited to, vaccines containing killed microorganisms (such as vaccines for flu, cholera, bubonic plague, and hepatitis A), vaccines containing live, attenuated virus or other microorganisms (such as vaccines for yellow fever, measles, rubella, and mumps), live vaccine (such as vaccines for tuberculosis), toxoid (such as vaccines for tetanus, diphtheria, and crotalis atrox), subunit of inactivated or attenuated microorganisms (such as vaccines for HBV, VLP, and HPV), conjugate vaccines (such as vaccines for H influenzae type B), recombinant vector, DNA vaccination. In one embodiment, the at least one vaccine includes but is not limited to rubella, polio, measles, mumps, chickenpox, typhoid, shingles, hepatitis A, hepatitis B, diphtheria, pertussis, rotavirus, influenza, meningococcal disease, pneumonia, tetanus, rattlesnake venom, virus-like particle, or human papillomavirus, or anti-cancer vaccine.

In one embodiment, the at least one therapeutic agent includes at least one adjuvant. The at least one adjuvant may include but not be limited to one or more organic or inorganic compounds. The at least one adjuvant may include but not be limited to at least one of a liposome, virosome, lipid, phospholipid, mineral salt, single-stranded DNA, double-stranded RNA, lipopolysaccharide, molecular antigen cage, CpG motif, microbial cell wall or component thereof, squalene, oil emulsion, surfactant, saponin, isolated microbial toxin, modified microbial toxin, endogenous immunomodulator, or cytokine. In one embodiment, the at least one adjuvant and the at least one vaccine are located in at least one of the same cavities of the same frozen particle composition. In one embodiment, the at least one adjuvant and the at least one vaccine are located in different cavities of the same frozen particle composition. In one embodiment, two or more frozen particle compositions of a plurality of frozen particle compositions include one or more similar vaccines. In one embodiment, two or more frozen particle compositions of a plurality of frozen particle compositions include one or more dissimilar vaccines.

In one non-limiting example, a composition includes one or more frozen particles including paclitaxel and at least one other constituent including at least one frozen component including air, oxygen, nitrogen, carbon dioxide, hydrogen oxide, helium, neon, xenon, krypton, chlorine, bromine, methane, or argon.

In one non-limiting embodiment, a composition includes one or more frozen particles including one or more pegylated cytokines or one or more anti-tumor compounds; wherein the one or more frozen particles include nitrogen, air, oxygen, carbon dioxide, hydrogen oxide, helium, xenon, krypton, chlorine, bromine, methane, or argon.

Adhesive Agents

In one embodiment, at least one adhesive agent is included in one or more frozen particle compositions. In one embodiment, the at least one adhesive agent includes at least one monomer, prepolymer, polymer, or copolymer. In one embodiment, the at least one adhesive agent includes at least one monomer of self-polymerizing agent. In one embodiment, the at least one adhesive agent is configured to polymerize upon administration to at least one substrate. In one embodiment, the at least one adhesive agent is configured to polymerize at or above the temperature of the at least one substrate. In one embodiment, the at least one adhesive agent is configured to polymerize at or above the temperature of at least one biological tissue. In one embodiment, the at least one adhesive agent is configured to polymerize at or above the temperature of at least one subject.

In one embodiment, the at least one adhesive agent includes one or more of a cement, glue, paste, fixative, or bonding agent. In one embodiment, the at least one adhesive agent includes one or more of a solid, liquid, or gas.

In one embodiment, the at least one adhesive agent is at least one of non-toxic, biocompatible, biodegradable or bioresorbable. In one embodiment, the at least one adhesive agent resists biodegradation or bioresorption. In one embodiment, the at least one adhesive agent is not biocompatible, or may induce a response from the at least one biological tissue, or subject's body. In one non-limiting example, one or more frozen particle compositions are administered with or contain at least one therapeutic agent, such as a vaccine, and optionally, at least one adhesive agent (which may act as an adjuvant).

In one embodiment, the at least one adhesive agent is degradable or resorbable (e.g., dissolvable sutures constructed from or secured with an adhesive). See e.g., Sierra, and Saltz, "Surgical Adhesives and Sealants," Technomic Pub. Co., 1996, which is incorporated herein by reference. In one embodiment, the at least one adhesive agent stimulates cell or tissue growth, allowing for healing of a wound (e.g., burn, surgery incision, etc.) while the adhesive agent itself subsequently degrades, dissolves, or is resorbed by the at least one substrate, including at least one biological tissue or the subject's body. In one embodiment, the at least one adhesive agent stimulates or increases tissue regeneration. In one embodiment, the at least one adhesive agent suppresses or decreases scarring or keloid formation or recurrence.

In one embodiment, one or more frozen particle compositions include at least one liquid adhesive agent. For example, the freezing point of acrylic or epoxy resins is generally approximately −10° C. to −15° C., while the freezing point of hydrogen oxide water is approximately 0° C. Thus, in one embodiment, one or more frozen hydrogen oxide particle compositions include at least one liquid adhesive agent.

In one embodiment, the at least one adhesive agent includes one or more of a hemostat, such as a mechanical hemostat (including but not limited to, porcine gelatin, bovine gelatin, oxidized regenerated cellulose, or polysaccharide spheres), an active hemostat (including but not limited to, bovine thrombin, human pooled thrombin, or recombinant thrombin), a flowable hemostat (including but not limited to, bovine gelatin and human thrombin, or porcine gelatin with or without thrombin), or a hemostat and sealant (such as fibrin sealants of human pooled fibrin; human fibrin; plasma, collagen, and bovine thrombin; animal fibrin or thrombin, or others). In one embodiment, the adhesive agent includes one or more of a sealant (such as polyethylene glycol (PEG) polymers, including dual PEG or single PEG). In one embodiment, the adhesive agent includes but is not limited to albumin (such as bovine serum albumin) and glutaraldehyde. (See, for example, Spotnitz and Burks, Transfusion, pp. 1502-1516, Vol. 48, 2008; which is incorporated herein by reference.)

In one embodiment, the at least one adhesive agent includes at least one naturally-occurring substance, such as gelatin, blood plasma, albumin, collagen, fibrin, fibrinogen (including lytic fragments, for example FPA, FPB, fragments D and E), hyaluronate, hyaluronan, glycosaminoglycans, chitin, thrombin, Factor XIII, or other substances. In one embodiment, the at least one adhesive agent includes at least one artificial or synthetic substance, such as an acrylic polymer or copolymer, acrylamide polymer or copolymer, polyacrylic acid (including but not limited to zinc polycarboxylate, resin bonding, or glass ionomer cement), epoxy, urethane, gum arabic, polyester, polyhydroxyalkanoate, poly (L-lactic acid), polyglycolide, polylactic acid, polyether, polyol, polyvinylpyrrolidone, pyroxylin, polymethyacrylate-isobutene-monoisopropylmaleate, siloxane polymer, poly-lactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, polyelectrolyte, maleic polyelectrolyte, cellulose, resilin, cyanoacrylate, isocyanate, (including but not limited to 2-octyl cyanoacrylate, 2-butyl-n-cyanoacrylate, monomeric n-butyl-2-cyanoacrylate, butyl-2-cyanoacrylate, methyl 2-cyanoacrylate, or its higher homologs (ethyl, butyl, octyl, etc.), or polyisohexylcyanoacrylate), fibrin, thrombin, firbrinogen, hyaluronate, chitin, Factor XIII, Factor XII, silk, nylon, collagen, glycosaminoglycan, selectin, polyurethane, methacrylate, polysulfide, polyanhydride, polydioxanone, poly-p-dioxanone, albumin, glutaraldehyde, polyethylene glycol, hydrogel, soy or other plant based adhesives, or gelatin. In at least one embodiment, the adhesive agent includes gecko glue. In at least one embodiment, the adhesive agent includes microscopic seta configured to adhere by van der Waals forces.

In one embodiment, the at least one adhesive agent includes one or more of a globin, hemoglobin, heme group, carbohydrate, cell or cell component, silicone, hydroxyapatite, acrylic polymer or copolymer, acrylamide polymer or copolymer, hyaluronate or hyaluronic acid, carboxymethylcellulose, healon, polymer or biopolymer, gelatin-resorcinol-formaldehyde (GRF) combination, a fibrin-collagen combination, or a fibrinogen-thrombin combination. In one embodiment, the at least one adhesive agent includes one or more naturally-occurring, artificial, or synthetic polymers, including but not limited to urethane prepolymers or polymers, cyano-based polymers, polyether, polyol, polyvinylpyrrolidone, pyroxylin/nitrocellulose, polymethylacrylate-isobutene-monoisopropylmaleate, acrylate polymers or siloxane polymers (such as acrylate terpolymer, polyphenylmethylsiloxane, hexamethyldisiloxane or isooctane solvent based polymers). (For other specific examples of adhesive agents see, e.g., U.S. Pat. Nos. 4,740,534 and 7,264,823; and U.S. Patent Application Nos. 20040097990, 20070161109, and 20070031474, each of which is incorporated herein by reference). In one embodiment, the at least one adhesive agent includes a combination of more than one adhesive agents.

In one embodiment, the at least one adhesive agent includes at least one crosslinking or derivatized agent. In one embodiment, the at least one adhesive agent is configured to form a crosslink bond with at least one component of at least one substrate. In one embodiment the crosslink bond of the at least one adhesive agent is configured for modulation by one or more of a chemical agent, change in pH, change in exposure to air, vacuum, change in moisture content, change in pressure, or change in temperature. In one embodiment, the formation of a crosslink bond of the at least one adhesive agent is configured for modulation by exposure of the at least one adhesive agent to one or more of electromagnetic energy, optical energy, thermal energy, laser energy, ionizing radiation, non-ionizing radiation, or sonic energy.

In one embodiment, one or more constituent of the at least one adhesive agent includes a crosslinked constituent (such as gelatin or albumin that is cross-linked with, for example, glutaraldehyde), or a derivatized constituent (such as derivatized collagen). In one embodiment, the at least one adhesive agent includes one or more constituents that are configured to crosslink with one or more substances in the at least one biological tissue. The crosslinking bond can form upon administration of the at least one adhesive agent to the at least one biological tissue, or upon administration of at least one of a chemical agent (such as an acid, base, enzyme, epoxide, diepoxide, 1,4-butanediol diglycidyl ether, glutaraldehyde, polysaccharide, or other chemical agent), air, moisture (such as from a biological fluid), electromagnetic energy (including ultraviolet light), optical energy, thermal energy, laser energy, ionizing radiation, non-ionizing radiation, or sonic energy to the at least one adhesive agent.

In one embodiment, the at least one adhesive agent includes one or more protein glue, including but not limited to protein, peptide, or amino acid-based substances. In one embodiment, the at least one adhesive agent includes one or more naturally-occurring or synthetic component. In one embodiment, the at least one adhesive agent includes one or more naturally-occurring or synthetic polyphenolic protein from mussels, wherein the polyphenolic protein is optionally cross-linked by a catechol oxidase. In one embodiment, the at least one adhesive agent includes mussel adhesive protein. In one embodiment, the mussel adhesive protein includes lysine, hydroxylated amino acids, and dopa. In certain instances, the mussel adhesive protein includes dihydroxyphenylalanine. In one embodiment, the at least one adhesive agent includes prolamine. In one embodiment, the at least one adhesive agent includes one or more chemotactic agent, such as transforming growth factor beta (TGF-β).

In one embodiment, fibrin sealant or fibrin glue can be formed as indicated in the table herein, or from two components: one containing fibrinogen and calcium chloride solution and the other containing thrombin solution and epsilon amino caproic acid (EACA).

In one embodiment, the at least one adhesive agent includes one or more hydrogel. See, for example, U.S. Pat. No. 6,103,528, which is incorporated herein by reference. One non-limiting example of a hydrogel included in a composition as described herein includes polyethylene glycol, polylactic acid, polytrimethylene carbonate, polycarophil, carbopol, polyox, chitosan, polyvinylpyrrolidone, block polymers or block copolymers, polymethylvinyl ether-maleic anhydride, or other constituents. In certain embodiments, the hydrogel may include a constituent with a polymerizable end cap, such as an acrylate ester. In one embodiment, the at least one adhesive agent at least partially generates a wound dressing, such as a sheet, bandage, film, or other permeable, semi-permeable, or impermeable covering. In one embodiment, the at least one wound dressing at least partially includes natural, synthetic, or artificial skin or skin deposit. (See, for example, Boateng et al., J. Pharm. Sciences. vol. 97, pp. 2892-2923 (2008)).

Some specific non-limiting examples of particular adhesive agents that are included in at least one composition described herein are listed in Table II herein. (Adapted from Smith, Ch. 7, p. 574, Table 1; Ratner, et al, Biomaterials Science, Second Edition, 2004; Elsevier Acad. Press., which is incorporated herein by reference).

TABLE II

| Type of tissue | Components | Possible setting or bonding reaction |
|---|---|---|
| Cyanoacrylate | Butyl or isobutyl cyanoacrylate | Addition polymerization |
| Fibrin sealant | Fibrinogen (with or without Factor XIII) Thrombin, CaCl$_2$ | Clot formation |
| Factor XIII | | Clot formation |
| GRF glue | Gelatin, resorcinol, formaldehyde (glutaraldehyde or glyoxal can be used in addition to or instead of formaldehyde) | Condensation |
| Hydrogel | Block copolymers of PEG, polylactic acid and acrylate esters | Photoinitiated addition polymerization |
| Acrylic bone cement | Methyl methacrylate and polymethyl methacrylate | Pertoxide-amine initiated addition polymerization |

TABLE II-continued

| Type of tissue | Components | Possible setting or bonding reaction |
|---|---|---|
| Dental cements | Zinc oxide powder, phosphoric acid | Acid-base reaction, zinc complexation |
| Zinc phosphate | | Zinc complexation |
| Zinc polycarboxylate | Zinc oxide powder, aqueous polyacrylic acid | Acid-base reaction, zinc complexation |
| Glass ionomer (polyalkenoate) | Ca, Sr, Al silicate glass powder aqueous polyacrylic-itatomic acid or polyacrylic-maleic acid | Acid-base reaction, metal ion complexation |
| Resin-based | Aromatic or urethane dimethacrylate monomers, silicate or other glass fillers aqueous polyacrylic acid-itaconic acid-methacrylate comonomers | Peroxide-amine or photoinitiated polymerization and photoinitiated addition polymerization |
| Resin-modified glass ionomer | Hydroxyethyl methacrylate aromatic or urethane diamethacrylates, Ca, Sr, Al glass powder | |
| Dentin adhesive | Etchant: phosphoric acid primer: carboxylate or phosphate Monomers hydroxyethyl methacrylate/water/solvent Bonding agent: urethane or aromatic dimethacrylate monomers | Photoinitiated addition polymerization |

In one embodiment, the at least one adhesive agent is configured to convert to at least one therapeutic agent upon administration of the at least one adhesive agent. In one embodiment, the at least one adhesive agent is configured to undergo one or more of hydration, hydrolysis, hydrogenolysis, condensation, dehydration, or polymerization upon administration of the at least one adhesive agent. In one embodiment, the at least one adhesive agent includes a methacrylate. In one embodiment, the at least one adhesive agent includes at least one of poly(N,N-dimethyl-N-(ethoxycarbonylmethyl)-N-[2'-(methacryloyloxy)ethyl]-ammonium bromide) or poly(sulfobetaine methacrylate).

In one embodiment, the at least one adhesive agent is configured to form one or more of a hydrogen bond, ionic bond, covalent bond, or noncovalent bond with at least one substrate.

In certain instances, at least one adhesive agent is provided to at least one substrate, including but not limited to at least one biological tissue, in an inactive form. In certain instances, the at least one adhesive agent is configured to polymerize or activate during administration of the at least one adhesive agent to at least one substrate, or shortly thereafter.

In one embodiment, the at least one adhesive agent is compatible with moist or wet tissues. In one embodiment, the at least one adhesive agent distributes evenly over the tissue surface. In one embodiment, the at least one adhesive agent quickly forms a durable bond. In one embodiment, the bonding time of the at least one adhesive agent is controllable. In one embodiment, the bonding time of the at least one adhesive agent is controlled or regulated. In one embodiment, the at least one adhesive degrades in a relatively short period of time. In one embodiment, the at least one adhesive agent is configured to be resorbed by the tissue to which it is applied, or by the subject's body. In one embodiment, the at least one adhesive agent maintains an appropriate viscosity for the application, provides adequate working time prior to bonding or setting, develops good adhesion, modulates hemostasis, modulates wound healing, reduces fibrosis, or provides at least one antimicrobial effect. In one embodiment, the at least one composition including at least one adhesive provides a local depot for at least one therapeutic agent.

In one embodiment, the at least one adhesive agent includes an active surface (i.e. having a bioglass, calcium phosphate, or biochemically active surface that can stimulate an in vivo response). In one embodiment, the at least one adhesive agent assists in delivering one or more therapeutic agents, including but not limited to antibiotics, vaccines, growth factors (e.g., members of the Fibroblast Growth Factor, members of the Bone Morphogenic Protein family, members of the Transforming Growth Factor-beta family, or others), transcription factors, anti-inflammatory agents, pain relievers, hemostatic agents, chemotherapeutic agents (e.g., 5-fluorouracil, paclitaxel, or others), chemokines, cytokines, angiogenic or anti-angiogenic factors, enzymes, stem cells, cellular organelles, or other therapeutic agents described herein.

In one embodiment, the at least one adhesive agent is delivered as a precursor molecule that is configured to activate by an additional activation step or event. In one embodiment, two or more components are configured to combine upon administration of the at least one adhesive agent. In one embodiment, the combination of the two or more components modifies at least one property of the adhesive agent. In one embodiment, the at least one property includes one or more of initiation of adhesive bond formation, strength of adhesive bond, adhesive bonding time, bond flexibility, bond biodegradability, bond bioresorbability, bond biocompatibility, or durability of adhesive bond. In one embodiment, the at least one property includes one or more of polymerization of the adhesive agent, or crosslinking of the adhesive agent. In one embodiment, two or more frozen particle compositions are administered; wherein at least one administration parameter is different for the two or more frozen particle compositions. In one embodiment, the at least one administration parameter includes at least one of: constitution of the frozen particle composition, formulation of the frozen particle composition, size of the frozen particle compositions, shape of the frozen particle composition, angle of administration of the frozen particle composition, velocity of administration of the frozen particle composition, quantity of frozen particle compositions administered, rate of administration of more than one frozen particle composition, spatial location for administration of the frozen particle compositions, temporal location for administration of the frozen particle compositions, method of administration of the frozen particle compositions, timing of administration of the frozen particle compositions, modulation of administration of the frozen particle compositions, deposition of the frozen particle compositions, or rate of deposition of at least one agent included in the frozen particle compositions.

In one embodiment, the at least one adhesive agent maintains the approximation of tissue of at least one wound of a subject. In one embodiment, the at least one adhesive agent forms a bond that resists separation between at least two aspects of a substrate. In one embodiment, the at least one adhesive agent is administered to the at least one substrate, such as a biological tissue or structure, prior to, during, or subsequent to a surgical procedure. Specific, non-limiting examples of surgical procedures include thoracic surgery, cardiovascular surgery, vascular surgery, neurological surgery, plastic surgery or aesthetic surgery, ophthalmic surgery, skin or connective tissue surgery, or abdominal surgery.

In one embodiment, at least one frozen particle composition includes an adhesive agent which provides a means for the repair, closure, maintenance of approximately the same tissue of a wound, treatment of a wound, or joining at least one substrate to another or joining at least one aspect of a substrate to another aspect of the same or different substrate.

In one embodiment, and as described herein, compositions and methods relate to the same or different frozen particle compositions, and are administered simultaneously, sequentially, randomly, or in another order. In certain instances, the at least one composition is administered that contains at least one adhesive agent as well as one or more other agents, such as bonding agents, that include functional groups or reactive side chains.

In one non-limiting example, polymerizable dimethacrylate monomers mixed with composite formulations are administered to calcified tissue, such as bone or tooth. In another non-limiting example, acid etching or priming of the cell or tissue surface (such as a calcified surface), is achieved by administration of phosphoric acid or another acidic substance. In certain instances, the acidic substance includes functional groups, such as polycarboxylate or polyphosphate. Next, one or more agents can be administered that react with the functional groups, such as hydrophilic monomers (including but not limited to hydroxyethyl methacrylate).

In one embodiment, the at least one adhesive agent forms one or more of a hydrogen bond, ionic bond, covalent bond, or non-covalent bond upon administration to at least one substrate. In one embodiment the at least one adhesive agent includes at least one crosslinking or derivatized agent. In one embodiment, the at least one adhesive agent forms a crosslink bond with at least one component of at least one substrate to which the adhesive agent is administered. In one embodiment, the crosslink bond of the at least one adhesive agent is modulated by one or more of a chemical agent, change in pH, change in exposure to air, vacuum, change in moisture content, change in pressure, or change in temperature. In one embodiment, formation of a crosslink bond of the at least one adhesive agent is modulated by exposure of the at least one adhesive agent to one or more of electromagnetic energy, optical energy, thermal energy, laser energy, ionizing radiation, non-ionizing radiation, or sonic energy.

In one embodiment, adhesive agents can be selected for a particular use as described herein, based on factors including, but not limited to, viscosity, adhesive tenacity, kinetic rates of monomer formation, polymerization (with or without covalent cross-linking), ability to be cryoprecipitated, tensile strength, ability to restore biomechanical tissue integrity, in vivo effectiveness, or other factors. In certain instances, these or other factors can be measured and selection of the one or more particular adhesive agents can be based on those measurements. In certain instances, these or other factors can be measured by standard methods, including but not limited to, in vitro analysis, in vivo experiments (e.g., animal studies), ex vivo experiments, in planta experiments, or other methods.

In one embodiment, a method for providing at least one agent to at least one substrate comprises administering at least one frozen particle composition to at least one substrate, wherein the at least one frozen particle composition includes one or more frozen particles as described herein, and at least one agent.

In one embodiment, a method for providing at least one adhesive agent to at least one substrate comprises administering at least one frozen particle composition to at least one substrate, wherein the at least one frozen particle composition includes one or more frozen particles as described herein, and at least one adhesive agent.

In one embodiment, a method of maintaining the approximation of tissue of at least one wound of a subject comprises administering at least one frozen particle composition to at least one wound of a subject for a time sufficient to maintain the approximation of tissue of the at least one wound; wherein the at least one frozen particle composition includes one or more frozen particle compositions including at least one agent (such as an adhesive agent, biological remodeling agent, reinforcement agent, therapeutic agent, abrasive, or explosive material) as described herein.

In one embodiment, the at least one frozen particle composition includes a detectable state that varies with its adhesive state. In one embodiment, the adhesive agent includes one or more eposy adhesive, acrylic adhesive, urethane adhesive, polyurethane adhesive, silicone adhesive, cationic adhesive, anerobic adhesive, urethane acrylate, polyester acrylate, methacrylate, methyacrylate, or cyanoacrylate.

In one embodiment, the at least one adhesive agent includes at least one α-cyanoacrylate and a fluorescent compound including at least one of a bis-benzoxazolyl compound, pyrylium salt, quantum dot, or coumarin compound. In one embodiment, the at least one adhesive agent includes an α-cyanoacrylate and 2,5-bis-(5-tert-butyl-2-benzoxasolyl)-thiophene. In one embodiment, the at least one adhesive agent includes one or more of a base component, initiator component, or activator component. In one embodiment, the at least one adhesive agent further includes at least one curing component. In one embodiment, the at least one adhesive agent includes at least one photopolymerizable adhesive, photocurable adhesive, thermal curable adhesive, free radical curable adhesive, or aerobic curable adhesive. In one embodiment, the at least one adhesive agent includes one or more adhesive agent configured to polymerize upon exposure to infrared light, ultraviolet light, x-ray, visible light, or other electromagnetic radiation.

In one embodiment, the adhesive agent includes at least one dye coinitiator. In one embodiment, the at least one dye coinitiator includes at least one of a bis-benzoxazolyl compound, pyrylium salt, QTX, safranine O, fluorescein, eosin yellow, eosin Y, eosin B, ethyl eosin, eosin bluish, erythrosine B, erythrosine yellowish blend, toluidine blue, 4',5'-dibromofluorescein, Rose Bengal B, cyanine, pyronin GY, cresyl violet, brilliant green, lissamine green BN, rhodamine B, methylene blue, crystal violet, phosphine oxide, or coumarin compound.

Biological Remodeling Agents

In one embodiment, one or more frozen particle compositions include at least one biological remodeling agent. In one embodiment, the at least one biological remodeling agent includes one or more extracellular matrix components. In one embodiment, the at least one biological remodeling agent provides at least one chemical or biochemical function to the at least one biological tissue. In one embodiment, the biological remodeling agent promotes growth of at least one biological tissue. In one embodiment, the at least one biological remodeling agent promotes at least one of cell migration, cell attachment, cell retention, cell differentiation, cell proliferation, apoptosis, angiogenesis, diffusion of materials, nucleic acid expression, protein translation, protein modification, protein secretion, carbohydrate production, carbohydrate secretion, fat production, or fat secretion.

In one embodiment, the at least one biological remodeling agent promotes at least partial construction or at least partial reconstruction of at least one biological tissue. In one embodiment, the at least one biological remodeling agent includes at least one cellular or tissue scaffolding component (e.g., collagen, elastin, protein, carbohydrate, nucleic acid, organic or inorganic agent, or other component). In one embodiment, the at least one biological remodeling agent includes at least one cell (e.g., endogenous cell, exogenous cell, transgenic cell, progenitor cell, allogeneic cell, neonatal cell, embryonic cell, stem cell, differentiated cell, blood cell, chondrocyte, endothelial cell, hepatocyte, keratinocyte, myocyte, osteoblast, osteoclast, osteocyte, mesenchymal cell, fibroblast, etc.), other cells are described herein. (See, for example, Nolte et al., Cells Tissues Organs vol. 187, pp. 165-176 (2008), which is incorporated herein by reference.)

In one embodiment, the at least one biological remodeling agent provides a scaffold or matrix for growth, regrowth, restructuring, remodeling, or physically, chemically, or biologically structuring one or more cells or biological tissues. In one embodiment, the at least one biological remodeling agent provides at least one mechanical structure to the at least one biological tissue. In one embodiment, the at least one biological remodeling agent provides a load-bearing structure to at least one biological tissue.

In one embodiment, the at least one biological remodeling agent includes one or more self-organizing structures, including at least one hydrogel, nanofiber, nanoparticle, or helical structure. (See, for example, Pokroy et al, Science vol. 323, pp. 237-240 (2009); U.S. Patent Application Publication No. 20080070304, each of which is incorporated herein by reference.) In one embodiment, the at least one biological remodeling agent includes one or more self-assembling nanofibers or nanoparticles.

In one embodiment, the at least one biological remodeling agent at least partially generates a wound dressing, such as a sheet, bandage, film, or other permeable, semi-permeable, or impermeable covering. In one embodiment, the at least one wound dressing at least partially includes natural, synthetic, or artificial skin, skin substitute, or skin deposit. In one embodiment, the at least one biological remodeling agent includes at least one nanotube (such as a carbon nanotube, DNA nanotube, or other nanotube).

In one embodiment, the at least one biological remodeling agent includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, chemical debridement agent, immunogen, antigen, radioactive agent, apoptotic promoting factor, angiogenic factor, anti-angiogenic factor, hormone, enzymatic factor, enzyme, papain, collagenase, protease, peptidase, elastase, urea, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof. In one embodiment, the nutraceutical includes one or more of a flavonoid, antioxidant, beta-carotene, anthocyanin, alpha-linolenic acid, omega-3 fatty acids, yeast, bacteria, algae, other microorganisms, plant products, or animal products.

In one embodiment, the at least one biological remodeling agent is utilized in at least partially constructing or reconstructing at least a portion of one or more biological tissues or organs. In on embodiment, the at least one biological remodeling agent assists in the repair, enhancement, or replacement of at least a portion of at least one biological tissue structure or function. In one embodiment, the at least one biological remodeling agent assists in restoring, maintaining, or improving at least one tissue or organ function.

In one embodiment, at least one frozen particle composition including at least one biological remodeling agent or adhesive agent is utilized in at least partially generating at least one biological tissue de novo. In one embodiment, at least one frozen particle composition including at least one biological remodeling agent or adhesive agent is utilized in at least partially repairing at least one damaged or diseased biological tissue. In one embodiment, the at least one damaged or diseased biological tissue is located in vivo. In one embodiment, the at least one damaged or diseased biological tissue includes one or more wounds.

In one embodiment, the at least one biological remodeling agent is administered to at least one substrate, as described herein. In one embodiment, the at least one biological remodeling agent includes at least one nontoxic agent. In one embodiment, the at least one biological remodeling agent includes a biocompatible, bioresorbable, or biodegradable agent. In one embodiment, the at least one substrate to which the one or more frozen particle compositions is deposited or administered is at least one of biocompatible, bioresorbable, or biodegradable.

In one embodiment, at least one scaffold is utilized for construction, reconstruction, or remodeling of at least one biological tissue. In one embodiment, the at least one scaffold is at least partially generated by deposition or administration of one or more frozen particle compositions including at least one biological remodeling agent. In one embodiment, the at least one scaffold is at least one of biocompatible, bioresorbable, or biodegradable.

In one embodiment, a template or molding is utilized for deposition of one or more frozen particle compositions including at least one biological remodeling agent. In one embodiment, the frozen particle composition includes one or more of a biological remodeling agent, a therapeutic agent, abrasive, explosive material, adhesive agent, or other agent. In one embodiment, the template or molding is at least one of nontoxic, biocompatible, bioresorbable, or biodegradable. In one embodiment, the one or more biological remodeling agents, are deposited or administered directly onto at least one substrate that is utilized in constructing, reconstructing, or remodeling at least one biological tissue.

In one embodiment, one or more frozen particle compositions, including at least one biological remodeling agent, are delivered to at least one scaffold, including a three dimensional porous scaffold. In one embodiment, the scaffold includes means for cell attachment, means for cell proliferation, means for cell differentiation, means for cell migration, means for cell contracting, means for cell expression, means for cell matrix production, or means for cell spreading. In one embodiment, the at least one scaffold includes seeding at least one cell (e.g., a live cell) within at least one scaffold. In one embodiment, seeding at least one cell within the at least one scaffold occurs prior to, simultaneously with, or subsequent to, at least partially generating, implanting, or transplanting the at least one scaffold. In one embodiment, the at least one scaffold includes injecting at least one biological remodeling agent and at least one cell (e.g., a live cell) mixture to the at least one substrate for at least partially constructing, reconstructing, or remodeling at least one biological tissue. In one embodiment, the scaffold is at least partially generated, implanted, or transplanted and is eventually seeded with a subject's own cells, either naturally or artificially.

In one embodiment, the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxyapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, elastin, silicone, polyurethane, ceramic powder, pectin, wax, glycosaminoglycan, poly($\alpha$-hydroxyacid), selectin, glutaraldehyde, hydrophobic non-glycosylated protein, hydrogel, peptide hydrogel, or gelatin.

In one embodiment, the at least one biological remodeling agent includes one or more of Type I collagen, Type II collagen, Type III collagen, Type VII collagen, or Type X collagen. In one embodiment, the at least one biological remodeling agent includes one or more of elastin fibers or soluble elastin.

In one embodiment, the biological remodeling agent includes at least one member of the Transforming Growth Factor $\beta$ superfamily, including but not limited to bone morphogenetic/osteogenic proteins (BMPs/OPs), growth differentiation factors, activin A and B, inhibin A and B, Anti-mullerian hormone, Nodal, TGF-$\beta$ type receptors such as Activin Type I receptors, Activin Type II receptors, transducers/SMAD molecules, ligand inhibitors (e.g., Cerberus, chordin, Dan, Decorin, Follistatin, Gremlin, Lefty, LTBP1, Noggin, THBS1), co-receptors (e.g., BAMBI-Cripto), SARA, or other molecules. (See, for example, Aarabi et al., PLOS Med., vol. 4, Issue 9, pp. 1464-1470 (2007). In one embodiment, the at least one biological remodeling agent includes one or more of epidermal growth factor (EGF), platelet derived growth factor (PDGF), fibroblast growth factor (FGF), insulin-like growth factor (IGF-1), human growth hormone, granulocyte-colony stimulating factor (G-CSF), or granulocyte-macrophage colony-stimulating factor (GM-CSF). In one embodiment, one or more biological remodeling agents include at least one nucleic acid. In one embodiment, one or more biological remodeling agents include at least one RNA or DNA molecule. In one embodiment, the one or more biological remodeling agents include at least one of a protein, carbohydrate, or fat.

Some other non-limiting examples of biological remodeling agents, as well as the general but non-limiting solidification mechanism of each, are set forth in Table III below. Abbreviations include: OPF: oligo(poly(ethylene glycol) fumarate); P(CL/TMC): poly(-caprolactone-co-trimethylene carbonate); PDLLA: poly(D,L-lactide); PEG: poly(ethylene glycol); PEO: poly(ethylene oxide); PEO-PPO-PEO: polyethylene oxide-polypropylene oxide-polyethylene oxide; PhosPEG-dMA: poly(ethylene glycol)di[ethylphosphatidyl (ethylene glycol)methacrylate]; PLA(Glc-Ser): Poly(L-lactic acid-co-glycolic acid-co-L-serine); PLA-PEG: poly(lactic acid)-poly(ethylene glycol; PLAL-ASP: Poly(lactic acid-co-lysine)-poly(aspartic acid); PLGA: Poly (DL-lactic-co-glycolic acid); PLLA: poly(L-lactic acid); PLLA-PEG: poly(L-lactide-ethylene glycol); PNIPAAm: poly(N-isopropylacrylamide); P(NIPAAm-AAc): Poly(N-isopropylacrylamide-acrylic acid); PPF: poly(propylene fumarate); P(PF-co-EG): poly(propylene furmarate-co-ethylene glycol; PVA: poly(vinyl alcohol). (See, for example, Hou et al., M. Mater. Chem., vol. 14, pp. 1915-1923 (2004), which is incorporated herein by reference.)

TABLE III

| Biological Remodeling Agent | Solidification mechanism |
| --- | --- |
| Calcium phosphate | Ceramics setting |
| Chitosan | Thermal gelation |
| Methylcellulose | Thermal gelation |
| Alginate | Photo cross-linking or ionic gelation |
| Hyaluronic acid | Photo cross-linking |
| Agarose | Thermal gelation |
| Fibrin | Thermal gelation |
| Gelatin | Thermal gelation |
| Poly(aldehyde gluronate) | Chemical cross-linking |
| PEG or PEO | Photo cross-linking |
| PEO-PPO-PEO | Thermal gelation |
| PEO-PLLA-PEO | Photo cross-linking |
| PLA-g-PVA | Photo cross-linking |
| PEO-PLLA | Thermal gelation |
| PLGA-PEG | Thermal gelation |
| PEG-co-Poly($\alpha$-hydroxy acid) | Photo cross-linking |
| PVA, PLAL-ASP, P(CL/TMC), PLA(Glc-Ser), or Polyanhydrides | Photo cross-linking |
| PPF, OPF, or P(PF-co-EG) | Photo cross-linking or radical polymerization |
| PhosPEG-dMA | Photo polymerization |
| PNIPAAm-PEG, PNIPAAm-gelatin, P(NIPAAm-AAc) | Thermal gelation |
| PEG based hydrogels | Enzymatic cross-linking or Michael-type addition reaction |
| PLA-PEG-biotin | Self-assembly |

Substrates

In one embodiment, the one or more frozen particle compositions are administered or delivered to at least one substrate. In one embodiment, the at least one substrate includes at least one nontoxic, biodegradable, bioresorbable, or biocompatible substrate. In one embodiment, the at least one substrate includes one or more of a cell, tissue, organ, structure, or device. In one embodiment, the substrate includes at least a portion of which is naturally, artificially, or synthetically derived. In one embodiment, the substrate includes at least a portion of which is genetically altered. In one embodiment, the structure or device may include a prosthesis, cell matrix, tissue matrix, supplement, implement, bandage, tourniquet, wound dressing, splint, stent, patch, gauze, covering, shunt, needle, scalpel, matrix, sponge, mesh, woven fabric, knitted fabric, film, instrument, or other tool or item. (See, for example, U.S. Patent Application Publication No. 20070021816, which is incorporated herein by reference.) In one embodiment, the device includes at least one mechanical or electrical device. In one embodiment, the substrate includes at least one implantable substrate.

In one embodiment, the substrate is located in at least one of in situ, in vitro, in vivo, in utero, in planta, in silico, or ex vivo. In one embodiment, the at least one substrate is transplanted or implanted into at least one subject. In one embodiment, the at least one substrate is ingested by at least one subject. In one embodiment, the at least one substrate includes at least one biological tissue from at least one donor or recipient. In one embodiment, the at least one donor includes at least one cadaver.

In one embodiment, the substrate includes, but is not limited to, biological tissue as described herein. For example, biological tissue includes soft tissues (such as connective tissue, or other soft tissue), or hard tissues (including calcified tissues, such as bone or teeth). In one embodiment, a cell includes, but is not limited to, at least one of an autologous cell, allogenic, xenogenic, stem cell, or syngenic cell. The one or more cells may include endogenous or exogenous cells relative to a particular subject. In one embodiment, the at least one substrate includes one or more stem cells (e.g., hematopoietic stem cells, adipocyte stem cells, neuronal stem cells, embryonic stem cells, hepatic stem cells, dermal stem cells, pancreatic stem cells, stem cells related to bone, stem cells related to muscle, or others). Particular examples of cells and biological tissues are described herein at other sections.

In one embodiment, the at least one biological tissue includes but is not limited to, one or more of skin, scalp, hair, nail, nail bed, teeth, eye, ear, ovary, oviduct, tongue, tonsil, adenoid, liver, bone, pancreas, stomach, blood vessel, bone marrow, blood, lymph, heart, lung, brain, breast, kidney, bladder, urethra, ureter, gall bladder, uterus, prostate, testes, vas deferens, fallopian tubes, large intestine, small intestine, esophagus, oral cavity, nasal cavity, otic cavity, connective tissue, muscle tissue, or adipose tissue. In one embodiment, the at least one tissue includes one or more of a tendon, vein (e.g., femoral or saphenous vein), artery, or capillary. In one embodiment, the at least one biological tissue includes a mucosal surface. In one embodiment, the at least one biological tissue includes one or more of a plant part. In one embodiment, the at least one biological tissue includes one or more of a stalk, stem, leaf, root, or tendril.

In one embodiment, the treatment of at least one biological tissue includes one or more of ossicular chain reconstruction in otlogic surgery, nerve anastomosis (e.g. peripheral nerve anastomosis); cerebralspinal fluid sealing in neurological repair, vascular repair or anastomosis, ocular repair, gastrological repair, urological repair, skin closure, bronchial repair (e.g. bronchial stump leakage), alveolar repair, or dental fillings. In one embodiment, the at least one biological tissue includes fetal tissues or organs (e.g. in utero) and can include any of the tissues or organs described herein.

In one embodiment, the at least one biological tissue is located in at least one tissue or organ related to transplantation. In one embodiment, transplantation includes extraction or implantation of the at least one tissue or organ. In one embodiment, the at least one tissue or organ related to transplantation is extracted from at least one first biological source or subject and implanted into at least one second biological source or subject. In one embodiment, the at least one tissue or organ related to transplantation is cultured prior to implantation in a subject. In one embodiment, the tissue or organ related to transplantation is an artificial tissue or organ (e.g. a bladder, heart, kidney, liver, pancreas, skin, eye, lung, nerve, blood vessel, and others). In one embodiment, the tissue or organ related to transplantation involves at least two sources (i.e. multiple species, partially artificial or synthetic, multiple biological cells or tissues including stem cells). In one embodiment, the at least one tissue or organ related to transplantation includes at least one donor or recipient tissue or organ.

In one embodiment, the at least one substrate includes at least one cell mass. In one embodiment, the at least one cell mass includes at least one of a scar, pore, pit, eschar, granuloma, keloid, artheromatous plaque, abscess, pustule, scaling (e.g., psoriasis or eczema), infected tissue, hair follicle, necrotic tissue, stratum corneum, wrinkle, wound, tumor, skin structure, nevus, cyst, lesion, callus, neoplastic tissue, gangrenous tissue, or cellular deposit. In one embodiment, the at least one cell mass includes at least one benign or malignant tumor. In one embodiment, the at least one benign or malignant tumor relates to one or more of a melanoma, lymphoma, leukemia, sarcoma, blastoma, or carcinoma.

In one embodiment, the at least one cell mass is related to at least one blood clot, microorganism accumulation, blood vessel obstruction, duct obstruction, bowel obstruction, infection, gangrene, connective tissue destruction, tissue or organ damage, injury, white blood cell accumulation, or cancer.

In one embodiment, the at least one substrate includes one or more wounds. In one embodiment, the one or more wounds are located in at least one biological tissue or organ. In one embodiment, the one or more wounds are located in one or more of skin tissue, muscle tissue, eye tissue, nervous tissue, peritoneal tissue, an organ, connective tissue, neoplastic tissue, or bone tissue.

In one embodiment, the one or more wounds are located in at least one subject. The one or more wounds include but are not limited to at least one of an incision (including surgical incision such as for facial or other aesthetic construction or reconstruction, or other cranio-facial surgeries, laproscopic procedures, birthing assistance, or other surgical procedures), fracture, irritation, episiotomy, laceration, endovascular occlusion (e.g., aneurism), blood vessel anastomosis, nerve repair, abrasion, cerebral spinal fluid leak, puncture wound, penetration wound, gunshot wound, iatrogenic wound, severing, infection, ulcer, pressure sore, lesion, chemical burn (including but not limited to exposure to an irritant, plant, or synthetic chemical), dental caries, first-degree burn, second-degree burn, third-degree burn, fourth-degree burn, fifth-degree burn, or sixth-degree burn. In certain instances, the wound can be a result of a bite, such as a bite from an animal, insect, or arachnid.

In one embodiment, the at least one subject includes one or more of a vertebrate or invertebrate, insect cells, insects, bacteria, algae, plankton, or protozoa. In one embodiment, the at least one subject includes one or more of a reptile, mammal, amphibian, bird, or fish. In one embodiment, the at least one subject includes at least one human. In one embodiment, the at least one subject includes at least one of livestock, pet, zoo animal, undomesticated herd animal, wild animal, or product animal.

In one embodiment, the at least one subject includes at least one of a sheep, goat, frog, dog, cat, rat, mouse, vermin, monkey, duck, horse, cow, pig, chicken, shellfish, fish, turkey, llama, alpaca, bison, buffalo, ape, primate, ferret, wolf, fox, coyote, deer, rabbit, guinea pig, yak, chinchilla, mink, reindeer, elk, camel, fox, elk, deer, raccoon, donkey, or mule.

Detectable Materials

In one embodiment, the one or more frozen particle compositions include at least one of a polymer, biopolymer, nanoparticle, sensor, micro-syringe, circuit, or detection material. Such dectable material may allow for visualization of the one or more frozen particle compositions, the administration process, or provide other benefits (including but not limited to reinforcement, adhesive, biological remodeling, abrasive, explosive, or therapeutic benefits). In one embodiment, the nanoparticle includes one or more of a nanorod, nanobone, nanocapsule, or other particle. In one embodiment, the nanoparticle releases its payload when exposed to an energy source, including heat or light. In one embodiment, the nanoparticles have a time-release payload of, for example, one or more therapeutic agents, adhesive agents, biological remodeling agents, reinforcement agents, abrasives, explosive materials, or other agents.

In certain instances, the detection material can be located on or in the one or more frozen particle compositions, or it can be intermixed with the one or more frozen particle compositions. In certain instances, the detection material provides a "tracer" agent that allows for visualization of one or more locations of administration of the at least one composition, or the at least one frozen particle. In certain instances the detection material is located on the at least one frozen particle composition or the at least one frozen particle. In other instances, the detection material is separate from the at least one frozen particle composition or the at least one frozen particle. In certain instances, the detection material forms a mixture with the frozen particle composition or frozen particles. In certain instances, the detection material is separate from the one or more frozen particle compositions and is administered at approximately the same time, in approximately the same place, or in approximately the same manner as the one or more frozen particle compositions. In one embodiment, the detectable material is located in at least one cavity or compartment of the one or more frozen particle compositions.

In one embodiment, detection material includes a detectable label including but not limited to, a calorimetric label, a radioactive label, a light-emitting label (such as a luminescent compound, a fluorescent compound, a phosphorescent compound, or a quantum dot), a nucleic acid label, a protein label, an antibody label, a ligand label, a receptor label, a magnetic label, or other detectable label. In one embodiment, the at least one detection material includes but is not limited to, at least one electronic identification device. In one embodiment, the at least one electronic identification device includes at least one radio frequency identification device.

In one embodiment, the at least one detection material includes but is not limited to, at least one radioactive element. In one embodiment, the radioactive element includes but is not limited to, $^{32}P$, $^{35}S$, $^{13}C$, $^{131}I$, $^{191}Ir$, $^{192}Ir$, $^{193}Ir$, $^{201}Tl$, or $^{3}H$. In one embodiment, the at least one detection material includes at least one radioactive, luminescent, colorimetric or odorous substance. In one embodiment, the at least one calorimetric substance includes one or more of an inorganic, organic, biological, natural, artificial, or synthetic substance. The calorimetric or luminescent substance may include, but not be limited to a dye, pigment, or a light-emitting substance, such as a luminescent substance, a fluorescent substance, phosphorescent substance, or quantum dot. In one embodiment, the at least one colorimetric or luminescent substance is nontoxic, biocompatible, bioresorbable, or biodegradable.

Some examples of colorimetric or luminescent substances include, but are not limited to, colored agents that have an affinity for a cell or tissue, such as acid dyes (e.g., water-soluble anionic dyes), basic dyes (e.g., water-soluble cationic dyes), direct or substantive dyes (e.g., stains for nucleic acids, proteins, lipids, carbohydrates, cell populations, tissues, or organelles), mordant dyes, vat dyes, reactive dyes, disperse dyes, azo dyes, sulfur dyes, food dyes, solvent dyes, carbene dyes, or others. Some examples of chromophores that can be utilized include, but are not limited to, dyes that are based on or derivatives of acridine, anthraquinone, arymethane (e.g., diphenyl methane, triphenyl methane), —N=N azo structure, phthalocyanine, diazonium salts, —NO$_2$ nitro functional group, —N=O nitroso functional group, phthalocyanine, quinine, azin, eurhodin, safranin, indamin, indophenol, oxazin, oxazone, thiazin, thiazole, xanthene, fluorine, pyronin, fluorine, rhodamine, or others. In one embodiment, the colorimetric substance includes trypan blue.

In one embodiment, the colorimetric or luminescent substance includes one or more fluorescent tags, including but not limited to fluorescein, phycobilin, phycoerythrin, phycourobilin, chlorophyll, phycocyanin, allophycocyanin, green fluorescent protein, or others. In one embodiment, the luminescent substance includes at least one light-emitting substance, including but not limited e.g. bioluminescent substances, chemiluminescent substances, luciferin, isoluminol, luminescent minerals, etc.

In one embodiment, the at least one detection material includes but is not limited to, at least one of a diamagnetic particle, ferromagnetic particle, paramagnetic particle, super paramagnetic contrast agent, or other magnetic particle.

Some non-limiting examples of particular diamagnetic substances include wood, water, organic compounds (such as petroleum), metals (including copper, mercury, gold, bismuth), or benzoic acid.

Methods, Devices, Systems

As described herein, a device or machine (including a computer) may be utilized in various aspects relating to compositions, methods, or systems relating to one or more frozen particle compositions. Non-limiting examples of such aspects may include predicting or calculating various properties or characteristics relating to the one or more frozen particle compositions, any substrate, any subject, any administration device, or any administration protocol.

In one embodiment, a method is disclosed for making one or more frozen particle compositions, optionally including at least one agent. In one embodiment, a method is disclosed for administering or delivering one or more frozen particle compositions. One or more methods disclosed include computer-implemented methods.

In one embodiment, a method comprises administering at least one frozen particle composition including at least one agent to a substrate. In one embodiment, may provide promoting wound healing; promoting healing of skin, cartilage, or bone; filling of skin wrinkles or flaws; filling of connective tissue; treating vesico-ureteral reflux; treating urinary incontinence; fixing prostheses or materials to at least one biological tissue; or producing at least one film, gel, or membrane for use in vitro or in vivo to assist in a biological function.

In one embodiment, a method of providing at least one agent, such as a biological remodeling agent, to at least one substrate comprises administering one or more frozen particle compositions to at least one substrate, wherein the one or more frozen particle compositions include at least one biological remodeling agent as described herein. In one embodiment, a method of at least partially constructing or at least partially reconstructing at least one biological tissue or organ comprises administering one or more frozen particle compositions that include at least one agent (such as at least one of a biological remodeling agent, adhesive agent, therapeutic agent, reinforcement agent, abrasive, or explosive material) in such a manner that the at least one agent is deposited. In one embodiment, the method further includes abrading or ablating one or more surfaces of the at least one substrate prior to, during, or subsequent to the administering of the one or more frozen particle compositions. In one embodiment, the method of administering one or more frozen particle compositions is provided in such a manner as to induce at least one cellular event. In one embodiment, the at least one cellular event includes one or more of: cell migration, cell attachment, cell retention, cell differentiation, cell proliferation, apoptosis, diffusion of materials, angiogenesis, nucleic acid expression, protein translation, protein modification, carbohydrate production, carbohydrate secretion, protein secretion, fat production or fat secretion. In one embodiment, the method further includes administering at least one component including an optical, photonic, or electronic article. In one embodiment, the at least one article is configured to communicate with at least one computer system. In one embodiment, the at least one article is configured to monitor at least one characteristic of the at least one biological tissue.

In one embodiment, computer-aided tissue engineering (CATE) is utilized in the design (including tissue scaffold design), image processing, predicting, modeling, simulation, manufacturing, administration or delivery of at least one frozen particle composition, informatics (including computer-aided tissue classification and application for tissue identification and characterization at different tissue hierarchical levels), or other aspects of tissue reconstruction with one or more frozen particle compositions described. In one embodiment, computer-aided tissue engineering compares information regarding at least one of design, image processing, predicting, modeling, simulation, manufacturing, administration or delivery of at least one frozen particle composition, or informatics for at least one biological tissue with at least one dataset or database. In one embodiment, a dataset or database is generated from information regarding at least one of design, image processing, predicting, modeling, simulation, manufacturing, administration or delivery of at least one frozen particle composition, informatics, or other aspect of tissue reconstruction with one or more frozen particle compositions described.

In one embodiment, ink-jet printing is utilized for stereo-model fabrication, or for direct biological tissue construction, reconstruction, or remodeling through deposition or administration of one or more frozen particle compositions. (See, for example, Mironov, et al, Trends in Biotech. Vol. 21, No. 4; pp. 157-161 (2003), which is incorporated herein by reference.) In one embodiment, the one or more frozen particle compositions include one or more agents that fuse upon administration or deposition. (See, for example, Jakab, et al, Tissue Eng. Part A, Vol. 14, No. 3 pp. 413-421 (2008), which is incorporated herein by reference.)

In one embodiment, at least one of rapid prototyping (including but not limited to stereolithography), fused deposition modeling, three-dimensional printing, selective deposition modeling, solid free-form fabrication (SFF), selective laser sintering, laminated object manufacturing, gas foaming, solvent casting and particulate leaching, emulsification, freeze-drying, phase separation, shape deposition manufacturing, or other method is utilized with administration of one or more frozen particle compositions for tissue reconstruction. (See, for example, U.S. Patent Application Publication No. 20040075196; Barry, et al., Phil. Trans. R. Soc. A vol. 364, pp. 249-261 (2006); and U.S. Patent Application Publication No. 20080145639, each of which is incorporated herein by reference.) In one embodiment, a model is used for designing or developing the architecture of the at least one biological tissue prior to administering or depositing the one or more frozen particle compositions for at least partially constructing, at least partially reconstructing, or at least partially remodeling at least one biological tissue. In one embodiment, the one or more frozen particle compositions are administered or deposited directly onto at least one substrate for at least partially constructing, at least partially reconstructing, or at least partially remodeling at least one biological tissue. In one embodiment, the at least partial reconstruction, at least partial construction, or at least partial remodeling of at least one biological tissue includes depositing at least one agent of at least one frozen particle composition. In one embodiment, the at least partial reconstruction, at least partial construction, or at least partial remodeling of at least one biological tissue includes at least partially abrading or ablating at least one surface of at least one substrate (e.g., biological tissue) with at least one frozen particle composition.

In one embodiment, sample cells are grown ex vivo, introduced with scaffold in the appropriate environment for cell or tissue growth utilizing one or more frozen particle compositions, and the cells implanted or transplanted into at least one subject. (See, for example, Sun et al., Biotechnol. Appl. Biochem. vol. 39, pp. 29-47 (2004), which is incorporated herein by reference.)

Computer-aided tissue modeling utilized in conjunction with certain embodiments for administration of one or more frozen particle compositions includes imaging data acquisition. For example, a medical imaging modality must be capable of one or more of producing three-dimensional views of anatomy, differentiating heterogenous tissue types and displaying the vascular structure, as well as generating computational tissue models.

In one embodiment, computer-aided tissue modeling utilized in conjunction with certain embodiments for administration of one or more frozen particle compositions includes generating at least one of a two-dimensional plot or a three-dimensional model. In one embodiment, a two-dimensional plot or three-dimensional view of anatomical modeling includes one or more of geometry, morphology, volumetric representation, mechanical, deformation, kinematic modeling, contour-based modeling, surface extraction, or solid modeling. In one embodiment, anatomical modeling occurs by way of computer-assisted tomography (CAT) or computed tomography (CT) scan, positron emission tomography (PET) scan, magnetic-resonance imaging (MRI), ultrasound, electrical-impedance monitoring, x-ray, microscopy, multiphoton calcium-imaging, or other imaging technique or device. (See, for example, Girod et al, J. Cranio-Max. Surgery vol. 29, pp. 156-158 (2001), which is incorporated herein by reference.) In one embodiment, multiple three-dimensional images are assembled or integrated for modeling of the tissue or organ.

Computer-aided tissue information utilized in conjunction with administration of one or more frozen particle compositions includes one or more of cell or tissue classification, hard tissue classification, soft tissue classification, tumor diagnosis, morphometric or cytometric information, tumor cell detection, tissue properties, cell aggregation, cell or tissue growth, cell to cell interaction, or cell to tissue interaction.

In one embodiment, at least one computer system is configured to provide one or more instructions to one or more devices for deposition or administration of one or more frozen particle compositions. In one embodiment, at least one device is configured to deposit or administer one or more frozen particle compositions on any x, y, or z axis. In one embodiment, the at least one computer system provides one or more instructions for predicting, controlling, or varying the administration of one or more frozen particle compositions or deposition of at least one agent included in the one or more frozen particle compositions on any x, y, or z location. In one embodiment, the at least one computer system provides one or more instructions for temporal, spatial, or regional locations for deposition or administration of one or more frozen particle compositions. Other components of the at least one computer system or device are included in the figures as described.

Computer-aided tissue scaffold design and manufacturing utilized in conjunction with certain embodiments for administration of one or more frozen particle compositions includes one or more of tissue scaffold modeling, biomimetic design, tissue scaffold fabrication, hybrid scaffold and cells, cell pattern, printing and deposition, or blueprint and organ hierarchical modeling. For example, in one embodiment, at least one parameter for at least partially constructing, at least partially reconstructing, or at least partially remodeling at least one tissue that are considered in design and administration of one or more frozen particle compositions, includes one or more of porosity, pore size, interconnectivity, transport properties, cell-tissue formation, mechanical strength, facilitation of attachment or distribution, growth of regenerative tissue and facilitate the transport of nutrients or other factors.

In one embodiment, the one or more frozen particle compositions are administered to at least one substrate by way of biopolymer deposition layering. For example, technology related to a micronozzle-based layered manufacturing, a microsyringe-based deposition, three dimensional plotting (e.g., Bioplotter, Envision Tech., Marl, Germany), or micromolding (e.g., by vacuum-molding) are capable of being utilized with the one or more frozen particle composition deposition. (See, for example, U.S. Patent Application Publication No. 20060195179.)

In one embodiment, the reconstructed tissue manufactured by use of one or more frozen particle compositions includes at least one material that mimics natural structures or functions, or enhances natural tissue growth. For example, in one embodiment, one or more frozen particle compositions are included in "smart" tissue scaffolds including one or more of a sensor, syringe, therapeutic agent, electronic article, nanoscale device, micro-scale device, or feedback mechanism. For example, at least one biosensor, circuit, or other electronic article can be included for monitoring tissue growth, dissolution, deterioration, biochemical function, structural integrity or function, immunological reaction, or other activities or conditions; or for providing a feedback mechanism. In one embodiment, the at least one optical, photonic, or electronic article included in the at least one tissue or organ is capable of communicating with at least one computer system.

In addition, one or more agents are included in one embodiment of the tissue reconstructed with one or more frozen particle compositions. Such agents include at least one of a therapeutic agent, abrasive, explosive material, adhesive agent, reinforcement agent, biological remodeling agent, one or more cells, or other agent. In one embodiment, the reconstructed or remodeled tissue includes at least one gene-activated matrix that allows for incorporation of one or more specific genes when one or more cells are administered to the matrix, or are allowed to migrate to the matrix. In one embodiment, one or more frozen particle compositions are utilized in three-dimensional cell or organ printing.

As described herein, in one embodiment the at least one biological remodeling agent includes one or more of: scaffolding materials, cells, nutrients, growth factors, or other components for at least partially constructing at least one tissue or organ de novo. (See Sun, et al, Ibid.)

In one embodiment, a scaffold is constructed, at least in part by seeding living cells into the scaffold. As described herein, various materials are capable of being utilized as a scaffold by delivering one or more frozen particle compositions, or deposition of at least one agent included in one or more frozen particle compositions. In particular, materials including but not limited to, pastes, resins, gels, bone cements, cellulose, silicone, polyurethanes, hydrogels, chitosan, or ceramic powders can be used.

Also as described herein, one or more materials utilized for the scaffold can be used for cell seeding, delivery systems for one or more therapeutic agents, other agents, or for integrating one or more angiogenic factors, growth factors, cytokines, or other agents.

In one embodiment, a composition includes an ex vivo biological tissue or organ that is at least partially constructed or at least partially reconstructed by administering one or more frozen particle compositions. In one embodiment, the one or more frozen particle compositions include at least one of a therapeutic agent, adhesive agent, biological remodeling agent, explosive material, abrasive, or reinforcement agent.

In one embodiment, the ex vivo biological tissue or organ is at least partially constructed or at least partially reconstructed de novo by administering one or more frozen particle compositions. In one embodiment, the one or more frozen particle compositions are administered to at least one substrate. In one embodiment, the at least one substrate includes one or more of a cell, tissue, organ, structure, or device. In one embodiment, the composition further includes at least one article including an optical, photonic, or electronic article. In one embodiment, the at least one article is configured to communicate with at least one computer system. In one embodiment, the at least one article is configured to monitor at least one characteristic of the at least one biological tissue or organ. In one embodiment, the at least one characteristic of the at least one biological tissue or organ includes one or more of: tissue formation, tissue growth, cell proliferation, cell differentiation, apoptosis, dissolution, deterioration, biochemical function of at least one cell, biochemical function of at least one tissue, biochemical function of at least one organ, structural integrity, structural function, immunological reaction, or durability of the at least one biological tissue or organ. In one embodiment, the at least one characteristic of the at least one biological tissue or organ includes one or more of: tissue formation associated with at least one substrate, tissue growth associated with at least one substrate, cell proliferation associated with at least one substrate, cell differentiation associated with at least one substrate, apoptosis associated with at least one substrate, dissolution associated with at least one substrate, deterioration associated with at least one substrate, biochemical function of at least one cell or tissue associated with at least one substrate, structural integrity of at least one substrate, structural function of at least one substrate, immunological reaction to at least one substrate, or durability of at least one substrate.

In one embodiment, a composition comprises a support means for aiding in at least partially constructing or at least partially reconstructing at least one biological tissue or organ; and one or more frozen particle compositions as described herein. In one embodiment, the one or more frozen particle compositions include at least one biological remodeling agent, adhesive agent, explosive material, abrasive, reinforcement agent, or therapeutic agent. In one embodiment, the support means includes at least one substrate configured for biological tissue formation or tissue growth. In one embodiment, the support means includes one or more of a cell scaffold, a tissue scaffold, extracellular matrix, methylcellulose, agarose, cellulose, a cell, a polymer, or other substrate. In one embodiment, the support means includes at least one substrate configured for promoting one or more of: cell migration, cell attachment, cell retention, cell differentiation, cell proliferation, apoptosis, diffusion of materials, angiogenesis, nucleic acid expression, protein translation, protein modification, protein secretion, carbohydrate production, carbohydrate secretion, fat production, or fat secretion.

In one embodiment, the one or more frozen particle compositions are deposited on a pre-existing substrate scaffolding, such as a flat or honeycomb film. (See, for example, Nishikawa et al., Mat. Res. Soc. Symp. Proc. Vol. 724 pp, N11.7.1-N11.7.6 (2002).) In one embodiment, at least one agent included in one or more frozen particle compositions are deposited such that the scaffolding is formed entirely from such deposition.

In one embodiment, the one or more frozen particle compositions include one or more cells. In one embodiment, the one or more cells are deposited during administration of the one or more frozen particle compositions. In one embodiment, the one or more frozen particle compositions are administered to at least one substrate. In one embodiment, the one or more cells serve particular functions. In one embodiment, the one or more cells serve at least one function including: seeding the scaffold, populating the tissue, reducing an immune reaction, facilitating tissue function, promoting cellular or tissue formation, promoting cellular or tissue proliferation, promoting cellular or tissue differentiation, promoting cellular or tissue apoptosis, modulating diffusion of materials, or increasing tissue growth.

In one embodiment, at least one scaffold, or other substrate is at least partially generated in at least one of in vitro, in vivo, ex vivo, in utero, or in planta. In one embodiment, one or more cells are utilized for seeding at least one scaffold in at least one of in vitro, in vivo, ex vivo, in utero, or in planta. In one embodiment, the scaffold or other substrate is at least partially generated in at least one of in vitro, in vivo, ex vivo, in utero, or in planta, and subsequently is transplanted or implanted into at least one subject. In one embodiment, the subject includes the same subject in which the scaffold or other substrate was at least partially generated. In one embodiment, wherein the scaffold or other substrate is transplanted or implanted, the scaffold or other substrate is modified in vitro, in vivo, ex vivo, in utero, or in planta prior to transplantation or implantation into at least one subject. In one embodiment, the at least one scaffold or at least one remodeled or reconstructed tissue is transplanted or implanted one or more times. In at least on embodiment, at least one substrate, including at least one tissue scaffold, is at least partially generated in vivo, and subsequently relocated within the same subject. (See, for example, Ripamonti et al., J. Anat. Vol. 209, pp. 447-468 (2006), which is incorporated herein by reference.)

In one embodiment, construction, reconstruction, or remodeling of at least one biological tissue or organ includes at least one of designing a blueprint or model. In one embodiment, the blueprint or model includes a software representation containing bio-information, physical or material information, or anatomic or geometric information. In one embodiment, the blueprint or model includes a process model, including a software representation that contains the printing operation control commands, process planning, or toolpath generated for the blueprint or model and machine hardware and control system. In one embodiment, the blueprint or model includes a process machine, including at least one of a hardware representation that is capable of printing; and a tissue or organ culture system that is capable of maintaining or growing the printed living biological tissues. In one embodiment, the three dimensional organ or tissue printing with one or more frozen particle compositions includes at least one of pre-processing or developing plots or blueprints for the tissue or organ; processing or actual organ printing; or post-processing or organ conditioning and accelerated organ maturation.

In one embodiment, the blueprint or model includes a description or representation of details of organ anatomy, morphology, tissue heterogeneity, or vascular systems at different tissue or organ organizational scales. In one embodiment, deposition of at least one tissue remodeling agent includes a process planning program control system. In one embodiment, a toolpath program is included. In certain instances, the blueprint or model provides at least one description of the anatomy, geometry, internal architecture of an organ or tissue of interest (including tissue heterogeneity), individual tissue geometry and boundary distinction within the tissue or organ of interest; at least one definition of vascular networks and three dimensional topology in an organ of interest; or at least one database of information based on organ or tissue geometry, heterogeneity, and vascular network used for toolpath or other program generation of three-dimensional cell or organ printing.

In one embodiment, the blueprint or model is constructed from three dimensional organ anatomy, tomography, or geometry information provided by medical imaging data (for example, as provided for by CT, PET, MRI, ultrasound, x-ray, multiphoton calcium-imaging, or other imaging). Such images can be modified, simulated, transformed, processed (e.g., electronically processed), or modeled by a computer system, including by computer program, such as NURBS, polygonal modeling, or splines and patches modeling. (See, for example, Sun et al, Ibid.) For example, Boolean, scaling, Gaussian smoothing, homomorphic filtering, parametric estimation techniques, Monte Carlo simulations, wavelet based methods, smoothing, mirroring, gradient weighted partial differential equation smoothing (PDE), or other operations can be used to modify a CAD or other design. (See, for example, U.S. Patent Application Publication No. 20060233454, and U.S. Pat. No. 7,353,153, U.S. Pat. No. 7,212,958; each of which is incorporated herein by reference.) In one embodiment, a computer system utilized in at least partial tissue construction, reconstruction, or remodeling includes at least one software program interface to convert the CAD design or device into a heterogeneous material or assembly for formation of the tissue or organ by deposition of at least one agent included in one or more frozen particle compositions, or administration of one or more frozen particle compositions. (See, for example, U.S. Patent Application Publication No. 20060105011, which is incorporated herein by reference.)

In one embodiment, one or more adjacent areas of constructed or reconstructed tissues or organs include similar biological remodeling agents. In one embodiment, one or more adjacent areas of constructed or reconstructed tissues or organs include different biological remodeling agents. In one embodiment, one or more substrate scaffolds are utilized to at least partially construct, at least partially reconstruct, or at least partially remodel at least one tissue or at least one organ. In one embodiment, the one or more substrate scaffolds include low microporosity, for strong structural or mechanical load, while one or more adjacent areas include high microporosity as well as embedded angiogenic factors, cytokines, cells, or other agents for seeding the structural component(s).

In one embodiment, three-dimensional CAD based models of the desired tissue are capable of being modified by Boolean operations, or separated into components or elements that each are independently exportable to freeform-fabrication technologies. In one embodiment, heterogeneous blocks are assembled brick-like into a tissue or organ. In one embodiment, solid structural models are manufactured out of substrate materials including for example, quartz or Teflon®. The models are then infiltrated with vasculature, living tissue, cells, or other agents. (See, for example, Sun et al, Ibid.)

In one embodiment, a method includes accepting a first input associated with at least one characteristic of at least one biological tissue to be at least partially constructed or at least partially reconstructed; accepting a second input associated with at least one parameter of at least partially constructing or at least partially reconstructing the at least one biological tissue by administering one or more frozen particle compositions including at least one agent; and processing results of the first input and the second input. In one embodiment, the method is implemented by a computer, including a computer system.

In one embodiment, the processing results of the first input and the second input includes electronically processing results of the first input and the second input. In one embodiment, the processing results of the first input and the second input includes electronically processing results of the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, or modification of a CAD design.

In one embodiment, the at least one agent includes one or more of a therapeutic agent, adhesive agent, abrasive, reinforcement agent, explosive material, or biological remodeling agent. In one embodiment, the administering one or more frozen particle compositions includes administering the one or more frozen particle compositions to at least one substrate. In one embodiment, the at least one substrate includes one or more of a cell, tissue, organ, structure, or device.

In one embodiment, the first input includes one or more values related to the at least one characteristic of at least one biological tissue. In one embodiment, the first input includes one or more spatial addresses associated with the at least one characteristic of at least one biological tissue. In one embodiment, the first input includes one or more of x, y, or z coordinates associated with the at least one characteristic of at least one biological tissue. In one embodiment, the at least one characteristic of at least one biological tissue to be constructed or reconstructed includes one or more of: morphological feature, anatomical feature, histological feature, tissue hierarchical level, scaffold feature, vascular structure feature, heterogenous tissue feature, mechanical feature, volumetric feature, geometric feature, volumetric representation, mechanical feature, deformation, kinematic feature, surface contour feature, cytometric feature, cell aggregation, cell growth, cell-cell interaction, cell-tissue interaction, biomimetic design, cell pattern, cell deposition, organ hierarchical level, tissue microstructure, cellular microstructure, cell junction feature, tissue junction feature, cell-tissue classification, hard tissue classification, soft tissue classification, tumor diagnosis, or other feature.

In one embodiment, the first input includes one or more temporal addresses associated with the at least one characteristic of at least one biological tissue. In one embodiment, the first input includes one or more values derived from at least one image of the at least one biological tissue. In one embodiment, the at least one image includes one or more images acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, multiphoton calcium-imaging, photography, or in silico generation.

In one embodiment, the at least one characteristic of at least one biological tissue includes one or more of cellular type, cellular function, cellular size, cellular constitution, cellular architecture, cellular durability, cellular source, tissue type, tissue constitution, tissue size, tissue shape, tissue function, tissue architecture, tissue source, tissue durability, organ type, organ constitution, organ size, organ shape, organ function, organ architecture, organ source, or organ durability. In one embodiment, the at least one biological tissue is located in at least one of in situ, in vitro, in vivo, in utero, in planta, in silico, or ex vivo. In one embodiment, the at least one biological tissue is at least partially located in at least one subject.

In one embodiment, the method further comprises accepting a third input associated with at least one feature of the at least one subject. In one embodiment, the at least one feature of the at least one subject includes one or more of age, gender, genotype, phenotype, proteomic profile, or health condition.

In one embodiment, the first input includes one or more values derived from at least one image of the at least one biological tissue at least partially located in at least one subject. In one embodiment, the processing results of the first input and the second input includes determining at least one parameter of at least partially constructing or at least partially reconstructing the at least one biological tissue with one or more frozen particle compositions from one or more values derived from at least one image of the at least one biological tissue.

In one embodiment, the second input includes one or more values related to the at least one parameter of at least partially constructing or at least partially reconstructing the at least one biological tissue by administering one or more frozen particle compositions to the at least one substrate. In one embodiment, the at least one parameter of at least partially constructing or at least partially reconstructing the at least one biological tissue includes one or more of porosity of the at least one substrate, pore size of the at least one substrate, interconnectivity of the pores of the at least one substrate, transport properties of the at least one substrate, cell-tissue formation of the at least one substrate, mechanical strength of the at least one substrate, ability for attachment or distribution of the at least one agent included in the one or more frozen particle compositions to the at least one substrate, ability for attachment or distribution of one or more cells or tissues to the at least one substrate, facilitation of at least one nutrient, or tissue formation or tissue growth associated with the at least one substrate.

In one embodiment, the one or more values related to the at least one parameter of constructing or reconstructing the at least one biological tissue includes one or more predictive values. In one embodiment, the at least one parameter of at least partially constructing or at least partially reconstructing the at least one biological tissue by administering one or more frozen particle compositions includes one or more of: design of plot or model for administration of one or more frozen particle compositions, constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, method of administration of one or more frozen particle compositions, timing of administration of one or more frozen particle compositions, modulation of administration of one or more frozen particle compositions, deposition of one or more frozen particle compositions, or rate of deposition of at least one agent.

In one embodiment, the at least one parameter of at least partially constructing or at least partially reconstructing the at least one biological tissue by administering one or more frozen particle compositions includes at least one parameter relating to at least partially ablating or at least partially abrading one or more surfaces of the at least one biological tissue with the one or more frozen particle compositions. In one embodiment, the at least one parameter of at least partially constructing or at least partially reconstructing the at least one biological tissue by administering one or more frozen particle compositions includes at least one parameter relating to administering at least one of a therapeutic agent, adhesive agent, biological remodeling agent, reinforcement agent, abrasive, or explosive material with the one or more frozen particle compositions. In one embodiment, the spatial location for administration of one or more frozen particle compositions includes one or more of x, y, or z coordinates.

In one embodiment, the processing results includes comparing at least one value related to the first input associated with the at least one characteristic of at least one biological tissue to be at least partially constructed or at least partially reconstructed with at least one value related to at least one image of a target biological tissue. In one embodiment, the image of a target biological tissue includes an image of a similar biological tissue, or an image of a dissimilar biological tissue. In one embodiment, administering one or more frozen particle compositions includes depositing the at least one agent on the at least one substrate. In one embodiment, processing results includes comparing at least one value related to the second input associated with the at least one parameter of at least partially constructing or at least partially reconstructing the at least one biological tissue with at least one value related to another administration of one or more frozen particle compositions.

In one embodiment, processing results includes determining one or more differences in at least one value related to the first input and at least one value related to at least one image of the at least one biological tissue or a similar biological tissue. In one embodiment, processing results includes determining one or more differences in at least one value related to the second input associated with the at least one parameter of at least partially constructing or at least partially reconstructing the at least one biological tissue and at least one value related to another administration of one or more frozen particle compositions to the at least one substrate. In one embodiment, processing results includes generating one or more protocols for administering the one or more frozen particle compositions.

In one embodiment, processing results includes generating one or more blueprints for administering the one or more frozen particle compositions. In one embodiment, the one or more blueprints include at least one of a two-dimesional plot or a three-dimensional model. In one embodiment, the one or more blueprints include at least one representation of at least one of organ anatomy, morphology, tissue heterogeneity, scale of vascular system, geometry, internal architecture of an organ or tissue, internal or external boundary distinction of a tissue or organ, topology, or tomography.

In one embodiment, processing results includes: comparing one or more values related to the one or more characteristics of the at least one biological tissue that are determined at two or more different times to obtain one or more characteristic comparisons; comparing one or more values related to the at least one parameter of at least partially constructing or at least partially reconstructing the at least one biological tissue at two or more different times to obtain one or more parameter comparisons; comparing the one or more characteristic comparisons with the one or more parameter comparisons to obtain one or more characteristic-characteristic/parameter-parameter comparisons; and comparing the one or more characteristic-characteristic/parameter-parameter comparisons to one or more substantially similar results obtained for one or more other at least partially constructed or at least partially reconstructed biological tissues.

In one embodiment, the method further comprises displaying results of the processing. In one embodiment, displaying results of the processing includes displaying the results on one or more active displays. In one embodiment, displaying results of the processing includes displaying the results on one or more passive displays. In one embodiment, displaying results of the processing includes displaying the results of the processing in at least one of numeric format, graphical format, or audio format. In one embodiment, displaying results of the processing includes displaying a comparison of at least one biological tissue that has been at least partially constructed or at least partially reconstructed. In one embodiment, displaying results of the processing includes displaying a comparison of at least one subject with one or more other subjects. In one embodiment, displaying results of the processing includes displaying one or more differences in the comparison of at least one value related to the first input and at least one value related to at least one image of a biological tissue.

In one embodiment, displaying results of the processing includes displaying one or more differences in the comparison of at least one value related to the second input and at least one value related to another administration of one or more frozen particle compositions. In one embodiment, the method further includes transmitting one or more signals that include information related to the processing results of the first input and the second input. In one embodiment, transmitting one or more signals includes transmitting one or more signals associated with selection of one or more frozen particle compositions for administration. In one embodiment, transmitting one or more signals includes transmitting one or more signals associated with selection of one or more of a biological remodeling agent, adhesive agent, abrasive, therapeutic agent, reinforcement agent, or explosive material associated with the one or more frozen particle compositions. In one embodiment, transmitting one or more signals includes transmitting one or more signals associated with comparing the information related to the processing results of the first input and the second input.

In one embodiment, the one or more frozen particle compositions includes one or more of an adhesive agent, therapeutic agent, reinforcement agent, abrasive, explosive material, or biological remodeling agent.

In one embodiment, a method comprises accepting input associated with at least one parameter of at least partially constructing or at least partially reconstructing the at least one biological tissue by administering one or more frozen particle compositions; administering one or more frozen particle compositions including at least one agent including a biological remodeling agent, therapeutic agent, reinforcement agent, explosive material, abrasive, or adhesive agent; evaluating the at least one biological tissue for one or more indicators related to deposition of at least one agent, tissue formation, or tissue growth; and transmitting one or more signals that include information related to the accepting input and information related to the evaluating the at least one biological tissue.

In one embodiment, evaluating at least one biological tissue for one or more indicators includes evaluating at least one of an assay, image, or gross assessment of the at least one biological tissue prior to, during, or subsequent to at least one administration of the one or more frozen particle compositions. In one embodiment, the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay. In one embodiment, the image includes at least one image acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, multiphoton calcium-imaging, photography, or in silico generation.

In one embodiment, one or more indicators of tissue formation or growth include at least one of cell migration, cell attachment, cell retention, cell differentiation, cell proliferation, apoptosis, diffusion of materials, angiogenesis, nucleic acid expression, protein translation, protein modification, carbohydrate production, carbohydrate secretion, fat production, fat secretion, or protein secretion. In one embodiment, the input associated with at least one parameter of at least partially constructing or at least partially reconstructing the at least one biological tissue by administering one or more frozen particle compositions includes one or more of: constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, method of administration of one or more frozen particle compositions, timing of administration of one or more frozen particle compositions, modulation of administration of one or more frozen particle compositions, deposition of one or more frozen particle compositions, or rate of deposition of at least one agent.

In one embodiment, transmitting one or more signals includes transmitting one or more signals associated with selection of one or more frozen particle compositions for administration. In one embodiment, transmitting one or more signals includes transmitting one or more signals associated with selection of one or more of a biological remodeling agent, adhesive agent, abrasive, therapeutic agent, reinforcement agent, or explosive material associated with the one or more frozen particle compositions. In one embodiment, administering one or more frozen particle compositions includes administering the one or more frozen particle compositions to at least one substrate. In one embodiment, at least one substrate includes one or more of a cell, tissue, organ, structure, or device.

In one embodiment, the one or more frozen particle compositions includes one or more of an adhesive agent, therapeutic agent, reinforcement agent, abrasive, explosive material, or biological remodeling agent.

In one embodiment, a method comprises receiving one or more signals that include information related to accepting input associated with at least one parameter of at least partially constructing or at least partially reconstructing the at least one biological tissue by administering one or more frozen particle compositions; receiving one or more signals that include information related to evaluating the at least one biological tissue for one or more indicators of tissue formation or growth; and processing the information related to the input associated with at least one parameter of at least partially constructing or at least partially reconstructing the at least one biological tissue and the information related to the evaluating the at least one biological tissue.

In one embodiment, evaluating at least one biological tissue for one or more indicators includes evaluating at least one of an assay, image, or gross assessment of the at least one biological tissue prior to, during, or subsequent to at least one administration of one or more frozen particle compositions. In one embodiment, the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay.

In one embodiment, the image includes at least one image acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, multiphoton calcium-imaging, photography, or in silico generation. In one embodiment, one or more indicators of tissue formation or growth include at least one of: cell migration, cell attachment, cell retention, cell differentiation, cell proliferation, apoptosis, diffusion of materials, angiogenesis, nucleic acid expression, protein translation, protein modification, carbohydrate production, carbohydrate secretion, fat production, fat secretion, or protein secretion.

In one embodiment, the input associated with at least one parameter of at least partially constructing or at least partially reconstructing the at least one biological tissue includes one or more of: constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, method of administration of one or more frozen particle compositions, timing of administration of one or more frozen particle compositions, modulation of administration of one or more frozen particle compositions, deposition of one or more frozen particle compositions, or rate of deposition of at least one agent.

In one embodiment, receiving one or more signals includes receiving one or more signals associated with selection of one or more frozen particle compositions for administration. In one embodiment, receiving one or more signals includes receiving one or more signals associated with the selection of at least one of a biological remodeling agent, adhesive agent, abrasive, therapeutic agent, reinforcement agent, or explosive material associated with the one or more frozen particle compositions.

In one embodiment, administering one or more frozen particle compositions includes administering the one or more frozen particle compositions to at least one substrate. In one embodiment, the at least one substrate includes one or more of a cell, tissue, organ, structure, or device. In one embodiment, the one or more frozen particle compositions includes one or more of an adhesive agent, therapeutic agent, reinforcement agent, abrasive, explosive material, or biological remodeling agent.

In one embodiment, a method comprises comparing information regarding at least one parameter for at least partially constructing or at least partially reconstructing at least one biological tissue of a subject by administering one or more frozen particle compositions to the at least one subject and information regarding at least one clinical outcome following receipt by the at least one subject of one or more frozen particle compositions; and providing output information.

In one embodiment, the output information is based on the comparison. In one embodiment, the method further comprises determining at least one statistical correlation. In one embodiment, the method further comprises counting the occurrence of at least one clinical outcome. In one embodiment, the information regarding at least one parameter of at least partially constructing or at least partially reconstructing at least one biological tissue of a subject includes information regarding quantity of cells or tissue at least partially constructed or at least partially reconstructed. In one embodiment, the information regarding at least one parameter of at least partially constructing or at least partially reconstructing at least one biological tissue of a subject includes information regarding at least one cellular or tissue source.

In one embodiment, the information regarding at least one parameter of at least partially constructing or at least partially reconstructing at least one biological tissue of a subject includes information regarding at least one abnormal cellular or tissue source. In one embodiment, the information regarding at least one parameter of at least partially constructing or at least partially reconstructing at least one biological tissue of a subject includes information regarding at least one type of cell or tissue. In one embodiment, the one or more frozen particle compositions includes at least one agent including at least one adhesive agent, abrasive, reinforcement agent, therapeutic agent, biological remodeling agent, or explosive material.

In one embodiment, the information regarding at least one parameter of at least partially constructing or at least partially reconstructing at least one biological tissue of a subject includes information regarding at least one dimension of at least one agent deposited. In one embodiment, the information regarding at least one parameter of at least partially constructing or at least partially reconstructing at least one biological tissue of at least one subject includes information regarding at least one dimension of at least one depth, width, or breadth of cellular, tissue, or other material removal or destruction.

In one embodiment, the information regarding at least one clinical outcome following receipt by the at least one subject of one or more frozen particle compositions includes information regarding two or more subjects with one or more common attributes. In one embodiment, the one or more common attributes include one or more of genetic attributes, mental attributes, proteomic attributes, phenotypic attributes, or psychological attributes. In one embodiment, the one or more common attributes include one or more of height, weight, medical diagnosis, familial background, results on one or more medical tests, ethnic background, body mass index, age, presence or absence of at least one disease or condition, species, ethnicity, race, allergies, gender, thickness of tissue, blood vessel condition, hair or fur condition, skin condition, tissue condition, muscle condition, organ condition, nerve condition, brain condition, presence or absence of at least one biological, chemical, or therapeutic agent in the subject, pregnancy status, lactation status, genetic profile, proteomic profile, partial or whole genetic sequence, partial or whole proteomic sequence, medical condition, medical history, or blood condition.

In one embodiment, the output information includes at least one of a response signal, comparison code, comparison plot, diagnostic code, treatment code, test code, code indicative of at least one treatment received, code indicative of at least one prescribed treatment step, code indicative of at least one vaccination administered, code indicative of at least one therapeutic agent administered, code indicative of at least one diagnostic agent administered, code indicative of at least one interaction of an administered agent and at least one biological or chemical agent in the subject; a code indicative of at least one dispertion or location of at least one administered agent; code indicative of at least one detection material administered; code indicative of the depth of penetration of an administered agent, code indicative of the depth of deposition of an administered agent, or a code indicative of the condition of at least one location of an administered frozen particle composition.

In one embodiment, receipt by the at least one subject of one or more frozen particle compositions is pursuant to at least one clinical trial. In one embodiment, the method further comprises determining at least one correlation before the administration of the one or more frozen particle compositions to the at least one subject. In one embodiment, the method further comprises creating at least one inclusion criterion and at least one exclusion criterion for a clinical trial involving the one or more frozen particle compositions. In one embodiment, the method further comprises suggesting the inclusion of one or more of the at least one subject in at least one clinical trial. In one embodiment, the method further comprises suggesting the exclusion of one or more of the at least one subject in at least one clinical trial. In one embodiment, the method further comprises using one or more of the at least one correlation to predict at least one clinical outcome regarding at least one second subject.

In one embodiment, the at least one second subject has not received the one or more frozen particle compositions. In one embodiment, the method further comprises predicting at least one clinical outcome involving the at least one second subject, wherein the at least one second subject is a plurality of people; and segregating subject identifiers associated with the plurality of people in reference to the predicted at least one clinical outcome. In one embodiment, the method further comprises determining the eligibility of the at least one second subject for the at least one clinical trial.

In one embodiment, the one or more frozen particle compositions includes one or more of an adhesive agent, therapeutic agent, reinforcement agent, abrasive, explosive material, or biological remodeling agent.

In one embodiment, a method of predicting a clinical outcome of one or more frozen particle compositions treatment for at least one first subject, comprises: determining a similarity or a dissimilarity in information regarding at least one parameter for at least partially constructing or at least partially reconstructing at least one biological tissue of at least one first subject by administering one or more frozen particle compositions to the at least one first subject with information regarding at least one parameter of at least partially constructing or at least partially reconstructing at least one biological tissue of at least one second subject, wherein the at least one second subject attained a clinical outcome following receipt of one or more frozen particle compositions; and providing output information. In one embodiment, providing output information is based on the determination. In one embodiment, the information regarding at least one parameter of at least partially constructing or at least partially reconstructing at least one biological tissue of at least second subject includes information regarding quantity of cells or tissue at least partially constructed or at least partially reconstructed.

In one embodiment, the information regarding at least one parameter of at least partially constructing or at least partially reconstructing at least one biological tissue of at least one first subject includes information regarding at least one cellular or tissue source. In one embodiment, the information regarding at least one parameter of at least partially constructing or at least partially reconstructing at least one biological tissue of at least one first subject includes information regarding at least one abnormal cellular or tissue source. In one embodiment, the information regarding at least one parameter of at least partially constructing or at least partially reconstructing at least one biological tissue of at least one first subject includes information regarding at least one type of cell or tissue.

In one embodiment, the information regarding at least one parameter of at least partially constructing or at least partially reconstructing at least one biological tissue of at least one second subject includes information regarding at least one type of cell or tissue.

In one embodiment, the one or more frozen particle compositions includes at least one agent including at least one adhesive agent, abrasive, reinforcement agent, therapeutic agent, biological remodeling agent, or explosive material. In one embodiment, the information regarding at least one parameter of at least partially constructing or at least partially reconstructing at least one biological tissue of at least one first subject includes information regarding at least one dimension of at least one agent deposited. In one embodiment, the information regarding at least one parameter of at least partially constructing or at least partially reconstructing at least one biological tissue of at least one second subject includes information regarding at least one dimension of at least one agent deposited.

In one embodiment, the information regarding at least one parameter of at least partially constructing or at least partially reconstructing at least one biological tissue of at least one second subject includes information regarding at least one dimension of at least one depth, width, or breadth of cellular, tissue, or other material removal or destruction. In one embodiment, the information regarding at least one parameter of at least partially constructing or at least partially reconstructing at least one biological tissue of at least one first subject includes information regarding at least one dimension of at least one depth, width, or breadth of cellular, tissue, or other material removal or destruction. In one embodiment, the information regarding at least one clinical outcome following receipt by the at least one second subject of one or more frozen particle compositions includes information regarding two or more subjects with one or more common attributes. In one embodiment, the one or more common attributes include one or more of genetic attributes, mental attributes, proteomic attributes, phenotypic attributes, or psychological attributes.

In one embodiment, the one or more common attributes include one or more of height, weight, medical diagnosis, familial background, results on one or more medical tests, ethnic background, body mass index, age, presence or absence of at least one disease or condition, species, ethnicity, race, allergies, gender, thickness of tissue, blood vessel condition, hair or fur condition, skin condition, tissue condition, muscle condition, organ condition, nerve condition, brain condition, presence or absence of at least one biological, chemical, or therapeutic agent in the subject, pregnancy status, lactation status, genetic profile, proteomic profile, partial or whole genetic sequence, partial or whole proteomic sequence, medical condition, medical history, or blood condition.

In one embodiment, the output information includes at least one of a response signal, comparison code, comparison plot, diagnostic code, treatment code, test code, code indicative of at least one treatment received, code indicative of at least one prescribed treatment step, code indicative of at least one vaccination administered, code indicative of at least one therapeutic agent administered, code indicative of at least one diagnostic agent administered, code indicative of at least one interaction of an administered agent and at least one biological or chemical agent in the subject; a code indicative of at least one dispertion or location of at least one administered agent; code indicative of at least one detection material administered; code indicative of the depth of penetration of an administered agent, code indicative of the depth of deposition of an administered agent, or a code indicative of the condition of at least one location of an administered frozen particle composition.

In one embodiment, receipt by the at least one second subject of one or more frozen particle compositions is pursuant to at least one clinical trial. In one embodiment, the method further comprises determining at least one correlation before the administration of the one or more frozen particle compositions to the at least one first subject. In one embodiment, the method further comprises creating at least one inclusion criterion and at least one exclusion criterion for a clinical trial involving the one or more frozen particle compositions. In one embodiment, the method further comprises suggesting the inclusion of one or more of the at least one first subject in at least one clinical trial.

In one embodiment, the method further comprises suggesting the exclusion of one or more of the at least one first subject in at least one clinical trial. In one embodiment, the method further comprises using one or more of the at least one correlation to predict at least one clinical outcome regarding at least one second subject. In one embodiment, the at least one second subject has not received the one or more frozen particle compositions. In one embodiment, the method further comprises predicting at least one clinical outcome involving the at least one second subject, wherein the at least one second subject is a plurality of people; and segregating subject identifiers associated with the plurality of people in reference to the predicted at least one clinical outcome.

In one embodiment, the one or more frozen particle compositions includes one or more of an adhesive agent, therapeutic agent, reinforcement agent, abrasive, explosive material, or biological remodeling agent. In one embodiment, the at least one biological remodeling agent is included as part of a carrier that assists in synthesis or activation of the at least one biological remodeling agent.

In one embodiment, a system comprises: at least one computing device; one or more instructions that when executed on the at least one computing device cause the at least one computing device to receive a first input associated with a first possible dataset, the first possible dataset including data representative of one or more parameters for administering one or more frozen particle compositions. In one embodiment, the system further comprises one or more instructions that when executed on the at least one computing device cause the at least one computing device to compare a value associated with the first possible dataset with a second dataset including values of at least one predictive parameter for administering one or more frozen particle compositions.

In one embodiment, the system further comprises one or more instructions that when executed on the at least one computing device cause the at least one computing device to determine from the comparison at least one parameter for administering one or more frozen particle compositions. In one embodiment, the system further comprises one or more instructions that when executed on the at least one computing device cause the at least one computing device to generate at least one response based on the determination. In one embodiment, the system further comprises one or more instructions that when executed on the at least one computing device cause the at least one computing device to access the first possible dataset in response to the first input. In one embodiment, the system further comprises one or more instructions that when executed on the at least one computing device cause the at least one computing device to generate the first possible dataset in response to the first input.

In one embodiment, the system further comprises one or more instructions that when executed on the at least one computing device cause the at least one computing device to determine a graphical illustration of the first possible dataset. In one embodiment, the system further comprises one or more instructions that when executed on the at least one computing device cause the at least one computing device to determine a graphical illustration of the second possible dataset. In one embodiment, the at least one computing device includes one or more of a desktop computer, workstation computer, or computing system. In one embodiment, the at least one computing system includes one or more of a cluster of processors, a networked computer, a tablet personal computer, a laptop computer, a mobile device, a mobile telephone, or a personal digital assistant computer.

In one embodiment, a system comprises at least one computing device; one or more instructions that when executed on the at least one computing device cause the at least one computing device to receive a first input associated with a first possible dataset, the first possible dataset including data representative of one or more characteristics of at least one biological tissue or organ to be at least partially constructed or at least partially reconstructed by administering one or more frozen particle compositions.

In one embodiment, the system further comprises one or more instructions that when executed on the at least one computing device cause the at least one computing device to compare a value associated with the first possible dataset with a second dataset including values of at least one predictive characteristic of at least one biological tissue to be at least partially constructed or at least partially reconstructed by administering one or more frozen particle compositions.

In one embodiment, the system further comprises one or more instructions that when executed on the at least one computing device cause the at least one computing device to determine from the comparison at least one characteristic of the at least one biological tissue or organ to be at least partially constructed or at least partially reconstructed. In one embodiment, the system further comprises one or more instructions that when executed on the at least one computing device cause the at least one computing device to generate at least one response based on the determination. In one embodiment, the system further comprises one or more instructions that when executed on the at least one computing device cause the at least one computing device to access the first possible dataset in response to the first input. In one embodiment, the system further comprises one or more instructions that when executed on the at least one computing device cause the at least one computing device to generate the first possible dataset in response to the first input. In one embodiment, the system further comprises one or more instructions that when executed on the at least one computing device cause the at least one computing device to determine a graphical illustration of the first possible dataset. In one embodiment, the system further comprises one or more instructions that when executed on the at least one computing device cause the at least one computing device to determine a graphical illustration of the second possible dataset.

In one embodiment, the at least one computing device includes one or more of a desktop computer, workstation computer, or computing system. In one embodiment, at least one computing system includes one or more of a cluster of processors, a networked computer, a tablet personal computer, a laptop computer, a mobile device, a mobile telephone, or a personal digital assistant computer. In one embodiment, the at least one computing device is configured to communicate with at least one apparatus for selecting or generating one or more frozen particle compositions.

In one embodiment, a system comprises: a signal-bearing medium bearing one or more instructions for accepting a first input associated with at least one characteristic of at least one biological tissue to be at least partially constructed or at least partially reconstructed by administering one or more frozen particle compositions; one or more instructions for accepting a second input associated with at least one characteristic of at least one parameter of at least partially constructing or at least partially reconstructing the at least one biological tissue by administering one or more frozen particle compositions that include at least one agent; and one or more instructions for processing results of the first input and the second input. In one embodiment, the signal-bearing medium includes a computer-readable medium. In one embodiment, the signal-bearing medium includes a recordable medium. In one embodiment, the signal-bearing medium includes a communications medium.

In one embodiment, the system further comprises one or more instructions for displaying results of the processing. In one embodiment, the system further comprises one or more instructions for transmitting one or more signals that include information related to the processing results of the first input and the second input. In one embodiment, the system further comprises one or more instructions for administering one or more frozen particle compositions that include at least one agent including: biological remodeling agent, therapeutic agent, adhesive agent, abrasive, reinforcement agent, or explosive material. In one embodiment, the system further comprises one or more instructions for evaluating the at least one biological tissue for one or more indicators relating to one or more of: deposition of at least one agent, tissue formation, or tissue growth.

In one embodiment, a system comprises circuitry for accepting a first input associated with at least one characteristic of at least one biological tissue to be at least partially constructed or at least partially reconstructed by administering one or more frozen particle compositions; circuitry for accepting a second input associated with at least one characteristic of at least one parameter of at least partially constructing or at least partially reconstructing the at least one biological tissue by administering one or more frozen particle compositions that include at least one agent; and circuitry for processing results of the first input and the second input. In one embodiment, the system further comprises circuitry for displaying results of the processing. In one embodiment, the system further comprises circuitry for transmitting one or more signals that include information related to the processing results of the first input and the second input. In one embodiment, the system further comprises circuitry for administering one or more frozen particle compositions that include at least one agent including at least one biological remodeling agent, therapeutic agent, adhesive agent, abrasive, reinforcement agent, or explosive material. In one embodiment, the system further comprises circuitry for evaluating the at least one biological tissue for one or more indicators relating to one or more of deposition of at least one agent, tissue formation, or tissue growth.

In one embodiment, a computer program product comprises: a signal-bearing medium bearing one or more instructions for accepting a first input associated with at least one characteristic of at least one biological tissue to be at least partially constructed or at least partially reconstructed by administering one or more frozen particle compositions; one or more instructions for accepting a second input associated with at least one characteristic of at least one parameter of at least partially constructing or at least partially reconstructing the at least one biological tissue by administering one or more frozen particle compositions that include at least one agent; and one or more instructions for processing results of the first input and the second input. In one embodiment, the signal-bearing medium includes a computer-readable medium. In one embodiment, the signal-bearing medium includes a recordable medium. In one embodiment, the signal-bearing medium includes a communications medium. In one embodiment, the computer program product further comprises one or more instructions for displaying results of the processing. In one embodiment, the computer program product further comprises one or more instructions for transmitting one or more signals that include information related to the processing results of the first input and the second input.

In one embodiment, the computer program product further comprises one or more instructions for administering one or more frozen particle compositions that include at least one agent including: biological remodeling agent, therapeutic agent, adhesive agent, abrasive, reinforcement agent, or explosive material. In one embodiment, the computer program product further comprises one or more instructions for evaluating the at least one biological tissue for one or more indicators relating to one or more of: deposition of at least one agent, tissue formation, or tissue growth.

In one embodiment, a system comprises: a signal-bearing medium bearing one or more instructions for accepting a first input associated with at least one characteristic of at least one biological tissue to be at least partially constructed or at least partially reconstructed by administering one or more frozen particle compositions; one or more instructions for accepting a second input associated with at least one characteristic of at least one parameter of at least partially constructing or at least partially reconstructing the at least one biological tissue by administering one or more frozen particle compositions that include at least one agent; and one or more instructions for processing results of the first input and the second input. In one embodiment, the signal-bearing medium includes a computer-readable medium. In one embodiment, the signal-bearing medium includes a recordable medium. In one embodiment, the signal-bearing medium includes a communications medium. In one embodiment, the system further comprises one or more instructions for displaying results of the processing. In one embodiment, the system further comprises one or more instructions for transmitting one or more signals that include information related to the processing results of the first input and the second input.

In one embodiment, the system further comprises one or more instructions for administering one or more frozen particle compositions that include at least one agent including: biological remodeling agent, therapeutic agent, adhesive agent, abrasive, reinforcement agent, or explosive material. In one embodiment, the system further comprises one or more instructions for evaluating the at least one biological tissue for one or more indicators relating to one or more of: deposition of at least one agent, tissue formation, or tissue growth.

In one embodiment, a system comprises: at least one computer program, configured with a computer-readable medium, for use with at least one computer system and wherein the computer program includes a plurality of instructions including but not limited to: one or more instructions for accepting a first input associated with at least one characteristic of at least one biological tissue to be at least partially constructed or at least partially reconstructed by administering one or more frozen particle compositions; one or more instructions for accepting a second input associated with at least one characteristic of at least one parameter of at least partially constructing or at least partially reconstructing the at least one biological tissue by administering one or more frozen particle compositions that include at least one agent; and one or more instructions for processing results of the first input and the second input. In one embodiment, the system further comprises one or more instructions for displaying results of the processing. In one embodiment, the system further comprises one or more instructions for transmitting one or more signals that include information related to the processing results of the first input and the second input.

In one embodiment, the system further comprises one or more instructions for administering one or more frozen particle compositions that include at least one agent including: biological remodeling agent, therapeutic agent, adhesive agent, abrasive, reinforcement agent, or explosive material. In one embodiment, the system further comprises one or more instructions for evaluating the at least one biological tissue for one or more indicators relating to one or more of: deposition of at least one agent, tissue formation, or tissue growth. In one embodiment, the at least one computer system includes at least one computing device. In one embodiment, the at least one computing device is configured to communicate with at least one printing device, at least one imaging device, or at least one input device.

In one embodiment, a computer program product comprises: a signal-bearing medium bearing one or more instructions for accepting a first input associated with at least one characteristic of at least one biological tissue to be at least partially constructed or at least partially reconstructed by administering one or more frozen particle compositions; one or more instructions for accepting a second input associated with at least one characteristic of at least one parameter of at least partially constructing or at least partially reconstructing the at least one biological tissue by administering one or more frozen particle compositions including at least one agent; and one or more instructions for processing results of the first input and the second input.

In one embodiment, the signal-bearing medium includes a computer-readable medium. In one embodiment, the signal-bearing medium includes a recordable medium. In one embodiment, the signal-bearing medium includes a communications medium. In one embodiment, the computer program product further comprises one or more instructions for displaying results of the processing. In one embodiment, the computer program product further comprises one or more instructions for transmitting one or more signals that include information related to the processing results of the first input and the second input. In one embodiment, the computer program product further comprises one or more instructions for administering one or more frozen particle compositions that include at least one agent including: biological remodeling agent, therapeutic agent, adhesive agent, abrasive, reinforcement agent, or explosive material. In one embodiment, the computer program product further comprises one or more instructions for evaluating the at least one biological tissue for one or more indicators relating to one or more of: deposition of at least one agent, tissue formation, or tissue growth.

As described herein, at least one frozen particle composition or therapeutic composition described herein is useful in one or more methods, including one or more of a method for abrasion of at least one biological tissue surface of a subject by delivering at least one composition to at least one surface of at least one biological tissue of a subject in a manner sufficient to abrade the at least one surface of the at least one biological tissue; a method of delivering at least one therapeutic agent to at least one biological tissue; a method of vaccinating a subject; a method of treating a tissue related to transplantation; a method for cleaning one or more wounds; a method for debridement of tissue or cells; a method for removing material from one or more blood vessel, and others. These and other methods include utilizing one or more composition or therapeutic composition described herein.

In one embodiment, a method of providing at least one agent to at least one biological tissue of a subject comprises administering at least one frozen particle composition to at least one biological tissue, wherein the at least one frozen particle composition includes one or more frozen particles defining at least one cavity and at least one agent; and the at least one cavity containing at least one agent.

In one embodiment, a method of vaccinating a subject comprises administering to at least one biological tissue of a subject at least one frozen particle composition, wherein the at least one frozen particle composition includes one or more frozen particles defining at least one cavity; the at least one cavity containing at least one vaccine. In one embodiment, a method of vaccinating at least one substrate, such as a biological tissue, includes administering to the substrate at least one frozen particle composition, wherein the at least one frozen particle composition includes one or more frozen particles defining at least one cavity; the at least one cavity containing at least one vaccine.

In one embodiment, a method of providing at least one frozen particle composition to at least one biological tissue of a subject comprises administering at least one frozen particle composition to at least one biological tissue, wherein the at least one frozen particle composition includes one or more frozen particles including at least one cavity configured for holding at least one agent.

In one embodiment, a method for abrasion of at least one biological tissue surface of a subject includes delivering at least one composition to at least one surface of at least one biological tissue of a subject in a manner sufficient to abrade the at least one surface of the at least one biological tissue. As discussed herein, particular methods are disclosed for abrading or ablating at least one surface of at least one biological tissue.

In one particular example, skin abrasion for superficial resurfacing (e.g., microdermabrasion) can be used to treat acne, scars, hyperpigmentation, and other skin blemishes, as described herein. Microscissuining creates microchannels in the skin by eroding the outer layers of skin with sharp microscopic metal granules (Carlisle Scientific, Carlisle, Mass.), and Med Pharm Ltd (Charlbury, UK) has developed a novel dermal abrasion device (D3S) for the delivery of difficult to formulate therapeutics ranging from hydrophilic low molecular weight compounds to other biopharmaceuticals, and can be utilized in conjunction with administration of at least one composition described herein. (See e.g., Roberts, et al., Clin. Exp. Pharmacol. Physiol. vol. 24, pp. 874-9 (1997); Murthy, et al., J. Controlled Rel. vol. 93, pp. 49-57 (2003); each of which is incorporated herein by reference).

Abrading at least one surface of at least one biological tissue may entail debridement of at least one biological tissue. In certain instances, debridement may include removal or destruction of dead, damaged, or infected cells or tissues. In certain instances, debridement can be included as part of an additional course of treatment (e.g., surgery). In one embodiment, debridement may include penetrating one or more healthy cells or tissues in order to facilitate healing. In one embodiment, debridement may include penetrating one or more healthy cells or tissues near in proximity to one or more unhealthy cells or tissues of a subject.

In one embodiment, one or more of the debridement methods described herein include penetrating one or more cells or biological tissues of a subject with at least one frozen particle composition or therapeutic composition, wherein the one or more cells or tissues are chemically or physically partitioned or segregated from at least one other part of the tissue or another tissue. In one embodiment, a method for debridement of at least one biological tissue of a subject includes delivering at least one frozen particle composition or therapeutic composition to at least one biological tissue of a subject wherein the at least one biological tissue is partitioned from another biological tissue or part of another biological tissue, and at least one frozen particle composition or therapeutic composition penetrates the at last one biological tissue with or without removing any tissue. In certain instances, a therapeutic agent is included with the at least one frozen particle composition or therapeutic composition, as described herein. In certain instances, one or more reinforcement agents or one or more explosive materials can be included in the at least one frozen particle composition or therapeutic composition.

In one embodiment, a method for removing one or more materials from at least one biological tissue includes delivering or administering at least one frozen particle composition or therapeutic composition to the at least one biological tissue. In one embodiment, the at least one biological tissue includes one or more tissues described herein. In one embodiment, the one or more materials may include one or more materials described herein.

In one embodiment, a method for removing one or more materials from at least one blood vessel of at least one subject includes delivering at least one composition to at least one blood vessel of a subject in a manner sufficient to remove one or more materials.

In certain instances, a method for abrasion of at least one biological tissue or organ surface related to transplantation is included. In one embodiment, the at least one biological tissue or organ includes one or more of the biological tissues or organs described herein.

In one embodiment, delivering at least one composition to at least one surface of at least one biological tissue of a subject includes contacting the at least one surface of at least one biological tissue of a subject with the composition. In one embodiment, delivering at least one composition to at least one surface of at least one biological tissue of a subject includes contacting the at least one surface of at least one biological tissue of a subject with the one or more frozen particle compositions. In one embodiment, delivering at least one composition to at least one surface of at least one biological tissue of a subject includes rupturing one or more cells of at least one surface of at least one biological tissue of a subject with the one or more frozen particle compositions.

In one embodiment, a method described herein includes extracting or collecting material from the at least one abraded surface of at least one biological tissue. Such extraction or collection may include the use of at least one vacuum, aspirator, container, instrument, tool, device, chemical, laser, stylet, cannula, light source, scope (e.g., laprascope), needle, scalpel, shunt, stent, bag, film, filter, suction apparatus, tube, compressed gas, fluid (e.g., fluid stream or mist), magnifying apparatus, imaging device, computing device, or system.

In one embodiment, at least one of the needle, scalpel, or other tools or instruments utilized in extracting or collecting material from the at least one cell, tissue, or subject, includes one or more frozen particle compositions (e.g., frozen hydrogen oxide, or other agents as described herein). Thus, the one or more frozen particle compositions are fashioned or molded for use as microneedles or other instruments (e.g., scapels, blades, tools, etc.). In one embodiment, the one or more frozen particle compositions are administered prior to, during, or subsequent to surgery.

In one embodiment, the extracted or collected material includes at least one organic or inorganic material. In one embodiment, the material includes one or more cells from the at least one abraded surface of at least one biological tissue. In one embodiment, the at least one material includes at least part of one or more granuloma, eschar, callus, atheromatous plaque, abscess, pustule, scaling (e.g., psoriasis or eczema), infected tissue, microorganism accumulation, blood clot, blood vessel obstruction, duct obstruction, bowel obstruction, necrotic tissue, stratum corneum, hair follicle, nevus, wrinkle, keloid, biofilm, calculus, plaque, tartar, dandruff, keratin, collagen, dust, dirt, metal, glass, hair or fur, cellular secretion, microorganism, blood cell, particulate matter, or connective tissue.

As indicated herein, in one embodiment, a method for providing at least one therapeutic agent to at least one biological tissue of a subject is included. In one embodiment, the at least one therapeutic agent is delivered to at least one biological tissue prior to, during, or subsequent to surgery. In certain instances, at least one therapeutic agent includes one or more therapeutic agents described herein. In one embodiment, a method of providing at least one therapeutic agent to at least one biological tissue of a subject includes delivering at least one composition to at least one biological tissue, including one or more frozen hydrogen oxide particles including at least one therapeutic agent; wherein the at least one composition has at least one crystalline or amorphous phase.

In certain aspects, a method relates to vaccinating a subject by administering at least one composition that includes at least one vaccine. The composition can be administered singularly, or in conjunction with another treatment, such as surface abrasion therapy. In one embodiment, a method of vaccinating a subject includes administering to a subject at least one composition; wherein the at least one composition includes one or more frozen hydrogen oxide particles, and at least one vaccine; wherein the composition has at least one crystalline or amorphous phase.

In one embodiment, a method of vaccinating a subject includes administering to a subject at least one composition described herein. In an embodiment, the at least one composition includes one or more frozen particles, including at least one of air, oxygen, nitrogen, carbon dioxide, hydrogen oxide, helium, neon, xenon, krypton, chlorine, bromine, methane, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether; and at least one vaccine.

As disclosed herein for other embodiments, a method of vaccinating a subject includes administering at least one composition that includes at least one vaccine, as well as one or more abrasives, one or more reinforcement agents, or one or more explosive materials. In one embodiment, the vaccine described herein relates to a therapeutic or prophylactic vaccine, and in certain instances the vaccine relates to an anti-cancer vaccine. In one embodiment, the one or more abrasives are the same as the one or more reinforcement agents, or the one or more explosive materials. In one embodiment, the one or more abrasives are different than the one or more reinforcement agents. In one embodiment, the one or more abrasives are different than the one or more explosive materials.

In certain instances, for example with at least one vaccine composition or method relate to vaccinating wildlife animals (e.g. vaccinating raccoons for rabies, or bison for brucellosis). In certain instances, the vaccine compositions and methods described herein relate to vaccinating domesticated animals (such as cattle, horses, sheep, or goats). In certain instances, vaccine compositions and methods described herein relate to vaccinating a group of subjects, such as a population, a herd, a pride, a gaggle, a pack, flock, band, cluster, school, brood, troop, colony, or other group. In certain instances, vaccinating a group of subjects is included as a route to regulate or control infection within a group of subjects.

In one embodiment, the one or more frozen particle compositions are delivered or administered to the at least one substrate, such as at least one biological tissue, in a directed manner such that the tissue is etched, tattooed, shaped, carved, or otherwise modified. In one embodiment, the directed manner is predetermined based on information, such as from the at least one biological tissue, the subject, the at least one frozen particle composition, the context of the debridement, the health of the biological tissue, the health of the subject, or other information.

Devices

In one embodiment, one or more methods, devices, or systems described herein include making or administering one or more frozen particle compositions. In one embodiment, frozen particle compositions as described herein are made by one or more processes.

In one embodiment, at least one first fluid composition is contacted with at least one second fluid for a time and condition sufficient to form one or more frozen particle compositions as described herein.

In one embodiment, at least one agent (e.g., a reinforcement agent) is utilized to freeze with one or more components, or substances. In one embodiment, the at least one agent is a solid, and at least one substance or component is a liquid. The mixture or solution is frozen, and frozen particle compositions are generated as described herein.

In one embodiment, one or more frozen particle compositions are extruded by way of a die, or molding. In one embodiment, one or more frozen particle compositions are generated with assistance of at least one refrigerant or cryogen, including but not limited to liquid nitrogen.

In one embodiment, at least one agent (e.g., a reinforcement agent) is utilized to crystallize one or more components or substances. The crystallization is frozen, and frozen particle compositions are generated as described herein.

In one embodiment, one or more methods, devices, or systems described herein include delivering or administering one or more frozen particle compositions by high velocity impact. In one embodiment, the one or more devices that utilize high velocity impact delivery provide at least one of localized delivery, targeted delivery, sustained delivery, modulated delivery, feedback controlled delivery. In some instances, an example of a device that can be used for administering one or more of the compositions described herein includes a handheld device, such as a wand, a pen, a baton, a hose, a sprayer, a gun (e.g., a particle or pellet gun), or other handheld device. In certain instances, the device is at least part of a built-in delivery device, such as can be included in a wall, an overhead device, a corral, a gate, or a device that includes a cavity into which a subject can be placed for administration or delivery of at least one composition described herein. In certain instances, the device has robotic action. In any of these instances, the device can be remotely controlled, for example, by a human, computer system, or computer program.

In one embodiment, the device includes at least one nozzle, such as a venturi nozzle, de Laval nozzle, or virtual Laval nozzle. See, for example, U.S. Pat. Nos. 4,038,786; 4,707,951; and 5,779,523, each of which is incorporated herein by reference. In one embodiment, the device includes at least one amplifier to increase the flow or passage of the one or more frozen particle compositions through or out of the device. See, for example, U.S. Pat. No. 4,398,820, which is incorporated herein by reference. In one embodiment, the device includes at least one injector, such as an oblique injector, that allows for introduction of a fluid (e.g., a gas or liquid) to assist in moving the one or more frozen particle compositions through or out of the device. (See, for example, U.S. Pat. No. 4,555,872, which is incorporated herein by reference.)

In one embodiment, the one or more frozen particle compositions are made by freezing all or some of the particular components for the composition. Next, the frozen composition is extruded through orifices in a die and are either sliced during extrusion, ground down, or otherwise manipulated to form the frozen particle compositions described herein.

In one embodiment, administering or delivering the at least one frozen particle composition includes at least one of accelerating, ejecting, or propelling the frozen particle composition. In one embodiment, the method for administering at least one frozen particle composition includes at least one of accelerating, ejecting, or propelling the frozen particle composition toward at least one substrate. In one embodiment, the at least one frozen particle composition is accelerated, ejected, or propelled to or at a predetermined pressure or velocity for delivery of the at least one composition to a desired location on or in the at least one substrate (such as a biological tissue). In certain instances, the at least one frozen particle composition is accelerated, ejected, or propelled at a particular pressure, angle, or velocity. In certain instances, the at least one frozen particle composition is accelerated, ejected, or propelled at a predetermined pressure, angle, or velocity.

The angle, velocity or pressure determined for delivery of the at least one frozen particle composition depends on certain factors, including but not limited to, size and density of the frozen particle composition, content of the frozen particle composition, desired effect or outcome of administration of the frozen particle composition, density of the target tissue, density of surrounding tissue, type of tissue, architecture of the tissue, and other factors. In certain instances, the desired angle, velocity or pressure for accelerating, ejecting, or propelling the at least one frozen particle composition described herein will be the minimum angle, velocity or pressure needed to achieve desired penetration of the substrate (including a biological tissue) with the frozen particle composition, whether for surface abrasion, therapeutic delivery, or other goal.

In addition to the angle and velocity of accelerating, ejecting, or propelling the at least one composition, other factors affect the depth of penetration of a particular composition, including one or more characteristics of the particular composition (e.g., size, shape, or constitution of the frozen particle composition) or one or more characteristics of administration of the particular composition (e.g., the quantity of frozen particle compositions administered, distance between the delivery device and the target substrate).

The means for accelerating, ejecting, or propelling the one or more frozen particle compositions described herein are non-limiting, and may include general methods for making, formulating, and delivering the one or more frozen particle compositions. For example, the one or more frozen particle compositions may be delivered to at least one substrate (such as a biological tissue) by carrier gas under pressure, mechanical or electrical impulse assistance, centripetal or centrifugal force, or others, some of which are described herein. (See e.g., U.S. Pat. No. 4,945,050 and PCT application WO 92/01802, each of which is incorporated herein by reference). In certain instances, the one or more frozen particle compositions are made, propelled, accelerated, or ejected simultaneously. Thus, the frozen particle compositions can be made while propelled, the frozen particle compositions can be made while accelerated, the frozen particle compositions can be made while ejected, or any combination thereof.

In one embodiment, the one or more frozen particle compositions are delivered or administered by an inkjet printer-type apparatus or device, by a thermal bubble device, by ultrasound-mediated transdermal drug transport, or by other device. When a voltage is applied, an inkjet-type apparatus generates a pressure pulse by change in shape or size of a chamber containing a fluid (or solid), and the pressure pulse drives the contents from the chamber. In one particular instance, a high velocity device (such as a powderject, air guns, or slingshot type devices) is utilized for injection of particles formulated with at least one therapeutic agent, for example, for therapy or prevention of a disease or condition.

For example, a powderject system, as described by Kumar and Philip (Trop. J. Pharm. Res., vol. 6, No. 1, pp. 633-644 (2007), which is incorporated herein by reference) propels frozen drug particles into the skin by means of high-speed gas flow (such as helium) that is usually painless and causes minimal bleeding or damage to the skin. (See also e.g., Tang et al., Pharm. Res., vol. 19, pp. 1160-69 (2002), which is incorporated herein by reference). As described by Kumar and Philip, particles contained in a cassette between two polycarbonate membranes located at the end of a chamber (Trop. J. Pharm. Res., vol. 6, No. 1, pp. 633-644 (2007), which is incorporated herein by reference). As described by Kumar and Philip, the polycarbonate membranes are ruptured when a carrier gas enters the chamber under high pressure, and the rapid expansion of the gas forms a shock wave that travels down the nozzle at a speed of approximately 600-900 m/s. Kumar and Philip report drug particle velocities of up to about 800 m/s at the nozzle exit, and the momentum density of the particles within the gas flow can be optimized for desired depth of penetration upon delivery to a biological tissue. (Trop. J. Pharm. Res., vol. 6, No. 1, pp. 633-644 (2007), which is incorporated herein by reference). In the powderject system, particle velocity is controlled by nozzle geometry, membrane burst strength, and gas pressure. (See e.g., U.S. Pat. Nos. 5,630,796; and 5,699,880, which are incorporated herein by reference).

Metered-dose transdermal sprays may also be used for delivery of at least one composition as described herein. As described by Rathbone, et al., in one particular example, a topical solution containing a volatile then nonvolatile vehicle including a therapeutic agent is administered as a single-phase solution. (See Rathbone, et al., Modified Release of Drug Delivery Technology, NY, Marcel Dekker, Inc. vol. 126, pp. 471-619 (2004), which is incorporated herein by reference). A finite metered-dose application of the formulation to intact skin results in evaporation of the volatile component, leaving the remaining nonvolatile penetration enhancer or therapeutic agent to partition into the stratum corneum and creating a reservoir of the therapeutic agent(s). (See Rathbone, Ibid; and Kumar, et al., Trop. J. Pharm. Res., vol. 6, pp. 633-644 (2007), each of which is incorporated herein by reference).

In addition to these particular examples of devices that can be utilized for administration of the compositions described herein, the compositions can be administered in conjunction with other delivery devices or avenues. Likewise, the compositions described herein for abrasion of at least one biological tissue can be delivered to the at least one tissue by any means described herein. Some such means for delivery of the compositions described herein include, but are not limited to, ultrasound, iontophoresis (which involves applying an electrical potential across skin or other tissue in order to increase penetration of ionizable drugs), diffusion, electroporation, photomechanical waves (such as by producing pulses with Q-switched or mode-locked lasers to the skin or other tissue), needle-free injections, electro-osmosis, artificial vesicles, laser radiation, magnetophoresis (utilizing a diamagnetic substance for use with a magnetic field for increased penetration of the composition into the biological tissue), microscissuining, controlled heat aided delivery (which involves heating the skin prior to or during therapeutic administration), or tattoos and etchings.

In one embodiment, Rathbone et al. have described artificial vesicles that mimic cell vesicles (such as TRANSFERSOMES®, from IDEA AG, Germany) can be utilized for administration of one or more composition described herein. Artificial vesicles penetrate the skin barrier along the transcutaneous moisture gradient and causes "virtual" pores between the cells in an organ without affecting its biological properties. (See, e.g., Modified Release Drug Delivery Technology, NY, Marcel Dekker, Inc., vol. 126, pp. 471-619 (2004), which is incorporated herein by reference). In addition, liposomes, and niosomes also serve as carriers and can be utilized in administration of at least one composition described herein.

In one embodiment, the one or more frozen particle compositions are generated by spraying a jet or mist of the composition constituents into a low temperature environment (solid, liquid, gas, or any combination thereof) such that the compositions freeze and form frozen particles. In one embodiment, streams of frozen particles are extruded at low temperatures through fine ducts and into a low temperature environment. In one embodiment, the one or more frozen particles are propelled through a nozzle or other delivery apparatus. In one embodiment, the one or more frozen particles are delivered by utilizing flash boiling of a cold liquid. In one particular example, liquid nitrogen is flash boiled in order to accelerate, eject, or propel one or more frozen particles for delivery or administration to at least one cell, tissue, or subject. In one embodiment, the flash boiling is caused or enhanced by one or more laser pulses (e.g., an infrared laser pulse). In one embodiment, the one or more frozen particles are prepared, delivered, or administered by another means.

In certain instances, it is desirable to deliver the one or more frozen particle compositions to at least one cell or tissue, or administer the one or more frozen particle compositions to at least one subject. In at least one instance, the one or more frozen particle compositions include a plurality of frozen particle compositions that include two or more subsets of frozen particle compositions that are delivered or administered in sequential order. In one embodiment, the sequential order is predetermined, based on factors relating to, for example, the at least one cell or tissue, the at least one subject, or the at least one frozen particle composition or therapeutic composition. In one embodiment, the sequential order is determined during the course of delivery or administration of at least one of the one or more frozen particles or at least one frozen particle composition or therapeutic composition. In one embodiment, the sequential order is determined by a software program. In one embodiment, the sequential order of delivery is randomized.

In one embodiment, the sequential order includes one or more subsets of frozen particle compositions that vary in size, shape, weight, density, location of delivery or administration, time of delivery or administration, angle of delivery or administration, or velocity of delivery or administration. In one embodiment, one or more subsets of frozen particle compositions are delivered or administered according to a course of treatment (e.g., at least one subset of relatively small frozen particle compositions are administered first, followed by at least one subset of relatively larger frozen particle compositions; at least one subset of frozen particle compositions are administered in a relatively fast velocity, followed by at least one subset of frozen particle compositions administered by a relatively slow velocity; at least one subset of frozen particle compositions approximately shaped as spheroids are administered followed by at least one subset of frozen particle compositions approximately shaped as bullets, etc.).

In one embodiment, the at least one frozen particle composition is propelled using a pressure set at least about 1 psi, about 5 psi, about 10 psi, about 20 psi, about 30 psi, about 40 psi, about 50 psi, at least about 100 psi, at least about 200 psi, at least about 300 psi, at least about 400 psi, at least about 450 psi, at least about 500 psi, at least about 600 psi, at least about 700 psi, at least about 800 psi, at least about 900 psi, at least about 1000 psi, at least about 1100 psi, at least about 1200 psi, at least about 1300 psi, at least about 1400 psi, at least about 1500 psi, about 2000 psi, about 2500 psi, about 3000 psi, about 3500 psi, about 4000 psi, about 5000 psi, about 6000 psi, about 7000 psi, about 8000 psi, about 9000 psi, about 10000 psi, about 20000 psi, about 30000 psi, about 40000 psi, about 50000 psi, or any value therebetween.

In one embodiment, the at least one frozen particle composition is propelled to or at a predetermined velocity, predetermined rate of delivery, or predetermined angle for delivery of the at least one composition to a desired location of the at least one biological tissue. In one embodiment, the velocity, rate, or angle of administration of the one or more frozen particle compositions are variable. In one embodiment, a method of administering one or more frozen particle compositions includes varying the rate, velocity, or angle at which the frozen particle compositions are administered. In one embodiment, a method includes multiple administrations of the one or more frozen particle compositions, wherein at least two of the administrations include different velocities, rates, or angles of delivery.

In one embodiment, the at least one frozen particle composition is propelled to or at a velocity of approximately 1 m/s, approximately 5 m/s, approximately 10 m/s, approximately 20 m/s, approximately 30 m/s, approximately 40 m/s, approximately 50 m/s, approximately 60 m/s, approximately 70 m/s, approximately 80 m/s, approximately 90 m/s, approximately 100 m/s, approximately 200 m/s, approximately 300 m/s, approximately 400 m/s, approximately 500 m/s, approximately 600 m/s, approximately 700 m/s, approximately 800 m/s, approximately 900 m/s, approximately 1000 m/s, approximately 1500 m/s, approximately 2000 m/s, approximately 3000 m/s, approximately 4000 m/s, approximately 5000 m/s, or any value greater or therebetween.

In one embodiment, the at least one frozen particle composition is accelerated or ejected toward the at least one substrate (such as a biological tissue) to a velocity of approximately 1 m/s, approximately 5 m/s, approximately 10 m/s, approximately 20 m/s, approximately 30 m/s, approximately 40 m/s, approximately 50 m/s, approximately 60 m/s, approximately 70 m/s, approximately 80 m/s, approximately 90 m/s, approximately 100 m/s, approximately 200 m/s, approximately 300 m/s, approximately 400 m/s, approximately 500 m/s, approximately 600 m/s, approximately 700 m/s, approximately 800 m/s, approximately 900 m/s, approximately 1000 m/s, approximately 1500 m/s, approximately 2000 m/s, approximately 3000 m/s, approximately 4000 m/s, approximately 5000 m/s, or any value greater or therebetween.

In one embodiment, delivering at least one frozen particle composition to at least one substrate (such as a biological tissue) includes accelerating, ejecting, or propelling a plurality of frozen particle compositions toward the at least one substrate (including a biological tissue). Such a plurality of particles may include one embodiment wherein two or more frozen particle compositions of the plurality include one or more similar agents. Likewise, a plurality of frozen particle compositions may include one embodiment wherein two or more frozen particle compositions include one or more dissimilar agents. In one embodiment, the rate, velocity, or angle at which the one or more frozen particle compositions are administered is variable.

As described herein, a plurality of frozen particle compositions or frozen particles may include one or more subsets, which can be delivered or administered in an order of operations. In one embodiment, the order of operations includes delivery or administration in a pattern. In one embodiment, the order of operations includes delivery or administration in a predetermined pattern. In one embodiment, the order of operations includes delivery or administration in sequential order. In one embodiment, the order of operations includes delivery or administration at random.

For embodiments described herein, those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media can be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein can be expressed as source code and compiled or otherwise invoked as an executable instruction sequence. In some contexts, for example, C++ or other code sequences can be compiled or implemented in high-level descriptor languages (e.g., a logic-synthesizable language, a hardware description language, a hardware design simulation, and/or other such similar mode(s) of expression). For example, some or all of the logical expression can be manifested as a Verilog-type hardware description or other circuitry model before physical implementation in hardware. Those skilled in the art will recognize how to obtain, configure, and optimize suitable transmission or computational elements, material supplies, actuators, or other structures in light of these teachings.

Figure 7:
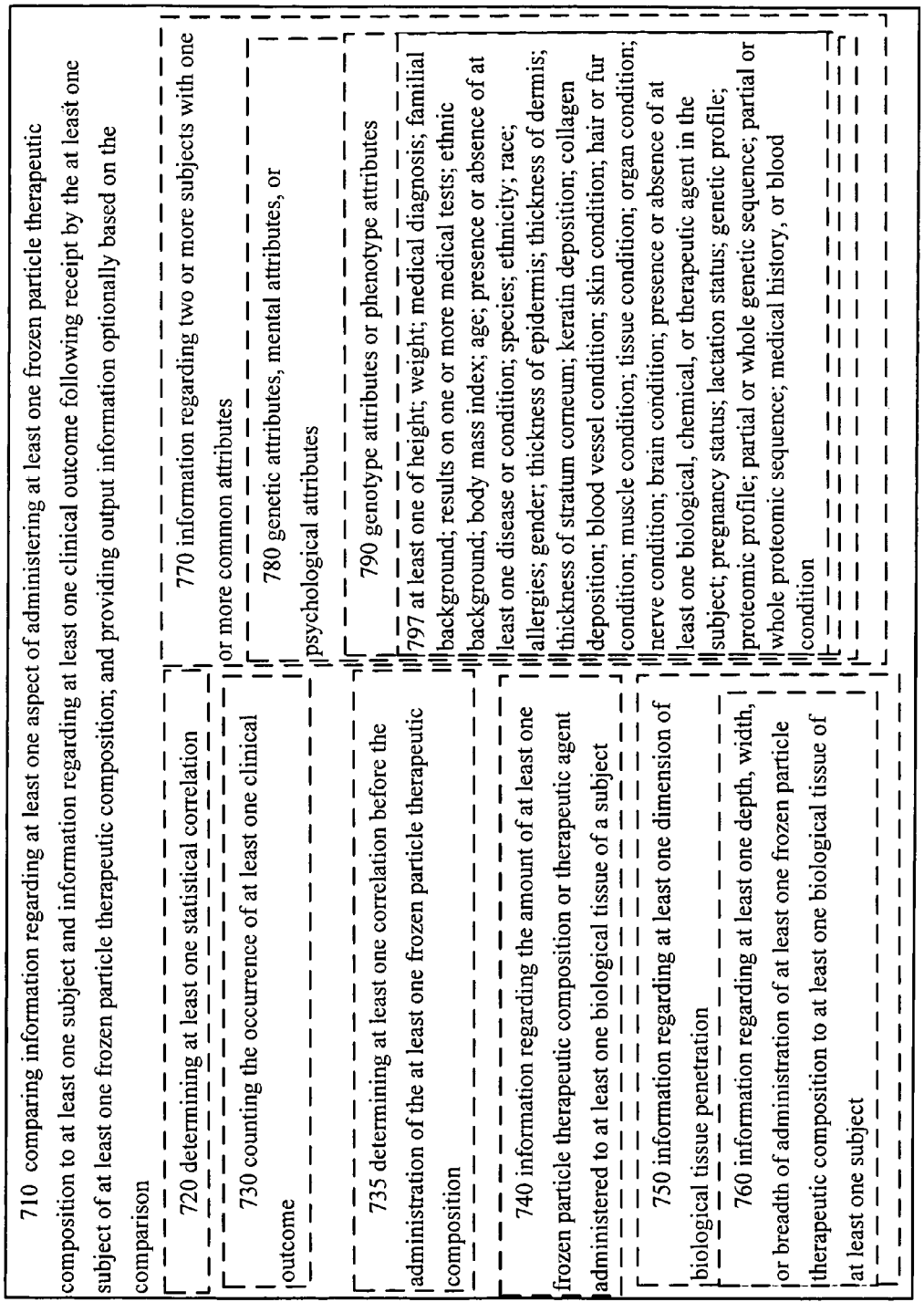
FIG. 7 illustrates a partial view of a method 700 that includes generating at least one response.
Figure 8:
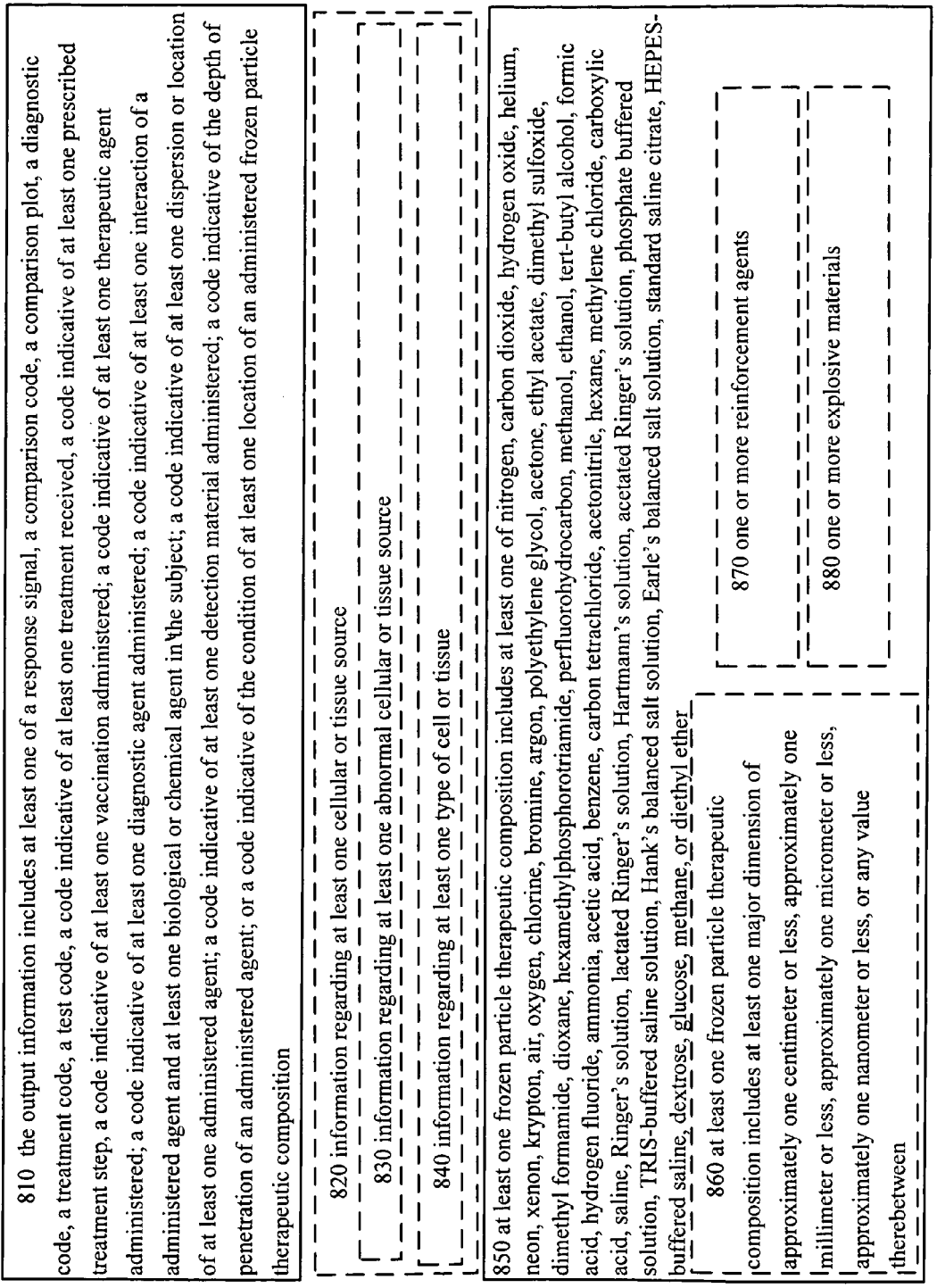
FIG. 8 illustrates a partial view of FIG. 7 in which embodiments may be implemented.

As indicated in FIGS. 7-9, one embodiment, a method 700 includes comparing 710 information regarding at least one aspect of administering at least one frozen particle composition to at least one subject and information regarding at least one clinical outcome following receipt by the at least one subject of at least one frozen particle composition; and providing output information optionally based on the comparison.

In one embodiment, the method includes determining at least one statistical correlation 720. In one embodiment, the method includes counting the occurrence of at least one clinical outcome 730. In one embodiment, the method includes determining at least one correlation before the administration of the at least one frozen particle composition 735. In one embodiment, information regarding at least one aspect of administering at least one frozen particle composition includes information regarding the amount of at least one frozen particle composition or therapeutic agent administered to at least one biological tissue of a subject 740. In one embodiment, the information regarding at least one aspect of administering or delivering at least one frozen particle composition includes information regarding at least one dimension of biological tissue penetration 750. In one embodiment, information regarding the at least one dimension of biological tissue penetration includes information regarding at least one of depth, width, or breadth of administration of at least one frozen particle composition to at least one biological tissue of at least one subject 760.

In one embodiment, the information regarding at least one aspect of administering at least one frozen particle composition includes information regarding two or more subjects with one or more common attributes 770. In one embodiment, the one or more common attributes include genetic attributes, mental attributes, or psychological attributes 780. In at least on embodiment, the one or more common attributes include genotype attributes or phenotype attributes 790.

In one embodiment, the one or more common attributes 797 include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; partial or whole proteomic sequence; medical history; lymph condition, or blood condition.

In one embodiment, the output information 810 includes at least one of a response signal, a comparison code, a comparison plot, a diagnostic code, a treatment code, a test code, a code indicative of at least one treatment received, a code indicative of at least one prescribed treatment step, a code indicative of at least one vaccination delivered; a code indicative of at least one therapeutic agent delivered; a code indicative of at least one diagnostic agent delivered; a code indicative of at least one interaction of a delivered agent and at least one biological or chemical agent in the subject; a code indicative of at least one dispersion or location of at least one delivered agent; a code indicative of at least one detection material delivered; a code indicative of the depth of penetration of a delivered agent; or a code indicative of the condition of at least one location of an administered or delivered frozen particle composition. In one embodiment, the at least one aspect of cellular or tissue abrasion or ablation includes information regarding at least one cellular or tissue source 820. In one embodiment, the information regarding at least one tissue source includes information regarding at least one abnormal cellular or tissue source 830. In one embodiment, the information regarding at least one cellular or tissue source includes information regarding at least one type of cell or tissue 840. In one embodiment, the cellular or tissue source includes at least one cell or biological tissue described herein.

In one embodiment, the at least one frozen particle composition or therapeutic composition includes at least one of nitrogen, carbon dioxide, hydrogen oxide, helium, neon, xenon, krypton, chlorine, bromine, methane, oxygen, air, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 850.

In one embodiment, the at least one frozen particle composition or therapeutic composition includes at least one major dimension of approximately one decimeter or less, or approximately one centimeter or less, approximately one millimeter or less, approximately one micrometer or less, approximately one nanometer or less, or any value therebetween 860.

In one embodiment, the at least one frozen particle composition or therapeutic composition includes one or more reinforcement agents 870. In one embodiment, the at least one frozen particle composition or therapeutic composition includes one or more explosive materials 880. In one embodiment, the receipt by the at least one subject of at least one frozen particle composition or therapeutic composition is pursuant to at least one clinical trial 900.

In one embodiment, the method includes creating at least one inclusion criterion and at least one exclusion criterion for a clinical trial involving the at least one frozen particle composition or therapeutic composition 910. In one embodiment, the method further comprises suggesting the inclusion of one or more of the at least one subject in at least one clinical trial 920. In one embodiment, the method further comprises suggesting the exclusion of one or more of the at least one subject in at least one clinical trial 930. In certain instances, multiple subjects from multiple clinical trials are included. In one embodiment, the method further includes using one or more of the at least one comparison to predict at least one clinical outcome regarding at least one second subject 940. In one embodiment, the at least one second subject has not received the at least one frozen particle composition or therapeutic composition 950. In one embodiment, the at least one second subject is a plurality of people; and the method further comprises segregating subject identifiers associated with the plurality of people in reference to the predicted at least one clinical outcome 960. In one embodiment, the at least one second subject is a plurality of people; and the method further comprises determining the eligibility of the at least one second subject for the at least one clinical trial 970.

Figure 11:
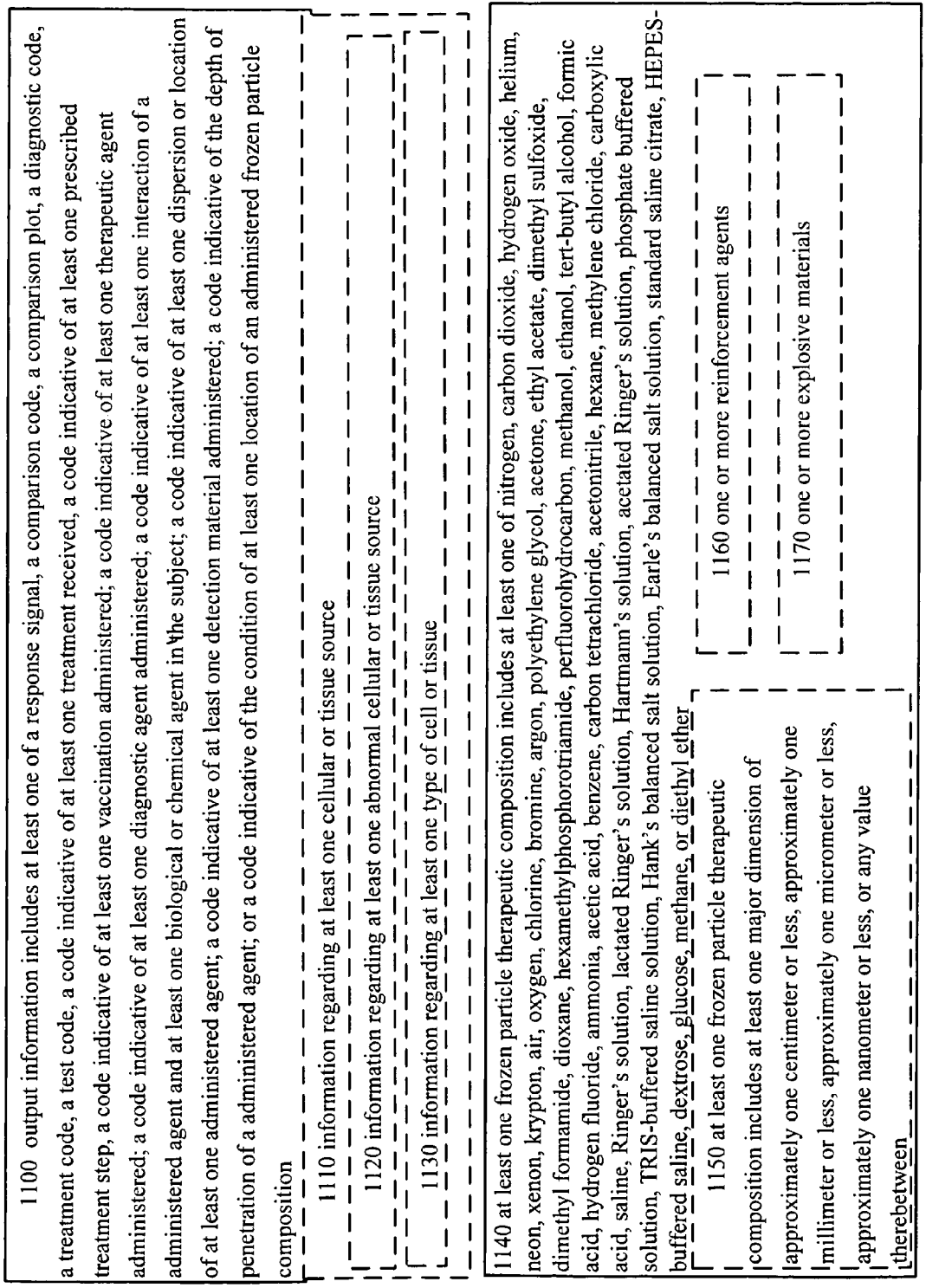
FIG. 11 illustrates a partial view of FIG. 10 in which embodiments may be implemented.

As indicated in FIGS. 10-12, at least one aspect includes a method 1000 relating to predicting a clinical outcome of administering at least one frozen particle therapeutic composition to at least one biological tissue of at least one first subject includes determining a similarity or a dissimilarity in information regarding at least one aspect of administering at least one therapeutic composition to the at least one biological tissue of the at least one first subject to information regarding at least one aspect of administering at least one therapeutic composition to the at least one biological tissue of the at least one second subject, wherein the at least one second subject attained a clinical outcome following receipt of the at least one frozen particle therapeutic composition; and providing output information optionally based on the determination 1010.

In one embodiment, the information regarding the at least one aspect of administering at least one frozen particle therapeutic composition includes information 1020 regarding the amount of at least one frozen particle therapeutic composition or therapeutic agent delivered to at least one biological tissue of a subject. In one embodiment, the information regarding the at least one aspect of administering at least one frozen particle therapeutic composition includes information 1030 regarding at least one dimension of biological tissue penetration. In one embodiment, the information regarding the at least one dimension of biological tissue penetration includes information 1040 regarding at least one of depth, width, or breadth of delivery of at least one frozen particle therapeutic composition to at least one biological tissue of at least one subject; or information 1050 regarding two or more subjects with common attributes.

In one embodiment, the one or more common attributes include genetic attributes, mental attributes, or psychological attributes 1060. In at least on embodiment, the one or more common attributes include genotype attributes or phenotype attributes 1070.

In one embodiment, the one or more common attributes 1080 include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; medical history; partial or whole proteomic sequence; lymph condition, or blood condition.

In one embodiment, the output information 1100 includes at least one of a response signal, a comparison code, a comparison plot, a diagnostic code, a treatment code, a test code, a code indicative of at least one treatment received, a code indicative of at least one prescribed treatment step, a code indicative of at least one vaccination delivered; a code indicative of at least one therapeutic agent delivered; a code indicative of at least one diagnostic agent delivered; a code indicative of at least one interaction of a delivered agent and at least one biological or chemical agent in the subject; a code indicative of at least one dispersion or location of at least one delivered agent; a code indicative of at least one detection material delivered; a code indicative of the depth of penetration of a delivered agent; or a code indicative of the condition of at least one location of an administered or delivered frozen particle composition or therapeutic composition. In one embodiment, the at least one aspect of cellular or tissue abrasion or ablation includes information regarding at least one cellular or tissue source 1110. In one embodiment, the information regarding at least one tissue source includes information regarding at least one abnormal cellular or tissue source 1120. In one embodiment, the information regarding at least one cellular or tissue source includes information regarding at least one type of cell or tissue 1130. In one embodiment, the cellular or tissue source includes at least one cell or biological tissue described herein.

In one embodiment, the at least one frozen particle composition includes at least one of nitrogen, carbon dioxide, hydrogen oxide, helium, neon, xenon, krypton, chlorine, bromine, methane, oxygen, air, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 1140.

In one embodiment, the at least one frozen particle composition or therapeutic composition includes at least one major dimension of approximately one decimeter or less, or approximately one centimeter or less, approximately one millimeter or less, approximately one micrometer or less, approximately one nanometer or less, or any value therebetween 1150.

In one embodiment, the at least one frozen particle composition or therapeutic composition includes one or more reinforcement agents 1160. In one embodiment, the at least one frozen particle composition or therapeutic composition includes one or more explosive materials 1170.

In one embodiment, the receipt by the at least one subject of at least one frozen particle composition or therapeutic composition is pursuant to at least one clinical trial 1200. In one embodiment, the method further comprises determining at least one correlation before the administration or delivery of the at least one frozen particle composition or therapeutic composition to at least one subject 1210. The at least one subject includes, but is not limited to at least one subject described herein.

In one embodiment, the method includes creating at least one inclusion criterion and at least one exclusion criterion for a clinical trial involving the at least one frozen particle composition or therapeutic composition 1220. In one embodiment, the method further comprises suggesting the inclusion of one or more of the at least one subject in at least one clinical trial 1230. In one embodiment, the method further comprises suggesting the exclusion of one or more of the at least one subject in at least one clinical trial 1240. In certain instances, multiple subjects from multiple clinical trials are included. In one embodiment, the method further includes using one or more of the at least one comparison to predict at least one clinical outcome regarding at least one second subject 1250. In one embodiment, the at least one second subject has not received the at least one frozen particle composition or therapeutic composition 1260. In one embodiment, the method includes predicting at least one clinical outcome involving the at least one second subject, and the at least one second subject is a plurality of people; and the method further comprises segregating subject identifiers associated with the plurality of people in reference to the predicted at least one clinical outcome 1270.

In one embodiment, the at least one second subject is a plurality of people; and the method further comprises determining the eligibility of the at least one second subject for the at least one clinical trial 1280.

Figure 14:
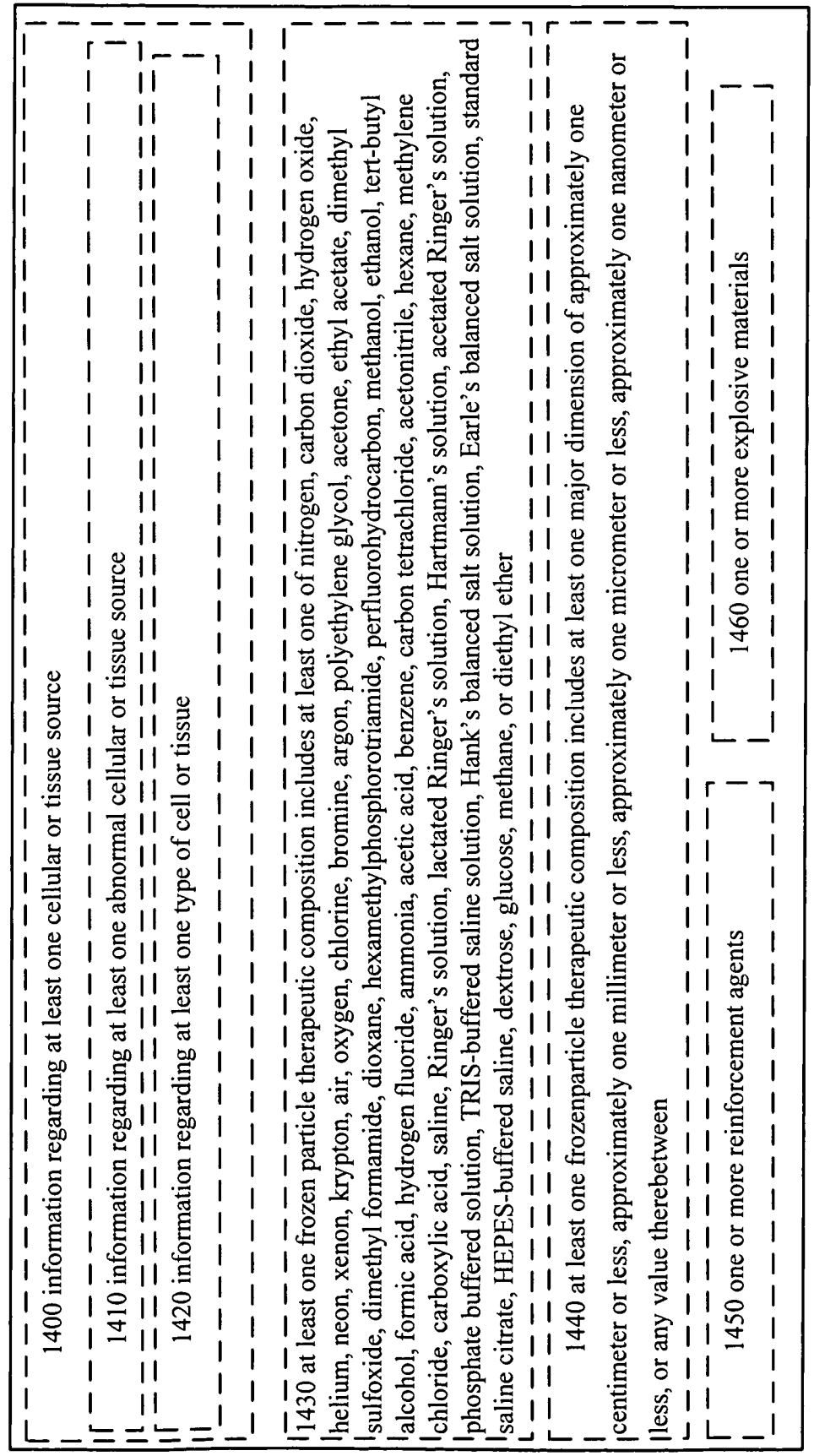
FIG. 14 illustrates a partial view of FIG. 13 in which embodiments may be implemented.

As shown in FIGS. 13-15, one embodiment includes a system 1300 including at least one computer program 1310, configured with a computer-readable medium, for use with at least one computer system and wherein the computer program includes a plurality of instructions including but not limited to one or more instructions 1320 for comparing information regarding at least one aspect of at least one therapeutic administration of at least one frozen particle composition or therapeutic composition to at least one subject. In one embodiment, information 1330 regarding amount of the at least one frozen particle composition, therapeutic composition, or therapeutic agent administered to at least one biological tissue of at least one subject. In one embodiment, information regarding at least one aspect of at least one therapeutic administration of at least one frozen particle composition or therapeutic composition includes information regarding at least one dimension of biological tissue penetration 1340. In one embodiment, information regarding at least one aspect of at least one therapeutic administration of at least one frozen particle composition or therapeutic composition includes information regarding at least one of depth, width, or breadth of administration of at least one frozen particle composition or therapeutic composition to at least one biological tissue of at least one subject 1350. In one embodiment, information regarding at least one aspect of at least one therapeutic administration includes information regarding two or more subjects with one or more common attributes 1360. In one embodiment, the computing device is configured to communicate with at least one imaging device. In one embodiment, the computing device is configured to communicate with at least one printing device. In one embodiment, the computing device is configured to communicate with at least one input device 1370.

In one embodiment, the information regarding at least one aspect of therapeutic administration of at least one therapeutic composition includes information regarding at least one cellular or tissue source 1400; information regarding at least one abnormal cellular or tissue source 1410; or information regarding at least one type of cell or tissue 1420. In one embodiment, at least one frozen particle composition or therapeutic composition includes at least one of nitrogen, carbon dioxide, hydrogen oxide, helium, neon, xenon, krypton, chlorine, bromine, methane, oxygen, air or argon. In one embodiment, the at least one frozen particle composition or therapeutic composition includes at least one of polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 1430. In one embodiment, at least one frozen particle composition or therapeutic composition includes at least one major dimension of approximately one decimeter or less, approximately one centimeter or less, approximately one millimeter or less, approximately one micrometer or less, approximately one nanometer or less, or any value therebetween 1440. In one embodiment, the at least one frozen particle composition or therapeutic composition includes one or more reinforcement agents 1450 or one or more explosive materials 1460.

In one embodiment, the receipt by the at least one subject of at least one frozen particle composition or therapeutic composition is pursuant to at least one clinical trial 1500. In one embodiment, the system further comprises determining at least one correlation before the delivery or administration of the at least one frozen particle composition or therapeutic composition to at least one subject 1510.

In one embodiment, the method includes creating at least one inclusion criterion and at least one exclusion criterion for a clinical trial involving the at least one frozen particle composition or therapeutic composition 1520. In one embodiment, the instructions further comprise suggesting the inclusion of one or more of the at least one subject in at least one clinical trial 1530. In certain instances, multiple subjects from multiple clinical trials are included.

In one embodiment, the instructions include suggesting the exclusion of one or more of the at least one subject in at least one clinical trial 1540.

In one embodiment, a method includes using one or more of the at least one comparison to predict at least one clinical outcome regarding at least one second subject 1550. In one embodiment, the at least one second subject has not received the at least one frozen particle composition or therapeutic composition 1560. In one embodiment, the at least one second subject is a plurality of people; and further comprising segregating subject identifiers associated with the plurality of people in reference to the predicted at least one clinical outcome 1570.

In one embodiment, the using one or more of the at least one comparison, wherein the at least one second subject is a plurality of people; and further comprising determining the eligibility of the at least one second subject for the at least one clinical trial 1580.

As indicated in FIG. 16, one embodiment relates to a system 1600 including at least one computer program 1610 configured with a computer-readable medium, for use with at least one computer system and wherein the computer program includes a plurality of instructions including but not limited to one or more instructions 1620 for comparing information regarding at least one aspect of at least one therapeutic administration of at least one frozen particle therapeutic composition to at last one subject, and information regarding at least one frozen particle therapeutic composition involving at least one biological tissue of at least one subject; and one or more instructions for applying one or more comparisons to the information regarding the at least one aspect of therapeutic administration of at least one frozen particle therapeutic composition to a plurality of people. In one embodiment, the computer program includes one or more instructions 1630 for segregating subject identifiers associated with the plurality of people in reference to at least one of the one or more applied comparisons. In one embodiment, information regarding at least one aspect of at least one therapeutic administration includes information 1640 regarding the amount of at least one frozen particle composition, therapeutic composition or therapeutic agent administered to at least one biological tissue of at least one subject; information 1650 regarding at least one dimension of biological tissue penetration; information 1660 regarding at least one of depth, width, or breadth of administration of at least one frozen particle therapeutic composition to at least one biological tissue of at least one subject. In one embodiment, the computer program includes one or more instructions 1670 for segregating individual identifiers associated with the plurality of people in reference to at least one characteristic shared by two or more subjects in the plurality of people.

As shown in FIG. 17, one embodiment relates to a computer program product 1700 that includes a signal bearing medium 1710 bearing at least one of one or more instructions 1720 for receiving a first input associated with a first possible dataset, the first possible dataset including data representative of one or more measurements relating to one or more physical attributes of a first subject; one or more instructions 1730 for comparing a value associated with the first possible dataset with a second dataset including values representative of predictive regimen parameters from a second subject with one or more similar or dissimilar physical attributes; one or more instructions 1740 for determining from the comparison at least one frozen particle therapeutic composition regimen for the first subject and output information; one or more instructions 1750 for accessing the first possible dataset in response to the first input; one or more instructions 1760 for generating the first possible dataset in response to the first input; one or more instructions 1770 for determining a graphical illustration of the first possible dataset; one or more instructions 1780 for determining a graphical illustration of the second possible dataset; and at least one generated output optionally based on the determination.

In one embodiment, the computer program product includes a signal bearing medium that includes a computer-readable medium 1790. In one embodiment, the signal bearing medium of the computer program product includes a recordable medium 1792. In one embodiment, the computer program product includes a signal bearing medium that includes a communications medium 1794.

Figure 18:
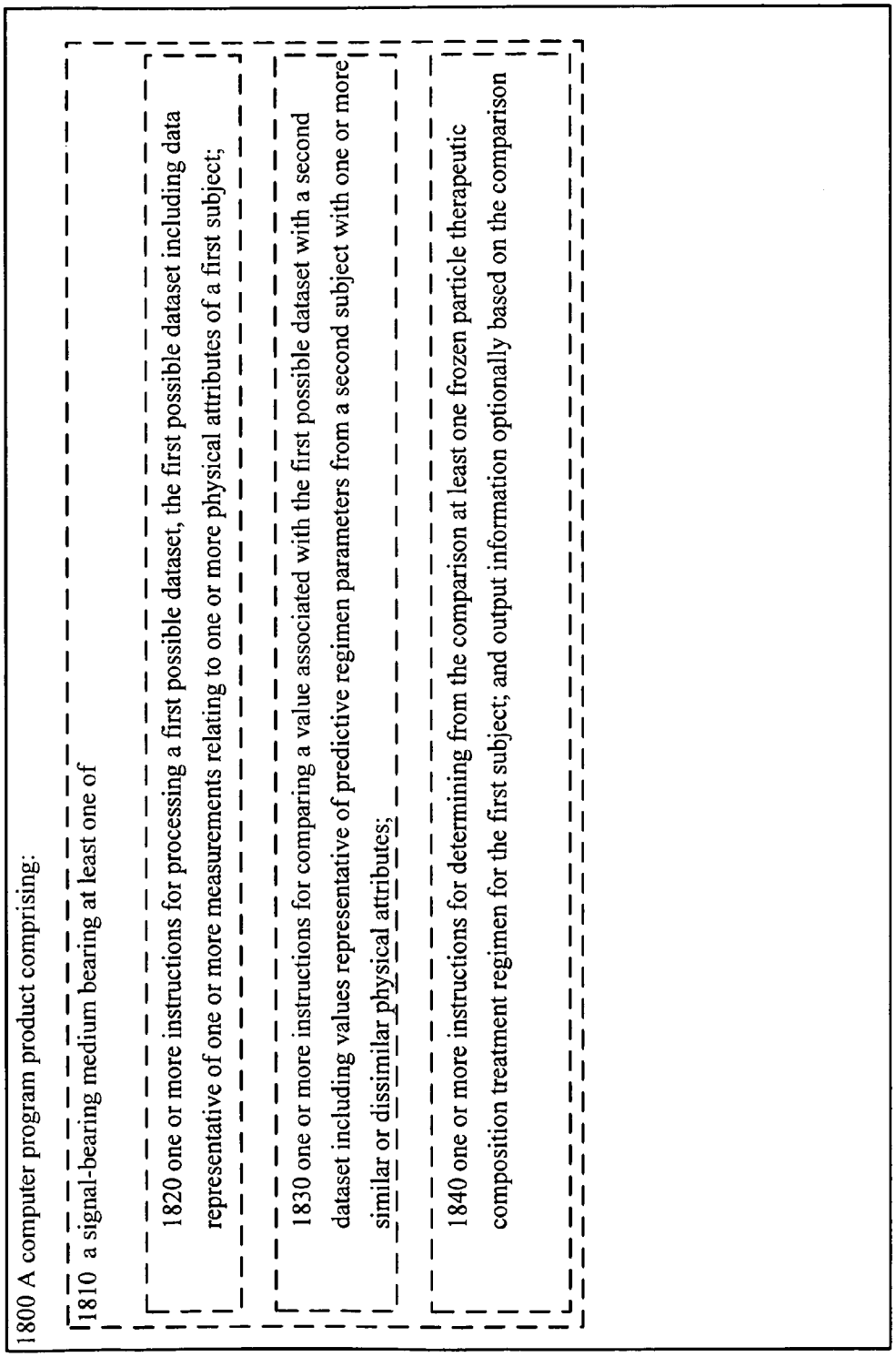
FIG. 18 illustrates a partial view of a computer program product 1800 for executing a computing process on a computing device.

As indicated in FIG. 18, one embodiment relates to a computer program product 1800 that includes a signal bearing medium 1810 bearing at least one of one or more instructions 1820 for processing a first possible dataset, the first possible dataset including data representative of one or more measurements relating to one or more physical attributes of a first subject; one or more instructions 1830 for comparing a value associated with the first possible dataset with a second dataset including values representative of predictive regimen parameters from a second subject with one or more similar or dissimilar physical attributes; one or more instructions 1840 for determining from the comparison at least one frozen particle composition or therapeutic composition treatment regimen for the first subject, and output information.

As indicated in FIG. 19, one embodiment relates to a computer program product 1900 that includes a signal bearing medium 1910 bearing at least one of one or more instructions 1920 responsive to a first possible dataset, the first possible dataset including data representative of one or more measurements relating to one or more physical attributes of a first subject; one or more instructions 1930 for comparing a value associated with the first possible dataset with a second dataset including values representative of predictive regimen parameters for a second subject with one or more similar or dissimilar physical attributes; one or more instructions 1940 for determining from the comparison at least one frozen particle composition or therapeutic composition treatment regimen for the first subject; and output information optionally based on the determination.

As shown in FIG. 20, one embodiment relates to a computer program product 2000 that includes a signal bearing medium 2010 bearing at least one of one or more instructions 2020 for receiving a first input associated with a first possible dataset, the first possible dataset including data representative of one or more measurements relating to one or more physical attributes of a subject; one or more instructions 2030 for comparing a value associated with the first possible dataset with a second dataset including values representative of parameters relating to one or more expected biological changes following administration of one or more frozen particle compositions or therapeutic compositions; one or more instructions 2040 for determining from the comparison at least one biological change following administration of one or more frozen particle compositions or therapeutic compositions to the subject; at least one generated output optionally based on the determination.

In one embodiment, the computer program product includes one or more instructions 2050 for accessing the first possible dataset in response to the first input. In one embodiment, the computer program product includes one or more instructions 2060 for generating the first possible dataset in response to the first input.

In one embodiment, the computer program product includes one or more instructions 2070 for determining a graphical illustration of the first possible dataset. In one embodiment, the computer program product includes one or more instructions 2080 for determining a graphical illustration of the second possible dataset. In one embodiment, the signal bearing medium includes a computer-readable medium 2090. In one embodiment, the signal bearing medium includes a recordable medium 2092. In one embodiment, the signal bearing medium includes a communications medium 2094.

As indicated in FIG. 21, one embodiment a computer program product 2100 includes a signal bearing medium 2110 bearing at least one of one or more instructions 2120 for processing a first input associated with a first possible dataset, the first possible dataset including data representative of one or more measurements relating to one or more physical attributes of a subject; one or more instructions 2130 for comparing a value associated with the first possible dataset with a second dataset including values representative of parameters relating to one or more expected biological changes following administration of one or more frozen particle compositions or therapeutic compositions; one or more instructions 2140 for determining from the comparison at least one biological change following administration of one or more frozen particle compositions or therapeutic compositions to the subject; at least one generated output optionally based on the determination.

As shown in FIG. 22, one embodiment relates to a computer program product 2200 includes a signal bearing medium 2210 bearing at least one of one or more instructions 2220 responsive to a first possible dataset, the first possible dataset including data representative of one or more measurements relating to one or more physical attributes of a subject; one or more instructions 2230 for comparing a value associated with the first possible dataset with a second dataset including values representative of parameters relating to one or more expected biological changes following administration of one or more frozen particle compositions or therapeutic compositions; one or more instructions 2240 for determining from the comparison at least one biological change following administration of one or more frozen particle compositions or therapeutic compositions to the subject; and output information optionally based on the determination.

Figure 24:
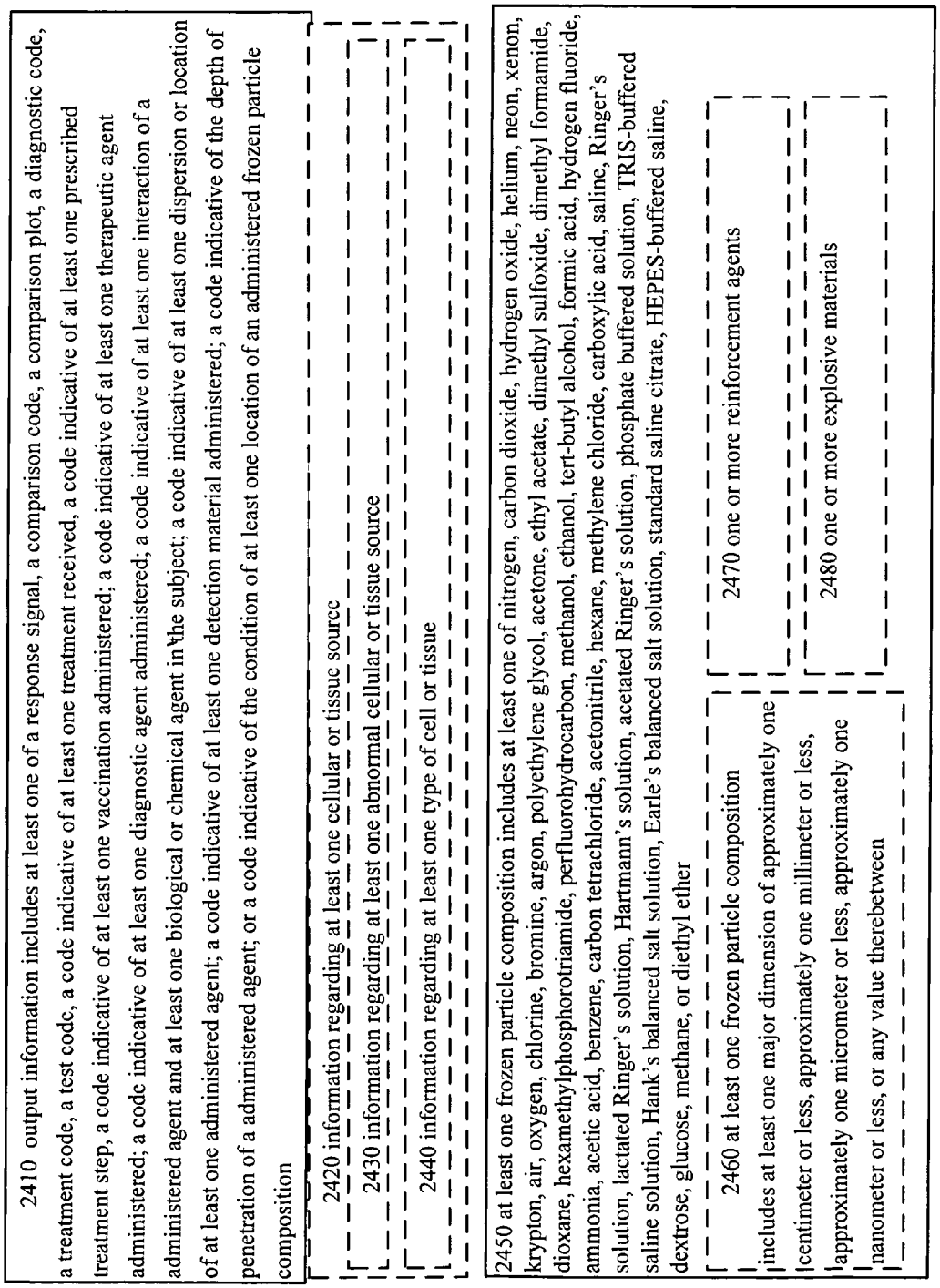
FIG. 24 illustrates a partial view FIG. 23 in which embodiments may be implemented.
Figure 25:
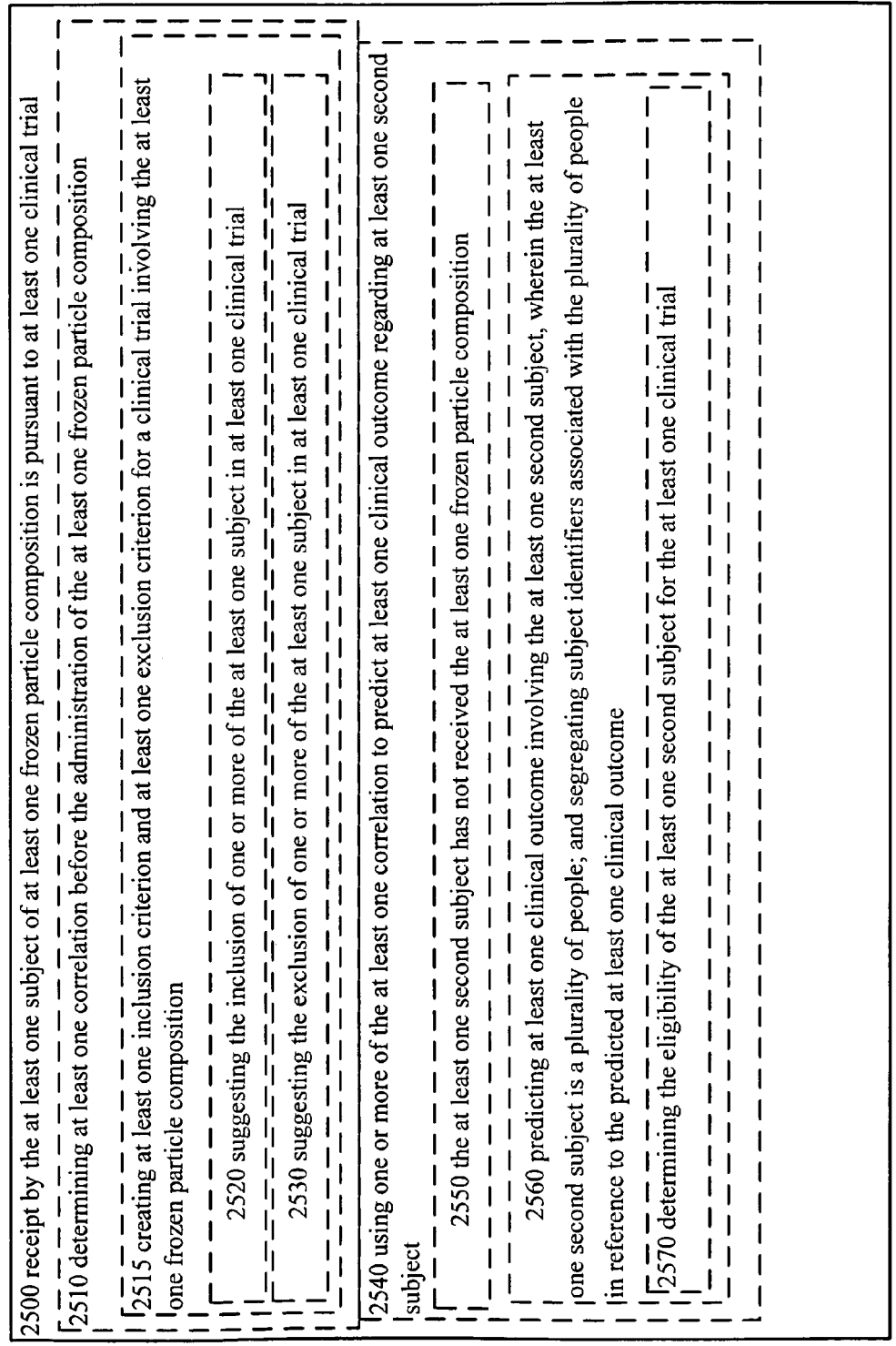
FIG. 25 illustrates a partial view FIG. 23 in which embodiments may be implemented.

As indicated in FIGS. 23-25, one embodiment, a method 2300 includes comparing 2310 information regarding at least one aspect of cellular or tissue abrasion or ablation of at least one biological tissue of at least one subject and information regarding at least one clinical outcome following receipt by the at least one subject of at least one frozen particle composition or therapeutic composition; and providing output information optionally based on the determination. In one embodiment, the method includes determining at least one statistical correlation 2320. In one embodiment, the method includes counting the occurrence of at least one clinical outcome 2330. In one embodiment, the information regarding at least one aspect of cellular or tissue abrasion or ablation includes information regarding quantity of cells or tissue removed or destroyed 2340. In one embodiment, the information regarding at least one aspect of cellular or tissue abrasion or ablation includes information regarding at least one dimension of cellular or tissue removal or destruction, or removal or destruction of other materials, such as plaque, extracellular matrix, collagen, elastin, protein, or other materials 2350. In one embodiment, information regarding the at least one dimension of cellular removal or destruction includes information regarding at least one of depth, width, or breadth of cellular removal or destruction 2360.

In one embodiment, the information regarding at least one aspect of cellular or tissue abrasion or ablation includes information regarding two or more subjects with one or more common attributes 2370. In one embodiment, the one or more common attributes include genetic attributes, mental attributes, or psychological attributes 2380. In at least on embodiment, the one or more common attributes include genotype attributes or phenotype attributes 2390.

In one embodiment, the one or more common attributes 2397 include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; proteomic profile; partial or whole genetic sequence; medical history; partial or whole proteomic sequence; lymph condition, or blood condition.

In one embodiment, the output information 2410 includes at least one of a response signal, a comparison code, a comparison plot, a diagnostic code, a treatment code, a test code, a code indicative of at least one treatment received, a code indicative of at least one prescribed treatment step, a code indicative of at least one vaccination delivered; a code indicative of at least one therapeutic agent delivered; a code indicative of at least one diagnostic agent delivered; a code indicative of at least one interaction of a delivered agent and at least one biological or chemical agent in the subject; a code indicative of at least one dispersion or location of at least one delivered agent; a code indicative of at least one detection material delivered; a code indicative of the depth of penetration of a delivered agent; or a code indicative of the condition of at least one location of a delivered or administered frozen particle composition. In one embodiment, the at least one aspect of cellular or tissue abrasion or ablation includes information regarding at least one cellular or tissue source 2420. In one embodiment, the information regarding at least one tissue source includes information regarding at least one abnormal cellular or tissue source 2430. In one embodiment, the information regarding at least one cellular or tissue source includes information regarding at least one type of cell or tissue 2440. In one embodiment, the cellular or tissue source includes at least one cell or biological tissue described herein.

In one embodiment, the at least one frozen particle composition or therapeutic composition includes at least one of nitrogen, carbon dioxide, hydrogen oxide, helium, neon, xenon, krypton, chlorine, bromine, methane, oxygen, air, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 2450.

In one embodiment, the at least one frozen particle composition includes at least one major dimension of approximately one decimeter or less, or approximately one centimeter or less, approximately one millimeter or less, approximately one micrometer or less, approximately one nanometer or less, or any value therebetween 2460.

In one embodiment, the at least one frozen particle composition includes one or more reinforcement agents 2470. In one embodiment, the at least one frozen particle composition includes one or more explosive materials 2480. In one embodiment, the receipt by the at least one subject of at least one frozen particle composition is pursuant to at least one clinical trial 2500. In one embodiment, the method further comprises determining at least one correlation 2510 before the delivery or administration of the at least one frozen particle composition to at least one subject. The at least one subject includes, but is not limited to at least one subject described herein.

In one embodiment, the method includes creating at least one inclusion criterion and at least one exclusion criterion for a clinical trial involving the at least one frozen particle composition or therapeutic composition 2515. In one embodiment, the method further comprises suggesting the inclusion of one or more of the at least one subject in at least one clinical trial 2520. In one embodiment, the method further comprises suggesting the exclusion of one or more of the at least one subject in at least one clinical trial 2530. In certain instances, multiple subjects from multiple clinical trials are included. In one embodiment, the method further includes using one or more of the at least one correlation to predict at least one clinical outcome regarding at least one second subject 2540. In one embodiment, the at least one second subject has not received the at least one frozen particle composition or therapeutic composition 2550. In one embodiment, the method further comprises predicting at least one clinical outcome involving the at least one second subject, wherein the at least one second subject is a plurality of people; and segregating subject identifiers associated with the plurality of people in reference to the predicted at least one clinical outcome 2560. In one embodiment, the at least one second subject is a plurality of people; and the method further comprises determining the eligibility of the at least one second subject for the at least one clinical trial 2570.

Figure 27:
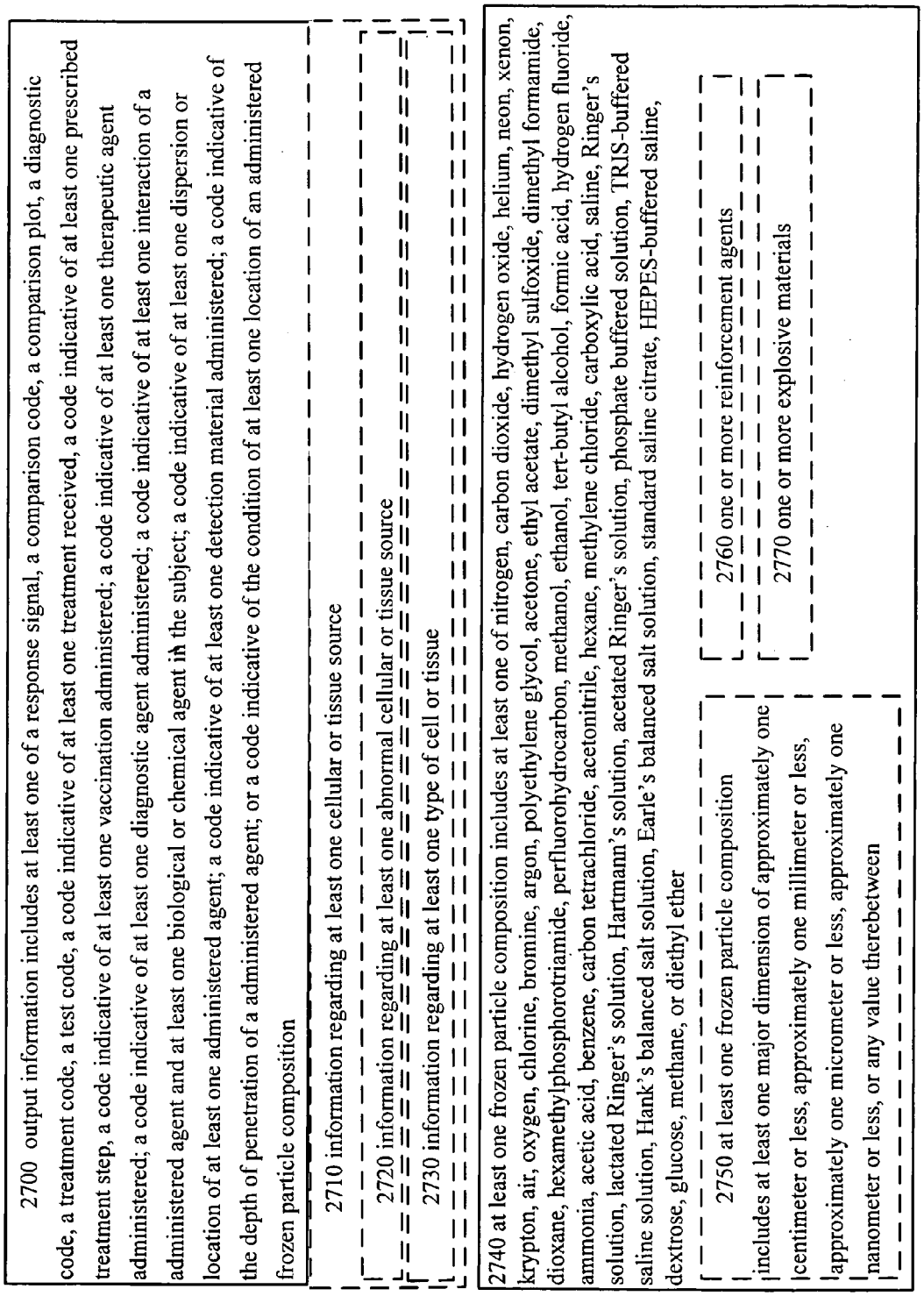
FIG. 27 illustrates a partial view of FIG. 26 in which embodiments may be implemented.
Figure 28:
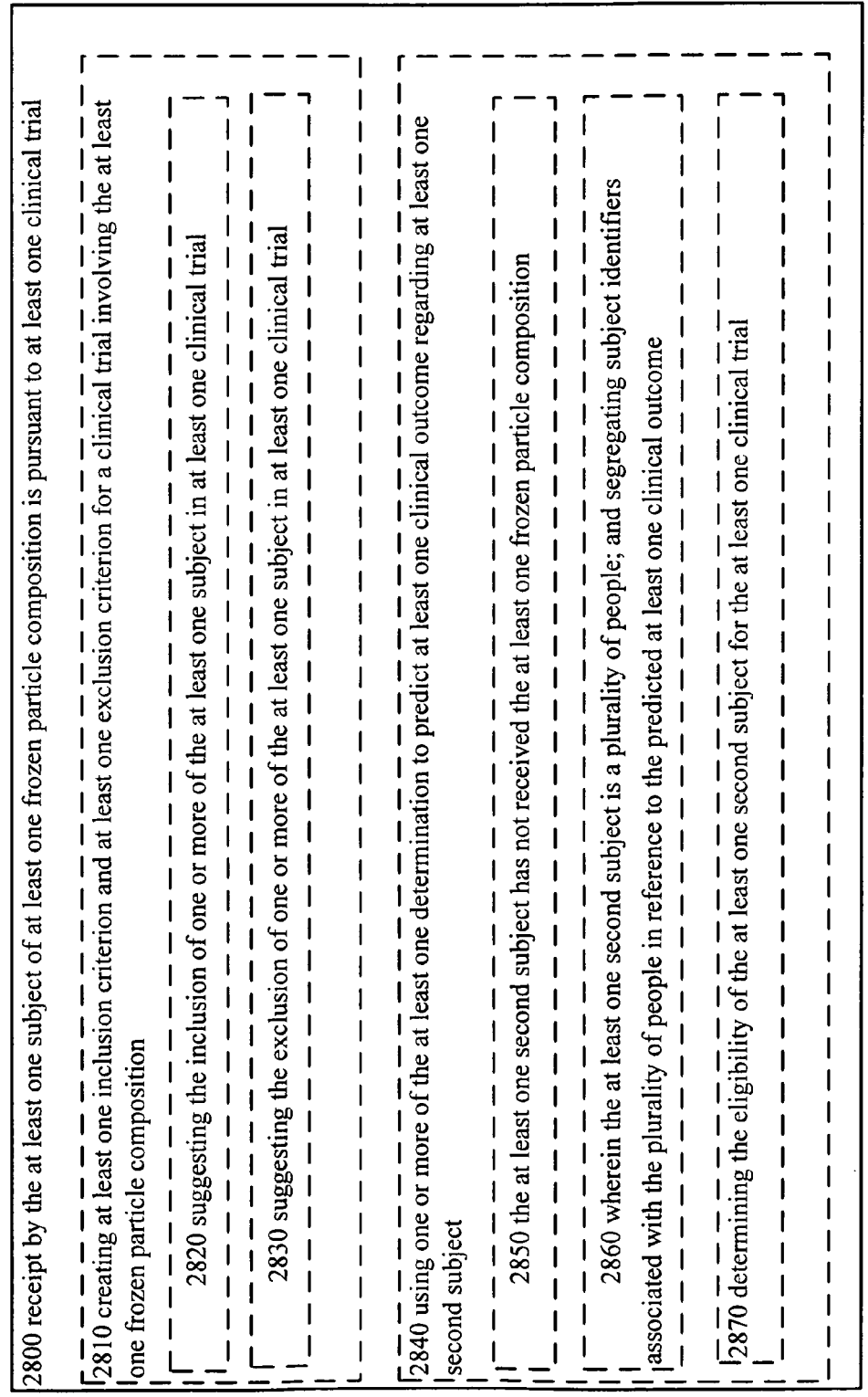
FIG. 28 illustrates a partial view of FIG. 26 in which embodiments may be implemented.

As indicated in FIGS. 26-28, one embodiment relates to a method 2600 of predicting a clinical outcome of at least one frozen particle composition treatment for at least one first subject includes determining 2610 a similarity or a dissimilarity in information regarding at least one aspect of cellular or tissue abrasion or ablation of at least one biological tissue of at least one first subject to information regarding at least one aspect of cellular or tissue abrasion or ablation of at least one biological tissue of at least one second subject, wherein the at least one second subject attained a clinical outcome following receipt of the at least one frozen particle composition or therapeutic composition; and providing output information optionally based on the determination.

In one embodiment, the information regarding at least one aspect of cellular or tissue abrasion or ablation includes information regarding the quantity of cells or tissue removed or destroyed 2620. In one embodiment, the information regarding at least one aspect of cellular or tissue abrasion or ablation includes information regarding at least one dimension of cellular, tissue, or other material removal or destruction 2630. In one embodiment, the at least one dimension of cellular removal or destruction includes information regarding at least one of depth, width, or breadth of cellular removal or destruction 2640. In one embodiment, the information regarding at least one aspect of cellular or tissue abrasion or ablation includes information regarding two or more subjects with one or more common attributes 2650.

In one embodiment, the one or more common attributes include but are not limited to genetic attributes, mental attributes, or psychological attributes 2660. In one embodiment, the one or more common attributes include genotype attributes or phenotype attributes 2670.

In one embodiment, the one or more common attributes include at least one of height; weight; medical diagnosis; familial background; results on one or more medical tests; ethnic background; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; medical history; genetic profile; proteomic profile; partial or whole genetic sequence; partial or whole proteomic sequence; lymph condition, medical history, or blood condition 2680.

In one embodiment, the output information includes at least one of a response signal, a comparison code, a comparison plot, a diagnostic code, a treatment code, a test code, a code indicative of at least one treatment received, a code indicative of at least one prescribed treatment step, a code indicative of at least one vaccination delivered; a code indicative of at least one therapeutic agent delivered; a code indicative of at least one diagnostic agent delivered; a code indicative of at least one interaction of a delivered agent and at least one biological or chemical agent in the subject; a code indicative of at least one dispersion or location of at least one delivered agent; a code indicative of at least one detection material delivered; a code indicative of the depth of penetration of a delivered agent; or a code indicative of the condition of at least one location of a delivered or administered frozen particle composition 2700.

In one embodiment, the information regarding at least one aspect of cellular or tissue abrasion or ablation includes information regarding at least one cellular or tissue source 2710. In one embodiment, the cellular or tissue source includes but is not limited to at least one biological tissue or cell described herein. In one embodiment, the information regarding at least one tissue source includes information regarding at least one abnormal cellular or tissue source 2720. In one embodiment, the information regarding at least one cellular or tissue source includes information regarding at least one type of cell or tissue 2730. In one embodiment, the information regarding at least one aspect of cellular or tissue abrasion or ablation includes information regarding at least one type of cell or tissue.

In one embodiment, the at least one frozen particle composition or therapeutic composition includes at least one of nitrogen, carbon dioxide, hydrogen oxide, helium, neon, xenon, krypton, chlorine, bromine, methane, oxygen, air or argon. In one embodiment, the at least one frozen particle composition or therapeutic composition includes at least one of polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 2740.

In one embodiment, the at least one frozen particle composition or therapeutic composition includes at least one major dimension of approximately one decimeter or less, or approximately one centimeter or less, or approximately one millimeter or less, or approximately one micrometer or less, or approximately one nanometer or less, or any value therebetween 2750.

In one embodiment, the at least one frozen particle composition or therapeutic composition includes one or more reinforcement agents 2760. In one embodiment, the at least one frozen particle composition or therapeutic composition includes one or more explosive materials 2770.

In one embodiment, the receipt by the at least one subject of at least one frozen particle composition or therapeutic composition is pursuant to at least one clinical trial 2800. In one embodiment, the method includes creating at least one inclusion criterion and at least one exclusion criterion for a clinical trial involving the at least one frozen particle composition or therapeutic composition 2810. In one embodiment, the method further comprises suggesting the inclusion of one or more of the at least one subject in at least one clinical trial 2820. In certain instances, multiple subjects from multiple clinical trials are included. In one embodiment, the method includes suggesting the exclusion of one or more of the at least one subject in at least one clinical trial 2830.

In one embodiment, a method includes using one or more of the at least one determination to predict at least one clinical outcome regarding at least one second subject 2840. In one embodiment, the at least one second subject has not received the at least one frozen particle composition or therapeutic composition 2850. In one embodiment, the at least one second subject is a plurality of people; and the method further comprises segregating subject identifiers associated with the plurality of people in reference to the predicted at least one clinical outcome 2860.

In one embodiment, the using one or more of the at least one comparison, wherein the at least one second subject is a plurality of people; and the method further comprises determining the eligibility of the at least one second subject for the at least one clinical trial 2870.

As indicated in FIGS. 29-30, at least one aspect relates to a system 2900 that includes at least one computing device 2910; one or more instructions 2920 that when executed on the at least one computing device cause the at least one computing device to receive a first input associated with a first possible dataset, the first possible dataset including data representative of one or more measurements relating to one or more physical attributes of a first subject; one or more instructions 2930 that when executed on the at least one computing device cause the at least one computing device to compare a value associated with the first possible dataset with a second dataset including values representative of predictive regimen parameters related to a second subject with one or more similar or dissimilar physical attributes; one or more instructions 2940 that when executed on the at least one computing device cause the at least one computing device to determine from the comparison at least one frozen particle composition treatment regimen for the first subject; and at least one generated output optionally based on the determination; one or more instructions 2950 that when executed on the at least one computing device cause the at least one computing device to access the first possible dataset in response to the first input; one or more instructions 2960 that when executed on the at least one computing device cause the at least one computing device to generate the first possible dataset in response to the first input; one or more instructions 2970 that when executed on the at least one computing device cause the at least one computing device to determine a graphical illustration of the possible dataset; or one or more instructions 3000 that when executed on the at least one computing device cause the at least one computing device to determine a graphical illustration of the second possible dataset. In one embodiment, the treatment regimen includes at least one of cellular or tissue removal, cellular or tissue ablation, debridement, delivery of at least one therapeutic agent, cleaning one or more wounds, removing material from at least one biological tissue, or removing material from at least one blood vessel 3005. In at least one nitrogen, carbon dioxide, hydrogen oxide, helium, neon, xenon, krypton, chlorine, bromine, methane, oxygen, air, argon, polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 3008.

In one embodiment, the at least one computing device includes one or more desktop computer, workstation computer, computing system including a cluster of processors, a networked computer, a tablet personal computer, a laptop computer, a mobile device, a mobile telephone, or a personal digital assistant computer 3010. In one embodiment, the at least one computing device is configured to communicate with a database to access the first possible dataset 3020. In one embodiment, the at least one computing device is configured to communicate with a frozen particle composition selecting apparatus, a frozen particle composition generating apparatus, or both 3030.

Figure 32:
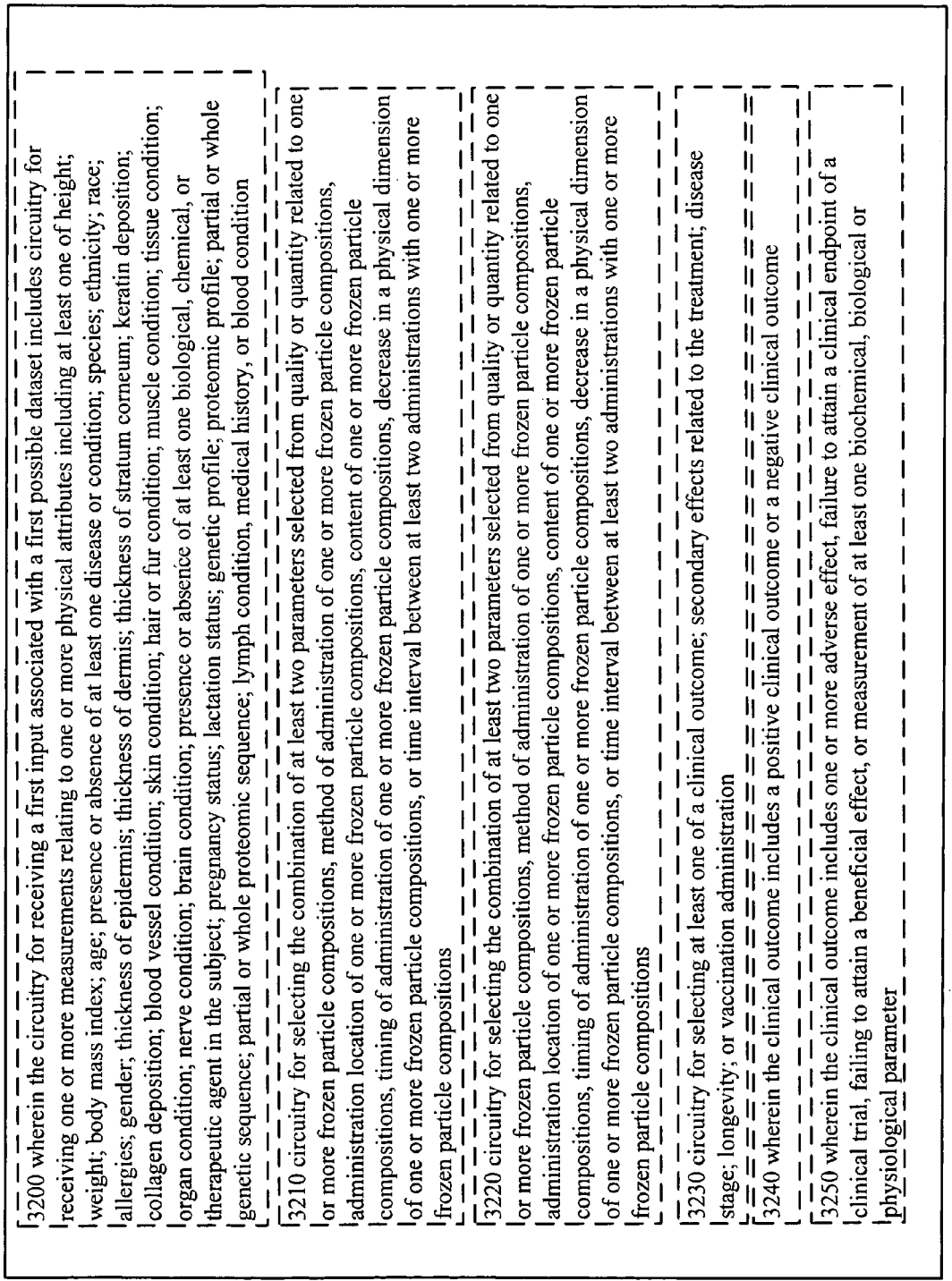
FIG. 32 illustrates a partial view of FIG. 31 in which embodiments may be implemented.

As shown in FIGS. 31-32, at least one aspect relates to a system 3100 including circuitry 3110 for receiving a first input associated with a first possible dataset, the first possible dataset including data representative of one or more measurements relating to one or more physical attributes of a first subject; circuitry 3120 for comparing a value associated with the first possible dataset with a second dataset including values representative of predictive regimen parameters related to a second subject with one or more similar or dissimilar physical attributes; circuitry 3125 for determining from the comparison at least one frozen particle composition treatment regimen for the first subject; circuitry 3128 for selecting at least one of quality or quantity related to one or more frozen particle compositions, method of administration of one or more frozen particle compositions, administration location of one or more frozen particle compositions, content of one or more frozen particle compositions, timing of administration of one or more frozen particle compositions, decrease in physical dimension of one or more frozen particle compositions or time interval between at least two deliveries with one or more frozen particle compositions.

In one embodiment, the system includes circuitry 3130 for determining from the comparison at least one frozen particle composition treatment regimen for the first subject; and circuitry 3140 for providing output information optionally based on the comparison. In one embodiment, the circuitry for receiving a first input associated with a first possible dataset includes circuitry 3200 for receiving one or more measurements relating to one or more physical attributes including at least one of height; weight; body mass index; age; presence or absence of at least one disease or condition; species; ethnicity; race; allergies; gender; thickness of epidermis; thickness of dermis; thickness of stratum corneum; keratin deposition; collagen deposition; blood vessel condition; skin condition; hair or fur condition; muscle condition; tissue condition; organ condition; nerve condition; brain condition; presence or absence of at least one biological, chemical, or therapeutic agent in the subject; pregnancy status; lactation status; genetic profile; medical history; proteomic profile; partial or whole genetic sequence; partial or whole proteomic sequence; medical history; lymph condition, or blood condition.

In one embodiment, the system includes circuitry 3210 for selecting the combination of at least two parameters selected from quality or quantity related to one or more frozen particle compositions, method of administration of one or more frozen particle compositions, administration location of one or more frozen particle compositions, content of one or more frozen particle compositions, timing of administration of one or more frozen particle compositions, decrease in a physical dimension of one or more frozen particle compositions, or time interval between at least two administrations or deliveries with one or more frozen particle compositions.

In one embodiment, the system includes circuitry 3220 for selecting the combination of at least two parameters selected from quality or quantity related to one or more frozen particle compositions, method of administration of one or more frozen particle compositions, administration location of one or more frozen particle compositions, content of one or more frozen particle compositions, timing of administration of one or more frozen particle compositions, decrease in a physical dimension of one or more frozen particle compositions, or time interval between at least two administrations with one or more frozen particle compositions.

In one embodiment, the system includes circuitry 3230 for selecting at least one of a clinical outcome; secondary effects related to the treatment; disease stage; longevity; or vaccination administration. In one embodiment, the clinical outcome 3240 includes a positive clinical outcome or a negative clinical outcome. In one embodiment, the clinical outcome includes one or more adverse effect, failure to attain a clinical endpoint of a clinical trial, failing to attain a beneficial effect, or measurement of at least one biochemical, biological or physiological parameter 3250.

FIGS. 33-35 illustrate a partial view of a system 3300 including at least one computer program 3310 configured with a computer-readable medium, for use with at least one computer system and wherein the computer program includes a plurality of instructions including but not limited to one or more instructions 3320 for determining at least one comparison between information regarding at least one aspect of cellular or tissue abrasion or ablation of at least one biological tissue of at least one subject and information regarding at least one clinical outcome following receipt by the at least one subject of at least one frozen particle composition. In one embodiment, the system includes one or more instructions 3330 for determining at least one statistical correlation. In one embodiment, the system includes one or more instructions 3340 for counting the occurrence of at least one clinical outcome. In one embodiment, information regarding at least one aspect of cellular or tissue abrasion or ablation includes information 3350 regarding quantity of cells or tissue removed or destroyed; information 3360 regarding at least one dimension of cellular, tissue or other material removal or destruction; information 3370 regarding at least one of depth, width, or breadth of cellular removal or destruction; or information 3380 regarding two or more subjects with one or more common attributes. In one embodiment, the information regarding at least one aspect of cellular or tissue abrasion or ablation includes information 3400 regarding at least one cellular or tissue source, including information 3410 regarding at least one abnormal cellular or tissue source or information 3420 regarding at least one type of cell or tissue.

In one embodiment, the at least one frozen particle composition or therapeutic composition includes at least one of polyethylene glycol, acetone, ethyl acetate, dimethyl sulfoxide, dimethyl formamide, dioxane, hexamethylphosphorotriamide, perfluorohydrocarbon, methanol, ethanol, tert-butyl alcohol, formic acid, hydrogen fluoride, ammonia, acetic acid, benzene, carbon tetrachloride, acetonitrile, hexane, methylene chloride, carboxylic acid, saline, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, or diethyl ether 3430. In one embodiment, at least one frozen particle composition includes at least one major dimension of approximately one decimeter or less, approximately one centimeter or less, approximately one millimeter or less, approximately one micrometer or less, approximately one nanometer or less, or any value therebetween 3440. In one embodiment, the at least one frozen particle composition includes one or more reinforcement agents 3450. In one embodiment, the at least one frozen particle composition includes one or more explosive materials 3460.

In one embodiment, the receipt by the at least one subject of at least one frozen particle composition or therapeutic composition is pursuant to at least one clinical trial 3500. In one embodiment, the system further comprises one or more instructions for determining at least one comparison before the delivery or administration of the at least one frozen particle composition or therapeutic composition to at least one subject 3510.

In one embodiment, the system includes one or more instructions for creating at least one inclusion criterion and at least one exclusion criterion for a clinical trial involving the at least one frozen particle composition or therapeutic composition 3520. In one embodiment, the system further comprises one or more instructions for suggesting the inclusion of one or more of the at least one subject in at least one clinical trial 3530. In certain instances, multiple subjects from multiple clinical trials are included.

In one embodiment, the system further includes one or more instructions for suggesting the exclusion of one or more of the at least one subject in at least one clinical trial 3540. In one embodiment, the system includes one or more instructions for using one or more of the at least one comparison to predict at least one clinical outcome regarding at least one second subject 3550. In one embodiment, the at least one second subject has not received the at least one frozen particle composition or therapeutic composition 3560. In one embodiment, the system includes predicting at least one clinical outcome involving the at least one second subject, wherein the at least one second subject is a plurality of people; and segregating subject identifiers associated with the plurality of people in reference to the predicted at least one clinical outcome 3570. In one embodiment, the at least one second subject is a plurality of people; and the system further comprises determining the eligibility of the at least one second subject for the at least one clinical trial 3580.

As indicated in FIG. 36, at least one aspect relates to a system 3600 that includes at least one computer program 3610, configured with a computer-readable medium, for use with at least one computer system and wherein the computer program includes a plurality of instructions including but not limited to one or more instructions 3620 for comparing information regarding at least one aspect of cellular or tissue abrasion or ablation of at least one biological tissue of at least one subject and information regarding at least one frozen particle composition involving the at least one biological tissue of at least one subject; and one or more instructions 3630 for applying one or more comparisons to information regarding at least one aspect of cellular or tissue abrasion or ablation regarding a plurality of people. In one embodiment, one or more instructions 3640 for segregating subject identifiers associated with the plurality of people in reference to at least one of the one or more applied comparisons. In one embodiment, the information regarding at least one aspect of cellular or tissue abrasion or ablation includes information 3650 regarding quantity of cells or tissue removed or destroyed; information 3660 regarding at least one dimension of cellular, tissue or other material removal or destruction; or information 3670 regarding at least one of depth, width, or breadth of cellular removal or destruction. In one embodiment, the system includes one or more instructions 3680 for segregating individual identifiers associated with the plurality of people in reference to at least one characteristic shared by two or more subjects of the plurality of people.

As indicated in FIG. 37, at least one aspect relates to a method 3700 comprising accepting a first input 3710 associated with at least one characteristic of at least one biological tissue to be at least partially constructed or at least partially reconstructed; accepting a second input 3720 associated with at least one parameter of at least partially constructing or at least partially reconstructing the at least one biological tissue by administering one or more frozen particle compositions including at least one agent. In one embodiment, the at least one agent 3730 includes one or more of a therapeutic agent, adhesive agent, abrasive, reinforcement agent, explosive material, or biological remodeling agent. In one embodiment, administering 3740 the one or more frozen particle compositions includes administering the one or more frozen particle compositions to at least one substrate. In one embodiment, the at least one substrate 3750 includes one or more of a cell, tissue, organ, structure, or device.

In one embodiment, the method includes processing results 3760 of the first input and the second input. In one embodiment, processing results of the first input and the second input includes electronically processing 3770 results of the first input and the second input. In one embodiment, processing results of the first input and the second input includes 3780 electronically processing results of the first input and the second input by utilizing one or more of Gaussian smoothing, scaling, homomorphic filtering, parametric estimation techniques, Boolean operations, Monte Carlo simulations, wavelet based techniques, mirroring, smoothing, gradient weighted partial differential equation smoothing, NURBS, polygonal modeling, splines and patches modeling, or modification of a CAD design.

As indicated in FIG. 38, in one embodiment, the first input 3810 includes one or more values related to the at least one characteristic of at least one biological tissue. In one embodiment, the first input includes one or more spatial addresses 3820 associated with the at least one characteristic of at least one biological tissue. In one embodiment, the first input includes one or more of x, y, or z coordinates 3830 associated with the at least one characteristic of at least one biological tissue.

In one embodiment, the at least one characteristic 3840 of at least one biological tissue to be at least partially constructed or at least partially reconstructed includes one or more of: morphological feature, anatomical feature, histological feature, tissue hierarchical level, scaffold feature, vascular structure feature, heterogenous tissue feature, mechanical feature, volumetric feature, geometric feature, volumetric representation, mechanical feature, deformation, kinematic feature, surface contour feature, cytometric feature, cell aggregation, cell growth, cell-cell interaction, cell-tissue interaction, biomimetic design, cell pattern, cell deposition, organ hierarchical level, tissue microstructure, cellular microstructure, cell junction feature, tissue junction feature, cell-tissue classification, hard tissue classification, soft tissue classification, tumor diagnosis, or other feature.

In one embodiment, the at least one characteristic 3850 of at least one biological tissue includes one or more of cellular type, cellular function, cellular size, cellular constitution, cellular architecture, cellular durability, cellular source, tissue type, tissue constitution, tissue size, tissue shape, tissue function, tissue architecture, tissue source, tissue durability, organ type, organ constitution, organ size, organ shape, organ function, organ architecture, organ source, or organ durability. In one embodiment, the first input 3860 includes one or more temporal addresses associated with the at least one characteristic of at least one biological tissue.

As indicated in FIG. 39, in one embodiment, the first input 3910 includes one or more values derived from at least one image of the at least one biological tissue. In one embodiment, the at least one image 3920 includes one or more images acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, multiphoton calcium-imaging, photography, or in silico generation.

In one embodiment, the at least one biological tissue 3930 is located in at least one of in situ, in vitro, in vivo, in utero, in planta, in silico, or ex vivo. In one embodiment, the at least one biological tissue 3940 is at least partially located in at least one subject. In one embodiment, the method further comprises accepting a third input 3950 associated with at least one feature of the at least one subject. In one embodiment, the at least one feature 3960 of the at least one subject includes one or more of age, gender, genotype, phenotype, proteomic profile, or health condition.

As indicated in FIGS. 40-41, In one embodiment, the processing results 4010 of the first input and the second input includes determining at least one parameter of at least partially constructing or at least partially reconstructing the at least one biological tissue with one or more frozen particle compositions from one or more values derived from at least one image of the at least one biological tissue. In one embodiment, the second input 4020 includes one or more values related to the at least one parameter of at least partially constructing or at least partially reconstructing the at least one biological tissue by administering one or more frozen particle compositions to the at least one substrate. In one embodiment, 4130 the one or more values related to the at least one parameter of constructing or reconstructing the at least one biological tissue includes one or more predictive values.

In one embodiment, the at least one parameter 4030 of at least partially constructing or at least partially reconstructing the at least one biological tissue includes one or more of porosity of the at least one substrate, pore size of the at least one substrate, interconnectivity of the pores of the at least one substrate, transport properties of the at least one substrate, cell-tissue formation of the at least one substrate, mechanical strength of the at least one substrate, ability for attachment or distribution of the at least one agent included in the one or more frozen particle compositions to the at least one substrate, ability for attachment or distribution of one or more cells or tissues to the at least one substrate, facilitation of at least one nutrient, or tissue formation or tissue growth associated with the at least one substrate.

In one embodiment, the at least one parameter 4040 of at least partially constructing or at least partially reconstructing the at least one biological tissue by administering one or more frozen particle compositions includes one or more of: design of plot or model for administration of one or more frozen particle compositions, constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, method of administration of one or more frozen particle compositions, timing of administration of one or more frozen particle compositions, modulation of administration of one or more frozen particle compositions, deposition of one or more frozen particle compositions, or rate of deposition of at least one agent.

In one embodiment, the at least one parameter 4110 of at least partially constructing or at least partially reconstructing the at least one biological tissue by administering one or more frozen particle compositions includes at least one parameter relating to at least partially ablating or at least partially abrading one or more surfaces of the at least one biological tissue with the one or more frozen particle compositions.

In one embodiment, the at least one parameter 4120 of at least partially constructing or at least partially reconstructing the at least one biological tissue by administering one or more frozen particle compositions includes at least one parameter relating to administering at least one of a therapeutic agent, adhesive agent, biological remodeling agent, reinforcement agent, abrasive, or explosive material with the one or more frozen particle compositions.

In one embodiment, the spatial location 4140 for administration of one or more frozen particle compositions includes one or more of x, y, or z coordinates. In one embodiment, the processing results 4150 includes comparing at least one value related to the first input associated with the at least one characteristic of at least one biological tissue to be at least partially constructed or at least partially reconstructed with at least one value related to at least one image of a target biological tissue. In one embodiment 4160, the image of a target biological tissue includes an image of a similar biological tissue, or an image of a dissimilar biological tissue.

Figure 42:
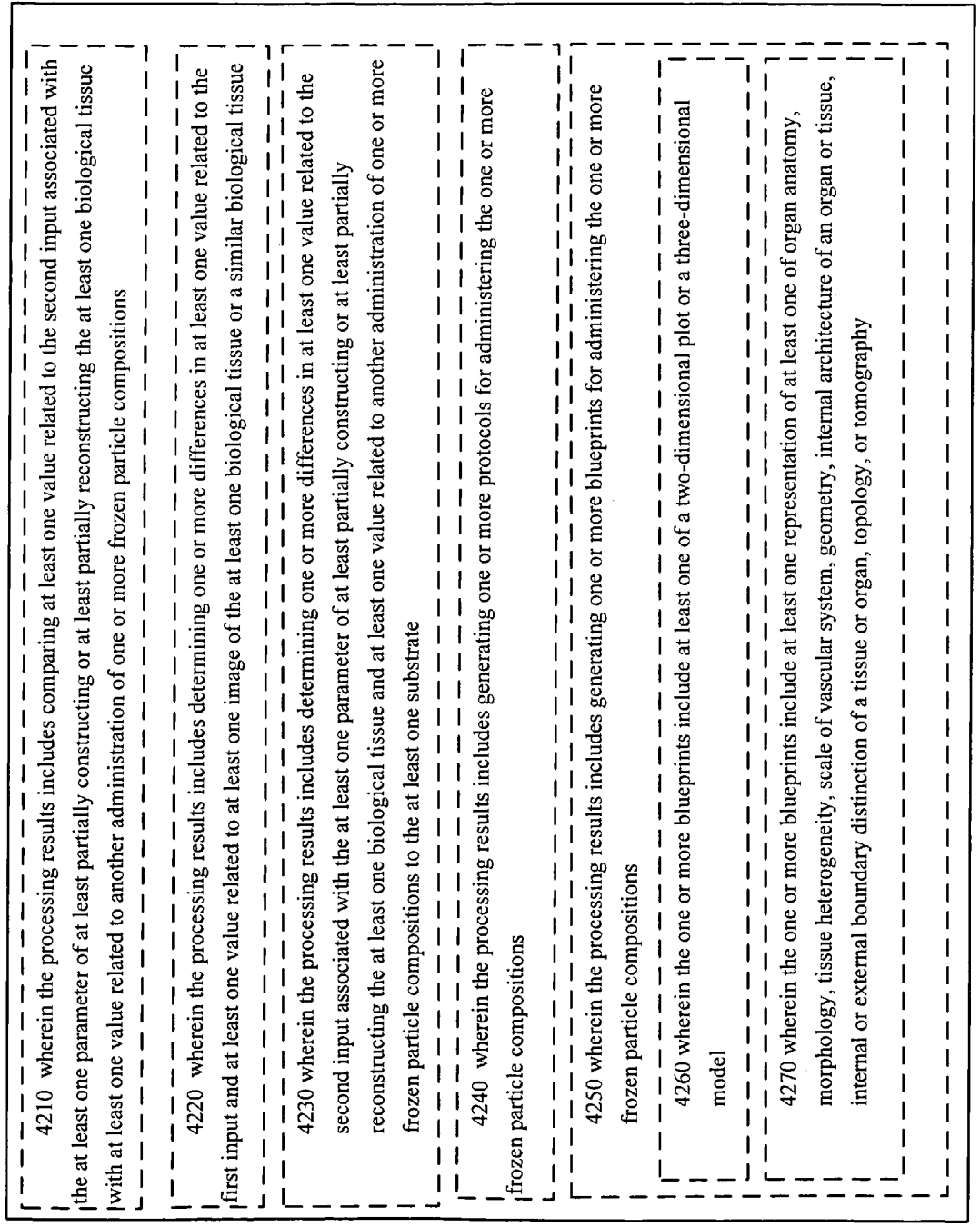
FIG. 42 illustrates a partial view of FIG. 37 in which embodiments may be implemented.

As indicated in FIG. 42, the processing results 4210 includes comparing at least one value related to the second input associated with the at least one parameter of at least partially constructing or at least partially reconstructing the at least one biological tissue with at least one value related to another administration of one or more frozen particle compositions. In one embodiment 4220, the processing results includes determining one or more differences in at least one value related to the first input and at least one value related to at least one image of the at least one biological tissue or a similar biological tissue. In one embodiment 4230, the processing results includes determining one or more differences in at least one value related to the second input associated with the at least one parameter of at least partially constructing or at least partially reconstructing the at least one biological tissue and at least one value related to another administration of one or more frozen particle compositions to the at least one substrate.

In one embodiment 4240, the processing results includes generating one or more protocols for administering the one or more frozen particle compositions. In one embodiment 4250, the processing results includes generating one or more blueprints for administering the one or more frozen particle compositions. In one embodiment 4260, the one or more blueprints include at least one of a two-dimesional plot or a three-dimensional model. In one embodiment 4270, the one or more blueprints include at least one representation of at least one of organ anatomy, morphology, tissue heterogeneity, scale of vascular system, geometry, internal architecture of an organ or tissue, internal or external boundary distinction of a tissue or organ, topology, or tomography.

Figure 43:
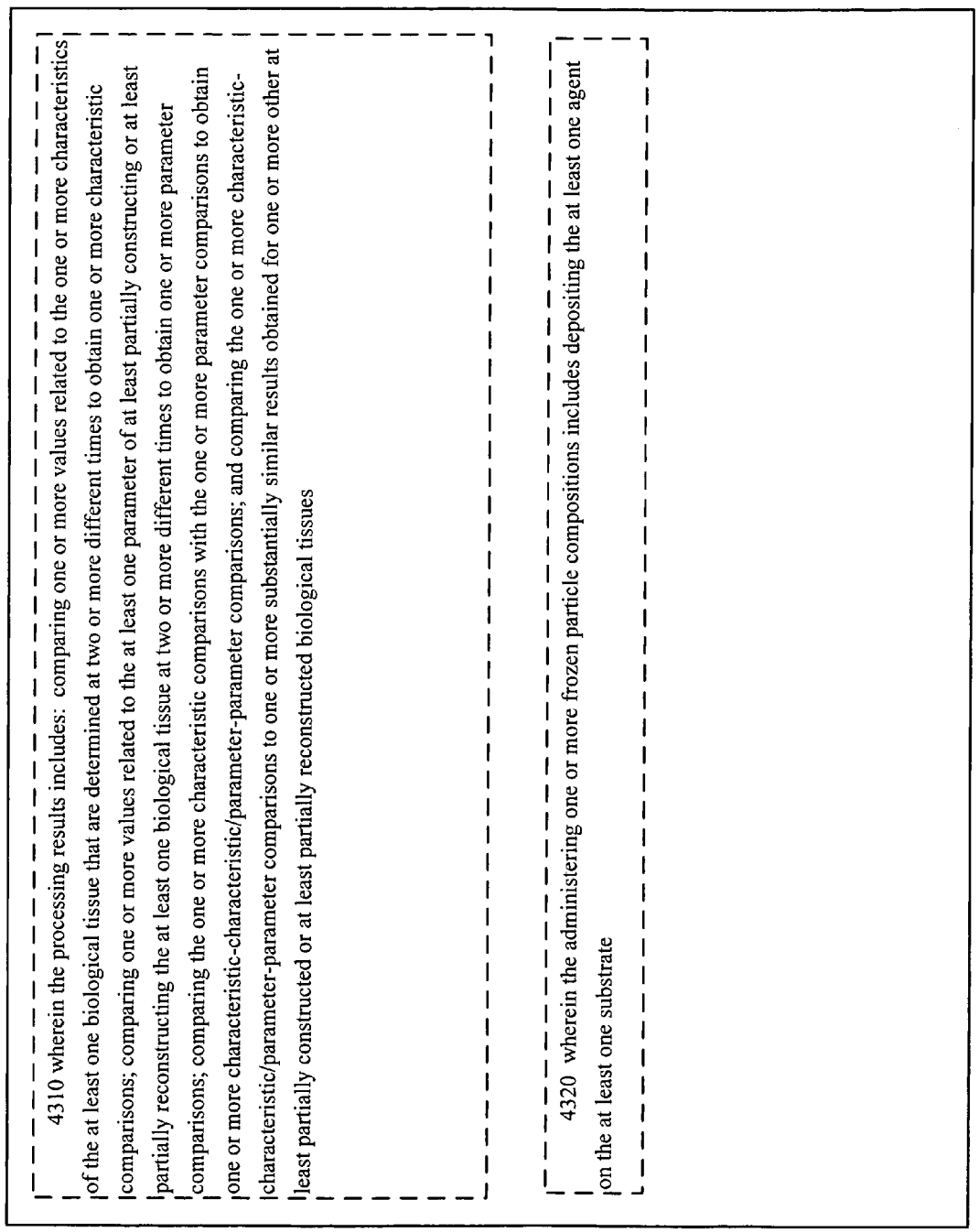
FIG. 43 illustrates a partial view of FIG. 37 in which embodiments may be implemented.

As indicated in FIG. 43, the processing results 4310 includes: comparing one or more values related to the one or more characteristics of the at least one biological tissue that are determined at two or more different times to obtain one or more characteristic comparisons; comparing one or more values related to the at least one parameter of at least partially constructing or at least partially reconstructing the at least one biological tissue at two or more different times to obtain one or more parameter comparisons; comparing the one or more characteristic comparisons with the one or more parameter comparisons to obtain one or more characteristic-characteristic/parameter-parameter comparisons; and comparing the one or more characteristic-characteristic/parameter-parameter comparisons to one or more substantially similar results obtained for one or more other at least partially constructed or at least partially reconstructed biological tissues. In one embodiment 4320, the administering one or more frozen particle compositions includes depositing the at least one agent on the at least one substrate.

Figure 44:
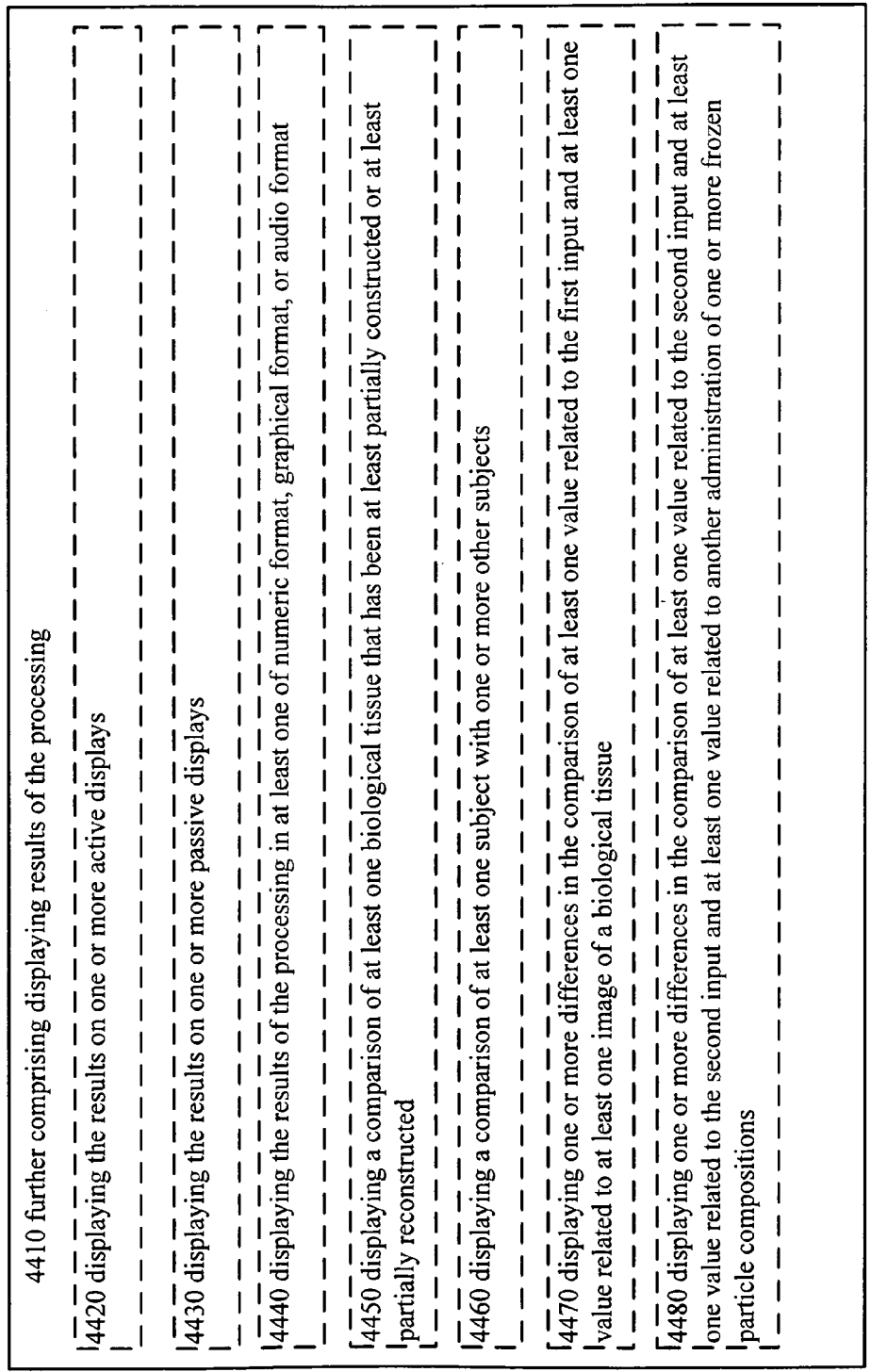
FIG. 44 illustrates a partial view of FIG. 37 in which embodiments may be implemented.

As indicated in FIG. 44, the method further comprises 4410 displaying results of the processing. In one embodiment 4420, the displaying results of the processing includes displaying the results on one or more active displays. In one embodiment 4430, the displaying results of the processing includes displaying the results on one or more passive displays. In one embodiment 4440, the displaying results of the processing includes displaying the results of the processing in at least one of numeric format, graphical format, or audio format.

In one embodiment 4450, the displaying results of the processing includes displaying a comparison of at least one biological tissue that has been at least partially constructed or at least partially reconstructed. In one embodiment 4460, the displaying results of the processing includes displaying a comparison of at least one subject with one or more other subjects. In one embodiment 4470, the displaying results of the processing includes displaying one or more differences in the comparison of at least one value related to the first input and at least one value related to at least one image of a biological tissue. In one embodiment 4480, the displaying results of the processing includes displaying one or more differences in the comparison of at least one value related to the second input and at least one value related to another administration of one or more frozen particle compositions.

Figure 45:
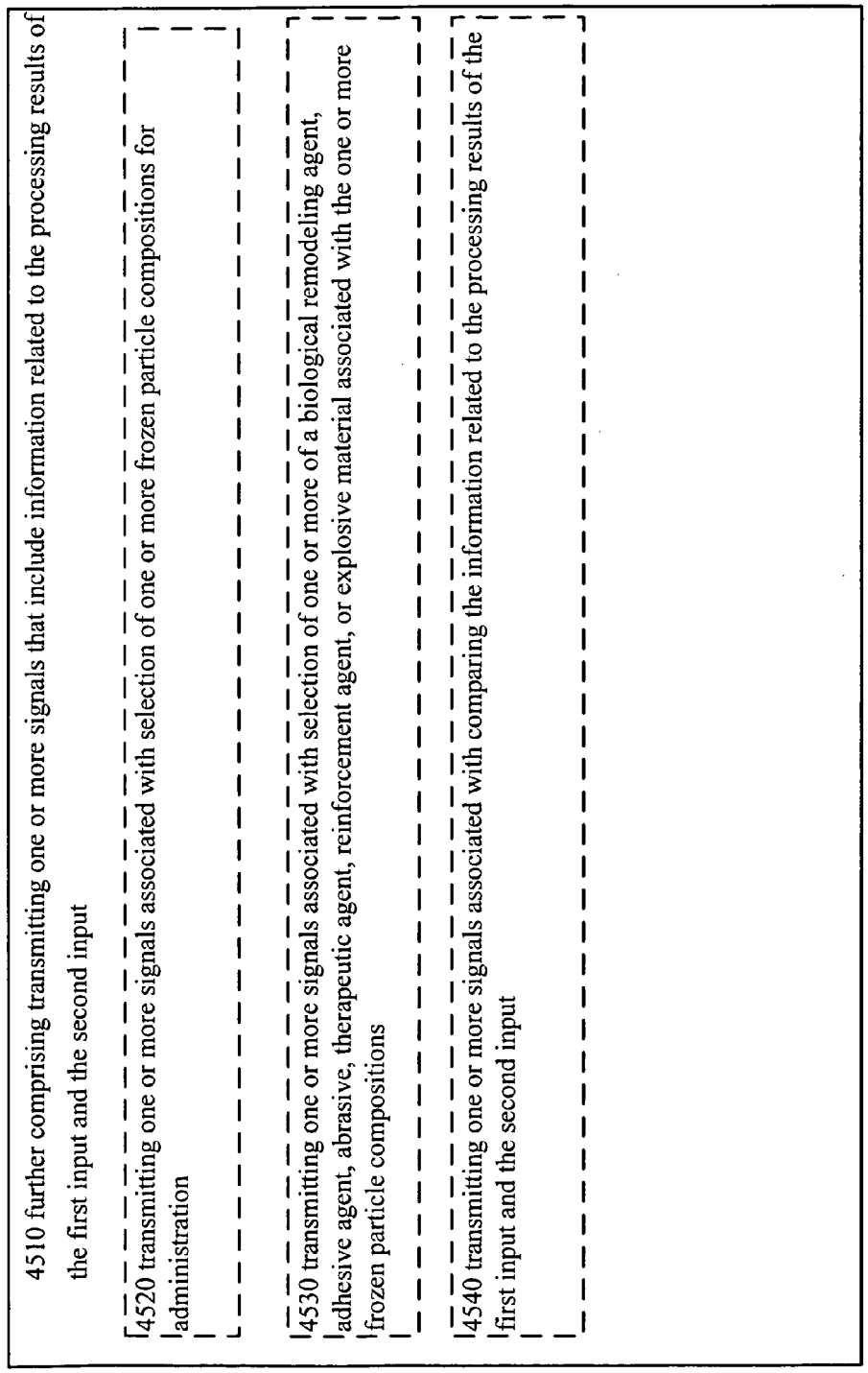
FIG. 45 illustrates a partial view of FIG. 37 in which embodiments may be implemented.

As indicated in FIG. 45, the method further comprises transmitting 4510 one or more signals that include information related to the processing results of the first input and the second input. In one embodiment 4520, the transmitting one or more signals includes transmitting one or more signals associated with selection of one or more frozen particle compositions for administration. In one embodiment 4530, the transmitting one or more signals includes transmitting one or more signals associated with selection of one or more of a biological remodeling agent, adhesive agent, abrasive, therapeutic agent, reinforcement agent, or explosive material associated with the one or more frozen particle compositions. In one embodiment 4540, the transmitting one or more signals includes transmitting one or more signals associated with comparing the information related to the processing results of the first input and the second input.

As indicated in FIG. 46, the one or more frozen particle compositions 4610 include one or more frozen particles including at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

In one embodiment 4620, the at least one agent includes one or more of an adhesive agent, therapeutic agent, reinforcement agent, abrasive, explosive material, or biological remodeling agent. In one embodiment 4630, at least one of the adhesive agent, therapeutic agent, reinforcement agent, abrasive, explosive material, or biological remodeling agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

As indicated in FIG. 47, the one or more explosive materials 4710 include at least one of a carbonate, carbon dioxide, nitroglycerine, acid, base, epoxy, acrylic polymer or copolymer, acrylamide polymer or copolymer, urethane, hypoxyapatite, or reactive metal. In one embodiment 4720, the at least one adhesive agent includes one or more of an acrylic polymer or copolymer, acrylamide polymer or copolymer poly-mer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin.

In at least one embodiment 4730, the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter.

As indicated in FIG. 48, the therapeutic agent 4810 includes at least one of an anti-tumor agent, antimicrobial agent, anti-viral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof.

In one embodiment 4820 the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast. In one embodiment, 4830, the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly(α-hydroxyacid), selectin, glutaraldehyde, hydrophobic non-glycosylated protein, hydrogel, peptide hydrogel, or gelatin. In one embodiment 4840, the at least one biological remodeling agent includes one or more of Type I collagen, Type II collagen, Type III collagen, Type VII collagen, Type X collagen, elastin fibers, or soluble elastin. In one embodiment 4850, the at least one biological remodeling agent is included as part of a carrier that assists in synthesis or activation of the at least one biological remodeling agent.

As indicated in FIGS. 49-51, a method 4900 comprises accepting input 4910 associated with at least one parameter of at least partially constructing or at least partially reconstructing at least one biological tissue by administering one or more frozen particle compositions; administering 4920 one or more frozen particle compositions including at least one agent; wherein 4930 the at least one agent includes one or more of a biological remodeling agent, therapeutic agent, reinforcement agent, explosive material, abrasive, or adhesive agent; evaluating 4940 the at least one biological tissue for one or more indicators related to deposition of at least one agent, tissue formation, or tissue growth; and transmitting 5110 one or more signals that include information related to the accepting input and information related to the evaluating the at least one biological tissue.

In one embodiment 4950, the evaluating at least one biological tissue for one or more indicators includes evaluating at least one of an assay, image, or gross assessment of the at least one biological tissue prior to, during, or subsequent to at least one administration of the one or more frozen particle compositions. In one embodiment 4960, the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay.

In one embodiment 5020, the image includes at least one image acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, multiphoton calcium-imaging, photography, or in silico generation. In one embodiment 5030, wherein the one or more indicators of tissue formation or growth include at least one of cell migration, cell attachment, cell retention, cell differentiation, cell proliferation, apoptosis, diffusion of materials, angiogenesis, nucleic acid expression, protein translation, protein modification, carbohydrate production, carbohydrate secretion, fat production, fat secretion, or protein secretion.

In one embodiment 5040, the input associated with at least one parameter of at least partially constructing or at least partially reconstructing the at least one biological tissue by administering one or more frozen particle compositions includes one or more of: constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, method of administration of one or more frozen particle compositions, timing of administration of one or more frozen particle compositions, modulation of administration of one or more frozen particle compositions, deposition of one or more frozen particle compositions, or rate of deposition of at least one agent.

In one embodiment 5120, the transmitting one or more signals includes transmitting one or more signals associated with selection of one or more frozen particle compositions for administration. In one embodiment 5130, the transmitting one or more signals includes transmitting one or more signals associated with selection of one or more of a biological remodeling agent, adhesive agent, abrasive, therapeutic agent, reinforcement agent, or explosive material associated with the one or more frozen particle compositions. In one embodiment 5140, the administering one or more frozen particle compositions includes administering the one or more frozen particle compositions to at least one substrate. In one embodiment 5150, the at least one substrate includes one or more of a cell, tissue, organ, structure, or device. In one embodiment 5160, the one or more frozen particle compositions include one or more frozen particles including at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

As indicated in FIG. 52, the at least one agent 5210 includes one or more of an adhesive agent, therapeutic agent, reinforcement agent, abrasive, explosive material, or biological remodeling agent. In one embodiment 5220, the adhesive agent, therapeutic agent, reinforcement agent, abrasive, explosive material, or biological remodeling agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

In one embodiment 5230, the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal. In one embodiment 5240, the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropyl-maleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin.

As indicated in FIG. 53, the one or more reinforcement agents 5310 include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter.

In one embodiment 5320, the therapeutic agent includes at least one of an anti-tumor agent, antimicrobial agent, antiviral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof. In one embodiment 5330, the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast.

In one embodiment 5340, the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly($\alpha$-hydroxyacid), selectin, glutaraldehyde, hydrophobic non-glycosylated protein, hydrogel, peptide hydrogel, or gelatin.

In one embodiment 5350, the at least one biological remodeling agent includes one or more of Type I collagen, Type II collagen, Type III collagen, Type VII collagen, Type X collagen, elastin fibers, or soluble elastin.

As indicated in FIG. 54, a method 5400 comprises receiving 5410 one or more signals that include information related to accepting input associated with at least one parameter of at least partially constructing or at least partially reconstructing the at least one biological tissue by administering one or more frozen particle compositions; receiving 5420 one or more signals that include information related to evaluating the at least one biological tissue for one or more indicators of tissue formation or growth; and processing 5430 the information related to the input associated with at least one parameter of at least partially constructing or at least partially reconstructing the at least one biological tissue and the information related to the evaluating the at least one biological tissue. In one embodiment 5440, the evaluating at least one biological tissue for one or more indicators includes evaluating at least one of an assay, image, or gross assessment of the at least one biological tissue prior to, during, or subsequent to at least one administration of one or more frozen particle compositions.

In one embodiment 5450, the assay includes at least one technique that includes spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay. In one embodiment 5460, the image includes at least one image acquired by one or more of optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, multiphoton calcium-imaging, photography, or in silico generation.

As indicated in FIG. 55, the one or more indicators 5510 of tissue formation or growth include at least one of: cell migration, cell attachment, cell retention, cell differentiation, cell proliferation, apoptosis, diffusion of materials, angiogenesis, nucleic acid expression, protein translation, protein modification, carbohydrate production, carbohydrate secretion, fat production, fat secretion, or protein secretion.

In one embodiment 5520, the input associated with at least one parameter of at least partially constructing or at least partially reconstructing the at least one biological tissue includes one or more of: constitution of the one or more frozen particle compositions, formulation of the one or more frozen particle compositions, size of the one or more frozen particle compositions, shape of the one or more frozen particle compositions, angle of administration of the one or more frozen particle compositions, velocity of administration of the one or more frozen particle compositions, quantity of frozen particle compositions administered, rate of administration of more than one frozen particle composition, spatial location for administration of one or more frozen particle compositions, temporal location for administration of one or more frozen particle compositions, method of administration of one or more frozen particle compositions, timing of administration of one or more frozen particle compositions, modulation of administration of one or more frozen particle compositions, deposition of one or more frozen particle compositions, or rate of deposition of at least one agent.

In one embodiment 5530, the receiving one or more signals includes receiving one or more signals associated with selection of one or more frozen particle compositions for administration. In one embodiment 5540, the receiving one or more signals includes receiving one or more signals associated with the selection of at least one of a biological remodeling agent, adhesive agent, abrasive, therapeutic agent, reinforcement agent, or explosive material associated with the one or more frozen particle compositions.

As indicated in FIG. 56, in one embodiment 5610, the administering one or more frozen particle compositions includes administering the one or more frozen particle compositions to at least one substrate. In one embodiment 5620, the at least one substrate includes one or more of a cell, tissue, organ, structure, or device. In one embodiment 5630, the one or more frozen particle compositions include one or more frozen particles including at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

In one embodiment 5640, the at least one agent includes one or more of an adhesive agent, therapeutic agent, reinforcement agent, abrasive, explosive material, or biological remodeling agent. In one embodiment 5650, the adhesive agent, therapeutic agent, reinforcement agent, abrasive, explosive material, or biological remodeling agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

As indicated in FIG. 57, the one or more explosive materials 5710 include at least one of a carbonate, carbon dioxide, nitroglycerine, acid, base, epoxy, acrylic polymer or copolymer, acrylamide polymer or copolymer, urethane, hypoxyapatite, or reactive metal. In one embodiment 5720, the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropyl-maleate, siloxane polymer, polylactic-co-glycolic-acid, poly-3-hydroxybutyrate, poly-4-hydroxybutyrate, polyhydroxy-valerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin. In one embodiment 5730, the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter.

In one embodiment 5740, the therapeutic agent includes at least one of an anti-tumor agent, antimicrobial agent, antiviral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof.

In one embodiment 5810, the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast. In one embodiment 5820, the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly($\alpha$-hydroxyacid), selectin, glutaraldehyde, hydrophobic non-glycosylated protein, hydrogel, peptide hydrogel, or gelatin. In one embodiment 5830, the at least one biological remodeling agent includes one or more of Type I collagen, Type II collagen, Type III collagen, Type VII collagen, Type X collagen, elastin fibers, or soluble elastin.

In one embodiment 5840, the at least one biological remodeling agent is included as part of a carrier that assists in synthesis or activation of the at least one biological remodeling agent.

As indicated in FIG. 59, a method 5900 comprises comparing information 5910 regarding at least one parameter for at least partially constructing or at least partially reconstructing at least one biological tissue of a subject by administering one or more frozen particle compositions to the at least one subject and information regarding at least one clinical outcome following receipt by the at least one subject of one or more frozen particle compositions; and providing output information 5920. In one embodiment 5930, the output information is based on the comparison. In one embodiment 5940, the method further comprises determining at least one statistical correlation. In one embodiment 5950, the method further comprises counting the occurrence of at least one clinical outcome. In one embodiment 5960, the information regarding at least one parameter of at least partially constructing or at least partially reconstructing at least one biological tissue of a subject includes information regarding quantity of cells or tissue at least partially constructed or at least partially reconstructed. In one embodiment 5970, the information regarding at least one parameter of at least partially constructing or at least partially reconstructing at least one biological tissue of a subject includes information regarding at least one cellular or tissue source. In one embodiment 5980, the information regarding at least one parameter of at least partially constructing or at least partially reconstructing at least one biological tissue of a subject includes information regarding at least one abnormal cellular or tissue source. In one embodiment 5990, the information regarding at least one parameter of at least partially constructing or at least partially reconstructing at least one biological tissue of a subject includes information regarding at least one type of cell or tissue.

As indicated in FIG. 60, the at least one agent 6010 includes at least one agent including at least one adhesive agent, abrasive, reinforcement agent, therapeutic agent, biological remodeling agent, or explosive material. In one embodiment 6020, the information regarding at least one parameter of at least partially constructing or at least partially reconstructing at least one biological tissue of a subject includes information regarding at least one dimension of at least one agent deposited. In one embodiment 6030, the information regarding at least one parameter of at least partially constructing or at least partially reconstructing at least one biological tissue of at least one subject includes information regarding at least one dimension of at least one depth, width, or breadth of cellular, tissue, or other material removal or destruction. In one embodiment 6040, the information regarding at least one clinical outcome following receipt by the at least one subject of one or more frozen particle compositions includes information regarding two or more subjects with one or more common attributes.

In one embodiment 6050, the one or more common attributes include one or more of genetic attributes, mental attributes, proteomic attributes, phenotypic attributes, or psychological attributes. In one embodiment 6060, the one or more common attributes include one or more of height, weight, medical diagnosis, familial background, results on one or more medical tests, ethnic background, body mass index, age, presence or absence of at least one disease or condition, species, ethnicity, race, allergies, gender, thickness of tissue, blood vessel condition, hair or fur condition, skin condition, tissue condition, muscle condition, organ condition, nerve condition, brain condition, presence or absence of at least one biological, chemical, or therapeutic agent in the subject, pregnancy status, lactation status, genetic profile, proteomic profile, partial or whole genetic sequence, partial or whole proteomic sequence, medical condition, medical history, or blood condition.

As indicated in FIG. 61, the output information 6110 includes at least one of a response signal, comparison code, comparison plot, diagnostic code, treatment code, test code, code indicative of at least one treatment received, code indicative of at least one prescribed treatment step, code indicative of at least one vaccination administered, code indicative of at least one therapeutic agent administered, code indicative of at least one diagnostic agent administered, code indicative of at least one interaction of an administered agent and at least one biological or chemical agent in the subject; a code indicative of at least one dispertion or location of at least one administered agent; code indicative of at least one detection material administered; code indicative of the depth of penetration of an administered agent, code indicative of the depth of deposition of an administered agent, or a code indicative of the condition of at least one location of an administered frozen particle composition.

In one embodiment 6120, receipt by the at least one subject of one or more frozen particle compositions is pursuant to at least one clinical trial. In one embodiment 6130, the method further comprises determining at least one correlation before the administration of the one or more frozen particle compositions to the at least one subject.

In one embodiment 6140, the method further comprises creating at least one inclusion criterion and at least one exclusion criterion for a clinical trial involving the one or more frozen particle compositions. In one embodiment 6150, the method further comprises suggesting the inclusion of one or more of the at least one subject in at least one clinical trial. In one embodiment 6160, the method further comprises suggesting the exclusion of one or more of the at least one subject in at least one clinical trial.

As indicated in FIG. 62, the method further comprising using one or more of the at least one correlation 6210 to predict at least one clinical outcome regarding at least one second subject. In one embodiment 6220, the at least one second subject has not received the one or more frozen particle compositions. In one embodiment 6230, the method further comprises predicting at least one clinical outcome involving the at least one second subject, wherein the at least one second subject is a plurality of people; and segregating subject identifiers associated with the plurality of people in reference to the predicted at least one clinical outcome. In one embodiment 6240, the method further comprises determining the eligibility of the at least one second subject for the at least one clinical trial.

In one embodiment 6250, the one or more frozen particle compositions include one or more frozen particles including at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

As indicated in FIG. 63, the at least one agent 6310 includes one or more of an adhesive agent, therapeutic agent, reinforcement agent, abrasive, explosive material, or biological remodeling agent. In one embodiment 6320, the adhesive agent, therapeutic agent, reinforcement agent, abrasive, explosive material, or biological remodeling agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer. In one embodiment 6330, the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal. In one embodiment 6340, the at least one adhesive agent includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin.

As indicated in FIG. 64, the one or more reinforcement agents 6410 include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter.

In one embodiment 6420, the therapeutic agent includes at least one of an anti-tumor agent, antimicrobial agent, antiviral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof. In one embodiment 6430, the at least one biological remodeling agent includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast.

As indicated in FIG. 65, the at least one biological remodeling agent 6510 includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde gluronate, Factor XIII, Factor XII, silk, nylon, collagen, silicone, polyurethane, ceramic powder, elastin, pectin, wax, glycosaminoglycan, poly($\alpha$-hydroxyacid), selectin, glutaraldehyde, hydrophobic non-glycosylated protein, hydrogel, peptide hydrogel, or gelatin. In one embodiment 6520, the at least one biological remodeling agent includes one or more of Type I collagen, Type II collagen, Type III collagen, Type VII collagen, Type X collagen, elastin fibers, or soluble elastin. In one embodiment 6530, the at least one biological remodeling agent is included as part of a carrier that assists in synthesis or activation of the at least one biological remodeling agent.

As indicated in FIG. 66, a method 6600 of predicting a clinical outcome of one or more frozen particle composition treatments for at least one first subject, comprises determining 6610 a similarity or a dissimilarity in information regarding at least one parameter for at least partially constructing or at least partially reconstructing at least one biological tissue of at least one first subject by administering one or more frozen particle compositions to the at least one first subject with information regarding at least one parameter of at least partially constructing or at least partially reconstructing at least one biological tissue of at least one second subject, wherein the at least one second subject 6620 attained a clinical outcome following receipt of one or more frozen particle compositions; and providing output information 6630.

In one embodiment 6640, providing output information is based on the determination. In one embodiment 6650, the information regarding at least one parameter of at least partially constructing or at least partially reconstructing at least one biological tissue of at least second subject includes information regarding quantity of cells or tissue at least partially constructed or at least partially reconstructed. In one embodiment 6660, the information regarding at least one parameter of at least partially constructing or at least partially reconstructing at least one biological tissue of at least one first subject includes information regarding at least one cellular or tissue source. In one embodiment 6670, the information regarding at least one parameter of at least partially constructing or at least partially reconstructing at least one biological tissue of at least one first subject includes information regarding at least one abnormal cellular or tissue source.

As indicated in FIG. 67, the information 6710 regarding at least one parameter of at least partially constructing or at least partially reconstructing at least one biological tissue of at least one first subject includes information regarding at least one type of cell or tissue. In one embodiment 6720, the information regarding at least one parameter of at least partially constructing or at least partially reconstructing at least one biological tissue of at least one second subject includes information regarding at least one type of cell or tissue. In one embodiment 6730, the at least one agent includes one or more of an adhesive agent, abrasive, reinforcement agent, therapeutic agent, biological remodeling agent, or explosive material. In one embodiment 6740, the information regarding at least one parameter of at least partially constructing or at least partially reconstructing at least one biological tissue of at least one first subject includes information regarding at least one dimension of at least one agent deposited.

In one embodiment 6750, the information regarding at least one parameter of at least partially constructing or at least partially reconstructing at least one biological tissue of at least one second subject includes information regarding at least one dimension of at least one agent deposited. In one embodiment 6760, the information regarding at least one parameter of at least partially constructing or at least partially reconstructing at least one biological tissue of at least one second subject includes information regarding at least one dimension of at least one depth, width, or breadth of cellular, tissue, or other material removal or destruction. In one embodiment 6770, the information regarding at least one parameter of at least partially constructing or at least partially reconstructing at least one biological tissue of at least one first subject includes information regarding at least one dimension of at least one depth, width, or breadth of cellular, tissue, or other material removal or destruction.

Figure 68:
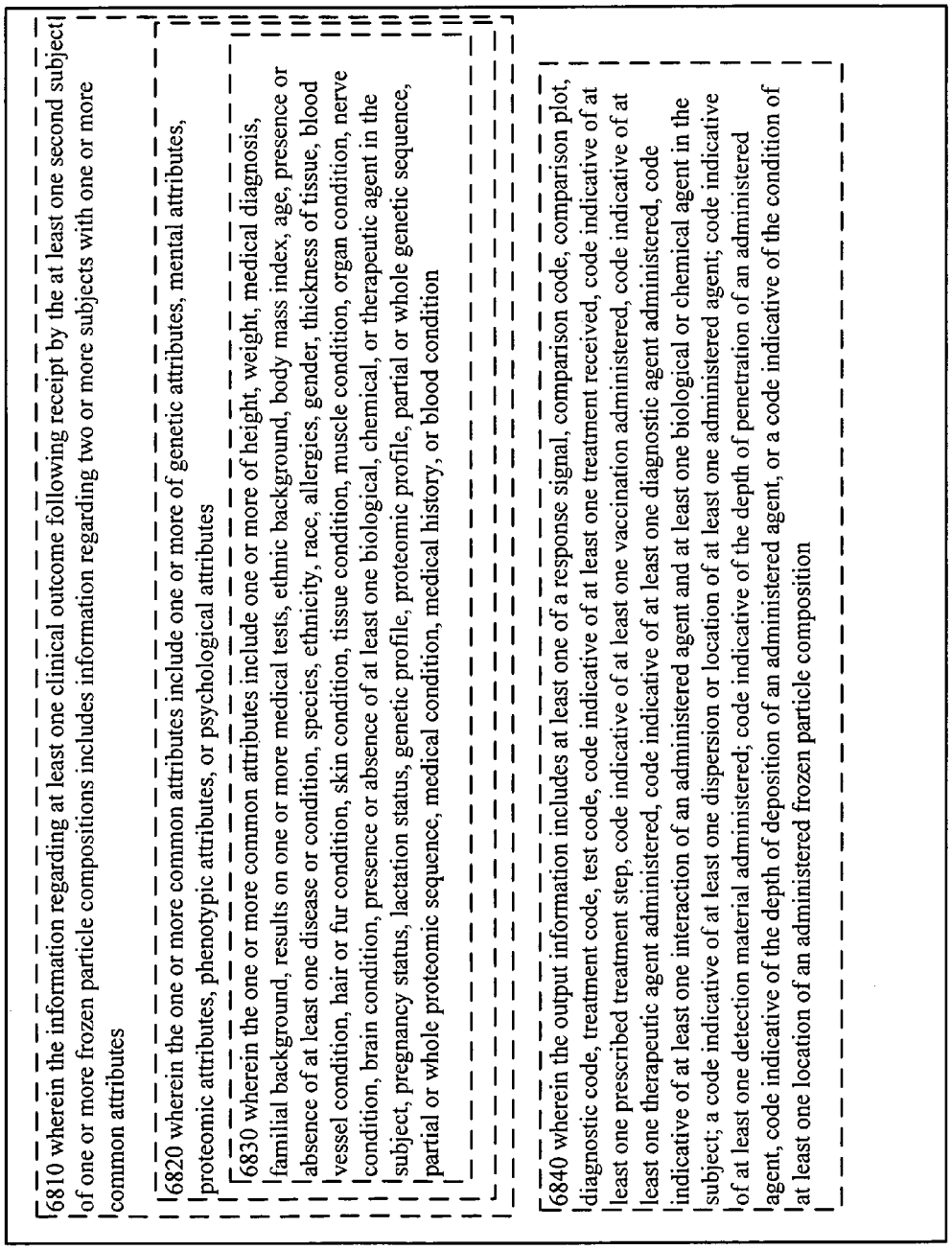
FIG. 68 illustrates a partial view of FIG. 66 in which embodiments may be implemented.

As indicated in FIG. 68, the information 6810 regarding at least one clinical outcome following receipt by the at least one second subject of one or more frozen particle compositions includes information regarding two or more subjects with one or more common attributes. In one embodiment 6820, the one or more common attributes include one or more of genetic attributes, mental attributes, proteomic attributes, phenotypic attributes, or psychological attributes. In one embodiment 6830, the one or more common attributes include one or more of height, weight, medical diagnosis, familial background, results on one or more medical tests, ethnic background, body mass index, age, presence or absence of at least one disease or condition, species, ethnicity, race, allergies, gender, thickness of tissue, blood vessel condition, hair or fur condition, skin condition, tissue condition, muscle condition, organ condition, nerve condition, brain condition, presence or absence of at least one biological, chemical, or therapeutic agent in the subject, pregnancy status, lactation status, genetic profile, proteomic profile, partial or whole genetic sequence, partial or whole proteomic sequence, medical condition, medical history, or blood condition. In one embodiment 6840, the output information includes at least one of a response signal, comparison code, comparison plot, diagnostic code, treatment code, test code, code indicative of at least one treatment received, code indicative of at least one prescribed treatment step, code indicative of at least one vaccination administered, code indicative of at least one therapeutic agent administered, code indicative of at least one diagnostic agent administered, code indicative of at least one interaction of an administered agent and at least one biological or chemical agent in the subject; a code indicative of at least one dispersion or location of at least one administered agent; code indicative of at least one detection material administered; code indicative of the depth of penetration of an administered agent, code indicative of the depth of deposition of an administered agent, or a code indicative of the condition of at least one location of an administered frozen particle composition.

Figure 69:
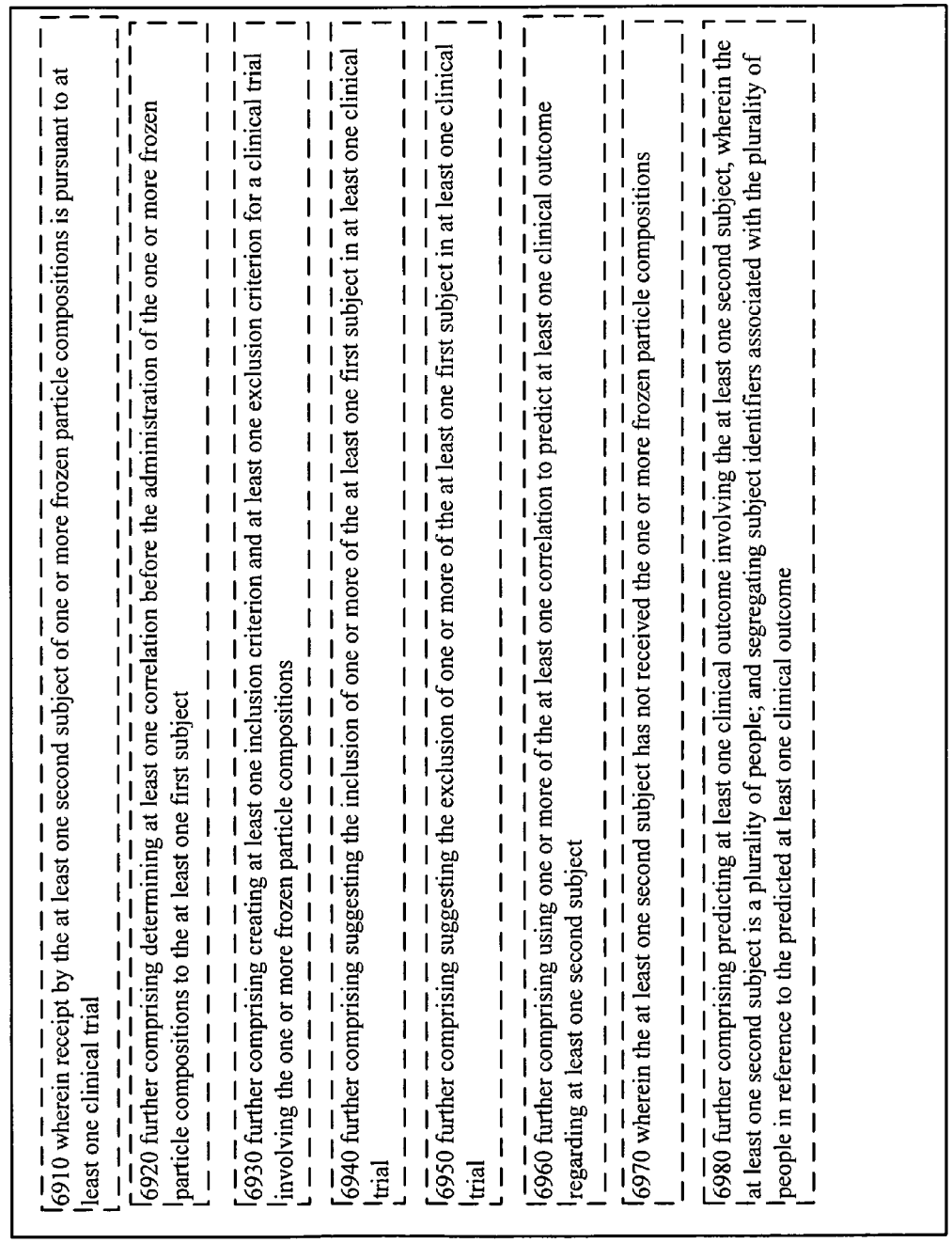
FIG. 69 illustrates a partial view of FIG. 66 in which embodiments may be implemented.

As indicated in FIG. 69, in one embodiment 6910, receipt by the at least one second subject of one or more frozen particle compositions is pursuant to at least one clinical trial. In one embodiment 6920, the method further comprises determining at least one correlation before the administration of the one or more frozen particle compositions to the at least one first subject. In one embodiment 6930, the method further comprises creating at least one inclusion criterion and at least one exclusion criterion for a clinical trial involving the one or more frozen particle compositions. In one embodiment 6940, the method further comprises suggesting the inclusion of one or more of the at least one first subject in at least one clinical trial. In one embodiment 6950, the method further comprises suggesting the exclusion of one or more of the at least one first subject in at least one clinical trial.

In one embodiment 6960, the method further comprises using one or more of the at least one correlation to predict at least one clinical outcome regarding at least one second subject. In one embodiment 6970, the at least one second subject has not received the one or more frozen particle compositions. In one embodiment 6980, the method further comprises predicting at least one clinical outcome involving the at least one second subject, wherein the at least one second subject is a plurality of people; and segregating subject identifiers associated with the plurality of people in reference to the predicted at least one clinical outcome.

As indicated in FIG. 70, in one embodiment 7010, the one or more frozen particle compositions include one or more frozen particles including at least one of hydrogen oxide, nitrogen, oxygen, air, helium, neon, argon, xenon, chlorine, bromine, carbon dioxide, acetone, ethyl acetate, dimethyl sulfoxide, dimethyl formamide, dioxane, tetrahydrofuran, acetonitrile, acetic acid, n-butanol, isopropanol, n-propanol, hexamethylphosphorotriamide, perfluorohydrocarbon, methanol, ethanol, tert-butyl alcohol, formic acid, hydrogen fluoride, ammonia, benzene, carbon tetrachloride, acetonitrile, hexane, dichloromethane, methylene chloride, carboxylic acid, saline, standard saline citrate, methane, toluene, chloroform, polyethylene glycol, acetic acid, Ringer's solution, lactated Ringer's solution, Hartmann's solution, acetated Ringer's solution, phosphate buffered solution, TRIS-buffered saline solution, Hank's balanced salt solution, Earle's balanced salt solution, standard saline citrate, HEPES-buffered saline, dextrose, glucose, methane, or diethyl ether.

In one embodiment 7020, the one or more frozen particle compositions include one or more of an adhesive agent, therapeutic agent, reinforcement agent, abrasive, explosive material, or biological remodeling agent. In one embodiment 7030, the adhesive agent, therapeutic agent, reinforcement agent, abrasive, explosive material, or biological remodeling agent is substantially in the form of at least one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, cell, membrane, nucleic acid, peptide, polypeptide, protein, oligosaccharide, polysaccharide, glycopeptide, glycolipid, sphingolipid, glycosphingolipid, glycoprotein, peptidoglycan, lipid, carbohydrate, metalloprotein, proteoglycan, chromosome, cell nucleus, acid, base, buffer, protic solvent, aprotic solvent, nitric oxide, nitric oxide synthase, nitrous oxide, amino acid, micelle, polymer, bone cement, copolymer, cell receptor, adhesion molecule, cytokine, chemokine, immunoglobulin, antibody, antigen, platelet, extracellular matrix, blood, plasma, cell ligand, zwitterionic material, cationic material, oligonucleotide, nanotube, or piloxymer.

In one embodiment 7040, the one or more explosive materials include at least one of a carbonate, carbon dioxide, nitroglycerine, acid, base, epoxy, acrylic polymer or copolymer, acrylamide polymer or copolymer, urethane, hypoxyapatite, or reactive metal.

As indicated in FIG. 71, the at least one adhesive agent 7110 includes one or more of an acrylic polymer or copolymer, acrylamide polymer or copolymer polymer or copolymer, acrylamide polymer or copolymer, polyacrylic acid, epoxy, urethane, gum arabic, polyester, polyhydroxyalkanoate, poly(L-lactic acid), polyglycolide, polylactic acid, polyether, polyol, polyvinylpyrrolidone, pyroxylin, polymethylacrylate-isobutene-monoisopropylmaleate, siloxane polymer, polylactic-co-glycolic-acid, poly-3-hydroxybutyrate, poly-4-hydroxybutyrate, polyhydroxyvalerate, polydydroxyhexanoate, polydyroxyoctanoate, polycaprolactone, poly(e-caprolactone), sialyl Lewis$^x$, heme group, hemoglobin, healon, carboxymethylcellulose, hydroxyapatite, silicone, cadherin, integrin, hydroxyapatite, polyelectrolyte, maleic polyelectrolyte, cellulose, resilin, cyanoacrylate, isocyanate, 2-octyl cyanoacrylate, 2-butyl-n-cyanoacrylate, n-butyl-2-cyanoacrylate, butyl-2-cyanoacrylate, methyl 2-cyanoacrylate, polyisohexylcyanoacrylate, fibrin, thrombin, fibrinogen, hyaluronate, chitin, Factor XIII, Factor XII, silk, nylon, collagen, glycosaminoglycan, selectin, polyurethane, methacrylate, or polysulfide, polyanhydride, polydioxanone, poly-p-dioxanone, silicone, albumin, glutaraldehyde, polyethylene glycol, or gelatin.

In one embodiment 7120, the one or more reinforcement agents include one or more of polyaramid, vinylester matrix, metal, ceramic, fiberglass, cellulose, broad carbide, aromatic polyamide, nylon, silk, rayon, acetate, modacrylic, olefin, acrylic, polyester, aromatic polyester, poly-lactic acid, vinyon, saran, spandex, vinalon, aromatic nylon, vinylidene chloride, modal, polybenzimidazole, sulfur, lyocell, orlon, zylon, high-performance polyethylene, polypyridobenzimidazole, vectran, acrylonitrile rubber, glass, copper, iron, steel, sodium, potassium, calcium, zinc, manganese, carbon, magnesium, silicon, silica, frozen hydrogen oxide ice, plant matter, animal matter, or mineral matter.

In one embodiment 7130, the therapeutic agent includes at least one of an anti-tumor agent, antimicrobial agent, antiviral agent, analgesic, antiseptic, anesthetic, diagnostic agent, anti-inflammatory agent, vaccine, cell growth inhibitor, cell growth promoter, immunogen, antigen, radioactive agent, apoptotic promoting factor, enzymatic agent, angiogenic factor, anti-angiogenic factor, hormone, vitamin, mineral, nutraceutical, cytokine, chemokine, probiotic, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof.

As indicated in FIG. 72, the at least one biological remodeling agent 7210 includes one or more of a blood cell, chondrocyte, endothelial cell, hepatocyte, keratinocyte, myocyte, osteoblast, osteoclast, osteocyte, mesenchymal cell, stem cell, progenitor cell, or fibroblast. In one embodiment 7220, the at least one biological remodeling agent includes one or more of calcium phosphate, albumin, cytokine, pegylated cytokine, bone, cartilage, globulin, fibrin, thrombin, glutaraldehyde-crosslinked pericardium, hide powder, hyaluronic acid, hydroxylapatite, keratin, ligament, nitinol, nucleic acid polymers, polyethylene, polyethylene glycol, polyethylene glycol diacrylate, polyethylene terephthalate fiber, polyglycol, polylactate, polytetrafluoroethylene, polylactic acid, polyglycolic acid, polycaprolactone, PURAMATRIX™ self-assembly peptide hydrogel fibers, linear aliphatic polyester, tendon, fibrinogen, hyaluronate, chitin, chitosan, methylcellulose, alginate, hyaluronic acid, agarose, cellulose, polyaldehyde glutonate, Factor XIII, Factor XII, silk, nylon, collagen, silicone, polyurethane, ceramic powder, elastin, pectin, wax, glycosaminoglycan, poly($\alpha$-hydroxyacid), selectin, glutaraldehyde, hydrophobic non-glycosylated protein, hydrogel, peptide hydrogel, or gelatin. In one embodiment 7230, the at least one biological remodeling agent includes one or more of Type I collagen, Type II collagen, Type III collagen, Type VII collagen, Type X collagen, elastin fibers, or soluble elastin. In one embodiment 7240, the at least one biological remodeling agent is included as part of a carrier that assists in synthesis or activation of the at least one biological remodeling agent.

Figure 73:
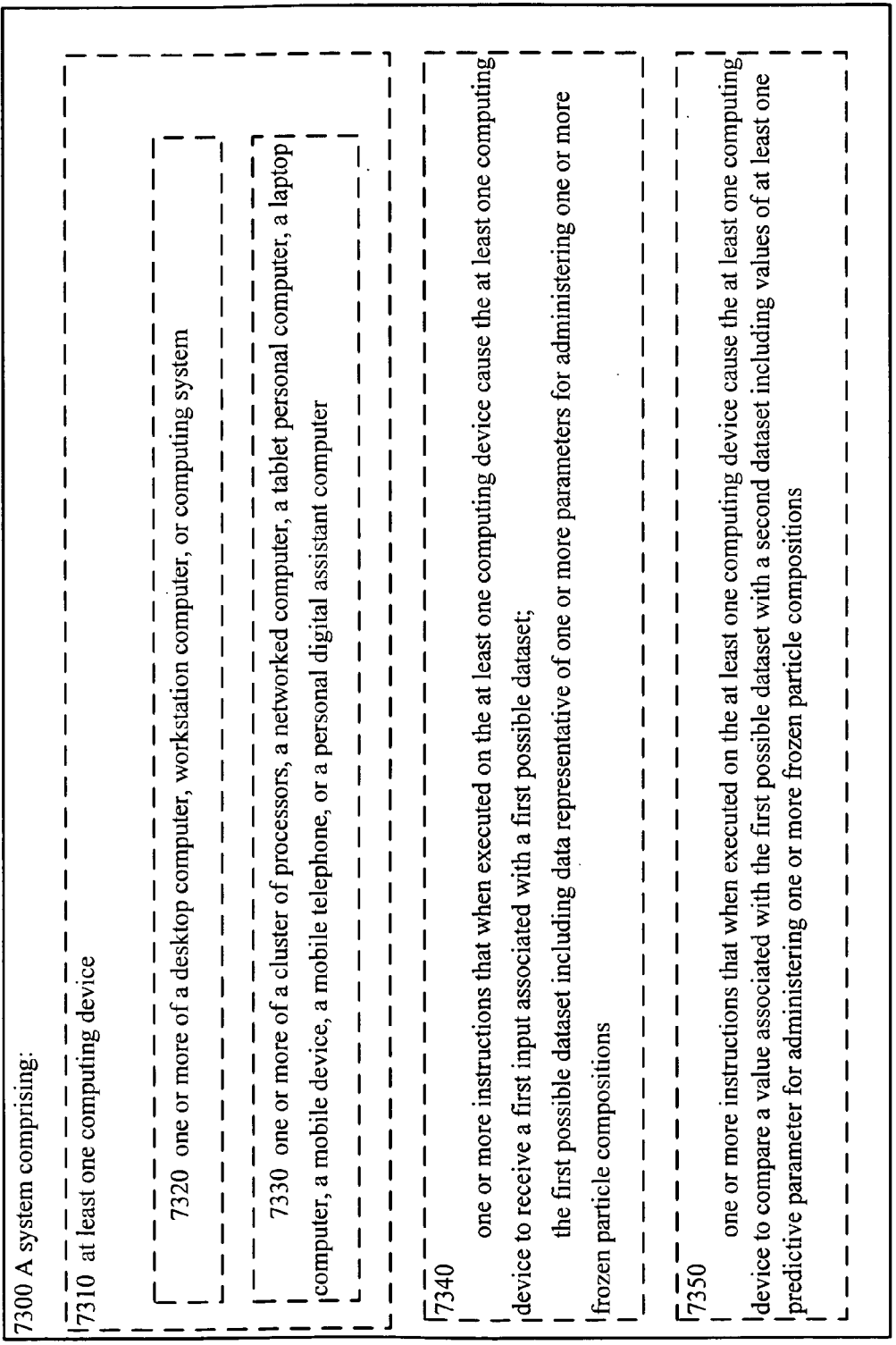
FIG. 73 illustrates a partial view of a system 7300 in which embodiments may be implemented.

As indicated in FIG. 73, a system 7300 comprises at least one computing device 7310; one or more instructions 7340 that when executed on the at least one computing device cause the at least one computing device to receive a first input associated with a first possible dataset, the first possible dataset including data representative of one or more parameters for administering one or more frozen particle compositions. In one embodiment 7350, the system further comprises one or more instructions that when executed on the at least one computing device cause the at least one computing device to compare a value associated with the first possible dataset with a second dataset including values of at least one predictive parameter for administering one or more frozen particle compositions. In one embodiment 7320, the at least one computing device includes one or more of a desktop computer, workstation computer, or computing system. In one embodiment 7330, the at least one computing system includes one or more of a cluster of processors, a networked computer, a tablet personal computer, a laptop computer, a mobile device, a mobile telephone, or a personal digital assistant computer.

As indicated in FIG. 74, the system further comprises one or more instructions 7460 that when executed on the at least one computing device cause the at least one computing device to determine a graphical illustration of the second possible dataset.

In one embodiment 7410, the system further comprises one or more instructions that when executed on the at least one computing device cause the at least one computing device to determine from the comparison at least one parameter for administering one or more frozen particle compositions. In one embodiment 7420, the system further comprises one or more instructions that when executed on the at least one computing device cause the at least one computing device to generate at least one response based on the determination. In one embodiment 7430, the system further comprises one or more instructions that when executed on the at least one computing device cause the at least one computing device to access the first possible dataset in response to the first input. In one embodiment 7440, the system further comprises one or more instructions that when executed on the at least one computing device cause the at least one computing device to generate the first possible dataset in response to the first input. In one embodiment 7450, the system further comprises one or more instructions that when executed on the at least one computing device cause the at least one computing device to determine a graphical illustration of the first possible dataset.

Figure 75:
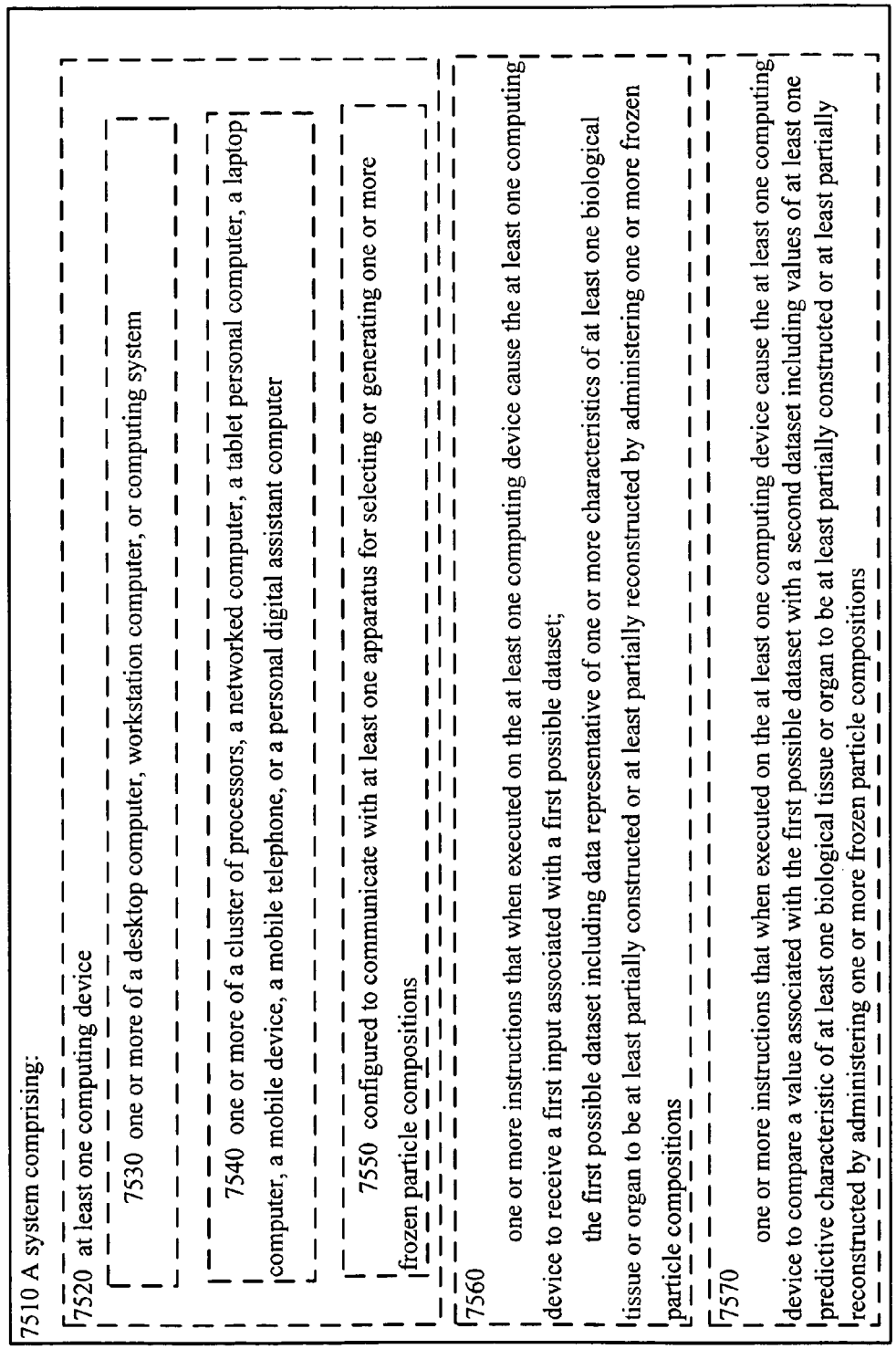
FIG. 75 illustrates a partial view of a system 7510 in which embodiments may be implemented.

As indicated in FIG. 75, a system 7510 comprises at least one computing device 7520; one or more instructions 7560 that when executed on the at least one computing device cause the at least one computing device to receive a first input associated with a first possible dataset, the first possible dataset including data representative of one or more characteristics of at least one biological tissue or organ to be at least partially constructed or at least partially reconstructed by administering one or more frozen particle compositions. In one embodiment 7570, the system further comprises one or more instructions that when executed on the at least one computing device cause the at least one computing device to compare a value associated with the first possible dataset with a second dataset including values of at least one predictive characteristic of at least one biological tissue or organ to be at least partially constructed or at least partially reconstructed by administering one or more frozen particle compositions.

In one embodiment 7530, the at least one computing device includes one or more of a desktop computer, workstation computer, or computing system. In one embodiment 7540, the at least one computing system includes one or more of a cluster of processors, a networked computer, a tablet personal computer, a laptop computer, a mobile device, a mobile telephone, or a personal digital assistant computer. In one embodiment 7550, the at least one computing device is configured to communicate with at least one apparatus for selecting or generating one or more frozen particle compositions.

As indicated in FIG. 76, the system further comprises one or more instructions 7610, that when executed on the at least one computing device cause the at least one computing device to determine a graphical illustration of the second possible dataset. In one embodiment 7620, the system further comprises one or more instructions that when executed on the at least one computing device cause the at least one computing device to determine from the comparison at least one characteristic of the at least one biological tissue or organ to be at least partially constructed or at least partially reconstructed by administering one or more frozen particle compositions. In one embodiment 7630, the system further comprises one or more instructions that when executed on the at least one computing device cause the at least one computing device to generate at least one response based on the determination.

In one embodiment 7640, the system further comprises one or more instructions that when executed on the at least one computing device cause the at least one computing device to access the first possible dataset in response to the first input. In one embodiment 7650, the system further comprises one or more instructions that when executed on the at least one computing device cause the at least one computing device to generate the first possible dataset in response to the first input. In one embodiment 7660, the system further comprises one or more instructions that when executed on the at least one computing device cause the at least one computing device to determine a graphical illustration of the first possible dataset.

Figure 77:
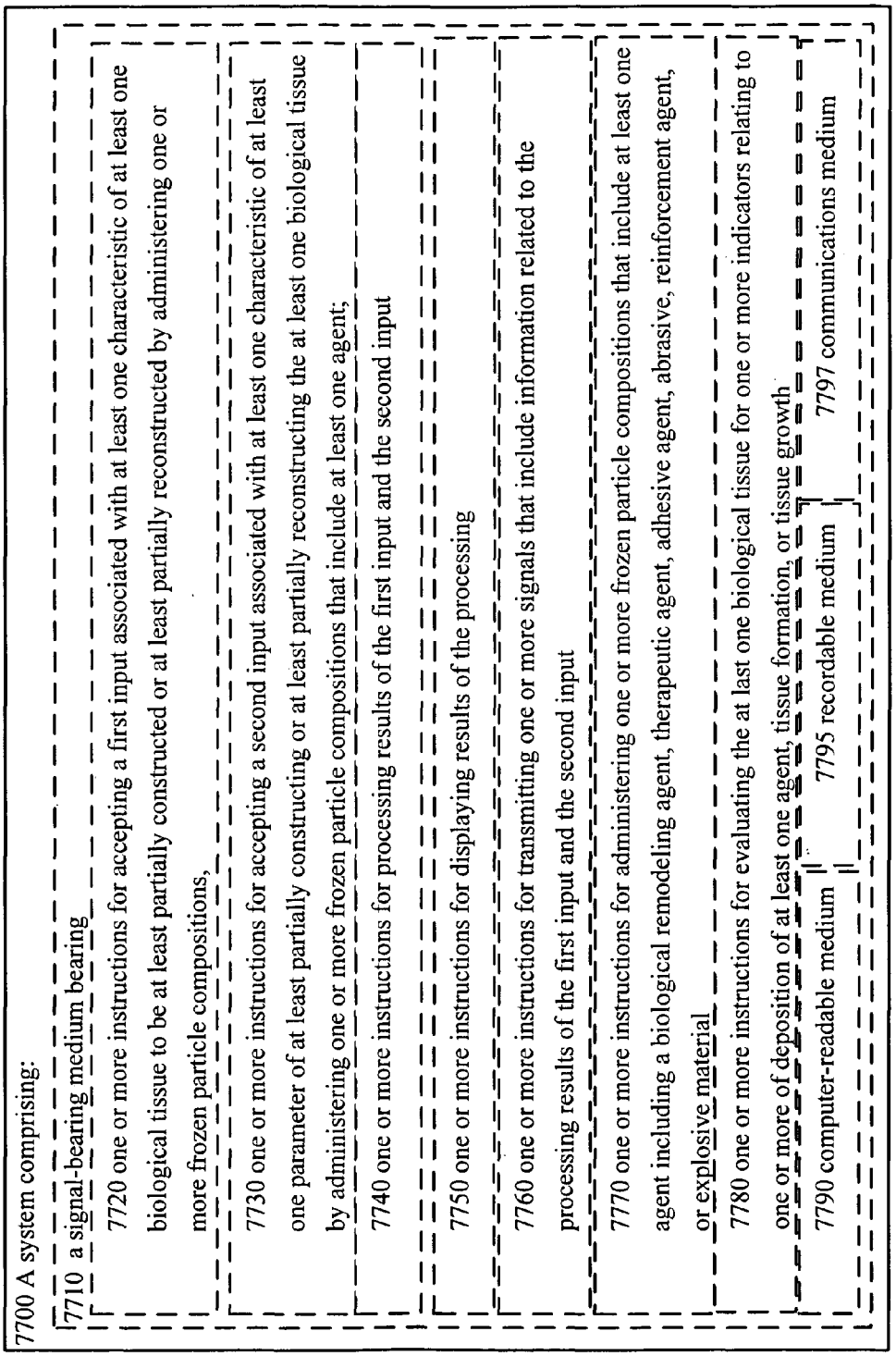
FIG. 77 illustrates a partial view of a system 7700 in which embodiments may be implemented.

As indicated in FIG. 77, a system 7700 comprises a signal-bearing medium 7710 bearing one or more instructions 7720 for accepting a first input associated with at least one characteristic of at least one biological tissue to be at least partially constructed or at least partially reconstructed by administering one or more frozen particle compositions; one or more instructions 7730 for accepting a second input associated with at least one characteristic of at least one parameter of at least partially constructing or at least partially reconstructing the at least one biological tissue by administering one or more frozen particle compositions that include at least one agent; and one or more instructions 7740 for processing results of the first input and the second input. In one embodiment 7750, the system further comprising one or more instructions for displaying results of the processing.

In one embodiment 7760, the system further comprises one or more instructions for transmitting one or more signals that include information related to the processing results of the first input and the second input. In one embodiment 7770, the system further comprises one or more instructions for administering one or more frozen particle compositions that include at least one agent including: biological remodeling agent, therapeutic agent, adhesive agent, abrasive, reinforcement agent, or explosive material. In one embodiment, the system 7780 further comprises one or more instructions for evaluating the at least one biological tissue for one or more indicators relating to one or more of: deposition of at least one agent, tissue formation, or tissue growth.

In one embodiment 7790, the signal-bearing medium includes a computer-readable medium. In one embodiment 7795, the signal-bearing medium includes a recordable medium. In one embodiment 7797, the signal-bearing medium includes a communications medium.

As indicated in FIG. 78, a computer program product 7800 comprises a signal-bearing medium 7810 bearing one or more instructions 7820 for accepting a first input associated with at least one characteristic of at least one biological tissue to be at least partially constructed or at least partially reconstructed by administering one or more frozen particle compositions; one or more instructions 7830 for accepting a second input associated with at least one characteristic of at least one parameter of at least partially constructing or at least partially reconstructing the at least one biological tissue by administering one or more frozen particle compositions that include at least one agent; and one or more instructions 7840 for processing results of the first input and the second input.

In one embodiment 7850, the computer program product further comprises one or more instructions for displaying results of the processing. In one embodiment 7860, the computer program product further comprises one or more instructions for transmitting one or more signals that include information related to the processing results of the first input and the second input. In one embodiment 7870, the computer program product further comprises one or more instructions for administering one or more frozen particle compositions that include at least one agent including biological remodeling agent, therapeutic agent, adhesive agent, abrasive, reinforcement agent, or explosive material.

In one embodiment 7880, the computer program product further comprises one or more instructions for evaluating the at least one biological tissue for one or more indicators relating to one or more of deposition of at least one agent, tissue formation, or tissue growth.

In one embodiment 7890, the signal-bearing medium includes a computer-readable medium. In one embodiment 7895, the signal-bearing medium includes a recordable medium. In one embodiment 7897, the signal-bearing medium includes a communications medium.

As indicated in FIG. 79, a system 7900 comprises circuitry 7910 for accepting a first input associated with at least one characteristic of at least one biological tissue to be at least partially constructed or at least partially reconstructed by administering one or more frozen particle compositions; circuitry 7920 for accepting a second input associated with at least one characteristic of at least one parameter of at least partially constructing or at least partially reconstructing the at least one biological tissue by administering one or more frozen particle compositions that include at least one agent; and circuitry 7930 for processing results of the first input and the second input. In one embodiment 7940, the system further comprises circuitry for displaying results of the processing. In one embodiment 7950, the system further comprises circuitry for transmitting one or more signals that include information related to the processing results of the first input and the second input. In one embodiment 7960, the system further comprises circuitry for administering one or more frozen particle compositions that include at least one agent including at least one biological remodeling agent, therapeutic agent, adhesive agent, abrasive, reinforcement agent, or explosive material. In one embodiment 7970, the system further comprises circuitry for evaluating the at least one biological tissue for one or more indicators relating to one or more of deposition of at least one agent, tissue formation, or tissue growth.

As indicated in FIG. 80, a system 8000 comprises at least at least one computer program 8010, configured with a computer-readable medium, for use with at least one computer system and wherein the computer program includes a plurality of instructions including but not limited to: one or more instructions 8020 for accepting a first input associated with at least one characteristic of at least one biological tissue to be at least partially constructed or at least partially reconstructed by administering one or more frozen particle compositions; one or more instructions 8030 for accepting a second input associated with at least one characteristic of at least one parameter of at least partially constructing or at least partially reconstructing the at least one biological tissue by administering one or more frozen particle compositions that include at least one agent; and one or more instructions 8040 for processing results of the first input and the second input.

In one embodiment 8050, the system further comprises one or more instructions for displaying results of the processing. In one embodiment 8060, the system further comprises one or more instructions for transmitting one or more signals that include information related to the processing results of the first input and the second input.

In one embodiment 8070, the system further comprises one or more instructions for administering one or more frozen particle compositions that include at least one agent including biological remodeling agent, therapeutic agent, adhesive agent, abrasive, reinforcement agent, or explosive material. In one embodiment 8080, the system further comprises one or more instructions for evaluating the at least one biological tissue for one or more indicators relating to one or more of deposition of at least one agent, tissue formation, or tissue growth.

Figure 81:
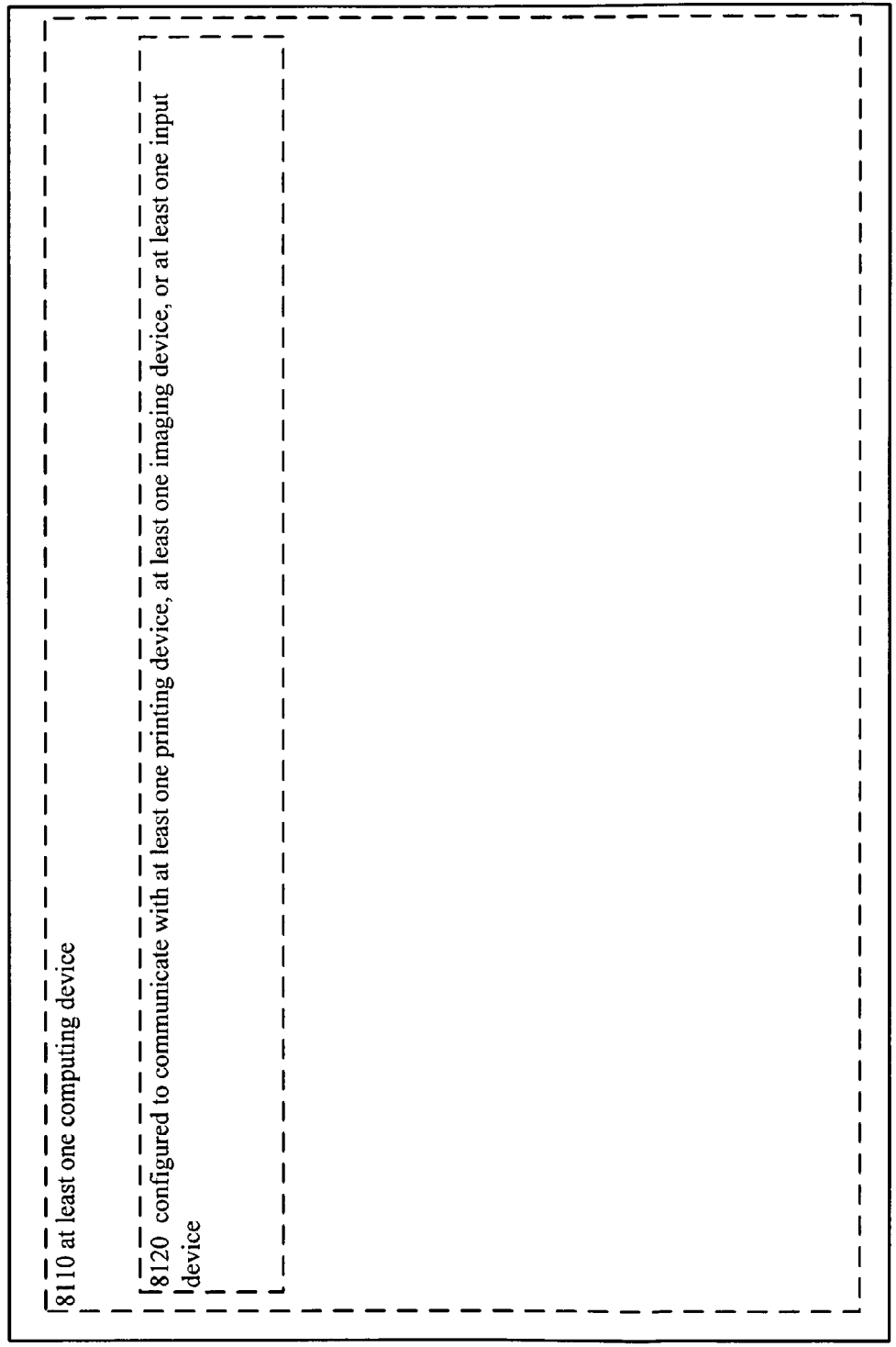
FIG. 81 illustrates a partial view of FIG. 80 in which embodiments may be implemented.

As indicated in FIG. 81, the system further comprises at least one computing device 8110. In one embodiment 8120, the at least one computing device is configured to communicate with at least one printing device, at least one imaging device, or at least one input device.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

For any of the various aspects and embodiments disclosed herein, one or more kits can be developed with the components described herein. In one embodiment, a kit includes one or more frozen particle compositions as described herein. In one embodiment, a kit includes one or more frozen particle compositions and at least one therapeutic agent as disclosed herein. In one embodiment, a kit includes one or more frozen particle compositions and one or more reinforcement agents. In one embodiment, a kit includes one or more frozen particle compositions and one or more explosive materials.

PROPHETIC EXAMPLES

Example 1

Compositions and Methods of Making Frozen Particles

Frozen particle compositions suitable for various embodiments described herein can be produced by controlling the pressure and temperature of hydrogen oxide that is introduced as a liquid, gas or frozen. Frozen particle compositions, including frozen hydrogen oxide ice Ic, are produced by cooling small hydrogen oxide droplets (~6 μm diameter) below −38° C. (See e.g., Murray, et al., Phys. Chem. Chem. Phys. vol. 8, pp. 186-192 (2006), which is incorporated herein by reference). Emulsions of 30-40% by weight of distilled and de-ionized hydrogen oxide in paraffin oil (Fisher Scientific) are agitated to produce hydrogen oxide droplets of mean diameters ranging from 5 to 35 μm as determined by optical microscopy. The droplets are cooled to −100° C. at a rate of 10° C./min by using a cryostat cooled with liquid nitrogen and containing a heater and temperature controller. Freezing liquid droplets with a median diameter of 5.6 μm or smaller can provide approximately 80% frozen ice Ic and approximately 20% frozen ice Ih. Following the procedures of Murray et al, selective production of ice Ic in pellet form produces quantities suitable for use in various embodiments described herein.

Frozen particles generated in this manner are utilized for abrasion of at least one biological tissue, including but not limited to skin. The frozen particle composition is administered to at least one biological tissue by, for example, accelerating, ejecting, or propelling the frozen particles by way of a carrier gas under pressure (e.g., air, carbon dioxide, nitrogen) through a tube, or other device directed toward at least one biological tissue, such as skin. Microdermabrasion, microscissuining, or other surface abrasion techniques are carried out in a similar fashion.

Example 2

Compositions and Methods of Making Frozen Particles

Frozen particles, including frozen hydrogen oxide ice Ic, are produced by depositing hydrogen oxide vapor onto a copper plate held at low temperatures in vacuo. Purified (deionized) hydrogen oxide is added to a vessel at approximately 25° C. and the hydrogen oxide vapor is condensed onto a metal plate held at approximately −196° C. in vacuo. The deposited amorphous ice is heated (at 10° C./min) to approximately −93° C. and is converted to crystalline cubic ice (ice Ic). Ice Ic is stable when stored under liquid nitrogen (See e.g., Johari, et al., J. Phys. Chem, vol. 94, pp. 1212-1214 (1990), which is incorporated herein by reference). An example of an apparatus that is used to produce frozen hydrogen oxide ice Ic is described in Hallbrucker et al (J. Phys. Chem., vol. 93, pp. 4986-4990 (1989), which is incorporated herein by reference).

Example 3

Compositions and Methods of Making Frozen Particles

Frozen hydrogen oxide ice Ic particles are produced from small hydrogen oxide droplets in an example of a "pelletizer" apparatus similar to those described by, for example, U.S. Pat. No. 4,617,064; U.S. Pat. No. 6,306,119, which are incorporated herein by reference. Frozen hydrogen oxide ice Ic particles are formed by spraying hydrogen oxide droplets of the desired size into a cooling chamber filled with a cold inert gas maintained at the desired temperature, for example, nitrogen gas maintained at approximately −100° C. to promote formation of ice Ic. Spray droplet size is maintained by variation of nozzle/orifice size and hydrogen oxide pressure to yield droplet diameters ranging from nanometers to centimeters. Frozen hydrogen oxide ice Ic, ice Ih, amorphous low density ice, amorphous high density ice, and other forms are produced by controlling the temperature and pressure of the cooling chamber. Cubic hydrogen oxide ice Ic particles are formed in a step-wise process, by maintaining the chamber at a very low temperature (approximately −196° C.) with increased pressure, which first promotes formation of amorphous hydrogen oxide ice. Next, the chamber is heated to approximately −93° C., which results in transformation to cubic hydrogen oxide ice (ice Ic) particles.

The hydrogen oxide ice particles are propelled into a delivery system (such as tubing and nozzle) by nitrogen gas under pressure. The delivery system is maintained at the appropriate temperature for preservation of the hydrogen oxide particle structure, (e.g., approximately −93° C. for ice Ic structure).

Example 4

Compositions and Methods of Making Frozen Carbon Dioxide Particles

Carbon dioxide frozen particles are produced from small carbon dioxide droplets in a "pelletizer" similar to those described by, for example, U.S. Pat. No. 4,617,064; and U.S. Pat. No. 6,306,119; each of which is incorporated herein by reference. Carbon dioxide frozen particles are formed by spraying liquid carbon dioxide droplets into a cooling chamber maintained at low temperatures (e.g., approximately −100° C.). Droplet size is regulated by varying nozzle or orifice size, and pressure. Carbon dioxide droplet diameters range, for example, from nanometers to centimeters. The frozen carbon dioxide particles are propelled into a delivery system (e.g., tubing and nozzle) by carrier gas, (e.g., air or nitrogen) under pressure. The carbon dioxide particles are maintained while in the delivery system at the appropriate temperature, (e.g., approximately −100° C.). Frozen carbon dioxide particles sublimate, or transition to a gas phase, at approximately −78.5° C. and 1 atm pressure.

Example 5

Compositions and Methods of Making Frozen DMSO Particles

Dimethyl sulfoxide (DMSO) frozen particles are produced from DMSO droplets, for example, in a "pelletizer" apparatus similar to those described by, for example, U.S. Pat. No. 4,617,064; U.S. Pat. No. 6,306,119; which are incorporated herein by reference. DMSO frozen particles are formed from spraying liquid DMSO droplets of the desired size into a cooling chamber that is maintained at low temperature, for example, less than approximately 18.5° C. Droplet size is regulated by varying nozzle or orifice size, and pressure, with compressed air as a carrier gas. Droplet size can be regulated by varying nozzle or orifice size, and DMSO pressure. DMSO droplet diameters range, for example, from nanometers to centimeters. The DMSO frozen particles are propelled by a carrier gas (e.g., air or nitrogen) under pressure to enter a delivery system (e.g., tubing and nozzle). In order to preserve DMSO particle structure, the delivery system is maintained at low temperature (e.g., less than approximately 18.5° C.).

Example 6

Methods of Assessment or Selection of Frozen Particles

According to various embodiments described herein, at least one frozen particle is made by lowering the temperature of liquid droplets of a selected material. Droplet and particle sizes are measured by imaging a spray or particle stream upon a background screen. The background screen is illuminated with a short pulse of light, for example, from an infrared laser beam (at approximately 805 nm), which is capable of pulsing at frequencies of approximately 1000 Hz.

A digital camera captures high resolution images of the droplets or particles. High-speed, real-time particle sizing software analyses the images to assess the diameter distribution for the particles and to determine the shape. The diameter of each droplet is determined automatically by referencing the number of dark pixels in the droplet image to the pixel area of a calibration circle. Droplet diameters between approximately 100 μm (±3.2%) and approximately 2000 μm (±0.03%) were measured with 95% confidence (See e.g., Ireland et al., 6th ASME-JSME Thermal Engineering Joint Conference (2003), which is incorporated herein by reference). Instruments, computer programs and protocols for measuring particle and droplet size are available, for example, from Oxford Lasers, Shirley, Mass. (e.g., world wide web at oxfordlasers.com, which is incorporated herein by reference).

Example 7

Methods of Assessment or Selection of Frozen Particles

According to various embodiments described herein, at least one frozen particle is made by lowering the temperature of liquid droplets of a selected material. Droplet and particle sizes are measured by laser diffraction. Laser diffraction based particle size analysis relies on particles passing through a laser beam and scattering light at an angle that is directly related to their size. As particle size decreases, the observed scattering angle increases logarithmically. Scattering intensity is also dependent on particle size, and decreases with decreasing particle volume. Thus, large particles scatter light at narrow angles with high intensity whereas small particles scatter at wider angles but with low intensity. Laser diffraction is used for the non-destructive analysis of wet or dry samples, to measure particles in the size range 0.02 to 2000 micrometers (e.g., world wide web at chemie.de/articles/e/61205/, which is incorporated herein by reference). A laser diffraction instrument, protocols and analysis software are available, for example, from Malvern Instruments Ltd. (Malvern, Worcestershire, WR14 1XZ United Kingdom).

Example 8

Compositions and Methods of Making Frozen Particles Including a Reinforcement Agent One or more reinforcement agents are added to the frozen particles during the formation process. Among other things, reinforcement agents can increase the strength of frozen particles (e.g., increase the modulus of rupture of ice) and decrease the deformation of frozen particles (e.g., decrease the beam deflection of ice). As indicated in Table A below, glass fibers present at 9% (wt./vol.), for example, increase the modulus of rupture of ice by approximately 7-fold relative to ice derived from unreinforced hydrogen oxide ice (See e.g., Kingery, Science, vol. 134, pp. 164-168 (1960), which is incorporated herein by reference).

TABLE A

Strength of fresh ice with sawdust and Fiberglass, respectively, added. Additions were % wt./vol. (Kingery, Ibid).

| Addition (%) | Modulus of rupture (kg/cm²) | |
|---|---|---|
| | Sawdust (−17° C.) | Fiberglass (−20° C.) |
| 0 | 22.5 | 24.1 |
| 0.8 | 22.7 | 24.0 |
| 2.5 | 35 | 65.4 |
| 9.0 | 60 | 161 |
| 14.0 | 66.7 | N/A |

Figure 5:
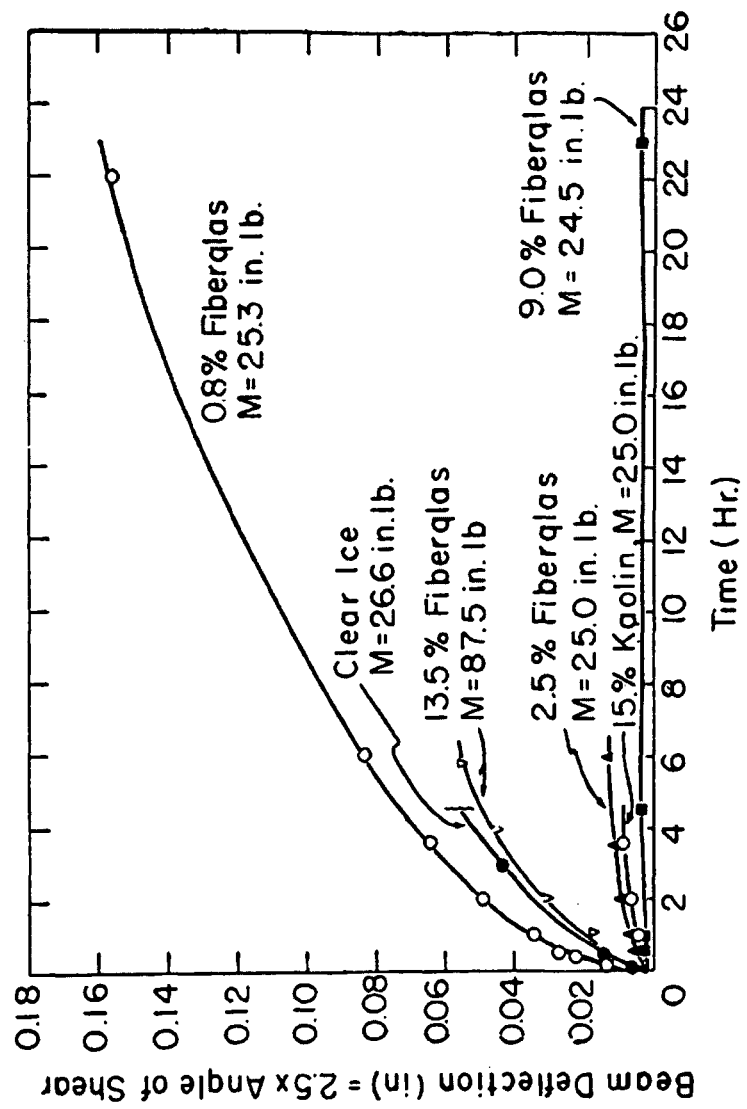
FIG. 5 illustrates the strength of hydrogen oxide samples reinforced with fiberglass or kaolin.

As indicated in FIG. 5, the beam deflection is less than 0.005 inches for hydrogen oxide ice that is reinforced with approximately 9.0% glass fibers and increases over time for hydrogen oxide ice that is reinforced with approximately 0.8% glass fibers (Kingery, Ibid). Furthermore, hydrogen oxide ice with approximately 9% (w/v) of glass fibers is not deformed over 23 hours under an applied force of approximately 24.5 in·lbs. As described in Kingery, et al, and as indicated in FIG. 5, beam deflection of hydrogen oxide ice with approximately 0.8% glass fibers is approximately 0.16 inches after 23 hours under 25.3 in·lbs. of force. Likewise, as indicated in FIG. 5, and according to Kingery et al, hydrogen oxide ice without reinforcement agents is deformed approximately 0.05 inches after 4 hours under approximately 26.6 in·lbs. of force. Additionally, aluminum and silica carbonate particles can be mixed at various volume fractions and co-milled under an argon atmosphere to produce nanocrystalline composites as reinforcement agents for frozen particle compositions. (See e.g., Kamrani, et al., Powder Met. vol. 50, pp. 276-282(7) (2007), which is incorporated herein by reference).

Example 9

Compositions and Methods of Making Frozen Particles

Frozen particles (e.g., carbon dioxide, DMSO, gelatin) are reinforced by incorporating one or more reinforcement agents, including but not limited to silica beads, fiberglass, polyethylene glycol, kaolin, or wood fibers.

Silica beads approximately 1 micrometer in diameter are mixed with hydrogen oxide at approximately 0° C. to make volume fractions including the approximate ranges, but not limited to, 0, 0.004, 0.04, 0.15, 0.29, 0.49 and 0.63 volume fraction. The volume fractions, or one or more particular volume fraction, are frozen in, for example, a cylindrical mold, at low temperatures (e.g., approximately −10° C.). Unconfined coaxial compression tests are used to determine the maximum stress (also known as the failure point) of the one or more frozen particles at defined temperatures and strain rates (See e.g., Yasui et al, Geophys. Res. Lett., vol. 35, L12206, (2008), which is incorporated herein by reference).

Figure 6:
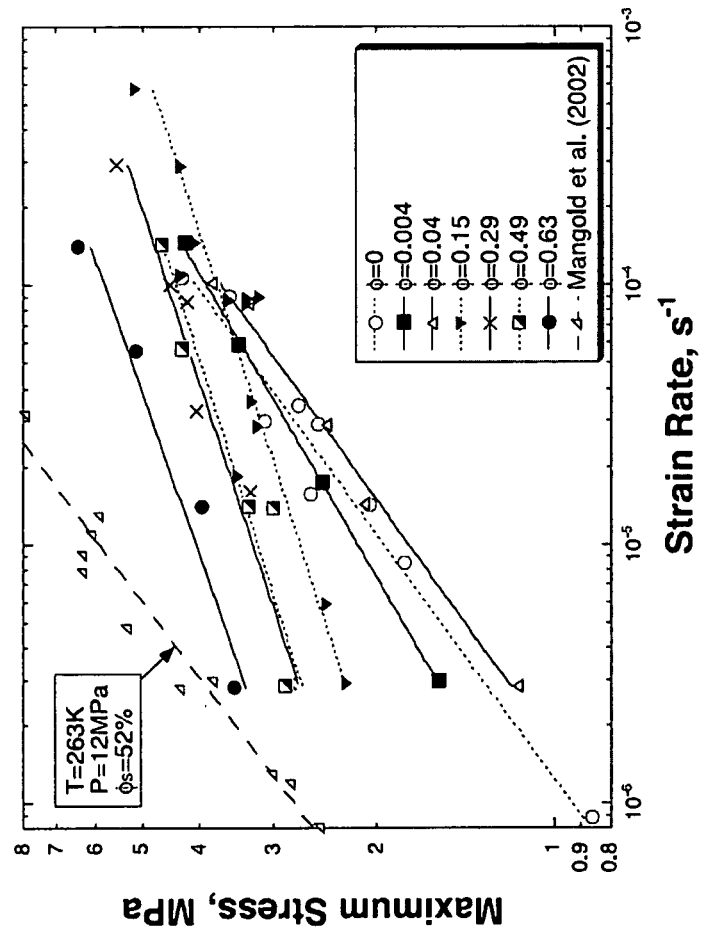
FIG. 6 illustrates the strength of hydrogen oxide samples reinforced with a reinforcement agent.

As indicated in FIG. 6, maximum stress values (MPa) increase for mixtures with an increased volume fraction of silica beads relative to the maximum stress for unreinforced hydrogen oxide ice. (See e.g., Yasui et al, Ibid.) φ=silica volume fraction The strength of specific frozen particles is altered by varying the composition of frozen particle mixtures containing one or more reinforcement agents. For example, Table B indicates the frozen particle strength of frozen particles including hydrogen oxide, DMSO, carbon dioxide, and gelatin, which contain at least one reinforcement agent. As indicated, the reinforced frozen particles exhibited increased strength compared to their unreinforced counterparts. As indicated in Table B, frozen particles containing at least one reinforcement agent at the volume fractions shown in the table displayed maximal strength in compression tests. (See also, FIGS. 5 and 6, as well as Table A herein for hydrogen oxide frozen particle strength).

TABLE B

Frozen particles and reinforcement agents leading to increased particle strength

| Particle Base | Fiber Glass | Saw Dust | Silica Beads | PEG | Kaolin |
|---|---|---|---|---|---|
| Ice | 0.15* | 0.14 | 0.63 | ND | 0.15 |
| DMSO | 0.15 | 0.14 | 0.63 | ND | 0.15 |
| carbon dioxide | 0.15 | 0.14 | 0.63 | ND | 0.15 |
| gelatin | 0.15 | 0.14 | 0.63 | ND | 0.15 |

Volume fraction for reinforcement agents in frozen particle base materials is given.
ND = Not Determined. (Yasui, et al.)

Example 10

Vaccine Compositions and Methods of Making Frozen Particles

As described herein, immunization of a subject with a vaccine is accomplished by way of introduction of the vaccine through, for example, subcutaneous, transcutaneous or intramuscular administration. (See e.g., Berzofsky et al, Nat. Rev. Immunol. vol. 1, pp. 209-219, (2001), which is incorporated herein by reference). Non-limiting examples of frozen particle vaccines are described herein, and include one or more immunogens. The immunogen therapeutic compositions are made, for example, in solution or as a solid in suspension or as a colloid created from, for example, buffered solutions (e.g., phosphate, citrate, lactate, pyruvate or an organic acid buffer) that optimize the stability and immunogenicity of the vaccine.

Storage stability of vaccines depends upon many factors, including vaccine formulation and storage temperature. For example, an influenza subunit vaccine formulated with trehalose, and Hepes buffered saline, is stable at room temperature for approximately 26 weeks (See e.g., Amorij et al, Pharm. Res. vol. 25, pp. 1256-1273 (2008), which is incorporated herein by reference).

Vaccines with adjuvants such as: N-acetyl muramyl-l-alanyl-d-isoglutamine, also called muramyl dipeptide (MDP) or monophosphoryl lipid A (MPL) elicit enhanced cellular and humoral immunity (See e.g., Aguilar et al Vaccine vol. 25, pp. 3752-62 (2007), which is incorporated herein by reference).

Furthermore, stable genetic transformation and vaccination of intact plant cells has been achievable by particle bombardment processes (See e.g., Klein et al PNAS vol. 85, pp. 8502-8505 (1988), and Klein et al BioTech vol. 24, pp. 384-386 (1992); each of which is incorporated herein by reference).

One or more hydrogen oxide frozen particle vaccine compositions, including, for example, one or more buffers, one or more immunogens (e.g., viral protein subunits) and one or more adjuvants, as a solution or suspension, are made by spraying the compositions through an orifice or nozzle. Each vaccine composition is propelled by a pressurized gas (e.g., compressed air) into a cooling chamber maintained at, for example, approximately −40° C.

The vaccine composition is delivered to at least one biological tissue of a subject, for example, by propelling the particles via a carrier gas under pressure (e.g., air, carbon dioxide, nitrogen) through a tube directed toward at least one biological tissue (including but not limited to plant callus, plant leaves, plant roots, plant stems, vasculature, lymphatic, lymph node, epidermis, subcutaneous, intramuscular, oral, nasal, pulmonary, intraperitoneal or rectal tissue).

Alternatively, the vaccine composition is delivered to at least one biological tissue of a subject, for example, by first forming the frozen particle vaccine compositions through spraying composition droplets into a cryogen bath (e.g., liquid nitrogen). The frozen particle compositions are subsequently delivered to at least one biological tissue by flash boiling liquid nitrogen, and propelling the frozen particle compositions through a tube or barrel, for example, to at least one biological tissue of a subject.

Frozen particle vaccine compositions containing one or more reinforcement agents (e.g., silica beads) and of the appropriate size and shape (e.g., bullet, spheroid, high aspect ratio shape) penetrate the at least one biological tissue when propelled to high velocity by a carrier gas. In one non-limiting example, a vaccine composition approximately 20-70 ηm in size penetrates the epidermis when the composition is accelerated to high speed with a powder jet injector (PowerJect, PowerJect Pharmaceuticals) (Amorij et al, Ibid.).

Similarly, one group found that using the Bio-Rad HELIOS Gene Gun® and microparticle-delivery of pCMV-S DNA vaccination in mice resulted in greater numbers of animals achieving immunity than those receiving intramuscular injection. (See, e.g., Conn et al, Bio-Rad Tech Note 2726, available on the worldwide web at bio-rad.com/LifeScience/pdf/Bulletin_2726.pdf, accessed Feb. 12, 2009, the content of which is incorporated herein by reference.)

For plant leaves, a high rate of infection with a Potyviridae virus was obtained by another group using the Bio-Rad HELIOS Gene Gun® and microparticle-delivery of the virus. (See, e.g., Kekarainen and Valkonen, Bio-Rad Tech Note 2531, available on the worldwide web at bio-rad.com/LifeScience/pdf/Bulletin_2531.pdf, accessed Feb. 12, 2009, the content of which is incorporated herein by reference.) The authors found optimal infection rates in plant leaves under a helium pressure of 150 psi or 200 psi, at a distance of 0 cm from the delivery device to the tissue. (Id. at page 2).

Example 11

Vaccine Compositions and Methods of Making Frozen Particles

Frozen particle vaccine compositions containing multiple immunogens, for example, toxoids (chemically modified toxins) from bacteria such as Clostridium tetani, Cornybacterium diphtheriae or Bordetella pertussis, stimulate immunity to multiple bacteria or toxins in a single vaccine composition.

Alternatively, multiple distinct immunogens, proteins, or peptides that are derived from a single pathogen are combined in a single frozen particle vaccine composition that immunizes a subject against a pathogenic virus or bacteria that mutates frequently. For example, multiple hemagglutinin or neuraminidase proteins, (e.g., H1N1, H3N2) from different viral strains (e.g., A/New Caledonia/H1N1, or A/Wellington/H3N2) or viral species of influenza (e.g., influenza A or influenza B) are combined in a single frozen particle vaccine composition and provides immunity to multiple strains or species. (See e.g., Kamps et al, Influenza Report, pp. 127-149 (2006); world wide web at influenzareport.com/ir/vaccines; each of which is incorporated herein by reference).

Alternatively, frozen particle vaccine compositions including one or more immunogens, antigens or proteins (e.g., influenza A/New Caledonia/(H1N1)) are combined with one or more frozen particle vaccine compositions containing one or more different antigens (e.g., influenza B/Shanghai or influenza A/Wellington/(H3N2)). Such a frozen particle vaccine composition combination provides immunity against seasonal variants of viral pathogens.

In one non-limiting example, combinations of frozen particle vaccine compositions including specific antigens from selected influenza variants or strains target a seasonal flu epidemic. (Kamps et al, Ibid.) Combination of frozen particle compositions are made containing one or more different antigens or epitopes, wherein the one or more different antigens or epitopes are derived from mutant or variant HIV proteins that evolve during HIV infection (See e.g., Berzofsky et al, J. Clin. Inv. vol. 114, pp. 450-462 (2004)). Such combination compositions immunize a subject against existing HIV mutants and anticipate the emergence of new HIV mutants or variants.

Alternatively, one or more frozen particle vaccine compositions are delivered to one or more mucosal tissues (e.g., nasal, oral, rectal, pulmonary) via propulsion using a "pellet gun," via inhalation, or ingestion by a subject. For example, an influenza vaccine lyophilized and delivered nasally as spherical particles, approximately 26.9 μm (mean diameter), induces mucosal (e.g., nasal IgA response) and systemic immunity (e.g., serum antibody response) to influenza virus (See e.g., Garmise et al, AAPS PharmSciTech. vol. 8:E81 (2007); Huang et al, Vaccine. vol. 23(6), pp. 794-801 (2004); each of which is incorporated herein by reference).

Alternatively, the one or more frozen particle vaccine compositions are delivered to one or more pulmonary surfaces of the subject via propulsion by way of a "pellet gun," by using flash boiled liquid nitrogen as a propellant, or by inhalation. Frozen particle influenza vaccine compositions administered to one or more pulmonary surfaces of a subject elicit mucosal and systemic humoral, as well as cell-mediated immune responses to influenza (See e.g., Amorij et al Vaccine. vol. 25, pp. 8707-8717 (2007), which is incorporated herein by reference).

Example 12

Compositions and Methods of Making Frozen Particles

Frozen particle compositions of the appropriate size and shape, including botulinum toxin, an optimal buffer (e.g., Hepes buffer), one or more stabilizing agents, and one or more reinforcement agents are administered through the skin of a subject to neuromuscular junctions. Botulinum toxin inhibits acetylcholine release, which blocks synapse formation, and temporarily paralyzes the corresponding musculature.

Frozen particle compositions containing a recommended dose of botulinum toxin (See e.g., Borodic, U.S. Pat. No. 5,183,462, which is incorporated herein by reference), and at least one reinforcement agent (e.g., polymer) are administered to skeletal muscles using a delivery system derived from inkjet printer technology (See e.g., world wide web at en.wikipedia.org/wiki/Inkjet Printer) that sprays picoliter quantities of the frozen particle compositions at high velocity (e.g., 50 m/sec) toward the skin of the subject. Botulinum toxin is typically administered by subcutaneous injection (generally with a 26 gauge hypodermic needle). Botulinum toxin is approved by the FDA for therapy of strabismus (crossed-eyes), blepharospasm (uncontrolled blinking), and other facial nerve disorders including hemifacial spasm. It is also approved for treatment of cervical dystonia and glabellar (frown) lines (See e.g., Jankovic, J. Neurol. Neurosurg. Psychiatry vol. 75, pp. 951-957 (2004), which is incorporated herein by reference).

In addition, botulinum toxin is included in the treatment of focal or segmental dystonia (e.g., oromandibular-facial-lingual dystonia, laryngeal dystonia, limb dystonia). Dystonias are neurological disorders with repetitive and patterned contractions of muscles that cause abnormal movements and postures. For example, cervical dystonia subjects are injected with, for example, approximately 100 I.U of botulinum toxin, distributed over 3-5 injection sites, spaced 5-15 mm apart, across the length of the sternomastoid muscle. (Borodic, Ibid.)

Frozen particle compositions containing botulinum toxin are administered to facial muscles that underlie frown lines, wrinkles, and "crow's feet." For example, botulinum toxin is targeted to: 1) the corrugator and procerus muscles to treat vertical glabellar eyebrow furrows; 2) to multiple sites in the frontalis muscle to eliminate horizontal lines in the forehead; or 3) to the lateral orbicularis oculi to treat crow's feet.

Frozen particle compositions containing an optimal dose of botulinum toxin (e.g., 0.2-0.4 I.U./kg) are administered over the length of a specific facial muscle (e.g., orbicularis oculi) by use of a delivery system with an inkjet nozzle. As described herein, picoliter volumes of one or more frozen particle compositions are sprayed at a velocity that achieves a desired or predetermined depth (for example, 5-8 mm; Borodic, Ibid.). The velocity is also altered according to the size, shape, and constituents of the frozen particle composition.

Example 13

Methods of Administering Frozen Particle Therapeutic Compositions

Frozen hydrogen oxide particles of ice Ic form and at least one therapeutic agent or at least one diagnostic agent are formulated for treatment of hematological cancers (e.g., leukemia or lymphoma) or solid tumors (e.g., carcinoma, sarcoma). For example, at least one of neo-adjuvant therapy, adjuvant therapy, chemotherapy, antibody therapy, or immunotherapy are employed In one non-limiting embodiment, frozen hydrogen oxide particles are used for adjuvant therapy of cancers treated with surgery such as colon cancer, lung cancer, and breast cancer. At least one frozen particle hydrogen oxide therapeutic composition containing one or more reinforcement agents (e.g., silica beads, Kevlar®), one or more buffers, one or more stabilizing agents (e.g., one or more saccharides), and one or more cancer therapeutic agents (such as one or more chemotherapy drugs, antibodies, biological agents (e.g., antibodies, cytokines or peptides), or one or more chemotherapeutic agents) are administered to an area proximal to a region of at least one biological tissue where a tumor is present or believed to be present. Optionally, resection of at least a part of a tumor can be performed, with or without additional administration of the at least one frozen particle therapeutic composition.

The at least one frozen particle therapeutic composition is administered in such a manner as described herein, that allows for desired depth of penetration of the at least one biological tissue. In one embodiment, the at least one frozen particle therapeutic composition is administered to a depth that allows for at least one of intracellular or intercellular delivery. For example, the at least one frozen particle therapeutic composition is administered to a depth that allows for delivery to at least one of epithelium, endothelium, vasculature, lymphatic vessels, lymph nodes or mucosa.

Specifically, if metastasis is present or believed to be present in the subject, administration of the at least one frozen particle therapeutic composition is delivered to such region of metastases or micro-metastases are believed to be present.

Frozen particle hydrogen oxide therapeutic compositions provided as an adjuvant therapy are administered by spraying at least one composition under pressure with a carrier gas through a nozzle designed to uniformly distribute particles over at least one biological tissue at sufficient velocity to penetrate the tissue exposed during tumor resection.

Advanced colon cancer (e.g., stage II, III) is treated surgically by removal of sections of colon containing tumor with margins of "normal" colon tissue and often includes removal of associated lymph nodes and mesentery (colectomy). Standard adjuvant therapy following surgery is systemic administration of a combination of chemotherapy drugs (e.g., 5-fluorouracil, leucovorin or oxaliplatin (FOLFOX)), (See e.g., Wolpin et al, CA Cancer J. Clin. vol. 57, pp. 168-185 (2007)). Systemic FOLFOX adjuvant therapy is associated with significant toxicities including gastrointestinal toxicity, neutropenia and neurotoxicity (Wolpin et al, Ibid.). Localized in situ delivery of FOLFOX by administration of frozen particle therapeutic compositions permits delivery of a lower dose.

Administration of at least one frozen particle hydrogen oxide therapeutic composition containing at least one therapeutic antibody includes, for example, bevacizumab (an anti-vascular endothelial growth factor) or cetuximab (an anti-epidermal growth factor receptor). Bevacizumab and cetuximab both target the tumor-associated vasculature and tumor cells in the remaining colon sections and the surrounding tissues, mesentery and lymph nodes. Localized administration of therapeutic antibodies provides sustained protection from recurrence of colon tumors at the site of tumor resection and in the surrounding tissues. (Wolpin et al, Ibid.). Following surgery and adjuvant therapy with one or more frozen particle hydrogen oxide therapeutic compositions, including at least one of one or more chemotherapy drugs, or one or more antibodies, the remaining colon sections are spliced together (i.e. anastomosis) or an artificial orifice (i.e. stoma) is inserted to restore a functional colon.

Example 14

Methods of Administering Frozen Particle Therapeutic Compositions

Frozen particle hydrogen oxide therapeutic compositions including one or more cancer therapeutics or one or more cancer diagnostics are used to treat cancers in distal locations from the primary tumor or initial tumor site treated with surgery or radiation. For example, colon cancer cells often metastasize to the liver ((Wolpin et al, Ibid.). At the time of surgical resection of colon cancer tumors, one or more frozen particle hydrogen oxide therapeutic compositions including at least one cancer therapeutic, such as one or more cytotoxic drugs (e.g., fluouracil), antibodies (e.g., cetuximab), radioisotopes conjugated to antibodies (e.g., $^{131}$I-cetuximab), or one or more mixtures of at least one cytotoxic drug and at least one biological-based therapeutic agent are administered to the liver and surrounding tissues.

Administration of the at least one frozen particle hydrogen oxide therapeutic composition is accomplished by traditional surgery or laparoscopic surgery that allows access to the liver (or other organs to be treated). Administration of at least one frozen particle hydrogen oxide therapeutic composition directly to the liver and the surrounding vasculature allows for intracellular or intercellular penetration and release of at least one anti-cancer therapeutic for treatment of any existing or suspected colon cancer mestastases or micro-metastases.

As described herein, the at least one frozen particle hydrogen oxide therapeutic composition including one or more cancer therapeutics are administered by way of a spraying device. Such a spraying device includes an insulated tube and nozzle, as well as a valve that controls the flow of particles. In the case of traditional surgery for tumor or tissue resection, the at least one frozen particle hydrogen oxide therapeutic composition is sprayed directly onto the target tissue or tissues. Whereas in the case of laparoscopic surgery for tumor or tissue resection, the at least one frozen particle hydrogen oxide therapeutic composition is sprayed through a trocar (a hollow tube approximately 10 millimeters in diameter).

In certain spraying devices, the at least one frozen particle hydrogen oxide therapeutic composition is administered by way of a carrier gas. The depth of penetration by the at least one therapeutic composition is controlled by regulating the carrier gas pressure as well as the consequent particle velocity. The at least one therapeutic composition optionally includes one or more tracer agents or is delivered simultaneously with one or more tracer agents. Some non-limiting examples of tracer agents include dyes, stains or fluorescent compounds that mark the tissue area sprayed. The one or more tracer agents can optionally monitor or provide feedback as to the quantity or quality (in the case of multiple therapeutic compositions administered simultaneously or over time) of the at least one therapeutic composition administered to a specific site.

In one embodiment, the at least one frozen particle hydrogen oxide therapeutic composition including at least one cancer therapeutic further includes hematoxylin and eosin stains mixed at a known ratio (e.g., 1:10). Alternatively, a batch of the at least one frozen particle hydrogen oxide therapeutic composition is administered in a mixture or in separate applications frozen particles including hematoxylin and eosin stains. Staining of tissues is visualized by inspection with a low power microscope (e.g., dissection microscope) or with a laparoscope, which allows for assessment of the relative quantity or quality of the at least one therapeutic composition administered to the tissue. Staining of the tissues further provides a guide as to the region that received the at least one therapeutic composition.

Example 15

Methods of Administering Frozen Particle Therapeutic Compositions

Frozen particle hydrogen oxide therapeutic compositions including carbon dioxide and at least one cancer therapeutic are administered to at least one tumor or tissue suspected of being cancerous. Upon administration, the frozen particle hydrogen oxide therapeutic compositions penetrate one or more tumor cells, warm to ambient temperature, and undergo rapid sublimation and gaseous expansion of the carbon dioxide. This rapid reaction produces a small explosion that destroys at least one tumor cell as well as one or more adjacent cells. In addition, administration of the frozen particle therapeutic compositions at low temperatures (e.g., lower than approximately −78.5° C., which is the approximate sublimation temperature for carbon dioxide at 1 atm pressure), freezes cells and tissues, causing tumor cell death (See e.g., Vergnon et al, Eur. Respir. J. vol. 28 pp. 200-218 (2006); incorporated herein by reference).

Alternatively, carbon dioxide gas is entrapped in frozen particles by placing the liquid phase (e.g., hydrogen oxide) under high pressure in the presence of carbon dioxide gas. (See e.g., U.S. Pat. Nos. 4,289,794; 4,289,790; 4,262,029; 5,439,698, each of which is incorporated herein by reference). Administration of the at least one therapeutic composition is conducted as described herein. In one embodiment, the use of a tube and nozzle is used that sprays the frozen particle therapeutic compositions under pressure in a carrier gas (e.g., carbon dioxide, nitrogen). Administration of the at least one therapeutic composition is carried out as an adjuvant therapy in conjunction with tumor resection, or as an alternative when tumor resection is not favored. For example lung cancer tumors are generally inoperable when such tumors are adjacent to airways, or infiltrate central airways including the trachea, main stem bronchi or multiple lung lobes. Additionally, subjects with compromised respiration (e.g., those with lung disease, heart disease or advanced age) are generally not candidates for surgery (See e.g., Spiro et al, Amer. J. Respir. Crit. Care Med., vol. 172, pp. 523-529 (2005); which is incorporated herein by reference).

Carbon dioxide frozen particle therapeutic compositions including one or more chemotherapeutic drugs (e.g., cisplatin, docetaxel, vinorelbine), targeted drugs (e.g., gefitnib, erlotnib), or biological-based agents (e.g., cetuximab, panitumumab, bevacizumab) are administered directly onto lung cancer tumors. Administration is conducted via endoluminal bronchoscopy or by video-assisted thoracoscopy by means of an insulated tube and nozzle integral to the endoscopic device. Frozen particle composition velocities and spray rate are controlled by a valve between the spray head and the cooling chamber of the "pelletizer." (See e.g., U.S. Pat. Nos. 6,306,119, or 6,764,493, each of which is incorporated herein by reference). Precise localization and administration of the frozen particle therapeutic compositions are accomplished by bronchoscopy and endoscopy with fluoroscopy used to mark the field(s) of interest.

Methods for endoscopic targeting of tumors are described, for example, in Huber et al (Chest vol. 107, pp. 463-470 (1995); which is incorporated herein by reference). Moreover, computed tomography, magnetic resonance imaging, positron emission tomography or other techniques are used to locate lung cancer tumors.

Frozen particle therapeutic composition administration by using endoscopic procedures or as an adjuvant therapy in conjunction with traditional surgery is used for various regions of existing or potential carcinogenesis, including mediastinal lymph nodes, vasculature, chest wall and other thoracic sites.

Alternatively, frozen particle therapeutic compositions are delivered during traditional surgery for lung cancer and used to treat inoperable tumors remaining following lobectomy, wedge resection, and pneumonectomy, as well as to treat margins of lobe, wedge or lung excisions to reduce recurrence of lung cancer (See e.g., the worldwideweb at en.wikipedia.org/wiki/Lung_cancer#Surgery; which is incorporated herein by reference). Without wishing to be bound by any particular theory, frozen particle carbon dioxide therapeutic compositions maintained at approximately −80° C. while administered to tumors rapidly freeze the tumor cells leading to formation of ice crystals in tumor cells that destroy cell organelles (e.g., mitochondria) leading to death of the tumor cells. (Vergnon et al, Ibid.)

Similarly, frozen particle therapeutic compositions containing at least one radioactive element deliver radiation to lung cancer tumor cells. One non-limiting example utilizes frozen particle therapeutic compositions including $^{192}$Iridium for irradiating lung tumors that obstruct major airways. Administration of the frozen particle therapeutic compositions is conducted using an endoscope and a wire to place the radioactive compositions in at least one lung tumor. Without wishing to be bound to any theory, tumor cell irradiation results in single-stranded DNA breaks that induce apoptosis and reduce rates of cell division (Vergnon et, Ibid.).

Example 16

Compartmentalized Frozen Particle Therapeutic Compositions

Frozen particles formed in a bullet-shaped mold with hollow cores or cavities that can be filled with therapeutics are useful for delivering at least one therapeutic agent to a variety of specific tissues, cells and organ or body locations. Hollow bullet-shaped frozen particles can be filled with a therapeutic agent such as one or more of an antibody, cytokine, DNA, small interfering RNA, microRNA, aptamer, cytotoxic agent (e.g. a xenobiotic, synthetic, or radioactive agent) that are in aqueous solution (e.g. sodium phosphate buffer) or form a suspension. Alternatively, hollow frozen bullets can be filled with one or more liquid or solid polymers or nanoparticles that contain at least one therapeutic agent (e.g. at least one prodrug) that requires activation.

In one particular embodiment, at least one therapeutic agent is frozen in carbon dioxide. The frozen carbon dioxide/therapeutic agent mixture or solution is used to fill pre-formed hollow bullet-shaped frozen particles. In certain embodiments, the hollow bullet-shaped frozen particles are formed and filled simultaneously. The temperature and pressure of the frozen particles are adjusted according to the particular constituents and specific parameters of the desired frozen particle.

Administration of at least one compartmentalized therapeutic frozen particle composition with a spraying device allows for localized delivery of at least one therapeutic agent to specific cells or tissues, such as one or more tumors. In certain embodiments, administration of at least one compartmentalized therapeutic frozen particle composition is directed to one or more adjacent, metastatic, or affected tissues including lymph nodes, lymphatic vessels, blood vessels, and organs (e.g. liver, lung, and kidney).

The size, shape or delivery velocity of the at least one compartmentalized frozen particle composition can be controlled in order to deliver the at least one particle composition to a desired location or penetration depth. In certain embodiments, the compartmentalized frozen particle composition includes at least one therapeutic agent (e.g. a cytotoxic agent) that is delivered intracellularly, intercellularly, or into the lumen of vasculature, lymphatics, alveoli, bladder, intestine, lungs or into a specific tissue (e.g. endoderm, smooth muscle, skeletal muscle, prostate).

In one example, hollow bullet-shaped frozen particle compositions containing a prodrug, such as capecitabine, can be delivered intracellularly to tumor cells (e.g. colon carcinoma) where capecitabine is metabolized to 5-fluorouracil, an active cytotoxic agent. Administration of at least one frozen particle composition including capecitabine specifically to tumor cells and optionally to proximal tissues allows for the potential to increase the therapeutic dose to tumor cells, while reducing systemic exposure (which can lead to toxicity and side effects, including angina and myocardial infarction, diarrhea, nausea, neutropenia, anemia and thrombocytopenia).

Alternatively, in one embodiment, intracellular delivery of at least one frozen particle composition including capecitabine that is encapsulated in biodegradable polymeric nanoparticles, releases capecitabine in a pH-dependent manner. (See for example, Shenoy et al, Pharm. Res. vol. 22, pp. 2107-2114 (2005), which is incorporated herein by reference). Since tumor cells generally have a lower pH than non-tumor cells, the capecitabine is released in higher amounts in the tumor environment.

Alternatively, in one embodiment, at least one frozen particle includes capecitabine and one or more polymeric nanoparticles composed of at least poly($\in$-caplactone) (PCL), a non-pH sensitive polymer that is able to release capecitabine as the frozen particle melts or sublimates. (See, for example, Shenoy et al, Ibid.).

Example 17

Compartmentalized Frozen Particle Therapeutic Compositions Including Reinforcement Agents for Transdermal Administration Frozen particle compositions that include at least one therapeutic agent in one or more distinct regions of the particles are useful for transdermal administration of at least one therapeutic to various layers of the skin or to underlying tissues, organs and structures. For example, treatment of certain skin disorders, such as psoriasis, is currently limited to topical administration of a therapeutic agent (e.g. coal tar, corticosteroids, vitamin $D_3$ analogs, or retinoids), systemic treatments (e.g. methotrexate, cyclosporin and retinoids), or UV irradiation (e.g. phototherapy) (See, for example, en.wikipedia/wiki/psoriasis2008, which is incorporated herein by reference). None of these current treatments are fully effective.

In one embodiment, at least one frozen particle composition including one or more psoriasis therapeutic agents located in one or more gradation layers of concentration, or as a coating on the particle is administered to the epidermis, dermis or hypodermis layer by controlling specific parameters, such as particle hardness, size, shape, reinforcement agent, or velocity. For example, frozen particle compositions including reinforced hydrogen oxide are propelled toward at least one biological tissue by "flash-boiling" liquid nitrogen to create nitrogen gas and propel the particle compositions by explosive force. The frozen particle compositions are reinforced with plant matter (such as silk fibers, or collagen fibers), or spun metallic fibers (such as tungsten, iron, manganese, carbon, titanium, or steel). The one or more frozen particle compositions are directed with a hose and nozzle device onto psoriatic skin. In addition, the frozen therapeutic particle compositions can be delivered to the dermis to further impact any pathogenic T cells or cytokines associated with the condition.

In one embodiment, hollow bullet-shaped frozen particle compositions containing one or more biological agent, for example etanercept (as an anti-TNF-α therapy), are administered to the dermal layer underlying areas of psoriatic skin. One or more other therapeutic agents can be combined with the one or more biological agent on the same frozen particle, or on different frozen particles for administration. For example, cytotoxic or cytostatic agents are administered to cells associated with psoriasis, including TI cells, $T_H17$ cells, dendritic cells, neutrophils or keratinocytes. (See, for example, Sabat et al, Exp. Derm. vol. 16, pp. 779-798 (2007), which is incorporated herein by reference). For example, therapeutic agents such as anti-CD3, anti-IL-23, anti-IL-17 or cyclosporin are included in one or more frozen particles to further treat psoriasis in the dermis or epidermis.

Example 18

Compartmentalized Frozen Particle Therapeutic Compositions Including Explosive Materials Hollow frozen particle compositions including one or more reinforcement agents and hydrogen oxide are filled with solid carbon dioxide. The hollow frozen particle compositions are useful for destroying, debriding, ablating, or eliminating unwanted cells or tissues such as fat, bone or tumor cells. In one embodiment, the hollow frozen particle compositions containing a solid carbon dioxide core produces an explosive force as the particle sublimates or melts during administration of the frozen particle compositions. The explosive force fragments, abrades, or destroys cells or tissues.

At least one sub-group of the frozen particle composition treatment course includes one or more of an antibiotic or other anti-microbial agent; one or more anti-inflammatory drugs; one or more anesthetics or analgesics; or one or more vasoconstrictors. Targeted delivery of hollow frozen particle compositions to unwanted cells or tissues is regulated by controlling, for example, frozen particle hardness, size, shape, reinforcement agents or explosive agents, and velocity. One or more frozen particle compositions are administered to at least one biological tissue by external (e.g. transdermal) methods, or internal (e.g. laparoscopic) methods. In one embodiment, a device (e.g. tube and spray nozzle) is integrated for administration of the one or more frozen particle compositions.

Compartmentalized frozen particle compositions are useful for destroying adipocytes or fatty tissue. Present treatments include liposuction, which is performed with a cannula attached to an aspirator that is inserted through small incisions proximal to unwanted fat and the cannula are drawn over the fat to dislodge it and aspirate it (See, for example, en.wikipedia.org/wiki/Liposuction2008, which is incorporated herein by reference).

In one embodiment, a tube and spray nozzle is integrated with the cannula for administration of frozen particles containing a solid carbon dioxide core and optionally, one or more therapeutic agents. For example, the operator sprays frozen particle compositions containing carbon dioxide toward the adipocytes or fatty tissue in order to remove or destroy the tissue. Next, the treated tissue is aspirated with the cannula.

In one embodiment, a laparoscope can be used with the delivery device to allow visualization of the fatty tissue as well as precise delivery of the one or more frozen particle compositions. In certain embodiments, the frozen particle compositions also include lidocaine or ibuprofen in order to minimize pain and inflammation often associated with liposuction. In certain embodiments, at least one vasoconstrictor, such as epinephrine, is included in the one or more frozen particles in order to minimize bleeding. In certain embodiments, antibiotics, such as penicillin or sulfonamide, are included to reduce infection.

Alternatively, frozen particle compositions including a solid carbon dioxide core, one or more antibiotics, analgesics, anti-inflammatory drugs or vasoconstrictors are delivered transdermally to adipose tissue by spraying the particle compositions as described herein, at the appropriate velocity to penetrate the epidermis, dermis or hypodermis. Following treatment of adipocytes or fatty tissue with the one or more frozen particles, liposuction is performed to remove the treated cells or tissues. In one embodiment, adipocytes are selectively treated with minimal effect on the underlying muscle cells, which reduces bruising or bleeding.

Example 19

Compositions and Methods of Administering Frozen Particles Including One or More Adhesive Agents and One or More Biological Remodeling Agents Frozen particles including hydrogen oxide, carbon dioxide, dimethylsulfoxide or a buffer (e.g. HEPES, Ringer's solution, sodium citrate, sodium phosphate, etc.) are formulated with at least one adhesive agent such as cyanoacrylate, polyethylene glycol polymers or albumin plus glutaraldehyde.

Frozen particle compositions including at least one adhesive agent are utilized in conjunction with standard methods to achieve hemostasis in patients undergoing surgery, for example, to repair large blood vessels such as the aorta, femoral or carotid arteries. Frozen particle compositions including bovine albumin and glutaraldehyde (BIOGLUE®, CryoLife, Inc., Kennesaw, Ga.) are utilized, for example, in repair of an aortic dissection or other blood vessel repair.

Frozen particle compositions including hydrogen oxide, glutaraldehyde, and bovine albumin are produced as described herein at other sections. In an embodiment, various different subsets of frozen particle compositions are produced, for example, one subset includes frozen hydrogen oxide particles including glutaraldehyde, while another subset is produced that includes frozen hydrogen oxide particles including bovine albumin.

In an embodiment, a single set of frozen particle compositions are produced, for example, including frozen hydrogen oxide particles including both glutaraldehyde and bovine albumin.

In an embodiment, a set of frozen particle compositions are produced, for example, that includes compartmentalized particles wherein both glutaraldehyde and bovine albumin are present on a particular particle, but each is partially or wholly sequestered in a separate compartment of the particular particle. Some examples of compartmentalized frozen particles are described herein at other sections.

In an embodiment, frozen particles include bovine albumin in a mass ratio of weight per volume of approximately 5%, approximately 10%, approximately 15%, approximately 20%, approximately 25%, approximately 30%, approximately 35%, approximately 40%, approximately 45%, approximately 50%, approximately 55%, approximately 60%, approximately 65%, approximately 70%, approximately 75%, or any value therebetween.

In an embodiment, frozen particles include glutaraldehyde in a mass ratio of weight per volume of approximately 1%, approximately 2%, approximately 3%, approximately 4%, approximately 5%, approximately 6%, approximately 7%, approximately 8%, approximately 9%, approximately 10%, approximately 11%, approximately 12%, approximately 15%, approximately 16%, approximately 17%, approximately 18%, approximately 19%, approximately 20%, or any value therebetween.

One or more sets of frozen particle compositions including hydrogen oxide, glutaraldehyde, and/or bovine albumin, as described herein, are administered to the false lumen of the dissected aorta or other blood vessel in need of repair, at the distal and proximal anastomotic sites.

In an embodiment, a set of frozen particle compositions including bovine albumin and glutaraldehyde is administered alone or in conjunction with (sequentially or simultaneously with) other frozen particle compositions that optionally include, for example, one or more of at least one therapeutic agent, at least one reinforcement agent, at least one explosive material.

In an embodiment, multiple sets of frozen particle compositions, including bovine albumin and glutaraldehyde on separate particles are administered simultaneously or sequentially to the biological tissue. These multiple sets of frozen particle compositions are optionally administered simultaneously or sequentially with other frozen particle compositions that include, for example, one or more of at least one therapeutic agent, at least one reinforcement agent, or at least one explosive material.

Depending on the thickness of the blood vessel to be repaired, as well as other factors, an adhesive layer is administered with a thickness of approximately 0.1 mm, approximately 0.2 mm, approximately 0.3 mm, approximately 0.4 mm, approximately 0.5 mm, approximately 0.6 mm, approximately 0.7 mm, approximately 0.8 mm, approximately 0.9 mm, approximately 1.0 mm, approximately 1.5 mm, approximately 2.0 mm, approximately 2.5 mm, approximately 3.0 mm, approximately 3.5 mm, approximately 4.0 mm, approximately 4.5 mm, approximately 5.0 mm, approximately 6.0 mm.

Optionally, subsequent to repair of the distal and proximal ends of the blood vessel, one or more support structural materials are inserted to replace damaged blood vessel sections. Some examples of structural material that can be utilized are described herein at other sections. For example, some non-limiting examples of structural material include one or more of tubing (such as plastic or rubber tubing, e.g. polyethylene terephthalate or polytetrafluoroethylene), a stent (optionally including one or more therapeutic agents), a matrix (such as extracellular matrix components, or an artificial or synthetic matrix), a rod or other physical support.

Following insertion of the optional support structure, one or more sets of frozen particle compositions are administered to the repaired blood vessel to secure the structure or assist in modulating hemostasis. One or more sets of frozen particle compositions are also optionally administered to the junctions between the support structure and the vasculature.

Example 20

Compositions and Methods of Administering Frozen Particles Including One or More Adhesive Agents and One or More Biological Remodeling Agents Surgical incisions, burns, and other traumatic injuries result in damage to the dermis or hypodermis skin layers. Frozen particles including at least one adhesive agent, and optionally one or more of a growth factor, an anesthetic, or an antibiotic are administered to the biological tissue to secure would closure, including securing skin grafts. The frozen particles are administered alone or in conjunction with surgical staples or sutures.

In an embodiment, one or more frozen particles including thrombin (e.g., activated thrombin) or fibrinogen are administered. As described in other sections herein, thrombin and fibrinogen can be included as part of a single frozen particle (including, for example, provided in compartments of a single frozen particle), a single set of frozen particles, or separately as part of different frozen particles or different sets of frozen particles. As described herein, if multiple sets of frozen particles are administered, the sets can be administered simultaneously or sequentially.

In an embodiment, one or more frozen particles including at least one adhesive agent include a biodegradable polymer that encapsulates at least one therapeutic agent (such as a growth factor, antibiotic, anesthetic or other agent). For example, poly($\in$-caprolactone) (PCL) allows for controlled or sustained release of a therapeutic agent for a specific location (See, for example, Shenoy et al, Ibid., which is incorporated herein by reference).

In an embodiment, one or more frozen particles include activated thrombin at a concentration of approximately 0.5 IU/mL, approximately 1.0 IU/mL, approximately 1.5 IU/mL, approximately 2.0 IU/mL, approximately 2.5 IU/mL, approximately 3.0 IU/mL, approximately 3.5 IU/mL, approximately 4.0 IU/mL, approximately 4.5 IU/mL, approximately 5.0 IU/mL, approximately 5.5 IU/mL, approximately 6.0 IU/mL, approximately 6.5 IU/mL, approximately 7.0 IU/mL, approximately 7.5 IU/mL, approximately 8.0 IU/mL, approximately 8.5 IU/mL, approximately 9.0 IU/mL, or any value therebetween.

In an embodiment, one or more frozen particles include fibrinogen at a concentration of approximately 20 mg/mL, 30 mg/mL, 40 mg/mL, 50 mg/mL, 60 mg/mL, 70 mg/mL, 80 mg/mL, 90 mg/mL, 100 mg/mL, 110 mg/mL, 115 mg/mL, 120 mg/mL, 130 mg/mL, 140 mg/mL, 150 mg/mL, or any value therebetween.

Since activated thrombin reacts with fibrinogen by way of proteolysis to form a fibrin adhesive, the concentration of either fibrinogen or thrombin can be increased or decreased, depending on the desired goal of wound closure. (See, e.g., Spotnitz et al. Transfusion, vol. 48, pp. 1502-1516 (2008); Evans et al., Braz. J. Urol. vol. 32, pp. 131-141 (2006), each of which is incorporated herein by reference.) For example, if a skin graft is involved in the wound repair and a slow rate of adherence is desired in order to accurately place the graft on the wound, the concentration of either thrombin or fibrinogen can be reduced. Alternatively, separate sets of one or more frozen particles can be administered, wherein the concentration of at least one adhesive agent varies within a set or between the separate sets of frozen particles. Optionally, one or more frozen particles can include at least one proteolytic inhibitor, such as aprotinin, in order to prolong the fibrin adhesive effect. (See, e.g., Spotnitz et al, Ibid., which is herein incorporated by reference).

Optionally, one or more of the frozen particles includes at least one detection material (e.g., a non-reactive, biodegradable dye or non-toxic contrast agent) that allows for visual detection of application of the one or more frozen particles. In an embodiment, the one or more frozen particles including at least one detection material also include at least one other agent (e.g., at least one adhesive agent, or at least one therapeutic agent). (See, e.g., worldwide web at kolorjectchemicals.com/natural-food-color.html, visited on Nov. 25, 2008, which is incorporated herein by reference.)

Optionally, frozen particles are administered that include one or more growth factor (e.g., keratinocyte growth factor, vascular endothelial growth factor A, epidermal growth factor, fibroblast growth factor, or hepatocyte growth factor) to promote engraftment. (See, for example, Nolte et al, Cells Tissue Organs, vol. 187, pp. 165-176 (2008); Boateng et al., J Pharm. Sci. vol. 97, pp. 2892-2923 (2008), each of which is incorporated herein by reference). In addition or instead of these growth factors, one or more frozen particles include one or more of collagen, hyaluronic acid, glycosaminoglycans, or other extracellular matrix components, at least one of which is encapsulated in a PCL polymer. (See, for example, Boateng et al., Ibid, which is incorporated herein by reference.)

In an embodiment, compartmentalized frozen particles including one or more of activated thrombin, fibrinogen, antibiotic (e.g., minocycline, gentamycin, oxoflacin, or tetracycline), or PCL-encapsulated extracellular matrix or growth factor are administered to a wound.

In an embodiment, one or more frozen particles include one or more cells (e.g., pluripotent stem cells, mesenchymal stem cells, fibroblasts, keratinocytes, dermal progenitor cells) to assist in wound repair, including skin engraftment. For example, dermal fibroblasts suspended in cryogenic media (e.g., containing 10% dimethylsulfoxide) are included in one or more frozen particles. In the same or different frozen particle, one or more of at least one growth factor, at least one extracellular matrix component, or at least one adhesive agent are included. Optionally, one or more of the agents included in the frozen particles are encapsulated by PCL or another polymer. The frozen particles can be administered simultaneously or sequentially.

In an embodiment, several different sets of frozen particles are administered in order to establish layers of, for example, extracellular matrix, fibroblasts, fibrin sealant, and keratinocytes can be administered in multiple layers with or without an additional skin graft. In an embodiment, the skin graft itself has been derived artificially or synthetically, at least in part, by administration of frozen particles including various skin components to at least one biological tissue or a synthetic matrix (e.g., biodegradable sponge or polymer matrix).

Optionally, as in the case of burns or other wounds in which necrotic tissue is present, frozen particles are administered to debride tissue prior to would closure or skin engraftment. Frozen particles including one or more of at least one antibiotic (e.g., neomycin, polymixin B, or gramicidin), or at least one anesthetic (e.g., lidocaine). As described herein at other sections, debridement of cells or tissue is regulated by several factors, including characteristics of the one or more frozen particles (e.g., size, shape, or constitution of any particular frozen particle), as well as characteristics of administration of the one or more frozen particles (e.g., velocity of delivery, angle of delivery, quantity of particles delivered, or rate of delivery).

In an embodiment in which tissue is debrided, a device is utilized to administer the one or more frozen particles, as described herein at other sections. In an embodiment, a tube and nozzle is utilized to administer the one or more frozen particles, with an optional aspirator tube to remove liquid and tissue as debridement occurs.

Example 21

Compositions and Methods of Administering Frozen Particles Including One or More Biological Remodeling Agents One or More Therapeutic Agents, One or More Adhesive Agents, and One or More Reinforcement Agents for Tissue Reconstruction Frozen particle compositions including one or more of a reinforcement agent, antibiotic, therapeutic agent, polymer, adhesive, stem cell, or progenitor cell are utilized for debriding damaged or necrotic tissue, such as bone and cartilage. Subsequently, one or more frozen particle compositions as described are utilized for reconstructing the tissue, in addition to or instead of one or more frozen particle compositions including one or more of a growth factor, progenitor cell or stem cell.

For example, joint restructuring or replacement is a common surgical procedure for joints such as knee or hip joints. Knee replacement surgery is performed as a partial or total knee joint replacement. Standard knee replacement generally includes replacing or supplementing diseased or damaged joint surfaces with bone grafts (e.g., autologous or cadaveric bone grafts) or synthetic materials (e.g., metal, plastic, or rubber substrates).

Optionally, computer systems are used to model the bone defect, based on imaging studies (e.g., x-ray, computed tomography (CT), or other imaging). Among other things, imaging the bone or other tissue (e.g., cartilage), allows for assessment of the defect, or analysis of the present joint structure, allows for assistance in designing repair or replacement of the joint, and provides guidance for delivery of the frozen particle compositions. In certain instances, the frozen particle compositions are delivered by way of a piezoelectric or inkjet printer device that is directly or indirectly under the control of a computer system.

In an embodiment, a CT scan is used to develop a three-dimensional image of the joint to be reconstructed. For a knee joint, for example, regions from the distal femur and proximal tibia, including synovial and cartilage, can be imaged for assessment. Computer systems and methods for designing and repairing the joint(s) can also be used for comparing the present state of the subject's joint with that of a healthy individual. Thus, the repair may include reconstructing or restructuring the joint according to healthy or undamaged joints.

Optionally, a computer system also controls a robotic arm or other automated instrument containing a piezoelectric or inkjet printer device, or sprayer for administration of one or more frozen particle compositions in the reconstruction of the joint. In certain instances, the subject's damaged or diseased joint is ablated or debrided with one or more frozen particle compositions in addition to or instead of reconstructing the joint. In certain instances, one or more frozen particles are delivered to a substrate (e.g., natural, artificial, or synthetic materials) used in reconstructing the subject's knee joint. In certain instances, the substrate includes an artificial knee joint or a cadaveric knee joint.

In the case where the subject's joint is ablated or debrided, one or more frozen particle compositions are administered to the subject's joint (optionally with assistance of a computer system). The ablation or debridement may be performed before, during, or subsequent to the administration of one or more frozen particle compositions related to stabilizing the joint or reconstructing the joint. For example, frozen particle compositions including reinforcement agents (e.g., silica beads, fiberglass, polyethylene glycol) are propelled toward the subject's knee joint at or to a predetermined velocity that allows for delivery of the compositions into the various layers of the joint (i.e., skin, subcutaneous layers, synovial membrane, etc.).

In an embodiment, an arthroscopic device is utilized for delivery of one or more frozen particle compositions to the knee joint. A computer system can assist a surgeon in ablating or debriding the cartilage and/or bone to the proper depth by delivering the frozen particle compositions at a predetermined or preselected set of parameters. The predetermined or preselected parameters include, but are not limited to, size of frozen particle compositions, shape of frozen particle compositions, constitution of frozen particle compositions, velocity at which frozen particle compositions are delivered, angle at which frozen particle compositions are delivered, timing for delivery of specific frozen particle compositions, or programs for cycling any one or more parameters. In an embodiment, ablation is performed on a knee joint with guidance provided by a computer system or imaging apparatus. During or subsequent to ablation, frozen particle compositions containing therapeutic agents (such as at least one antibiotic or anti-inflammatory agent) are administered to the joint.

In an embodiment, the joint is reconstructed by utilizing a computer system for imagine or modeling the joint. Optionally, the computer system is directly or indirectly linked to a sprayer or piezoelectric or inkjet printer device capable of administering one or more frozen particle compositions. In certain instances, the frozen particle compositions administered to reconstruct the joint include scaffolding materials of natural, artificial, or synthetic origin (examples of specific agents include, but are not limited to, antibodies; growth factors; e.g., bone morphogenic protein; polymers; e.g., polylactic acid, polylactic acid-co-glycolic acid; or adhesives; e.g., polyethylmethacrylate/tetrahydrofurfuryl methacrylate, hydroxyapatite, etc.), or an amphiphilic polymer. In one embodiment, the delivery of one or more adhesive agents or at least one biological remodeling agents, includes at least one temporally-regulated method. (See, e.g., Davies, et al. Advanced Drug Delivery Reviews, vol. 60, pp. 373-387 (2008); or Kanczler et al. Biomaterials, vol. 29, pp. 1892-1900 (2008), each of which is incorporated herein by reference.)

In an embodiment, scaffolding materials solidify in situ at physiological temperature and pH, and may include, but not be limited to, calcium phosphate cement with a biocompatible gelling agent and scaffold materials for cartilage regeneration (e.g., oligopoly-ethylene glycol fumarate, polyN-isopropylacrylamideco-acrylic acid, polyN-isopropylacrylamide-grafted gelatin, polyethylene oxide, alginate, fibrin, PLGA-g-PEG, pluronics, calcium phosphate/hyaluronic acid composites, hyaluronic acid gel and chitosan. See, e.g., Hou et al., J. Mat. Chem. vol. 14, pp. 1915-1923 (2004), which is incorporated by reference herein.

Optionally, one or more frozen particle compositions including scaffolding materials that promote adhesion of cell types that produce bone or cartilage are administered to assist in reconstructing the subject's joint. For example, integrin peptides with the arginine-glycine-aspartic acid (RGD) sequence can be covalently coupled with other scaffolding materials administered to the joint. Integrins are capable of promoting adhesion of cells, including osteoblasts, via their integrin receptors. See, e.g., Hou, et al., Ibid.

Optionally, one or more frozen particle compositions including antibodies or antibody fragments are chemically coupled with scaffold polymers that among other things, promote binding and retention of specific cell types within the scaffold, are administered to the subject's knee or a substrate used in reconstructing the knee. For example, anti-integrin $\alpha_v\beta_3$ antibodies recognize endothelial cells, and anti-integrin $\alpha_5$ antibodies recognize chondrocytes, both of which cell types can assist in reconstructing the joint. See, e.g., Hou et al, Ibid.

Optionally, one or more frozen particle compositions including one or more growth factors that are capable, for example, of promoting cell growth and/or cell differentiation are administered in reconstructing the knee joint. For example, bone morphogenic proteins, fibroblast growth factors, vascular endothelial growth factors, or other factors are encapsulated in polymer particles (e.g., vesicles) that form at least part of a scaffold to support reconstruction of the joint. See, e.g., Davies et al., Ibid. In an embodiment, one or more growth factors support the infiltration or growth of osteocytes, chondrocytes, or vascular cells.

In an embodiment, one or more frozen particle compositions including one or more of a progenitor cell, stem cell, osteoblast, chondrocyte, or endothelial cell are administered. In an embodiment, one or more subsets of frozen particle compositions include, but are not limited to compositions containing one or more of a scaffolding material, adhesive agent, or growth factor. In an embodiment, one or more subsets of frozen particle compositions are administered to the subject's joint simultaneously, sequentially, or cyclically.

In an embodiment, reconstruction of the joint is conducted by administering one or more subsets of frozen particle compositions through interaction or consultation with a computer system. In an embodiment, administration of one or more frozen particle compositions or one or more subsets of frozen particle compositions occurs in a stepwise fashion according to one or more parameters including, but not limited to, size of frozen particle compositions, shape of frozen particle compositions, constitution of frozen particle compositions, velocity at which frozen particle compositions are delivered, angle at which frozen particle compositions are delivered, timing for delivery of specific frozen particle compositions, or programs for cycling any one or more parameters.

In an embodiment, the joint is debrided, and the surface is prepared for reconstruction. Additionally, one or more frozen particle compositions or one or more subsets of frozen particle compositions are administered containing one or more of a scaffolding material, an adhesive agent, a therapeutic agent, a reinforcement agent, or an explosive agent. For example, calcium phosphate cement with a biocompatible gelling agent are included with one or more frozen particle compositions. In the same or different frozen particle compositions, growth factors (such as vascular endothelial growth factors or bone morphogenic factors) are included. In addition, in the same or different frozen particle compositions, osteoblast cells or osteoblast precursor cells are administered to the subject's joint or a substrate used for reconstructing the joint. In the same or different frozen particle compositions, at least one scaffold material, such as a polymer, is administered to the joint or a substrate used for reconstructing the joint. For example, oligopoly-ethylene glycol fumarate optionally with a chondrocyte growth factor (e.g., fibroblast growth factor) are included in one or more frozen particle compositions. In the same or different frozen particle compositions, frozen particle compositions including chondrocytes or condrocyte progenitor cells (e.g., mesenchymal stem cells) are administered to the joint.

In an embodiment, one or more steps of assessing the joint, preparing the joint, debriding or abrading the joint, or reconstructing the joint are aided by use of a computer system, including but not limited to CT imaging, computer-aided design (CAD), or computer-aided surgery (CAS). See, e.g., Bradley et al., Arch. Otolaryngol. Head Neck Surg. Vol. 34, pp. 1080-1084 (2008), which is incorporated by reference herein.

Example 22

Compositions and Methods of Administering Frozen Particles Including One or More Biological Adhesive Agents and One or More Biological Remodeling Agents Frozen particles containing one or more biological adhesive agents (for example, bispecific antibodies or bispecific proteins), are used to bind cells or tissues specifically to therapeutic targets, such as endothelial cells, leukocytes, epithelial cells, cancer cells, extracellular matrices, vasculature, lymphatics, tumors, and other tissues. For example, one or more frozen particles containing at least one bispecific receptor, antibody, ligand, or fusion proteins of one or more of receptors, antibodies, or ligands are used to selectively bind or adhere leukocytes, such as macrophages, monocytes, T cells, natural killer cells (NK cells), granulocytes, or other cells to target tissues, extracellular matrices, or other cell types (e.g., cancer cells, endothelial cells, or epithelial cells).

Moreover, one or more frozen particles optionally contain at least one biological adhesive agent and at least one leukocyte in separate sectors. In one embodiment, the sector includes a compartment.

In one embodiment, one or more biological adhesive agent is bound to a leukocyte (or other cell) in vitro prior to incorporation of the cell plus biological adhesive into the one or more frozen particle compositions. Optionally, one or more frozen particle compositions including at least one biological adhesive or at least one cell are delivered sequentially to a target tissue, matrix, or cell type.

Examples of one or more biological adhesive agents are disclosed herein at other sections, and include but are not limited to mammalian cell surface proteins, and glycoproteins. For example, adhesion molecules include CD44, immunoglobulin (Ig) superfamily members, integrins, cadherins, and selectins. These or other factors that are included in the disclosure specifically bind to protein or macromolecule ligands (e.g., intercellular adhesion molecule (ICAM), vascular cell adhesion molecule (VCAM), fibronectin, and hyaluronate), MADCAM, LFA-1, and others. Other cell surface receptors are included as biological adhesive agents, including but not limited to immunoglobulin Fc receptors (FcR), complement receptors (CR), and surface immunoglobulin (sIg).

Example 23

Compositions and Methods of Administering Frozen Particles Including One or More Biological Adhesive Agents for Administration to Tumor Tissue Frozen particles containing one or more biological-based adhesive agents are used to deliver and bind immune effector cells to primary or metastatic tumor cells, as well as tumor-associated stroma or extracellular matrices. Macrophages or monocytes that have the potential to kill tumor cells, and present tumor-associated antigens are recognized by antibodies that bind integrin receptors, such as VLA-4, β-1, β-2, Fcγ receptor I (CD64) or by cell adhesion peptides (e.g., YRGDS, YEILDV). (See, for example, Martin-Manso et al., Cancer Res., vol. 68, pp. 7090-7099 (2008); Wagner et al., Biomat., vol. 25, pp. 2247-2263 (2006); each of which is incorporated herein by reference). In addition, lymphocytes (such as T cells or B cells), as well as natural killer cells are capable of directed killing of tumor cells, and are included in specific embodiments disclosed herein.

Biological adhesive agents, including a bispecific antibody, such as anti-CD64 binding domain (e.g., single chain Fv (SCFv)) is fused to a second binding domain that recognizes a tumor-associated antigen (e.g., CA-125 (mucin 16), or melanoma-associated antigen (MAGE)). Mucin 16 binds macrophages to ovarian cancer cells, while MAGE binds macrophages to melanoma cancer cells. Generation, including design, construction, and production, of bispecific antibodies is generally known in the art. (See, for example, USPTO Application Publication No. 20080305105; Kufer et al., Trends in Biotech., vol. 22, pp. 238-244 (2004); each of which is incorporated herein by reference.)

Macrophage or monocyte cells are obtained from the peripheral blood of cancer patients or subjects. Monocytes are purified from peripheral blood leukocytes (standard reagents and protocols are available from, for example, StemCell Tech., Inc., Vancouver, B.C., Canada). Monocytes are activated by treatment in vitro with cytokines, such as interferon-γ. (See, for example, Kufer et al., Ibid.) Production of macrophage cells that are cytotoxic for tumor cells is described, for example, in Martin-Manso et al., Ibid. Cytotoxic macrophage cells are bound in vitro to a bispecific antibody (e.g., antibody that recognizes CD64 or MAGE), prior to incorporation into one or more frozen particle compositions for administration to a melanoma tumor.

Briefly, bispecific antibodies at 10-100 micrograms/mL in RPMI 1640 media, pH 7.4 (Invitrogen Corp., Carlsbad, Calif.), are incubated with monocyte cells for 1-4 hours at 5°-37° C. Monocyte cells with bound bispecific antibodies are washed by centrifugation and incorporated into one or more frozen particle compositions containing dimethylsulfoxide (10% vol/vol), RPMI 1640 media, and human serum (20% vol/vol).

One or more frozen particle compositions containing one or more monocyte cells, one or more biological adhesive agents, and media are delivered directly to tumor tissue by a device (for example, a spray device). Depending on various factors, including but not limited to, size of tumor, presence of metastatic tumor tissue, extent of any metastatic tissue, type of tissue of origin for the tumor, location of tumor, condition of the subject, or other factors, the depth of frozen particle penetration can be predicted or determined through design or alteration of frozen particle composition velocity, size, shape, and constituency of the one or more frozen particles.

Example 24

Compositions and Methods of Administering Frozen Particles Including One or More Biological Adhesive Agents for Administration to Tumor Tissue Immune effector cells (including monocytes, macrophages, natural killer cells, or lymphocytes) plus bound bispecific antibodies are delivered to tumor tissue, for example, at a site or organ (e.g. lung, liver) using a device (such as an endoscope, including a laparascope or thoracoscope). In one embodiment, a particle spraying device is introduced through a trocar and guided by way of an endoscope, delivers the frozen particle compositions including at least one immune effector cell with at least one biological adhesive to the target site. In one embodiment, the target site includes tumor tissue. In at least on embodiment, the target site includes tissue surrounding a tumor. In one embodiment, the target site includes tissue suspected of being cancerous. In one embodiment, the target site includes primary tumor tissue. In one embodiment, the target site includes metastatic cancer tissue.

In one embodiment, frozen particle compositions including at least one biological adhesive and at least one immune effector cell are administered as an adjunct therapy following surgery to resect diseased tissue, chemotherapy, radiation treatment, or other therapy. For example, frozen particle compositions including at least one biological adhesive that recognizes monocytes (e.g., anti-CD64) and MAGE are administered to tissue surrounding the surgical site, including lymph nodes or sites of suspected or anticipated metastasis.

Example 25

Compositions and Methods of Administering Frozen Particles Including One or More Biological Adhesive Agents to Melanoma Cells and Tumor-Associated Endothelial Cells At least one biological adhesive recognizing one or more integrin present on melanoma cells or tumor endothelial cells is used to bind immune effector cells to melanoma cells or tumor-associated endothelial cells. For example, one or more antibodies specific for the integrin $\alpha_v\beta_3$ and CD3 (a signaling part of the T cell antigen receptor) can be used in conjunction with cytotoxic T cells derived from melanoma subjects. See, for example, Berger et al., J. Clin. Invest. vol. 118, pp. 294-305 (2008), which is incorporated herein by reference.

One or more frozen particle compositions containing anti-$\alpha_v\beta_3$, anti-CD3, or cytotoxic T cells bind to melanoma cells directly or indirectly following binding to tumor neovasculature endothelium and extravasation. See, for example, Mahabeleshwar et al., Ibid. In one embodiment, the one or more frozen particle compositions are administered in multiple dimensions (e.g., x, y, z coordinates) to melanoma cells, neovasculature, and adjacent tissues (which may or may not be malignant). In one embodiment, primary tumor cells, metastatic tumor cells, neovasculature, and adjacent lymphatic ducts and lymph nodes are targeted. One or more frozen particle compositions delivered to the epidermis, dermis, and subcutaneous layers of a subject target melanoma cells in radial, vertical, and metastatic modes of growth. See, for example, Mahabeleshwar et al, Ibid.

In one embodiment, administration of the one or more frozen particle compositions in three dimensions is conducted with a computer-guided spraying device. The computer-guided device uses one or more computer systems, or one or more computer programs to derive or obtain data to predict or generate one or more frozen particle compositions based on specific characteristics. For example, the one or more frozen particle compositions are predicted or generated based on particle hardness, shape, size, constituency, or other factors. The one or more frozen particle composition administration is predicted or generated based on number of frozen particle compositions administered for any particular round of delivery, the velocity of delivery, the angle of delivery, the number of rounds of delivery of the same or different frozen particle compositions, the type of tissue receiving the frozen particle compositions, the condition of the tissue receiving the frozen particle compositions, and other factors. In this manner, the one or more frozen particle compositions are administered to a particular target tissue, and to a particular desired depth or breadth.

Example 26

Compositions and Methods of Administering Frozen Particles Including One or More Biological Adhesive Agents to Melanoma Cells One or more frozen particle compositions including one or more biological adhesive agents capable of specifically binding melanoma tumor cell surface receptors, including at least one receptor capable of signaling or initiating apoptosis are administered to melanoma cells. For example, at least one biological adhesive agent including at least one bispecific protein that recognizes melanoma tumor cell antigens (e.g., MAGE), as well as a pro-apoptotic cell surface receptor (e.g., death receptor 5 (DR5)) is delivered to melanoma cells for induction of apoptosis.

In one embodiment, binding of DR5 by an agonistic monoclonal antibody or apoptosis ligand 2/TNF-related apoptosis-inducing ligand (e.g., Apo2L/TRAIL) initiates signaling that leads to apoptotic death of the tumor cell. See, for example, Ashkenazi, Nat. Rev. Drug Discov., vol. 7, pp. 1001-1012 (2008). Some examples of agonistic antibodies that are capable of inducing apoptosis on tumor cells include, but are not limited to, mapatumumab and lexatumumab (Human Genome Sciences, Inc., Rockville, Md.; HGS), Apomab (Genentech Inc., South San Francisco, Calif.), AMG655 (Amgen, Inc., Thousand Oaks, Calif.), CS-1008 (Daiichi Sankyo Co., Ltd., Tokyo), and LBY-135 (Novartis Int'l AG, Basel).

In one embodiment, a bispecific protein including anti-MAGE binding domains (e.g., single chain Fv (SCFv)) and at least one agonistic anti-DR5 binding domain (e.g., SCFv from Apomab; Ashkenazi, Ibid) is administered in one or more frozen particle compositions directly to melanoma cells, or delivered to subcutaneous layers surround the melanoma cells.

In one embodiment, in addition to targeting primary tumor cells, tissue known to be metastatic, or suspected to be metastatic due to the epidemiology of the disease, are targeted. For example, melanoma is known to metastasize to the brain. In one embodiment, the brain receives one or more frozen particles alone or in combination with surgery (e.g., craniotomy), based on imaging studies done with computer-assisted tomography or magnetic resonance imaging. Frozen particle compositions including pro-apoptotic agonists or anti-MAGE binding proteins are used as adjuvant therapy following surgery (e.g., open surgery, stereotactic surgery, or stereotactic radiosurgery to remove or destroy melanoma metastatic cells.

In one embodiment, minimally invasive computer assisted surgery is used to remove tumor cells and tumor tissue, followed by administration of one or more frozen particle compositions as adjuvant therapy. For example, computer-aided surgery (CAS) is used with stereotactic surgery systems to target tumor cells that have infiltrated essential and/or highly vascularized brain tissues that are considered inaccessible or inoperable by standard methods.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations can be performed in other orders than those which are illustrated, or can be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

All publications and patent applications cited in this specification are incorporated herein by reference to the extent not inconsistent with the description herein and for all purposes as if each individual publication or patent application were specifically and individually indicated to be incorporated by reference for all purposes.

What is claimed is:

1. A method for providing at least one adhesive agent to at least one substrate, comprising:
administering at least one frozen particle composition to at least one substrate at a predetermined velocity, wherein the at least one frozen particle composition includes one or more frozen hydrogen oxide particles coated in at least one adhesive agent; wherein the at least one adhesive agent includes one or more epoxy adhesive, acrylic adhesive, urethane adhesive, polyurethane adhesive, anerobic adhesive, urethane acrylate, polyester acrylate, methyacrylate, or cyanoacrylate.

2. The method of claim 1, wherein the at least one adhesive agent includes at least one of a monomer, prepolymer, polymer, or copolymer.

3. The method of claim 1, wherein the substrate includes at least a portion of which is naturally, artificially, or synthetically derived.

4. The method of claim 1, wherein the substrate includes at least a portion of which is genetically altered.

5. The method of claim 1, wherein the at least one substrate includes one or more of a cell, tissue, organ, structure, or device.

6. The method of claim 5, wherein the structure includes one or more of a prosthesis, cell matrix, or tissue matrix.

7. The method of claim 1, wherein the at least one substrate is located in at least one of in situ, in vitro, in vivo, in utero, in planta, or ex vivo.

8. The method of claim 7, wherein the at least one substrate is transplanted or implanted into at least one subject.

9. The method of claim 7, wherein the at least one substrate is ingested by at least one subject.

10. The method of claim 7, wherein the at least one substrate includes at least one biological tissue from at least one donor or recipient.

11. The method of claim 1, wherein the at least one substrate includes one or more wounds.

12. The method of claim 1, further including varying the rate, velocity, or angle at which the at least one frozen particle composition is administered to at least one substrate.

13. The method of claim 1, further including administering to the at least one substrate at least one of a nanoparticle, detection material, sensor, micro-syringe, or circuit.

14. The method of claim 1, wherein the at least one frozen particle composition further includes one or more of a reinforcement agent, abrasive, explosive material, or biological remodeling agent.

15. The method of claim 1, wherein the at least one adhesive agent further includes at least one α-cyanoacrylate and a fluorescent compound including at least one of a bis-benzoxazolyl compound, pyrylium salt, quantum dot, or coumarin compound.

16. The method of claim 1, wherein the at least one adhesive agent further includes an α-cyanoacrylate and 2,5-bis-(5-tert-butyl-2-benzoxasolyl)-thiophene.

17. The method of claim 1, wherein the at least one adhesive agent further includes one or more of a base component, initiator component, or activator component.

18. The method of claim 1, wherein the at least one adhesive agent further includes at least one curing component.

19. A method of maintaining the approximation of tissue of at least one wound of a subject, comprising:
administering at least one frozen particle composition to at least one wound of a subject at a predetermined velocity, for a time sufficient to maintain the approximation of tissue of the at least one wound;
wherein the at least one frozen particle composition includes one or more frozen hydrogen oxide coated in at least one adhesive agent; wherein the at least one adhesive agent; wherein the at least one adhesive agent includes one or more epoxy adhesive, acrylic adhesive, urethane adhesive, polyurethane adhesive, anerobic adhesive, urethane acrylate, polyester acrylate, methyacrylate, or cyanoacrylate; and
wherein the one or more frozen hydrogen oxide particles have one or more phases including at least one of amorphous solid water, low density amorphous ice, high density amorphous ice, very high density amorphous ice, clathrate ice, hyperquenched glassy water, ice Ic, ice II, ice III, ice IV, ice V, ice VI, ice VII, ice VIII, ice IX, ice X, ice XI, ice XII, ice XIII, ice XIV, or ice XV.

* * * * *

UNITED STATES PATENT AND TRADEMARK OFFICE
CERTIFICATE OF CORRECTION

| | | |
|---|---|---|
| PATENT NO. | : 8,545,856 B2 | Page 1 of 1 |
| APPLICATION NO. | : 12/383264 | |
| DATED | : October 1, 2013 | |
| INVENTOR(S) | : Edward S. Boyden et al. | |

It is certified that error appears in the above-identified patent and that said Letters Patent is hereby corrected as shown below:

In the Claims

Column 150, claim 19, lines 59-60:

After "least one adhesive agent;" delete "wherein the at least one adhesive agent;"

Signed and Sealed this
Third Day of December, 2013

Margaret A. Focarino
*Commissioner for Patents of the United States Patent and Trademark Office*